(12) United States Patent
Teter et al.

(10) Patent No.: US 9,701,951 B2
(45) Date of Patent: *Jul. 11, 2017

(54) VARIANTS OF GLYCOSIDE HYDROLASES

(71) Applicant: Novozymes Inc., Davis, CA (US)

(72) Inventors: Sarah Teter, Mountainview, CA (US); Connie Ward, Hamilton, MT (US); Joel Cherry, Winters, CA (US); Aubrey Jones, Davis, CA (US); Paul Harris, Carnation, WA (US); Jung Yi, Sacramento, CA (US)

(73) Assignee: Novozymes, Inc., Davis, CA (US)

( * ) Notice: Subject to any disclaimer, the term of this patent is extended or adjusted under 35 U.S.C. 154(b) by 37 days.

This patent is subject to a terminal disclaimer.

(21) Appl. No.: 14/475,639

(22) Filed: Sep. 3, 2014

(65) Prior Publication Data

US 2015/0056664 A1   Feb. 26, 2015

Related U.S. Application Data

(60) Division of application No. 13/748,328, filed on Jan. 23, 2013, now abandoned, which is a division of application No. 13/009,524, filed on Jan. 19, 2011, now Pat. No. 8,383,385, which is a division of application No. 11/891,249, filed on Aug. 8, 2007, now Pat. No. 7,932,073, which is a continuation of application No. 10/926,223, filed on Aug. 25, 2004, now abandoned.

(60) Provisional application No. 60/497,809, filed on Aug. 25, 2003.

(51) Int. Cl.
| | |
|---|---|
| *C12N 9/42* | (2006.01) |
| *C12P 19/14* | (2006.01) |
| *C11D 3/386* | (2006.01) |
| *C12P 19/02* | (2006.01) |

(52) U.S. Cl.
CPC ........ *C12N 9/2437* (2013.01); *C11D 3/38645* (2013.01); *C12N 9/2434* (2013.01); *C12N 9/2445* (2013.01); *C12P 19/02* (2013.01); *C12P 19/14* (2013.01); *C12Y 302/01091* (2013.01); *C12Y 302/01176* (2013.01)

(58) Field of Classification Search
CPC .............................. C12N 9/2437; C12N 9/244
See application file for complete search history.

(56) References Cited

U.S. PATENT DOCUMENTS

| | | | |
|---|---|---|---|
| 6,117,664 | A | 9/2000 | Schulein et al. |
| 7,375,197 | B2 | 5/2008 | Adney et al. |
| 2005/0054039 | A1 | 3/2005 | Goedegebuur et al. |
| 2011/0177561 | A1 | 7/2011 | Goedegebuur et al. |

FOREIGN PATENT DOCUMENTS

| | | |
|---|---|---|
| EP | 0137280 A1 | 8/1984 |
| WO | 01/04284 A1 | 1/2001 |
| WO | 2004/016760 A2 | 2/2004 |

OTHER PUBLICATIONS

Becker et al., Biochem. J., vol. 356, pp. 19-30 (2001).
Boer et al., Eur. J. Biochem., vol. 270, pp. 841-848 (2003).
Guilfoile et al., Journal of the Minnesota Academy of Science, vol. 64, pp. 18-22 (1999).
Guilfoile et al., UniProt Accession No. Q9P8P3 (2000).
Shoemaker et al., Biotechnology, pp. 691-696 (Oct. 1983).
Song et al., Genbank Access No. AY 368686 (2010).
Stahlberg et al., J. Mol. Biol., vol. 264, pp. 337-349 (1996).
Stahlberg et al., J. Mol. Biol., vol. 305, pp. 79-93 (2001).
Wey et al., Current Microbiology, vol. 28, pp. 31-39 (1994).

*Primary Examiner* — Rebecca Prouty
(74) *Attorney, Agent, or Firm* — Robert Starnes

(57) ABSTRACT

The present invention relates to variants of a parent glycoside hydrolase, comprising a substitution at one or more positions corresponding to positions 21, 94, 157, 205, 206, 247, 337, 350, 373, 383, 438, 455, 467, and 486 of amino acids 1 to 513 of SEQ ID NO: 2, and optionally further comprising a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2 a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2, wherein the variants have glycoside hydrolase activity. The present invention also relates to nucleotide sequences encoding the variant glycoside hydrolases and to nucleic acid constructs, vectors, and host cells comprising the nucleotide sequences.

21 Claims, 20 Drawing Sheets

VARIANTS OF GLYCOSIDE HYDROLASES

CROSS-REFERENCE TO RELATED APPLICATION

This application is a divisional of U.S. application Ser. No. 13/748,328 filed on Jan. 23, 2013, now abandoned, which is a divisional of U.S. application Ser. No. 13/009,524 filed on Jan. 19, 2011, now U.S. Pat. No. 8,383,385, which is a divisional of U.S. application Ser. No. 11/891,249 filed on Aug. 8, 2007, now U.S. Pat. No. 7,932,073, which is a continuation of U.S. application Ser. No. 10/926,223 filed on Aug. 25, 2004, now abandoned, which claims the benefit of U.S. Provisional Application No. 60/497,809 filed on Aug. 25, 2003. The content of these applications is incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

BACKGROUND OF THE INVENTION

Field of the Invention

The present invention relates to variants of a glycoside hydrolase having one or more improved properties relative to its parent enzyme, nucleic acids encoding the variants, methods of producing the variants, and methods of using the variants.

Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

Ståhlberg et al., 1996, *J. Mol. Biol.* 264: 337-349, describe activity studies and crystal structures of catalytically deficient mutants of cellobiohydrolase I from *Trichoderma reesei*. Boer and Koivula, 2003, *Eur. J. Biochem.* 270: 841-848, disclose the relationship between thermal stability and pH optimum studied with wild-type and mutant *Trichoderma reesei* cellobiohydrolase Cel7A.

WO 2004/016760 discloses variants of a *Hypocrea jecorina* cellobiohydrolase.

It would be an advantage in the art to provide glycoside hydrolase variants with improved properties for converting cellulosic materials to monosaccharides, disaccharides, and polysaccharides. Improved properties include altered temperature-dependent activity profiles, thermostability, pH activity, pH stability, substrate specificity, product specificity, and chemical stability.

It is an object of the present invention to provide variants of glycoside hydrolases with improved properties compared to its parent enzyme.

SUMMARY OF THE INVENTION

The present invention relates to isolated variants of a parent glycoside hydrolase, comprising a substitution at one or more positions corresponding to positions 21, 94, 157, 205, 206, 247, 337, 350, 373, 383, 438, 455, 467, and 486 of amino acids 1 to 513 of SEQ ID NO: 2, and optionally further comprising a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2, wherein the variants have glycoside hydrolase activity.

The present invention also relates to isolated polypeptides having glycoside hydrolase activity, wherein the amino acid sequences of the polypeptides differ from amino acids 1 to 513 of SEQ ID NO: 2 at one or more positions corresponding to positions 21, 94, 157, 205, 206, 247, 337, 350, 373, 383, 438, 455, 467, and 486 of amino acids 1 to 513 of SEQ ID NO: 2, and optionally further differs at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2.

The present invention also relates to isolated nucleotide sequences encoding the variant glycoside hydrolases or polypeptides having glycoside hydrolase activity and to nucleic acid constructs, vectors, and host cells comprising the nucleotide sequences.

The present invention also relates to methods for producing variants of a parent glycoside hydrolase or polypeptides having glycoside hydrolase activity in a host cell.

The present invention also relates to methods for obtaining a variant of a parent glycoside hydrolase, comprising:

(a) introducing a substitution at one or more positions corresponding to positions 21, 94, 157, 205, 206, 247, 337, 350, 373, 383, 438, 455, 467, and 486 of amino acids 1 to 513 of SEQ ID NO: 2, and optionally further introducing a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2, wherein the variant has glycoside hydrolase activity; and (b) recovering the variant.

The present invention further relates to methods of using the glycoside hydrolase variants in detergents and in the conversion of cellulose to glucose.

BRIEF DESCRIPTION OF THE FIGURES

FIGS. 15A and 15B show the genomic DNA sequence and the deduced amino acid sequence of an *Aspergillus fumigatus* be'ta-glucosidase (SEQ ID NOS: 56 and 57, respectively). The predicted signal peptide is underlined and predicted introns are italicized.

DETAILED DESCRIPTION OF THE INVENTION

Figure 1:
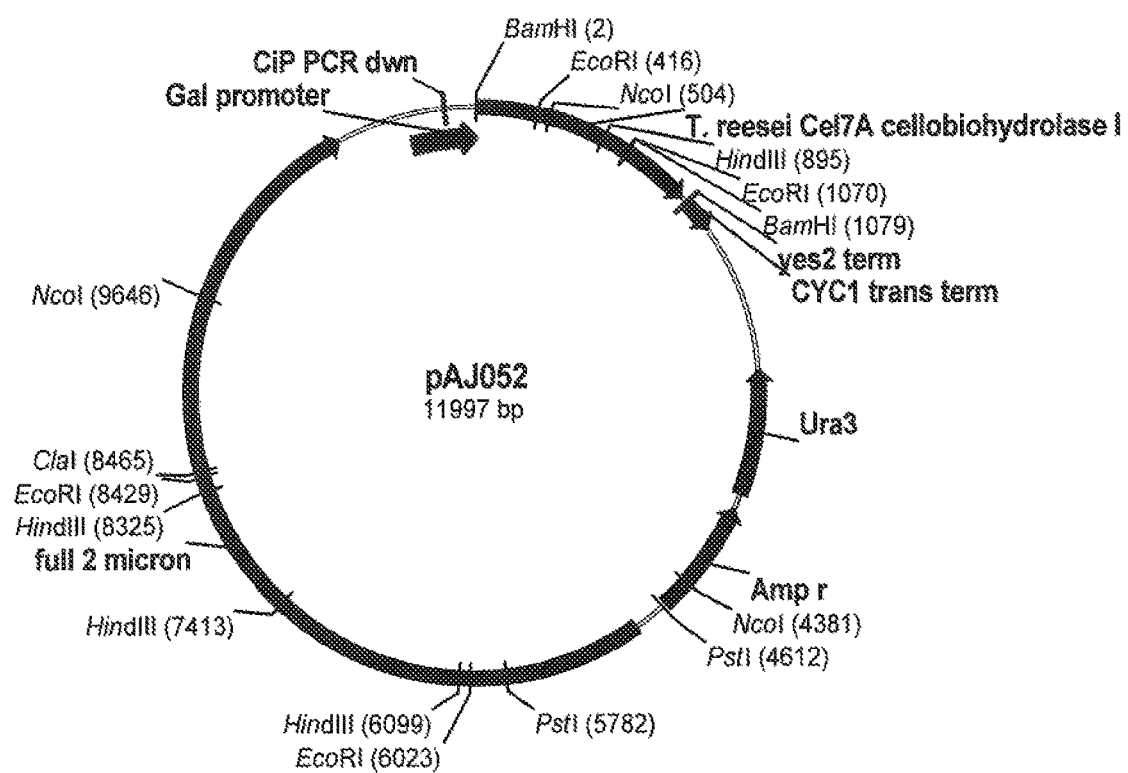
FIG. 1 shows a restriction map of pAJ052.

The present invention relates to isolated variants of a parent glycoside hydrolase, comprising a substitution at one or more positions corresponding to positions 21, 94, 157, 205, 206, 247, 337, 350, 373, 383, 438, 455, 467, and 486 of amino acids 1 to 513 of SEQ ID NO: 2, and optionally further comprising a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2, wherein the variant has glycoside hydrolase activity.

Definitions

The term "glycoside hydrolase" is defined herein as hydrolases described by Coutinho, P. M. and Henrissat, B., 1999, Carbohydrate-active enzymes: an integrated database approach, in "*Recent Advances in Carbohydrate Bioengineering*", H. J. Gilbert, G. Davies, B. Henrissat and B. Svensson eds., The Royal Society of Chemistry, Cambridge, pp. 3-12. Examples of glycoside hydrolases include, but are not limited to, cellobiohydrolase, endoglucanase, and exoglucanase. In a preferred embodiment, the glycoside hydrolases belong to Family 7 as defined by Coutinho, P. M. and Henrissat, B., 1999, supra.

The term "cellobiohydrolase" is defined herein as a 1,4-D-glucan cellobiohydrolase (E.C. 3.2.1.91) which catalyzes the hydrolysis of 1,4-beta-D-glucosidic linkages in cellulose, cellotetriose, or any beta-1,4-linked glucose containing polymer, releasing cellobiose from the non-reducing ends of the chain. For purposes of the present invention, cellobiohydrolase activity is determined according to the procedures described by Lever et al., 1972, *Anal. Biochem.* 47: 273-279 and by van Tilbeurgh et al., 1982, *FEBS Letters*, 149: 152-156; van Tilbeurgh and Claeyssens, 1985, FEBS *Letters*, 187: 283-288. In the present invention, the Lever et al. method was employed to assess hydrolysis of cellulose in corn stover, while the method of van Tilbeurgh et al. was used to determine the cellobiohydrolase activity on a fluorescent disaccharide derivative.

The term "endoglucanase" is defined herein as an endo-1,4-(1,3;1,4)-beta-D-glucan 4-glucanohydrolase (E.C. No. 3.2.1.4) which catalyses endohydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268.

The term "exoglucanase" is defined herein as a 1,4-beta-D-glucan glucohydrolase (E.C. 3.2.1.74) which catalyzes the hydrolysis of 1,4-linkages (O-glycosyl bonds) in 1,4-beta-D-glucans so as to remove successive glucose or cellobiose units. For purposes of the present invention, exoglucanase activity is determined according to the procedure described by Himmel et al., 1986, *J. Biol. Chem.* 261: 12948-12955.

Variant: The term "variant" is defined herein as a glycoside hydrolase comprising one or more alterations, such as substitutions, insertions, deletions, and/or truncations of one or more specific amino acid residues at one or more specific positions in the polypeptide.

Wild-Type Enzyme: The term "wild-type" glycoside hydrolase denotes a glycoside hydrolase expressed by a naturally occurring microorganism, such as a yeast or a filamentous fungus found in nature.

Parent Enzyme: The term "parent" glycoside hydrolase as used herein means a glycoside hydrolase to which modifications, e.g., substitution(s), insertion(s), deletion(s), and/or truncation(s), are made to produce the enzyme variants of the present invention. This term also refers to the polypeptide with which a variant is compared and aligned. The parent may be a naturally occurring (wild type) polypeptide, or it may even be a variant thereof, prepared by any suitable means. For instance, the parent protein may be a variant of a naturally occurring polypeptide which has been modified or altered in the amino acid sequence. A parent may also be an allelic variant which is a polypeptide encoded by any of two or more alternative forms of a gene occupying the same chromosomal locus.

Shuffling: The term "shuffling" means recombination of nucleotide sequence(s) between two or more homologous nucleotide sequences resulting in recombined nucleotide sequences (i.e., nucleotide sequences having been subjected to a shuffling cycle) having a number of nucleotides exchanged, in comparison to the starting nucleotide sequences.

Randomized library: The term "randomized library", "variant library", or "library" is defined herein as a library of variant polypeptides. Diversity in the variant library can be generated via mutagenesis of the genes encoding the variants at the DNA triplet level, such that individual codons are variegated, e.g., by using primers of partially randomized sequences in a PCR reaction. Several techniques have been described, by which one can create a diverse combinatorial library by variegating several nucleotide positions in a gene and recombining them, for example, where these positions are too far apart to be covered by a single (spiked or doped) oligonucleotide primer. These techniques include the use of in vivo recombination of the individually diversified gene segments as described in WO 97/07205 on page 3, lines 8 to 29. They also include the use of DNA shuffling techniques to create a library of full length genes, wherein several gene segments are combined, and wherein each segment may be diversified, e.g., by spiked mutagenesis (Stemmer, 1994, *Nature* 370: 389-391; U.S. Pat. Nos. 5,811, 238; 5,605,793; and 5,830,721). One can use a gene encoding a protein "backbone" (wild type parent polypeptide) as a template polynucleotide, and combine this with one or more single or double-stranded oligonucleotides as described in WO 98/41623 and WO 98/41622. The single-stranded oligonucleotides can be partially randomized during synthesis. The double-stranded oligonucleotides can be PCR products incorporating diversity in a specific region. In both cases, one can dilute the diversity with corresponding segments encoding the sequence of the backbone protein in order to limit the average number of changes that are introduced.

Recombination: The term "recombination" is defined herein as a process wherein nucleic acids associate with each other in regions of homology, leading to interstrand DNA exchange between those sequences. For purposes of the present invention, homologous recombination is determined according to the procedures summarized by Paques and Haber, 1999, *Microbiology and Molecular Biology Reviews* 63: 349-404. "Homologous recombination" is defined herein as recombination in which no changes in the nucleotide sequences occurs within the regions of homology relative to the input nucleotide sequences. For perfect homologous recombination, the regions should contain a sufficient number of nucleic acids, such as 15 to 1,500 base pairs, preferably 100 to 1,500 base pairs, more preferably 400 to 1,500 base pairs, and most preferably 800 to 1,500 base pairs, which are highly homologous with the corresponding nucleic acid sequence to enhance the probability of homologous recombination. The recombination may also occur by non-homologous recombination. "Non-homologous recombination" is defined herein as recombination where any mode of DNA repair incorporating strand exchange results in a nucleotide sequence different from any of the recombining sequences.

Improved property: The term "improved property" is defined herein as a characteristic associated with a variant which is improved compared to the parent glycoside hydrolase. Such improved properties include, but are not limited to, altered temperature-dependent activity profile, thermostability, pH activity, pH stability, substrate specificity, product specificity, and chemical stability.

Improved thermal activity: The term "improved thermal activity" is defined herein as an alteration of the temperature-dependent activity profile of a glycoside hydrolase variant at a specific temperature relative to the temperature-dependent activity profile of the parent glycoside hydrolase. The thermal activity value provides a measure of the enzyme's efficiency in performing catalysis of a hydrolysis reaction over a range of temperatures. A glycoside hydrolase has a specific temperature range wherein the protein is stable and retains its enzymatic activity, but becomes less stable and thus less active with increasing temperature. Furthermore, the initial rate of a reaction catalyzed by a glycoside hydrolase can be accelerated by an increase in temperature which is measured by determining thermal activity of a variant. A more thermoactive variant will lead to an increase in the rate of hydrolysis decreasing the time required and/or decreasing the enzyme concentration required for hydrolysis. Alternatively, a variant with a reduced thermal activity will catalyze a hydrolysis reaction at a temperature lower than the temperature optimum of the parent enzyme defined by the temperature-dependent activity profile of the parent.

Improved thermostability: The term "improved thermostability" is defined herein as a variant enzyme displaying retention of enzymatic activity after a period of incubation at elevated temperature relative to the parent enzyme. Such a variant may or may not display an altered thermal activity profile relative to the parent. For example, a variant may have an improved ability to refold following incubation at elevated temperature relative to the parent.

In a preferred embodiment, the thermal activity of the variant glycoside hydrolase is at least 1.5-fold, preferably at least 2-fold, more preferably at least 5-fold, most preferably at least 7-fold, and even most preferably at least 20-fold more thermally active than the wild type variant when activity on 4-methylumbelliferyl beta-D-lactoside at 64° C. or a higher temperature is compared to activity at 50° C., for 45 minutes at pH 5.0.

Improved product specificity: The term "improved product specificity" is defined herein as a variant enzyme displaying an altered product profile relative to the parent in which the altered product profile improves the performance of the variant in a given application relative to the parent. The term "product profile" is defined herein as the chemical composition of the reaction products produced by enzymatic hydrolysis.

Improved chemical stability: The term "improved chemical stability" is defined herein as a variant enzyme displaying retention of enzymatic activity after a period of incubation in the presence of a chemical or chemicals, either naturally occurring or synthetic, which reduce the enzymatic activity of the parent enzyme. Improved chemical stability may also result in variants better able to catalyze a reaction in the presence of such chemicals.

Conventions for Designation of Variants

In the present invention, a specific numbering of amino acid residue positions in the glycoside hydrolase variants is employed. For example, by aligning the amino acid sequences of known glycoside hydrolases, it is possible to designate an amino acid position number to any amino acid residue in any glycoside hydrolase enzyme.

Using the numbering system originating from the amino acid sequence of the glycoside hydrolase disclosed in SEQ ID NO: 2, aligned with the amino acid sequence of a number of other glycoside hydrolases, it is possible to indicate the position of an amino acid residue in a glycoside hydrolase in regions of structural homology.

Multiple alignments of protein sequences may be made, for example, using "ClustalW" (Thompson, J. D., Higgins, D. G. and Gibson, T. J., 1994, CLUSTAL W: Improving the sensitivity of progressive multiple sequence alignment through sequence weighting, positions-specific gap penalties and weight matrix choice, *Nucleic Acids Research* 22: 4673-4680). Multiple alignments of DNA sequences may be done using the protein alignment as a template, replacing the amino acids with the corresponding codon from the DNA sequence.

Pairwise sequence comparison algorithms in common use are adequate to detect similarities between protein sequences that have not diverged beyond the point of approximately 20-30% sequence identity (Doolittle, 1992, *Protein Sci.* 1: 191-200; Brenner et al., 1998, *Proc. Natl. Acad. Sci. USA* 95, 6073-6078). However, truly homologous proteins with the same fold and similar biological function have often diverged to the point where traditional sequence-based comparisons fail to detect their relationship (Lindahl and Elofsson, 2000, *J. Mol. Biol.* 295: 613-615). Greater sensitivity in sequence-based searching can be attained using search programs that utilize probabilistic representations of protein families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the protein of interest has one or more representatives in the protein structure databases. Programs such as GenTHREADER (Jones 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the protein of interest, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. These alignments can be used to predict the structurally and functionally corresponding amino acid residues in proteins within the same structural superfamily. This information, along with information derived from homology modeling and profile searches, can be used to predict which residues to mutate when moving mutations of interest from one protein to a close or remote homolog.

In describing the various glycoside hydrolase variants of the present invention, the nomenclature described below is adapted for ease of reference. In all cases, the accepted IUPAC single letter or triple letter amino acid abbreviation is employed.

Substitutions. For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing mutations at positions 205 and 411 substituting glycine (G) with arginine (R), and serine (S) with phenylalanine (F), respectively.

Deletions. For an amino acid deletion, the following nomenclature is used: Original amino acid, position*. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, new inserted amino acid. Accordingly the insertion of lysine after glycine at position 195 is designated "Gly195GlyLys" or "G195GK".

Multiple modifications. Variants comprising multiple modifications are separated by addition marks ("+"), e.g., "Arg170Tyr+Gly195Glu" or "R170Y+G195E" representing modifications at positions 170 and 195 substituting tyrosine and glutamic acid for arginine and glycine, respectively.

Parent Glycoside Hydrolases

In the present invention, the parent glycoside hydrolase is (a) a polypeptide comprising an amino acid sequence which has at least 70% identity with amino acids 1 to 513 of SEQ ID NO: 2; or (b) a polypeptide encoded by a nucleotide sequence which hybridizes under at least low stringency conditions with nucleotides 52 to 1539 of SEQ ID NO: 1, or its complementary strand.

In a first aspect, the parent glycoside hydrolase comprises an amino acid sequence which has a degree of identity to amino acids 1 to 513 of SEQ ID NO: 2 of at least 70%, preferably at least 75%, more preferably at least 80%, more preferably at least 85%, even more preferably at least 90%, most preferably at least 95%, and even most preferably at least 97%, which have glycoside hydrolase activity (hereinafter "homologous polypeptides"). For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Substantially homologous parent glycoside hydrolases may have one or more amino acid substitutions, deletions or additions. These changes are preferably of a minor nature, that is conservative amino acid substitutions as described above and other substitutions that do not significantly affect the three-dimensional folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, or protein A (Nilsson et al., 1985, *EMBO J.* 4: 1075; Nilsson et al., 1991, *Methods* Enzymol. 198: 3. See, also, in general, Ford et al., 1991, *Protein Expression and Purification* 2: 95-107. Examples of conservative modifications are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid modifications, which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as the reverse (Taylor, 1986, *Journal of Theoretical Biology* 119: 205-218.

Although the changes described above preferably are of a minor nature, such changes may also be of a substantive nature such as fusion of larger polypeptides of up to 300 amino acids or more both as amino- or carboxyl-terminal extensions.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type glycoside hydrolase. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Preferably, the parent glycoside hydrolase comprises the amino acid sequence of SEQ ID NO: 2; or an allelic variant thereof; or a fragment thereof that has glycoside hydrolase activity. In a preferred embodiment, the parent polypeptide comprises the amino acid sequence of SEQ ID NO: 2. In another preferred embodiment, the parent polypeptide comprises amino acids 1 to 513 of SEQ ID NO: 2; or an allelic variant thereof; or a fragment thereof that has glycoside hydrolase activity. In another preferred embodiment, the parent polypeptide comprises amino acids 1 to 513 of SEQ ID NO: 2. In another preferred embodiment, the parent polypeptide consists of the amino acid sequence of SEQ ID NO: 2; or an allelic variant thereof; or a fragment thereof that has glycoside hydrolase activity. In another preferred embodiment, the parent polypeptide consists of the amino acid sequence of SEQ ID NO: 2. In another preferred embodiment, the parent polypeptide consists of amino acids 1 to 513 of SEQ ID NO: 2 or an allelic variant thereof; or a fragment thereof that has glycoside hydrolase activity. In another preferred embodiment, the parent polypeptide is encoded by the nucleotide sequence contained in plasmid pAJO52 which is contained in *Escherichia coli* NRRL B-30683, wherein the nucleic acid sequence encodes a polypeptide having glycoside hydrolase activity. In another preferred embodiment, the parent polypeptide is encoded by the mature polypeptide coding region contained in plasmid pAJO52 which is contained in *Escherichia coli* NRRL B-30683.

A fragment of SEQ ID NO: 2 is a polypeptide having one or more amino acids deleted from the amino and/or carboxyl terminus of this amino acid sequence. Preferably, a fragment contains at least 450 amino acid residues, more preferably at least 470 amino acid residues, and most preferably at least 490 amino acid residues.

In a second aspect, the parent glycoside hydrolase is encoded by a nucleotide sequence which hybridizes under low stringency conditions, preferably medium stringency conditions, more preferably medium-high stringency conditions, even more preferably high stringency conditions, and most preferably very high stringency conditions with a nucleotide probe which hybridizes under the same conditions with (i) nucleotides 52 to 1539 of SEQ ID NO: 1, (ii) the genomic nucleotide sequence comprising nucleotides 52 to 1539 of SEQ ID NO: 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO: 1 may be at least 100 contiguous nucleotides or preferably at least 200 contiguous nucleotides. Moreover, the subsequence may encode a polypeptide fragment which has glycoside hydrolase activity.

A subsequence of SEQ ID NO: 1, or homologue thereof, is a nucleotide sequence where one or more nucleotides have been deleted from the 5'- and/or 3'-end. Preferably, a subsequence contains at least 1350 nucleotides, more preferably at least 1410 nucleotides, and most preferably at least 1470 nucleotides.

The parent polypeptide may also be an allelic variant of a polypeptide that has glycoside hydrolase activity. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The nucleotide sequence of SEQ ID NO: 1 or a subsequence thereof, as well as the amino acid sequence of SEQ ID NO: 2, or a fragment thereof, may be used to design nucleotide probes to identify and clone DNA encoding parent polypeptides having glycoside hydrolase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin).

A genomic DNA or cDNA library prepared from such other organisms may be screened for DNA which hybridizes with the probes described above and which encodes a parent polypeptide having glycoside hydrolase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, or a subsequence thereof, the carrier material is used in a Southern blot. For purposes of the present invention, hybridization indicates that the nucleotide sequence hybridizes to a labeled nucleotide probe corresponding to the nucleotide sequence shown in SEQ ID NO: 1, its complementary strand, or a subsequence thereof, under low to very high stringency conditions. Molecules to which the probe hybridizes can be detected using, for example, X-ray film or any other detection means known in the art.

In a preferred embodiment, the nucleotide probe is a nucleotide sequence which encodes the polypeptide of SEQ ID NO: 2, or a subsequence thereof. In another preferred embodiment, the nucleotide probe is SEQ ID NO: 1. In another preferred embodiment, the nucleotide probe is nucleotides 52 to 1539 of SEQ ID NO: 1. In another preferred embodiment, the nucleotide probe is the nucleic acid sequence contained in plasmid pAJO52 which is contained in *Escherichia coli* NRRL B-30683, wherein the nucleic acid sequence encodes a polypeptide having glycoside hydrolase activity. In another preferred embodiment, the nucleotide probe is the mature polypeptide coding region contained in plasmid pAJO52 which is contained in *Escherichia coli* NRRL B-30683.

For long probes of at least 100 nucleotides in length, low to very high stringency conditions are defined as prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at least at 50° C. (low stringency), more preferably at least at 55° C. (medium stringency), more preferably at least at 60° C. (medium-high stringency), most preferably at least at 65° C. (high stringency), and even most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The parent glycoside hydrolase may be obtained from microorganisms of any genus. For purposes of the present invention, the term "obtained from" as used herein in connection with a given source shall mean that the parent glycoside hydrolase encoded by a nucleotide sequence is produced by the source or by a cell in which the nucleotide sequence from the source has been inserted. In a preferred embodiment, the parent glycoside hydrolase is secreted extracellularly.

The parent glycoside hydrolase may be a fungal glycoside hydrolase. In a preferred embodiment, the fungal glycoside hydrolase is a yeast glycoside hydrolase such as a *Candida, Kluyveromyces, Pichia, Saccharomyces, Schizosaccharomyces*, or *Yarrowia* glycoside hydrolase. In another preferred embodiment, the fungal glycoside hydrolase is a filamentous fungal glycoside hydrolase such as an *Acremonium, Agaricus, Alternaria, Aspergillus, Botryosphaeria, Ceriporiopsis, Chaetomidium, Claviceps, Cochliobolus, Coprinopsis, Coptotermes, Corynascus, Cryphonectria, Diplodia, Exidia, Fusarium, Gibberella, Holomastigotoides, Humicola, Irpex, Lentinula, Leptospaeria, Magnaporthe, Melanocarpus, Meripilus, Myceliophthora, Neurospora, Penicillium, Phanerochaete, Poitrasia, Pseudoplectania, Pseudotrichonympha, Rhizomucor, Scytalidium, Talaromyces, Thermoascus, Thielavia, Trichoderma, Trichophaea, Verticillium, Volvariella*, or *Xylaria* glycoside hydrolase.

In a more preferred embodiment, the parent glycoside hydrolase is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* glycoside hydrolase.

In another more preferred embodiment, the parent glycoside hydrolase is an *Acremonium cellulolyticus, Aspergillus aculeatus, Aspergillus awamori, Aspergillus fumigatus, Aspergillus foetidus, Aspergillus fumigatus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium solani, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Schizophyllum commune, Sclerotium rolfsii, Sporotrichum cellulophilum, Talaromyces emersonii, Thielavia terrestris, Trichoderma harzianum, Trichoderma koningii, Trichoderma longibrachiatum, Trichoderma reesei*, or *Trichoderma viride* glycoside hydrolase.

In an even more preferred embodiment, the parent glycoside hydrolase is a *Trichoderma reesei* glycoside hydrolase, and most preferably the *Trichoderma reesei* cellobiohydrolase I of SEQ ID NO: 2 or the mature polypeptide thereof. In another most preferred embodiment, the parent glycoside hydrolase is encoded by the nucleotide sequence contained in plasmid pAJO52 which is contained in *Escherichia coli* NRRL B-30683, wherein the nucleotide sequence encodes a polypeptide having glycoside hydrolase activity. In another most preferred embodiment, the parent glycoside hydrolase is encoded by the mature polypeptide coding region contained in plasmid pAJO52 which is contained in *Escherichia coli* NRRL B-30683.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The parent glycoside hydrolase may also be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. The nucleotide sequence encoding a glycoside hydrolase may then be derived by similarly screening a genomic or cDNA library of another microorganism or mixed DNA sample. Once a nucleotide sequence encoding a glycoside hydrolase has been detected with suitable probe(s) as described herein, the sequence may be isolated or cloned by utilizing techniques which are known to those of ordinary skill in the art (see, e.g., J. Sambrook, E. F. Fritsch, and T. Maniatus, 1989, *Molecular Cloning, A Laboratory Manual*, 2d edition, Cold Spring Harbor, N.Y.).

As defined herein, an "isolated" glycoside hydrolase is a polypeptide which is essentially free of other non-glycoside hydrolase polypeptides, e.g., at least 20% pure, preferably at least 40% pure, more preferably at least 60% pure, even more preferably at least 80% pure, most preferably at least 90% pure, and even most preferably at least 95% pure, as determined by SDS-PAGE.

The parent glycoside hydrolase can also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

Essential amino acids in the parent glycoside hydrolase can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., glycoside hydrolase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Left.* 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204) and region-directed mutagenesis (Derbyshire et al., 1986, *Gene* 46:145; Ner et al., 1988, *DNA* 7:127).

Plasmids

The plasmid or plasmids used for preparing glycoside hydrolase variants may be any plasmid or vector that may be subjected to recombinant DNA procedures. The plasmid comprising a nucleotide sequence encoding a glycoside hydrolase may be prepared by ligating the nucleotide sequence into a suitable plasmid, or by any other suitable method. The plasmid preferably contains one or more selectable markers described herein which permit easy selection of transformed cells. The choice of plasmid will often depend on the host cell into which it is to be introduced.

In the present invention, the plasmid may be an autonomously replicating plasmid, i.e., a plasmid which exists as an extrachromosomal entity, the replication of which is distinct from chromosomal replication.

The plasmid replicator may be any plasmid replicator mediating autonomous replication which functions in a cell. The term "plasmid replicator" is defined herein as a sequence that enables a plasmid or vector to replicate in vivo. Examples of a plasmid replicator useful in a yeast cell are the 2 micron origin of replication, ARS1, ARS4, the combination of ARS1 and CEN3, and the combination of ARS4 and CEN6. Examples of a plasmid replicator useful in a filamentous fungal cell are AMA1 and ANSI (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

The linearizing of the plasmid(s) can be directed toward any site within the plasmid. The plasmid(s) may be linearized by any suitable methods known in the art, for example, digestion with one or more restriction enzymes. The linearized ends of the plasmid may be filled-in with nucleotides as described by Pompon el al., 1989, *Gene* 83: 15-24. However, it is preferred not to fill in the linearized ends as it might create a frameshift.

To facilitate the screening process, the plasmid is preferably an expression vector in which the nucleotide sequence in question is operably linked to additional segments required for transcription of the DNA. In general, the expression vector is derived from a plasmid, a cosmid or a bacteriophage, or may contain elements of any or all of these. For purposes of the present invention, the terms "plasmid" and "vector" are used interchangeably.

DNA Fragments

A library of DNA fragments to be randomly combined (or "shuffled") with homologous regions in the linearized plasmid(s) by in vivo recombination may be prepared by any suitable method. For example, the DNA fragment may be prepared by PCR amplification (e.g., error-prone PCR) of a plasmid comprising the nucleotide sequence, using specific primers, for example, as described in U.S. Pat. No. 4,683, 202 or Saiki et al., 1988, *Science* 239: 487-491. The DNA fragment may also be isolated from a plasmid comprising the desired nucleotide sequence by digestion with restriction enzymes, followed by isolation using, for example, electrophoresis.

The DNA fragment may alternatively be prepared synthetically by established standard methods, e.g., the phosphoamidite method described by Beaucage and Caruthers, 1981, *Tetrahedron Letters* 22: 1859-1869, or the method described by Matthes et al., 1984, *EMBO Journal* 3: 801-805. According to the phosphoamidite method, oligonucleotides are synthesized in an automatic DNA synthesizer, purified, annealed, ligated, and cloned into suitable plasmids.

The DNA fragment may also be of mixed synthetic and genomic, mixed synthetic and cDNA, or mixed genomic and cDNA origins prepared by ligating fragments of synthetic, genomic or cDNA origin, the fragments corresponding to various parts of the entire nucleotide sequence, in accordance with standard techniques.

The library of DNA fragments comprise one or more mutations of the nucleotide sequence, wherein the fragments comprise at least two regions, one or more regions which are homologous to the 5'-region or the 3'-region of the gap in the linearized nucleotide sequence and/or plasmid sequence and one or more second regions which are homologous to the 5'-region or the 3'-region of the DNA fragments of the library.

The regions of the DNA fragment may be any sequence that is homologous with the nucleotide sequence and/or plasmid sequence.

In a preferred embodiment, the regions of the DNA fragment are a 5'-region and/or a 3'-region that flank a gene that encodes a glycoside hydrolase, or a 5'-region and/or a 3'-region of a gene that encodes a glycoside hydrolase.

In another preferred embodiment, the DNA fragment or fragments are prepared under conditions resulting in low, medium or high random mutagenesis frequency. To obtain low mutagenesis frequency the nucleotide sequence(s) (comprising the DNA fragment(s)) may be prepared by a standard PCR amplification method (U.S. Pat. No. 4,683, 202 or Saiki et al., 1988, *Science* 239: 487-491). A medium or high mutagenesis frequency may be obtained by performing the PCR amplification under conditions which reduce the fidelity of replication by a thermostable polymerase and increase the misincorporation of nucleotides, for example, as described by Deshler, 1992, GATA 9: 103-106; Leung et al., 1989, *BioTechniques* 1: 11-15.

The PCR amplification may be combined with a mutagenesis step using a suitable physical or chemical mutagenizing agent, e.g., one which induces transitions, transversions, inversions, scrambling, deletions, and/or insertions.

In a preferred embodiment, the DNA fragment(s) to be shuffled preferably have a length of about 15 bp to 8 kb, more preferably about 30 bp to 6 kb, even more preferably about 40 by to 6 kb, even more preferably about 80 bp to 4 kb, and most preferably about 100 bp to 2 kb, to be able to interact optimally with the linearized plasmid.

Fungal Cells

The fungal cell, into which the mixture of plasmid/fragment nucleotide sequences are to be introduced, may be any fungal cell useful in the present invention. A "recombination fungal cell" is defined herein as a cell capable of mediating shuffling of a number of homologous nucleotide sequences.

In a preferred embodiment, the fungal recombination cell is a yeast cell. In a more preferred embodiment, the yeast recombination cell is a *Candida, Hansenula, Kluyveromyces, Pichia, Saccharomyces, Schizosaccharomyces*, or *Yarrowia* cell.

In a most preferred embodiment, the yeast recombination cell is a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

In another preferred embodiment, the fungal recombination cell is a filamentous fungal cell. In a more preferred embodiment, the filamentous fungal recombination cell is an *Acremonium, Aspergillus, Fusarium, Humicola, Mucor, Myceliophthora, Neurospora, Penicillium, Thielavia, Tolypocladium*, or *Trichoderma* cell.

In a most preferred embodiment, the filamentous fungal recombination cell is an *Aspergillus awamori, Aspergillus foetidus, Aspergillus japonicus, Aspergillus nidulans, Aspergillus niger*, or *Aspergillus oryzae* cell. In another most preferred embodiment, the filamentous fungal recombination cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred embodiment, the filamentous fungal recombination cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

In another most preferred embodiment, the *Aspergillus* cell is an *Aspergillus oryzae* cell.

In another most preferred embodiment, the *Aspergillus* cell is an *Aspergillus niger* cell.

In another most preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62-80 and O'Donnell et al., 1998, *Fungal Genetics and Biology* 23: 57-67; as well as taxonomic equivalents of *Fusarium venenatum* regardless of the species name by which they are currently known. In another most preferred embodiment, the *Fusarium venenatum* cell is a morphological mutant of *Fusarium venenatum* A3/5 or *Fusarium venenatum* ATCC 20334, as disclosed in WO 97/26330.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings* of the National Academy of Sciences USA 75: 1920.

In Vivo Recombination

A large number of variants or homologous genes can be combined in one transformation to efficiently create gene chimeras from the homologous genes. The shuffling of these genes, encoding improved variants, wild type genes, or a combination thereof, results in chimeras that can be expressed and followed by screening to identify those chimeras with the optimal combination of beneficial mutations. The process increases multi-fold the number of further improved variants that can be obtained compared to a process that uses only random mutagenesis (for a review, see Kuchner and Arnold, 1997, *TIBTech* 15: 523-530). Random mutagenesis introduces mutations into a target nucleotide sequence, creating deleterious mutations much more frequently than beneficial ones. In iterative rounds of such mutagenesis, deleterious mutations accumulate more rapidly than beneficial ones, effectively masking the identification of beneficial mutations during screening. The random recombination between two or more homologous nucleotide sequences that contain multiple single nucleotide changes in their nucleotide sequences potentially allows all those nucleotide changes contained in one variant to be separated from one another and to be randomly combined instead with any mutations present on other variants. This shuffling of mutations provides a means by which mutations from different parent sequences can be combined with each other randomly to increase the probability of combining nucleotide changes in a single nucleotide sequence.

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

Efficient recombination of multiple overlapping fragments using the in vivo recombination method is a means to generate chimeras from variants or homologous genes. An overlap as small as 15 bp is sufficient for recombination, and may be utilized for very easy domain shuffling of even distantly related genes. In domain shuffling, larger blocks of non-homologous DNA are randomly assorted by means of stretches of homology at their termini.

It is preferred that at least one shuffling cycle is a backcrossing cycle with the initially used DNA fragment or fragments, which may be the wild-type DNA fragment. This eliminates non-essential mutations. Non-essential mutations may also be eliminated by using wild-type DNA fragments as the initially used input DNA material.

More than two nucleotide sequences can be shuffled at the same time, and can be advantageous as a vast number of quite different variants can be made rapidly without an abundance of iterative procedures. When recombining many fragments from the same region, multiple overlapping of the fragments will increase the frequency of DNA interchange by itself, but it is also important to have a relatively high number of random crossovers in overlapping regions in order to recombine closely located variants/differences.

An overlap as small as 15 bp between two fragments is sufficient to obtain an efficient recombination. Therefore, overlapping in the range from 15 to 5000 bp, preferably from 30 bp to 500 bp, especially 30 bp to 100 bp is suitable in the present invention.

In the present invention, preferably 2 or more overlapping fragments, more preferably 2 to 50 overlapping fragments, and most preferably 2 to 10 overlapping fragments may advantageously be used as DNA fragments in a shuffling cycle.

Besides allowing creation of chimeric genes, employing overlapping fragments is a useful method for domain shuffling by creating small overlaps between DNA fragments from different domains and screening for the best combination. For example, in the case of three DNA fragments, the overlapping regions may be as follows: the first end of the first fragment overlaps the first end of the linearized plasmid, the first end of the second fragment overlaps the second end of the first fragment, and the second end of the second fragment overlaps the first end of the third fragment, the first end of the third fragment overlaps (as stated above) the second end of the second fragment, and the second end of the third fragment overlaps the second end of the linearized plasmid.

It is understood that when using two or more DNA fragments as the starting material, it is preferred to have continuous overlaps between the ends of the plasmid and the DNA fragments.

Even though it is preferred to shuffle homologous nucleotide sequences in the form of DNA fragment(s) and linearized plasmid(s), it is also possible to shuffle two or more linearized plasmids comprising homologous nucleotide sequences encoding polypeptides. However, in such a case, it is important to linearize the plasmids at different sites.

In the present invention, two or more linearized plasmids and one or more homologous DNA fragments can be used as the starting material to be shuffled. The ratio between the linearized plasmid(s) and homologous DNA fragment(s) preferably lie in the range from 20:1 to 1:50, and more preferably from 2:1 to 1:10 (mol plasmid:mol fragments) with the specific concentrations being from 1 pM to 10 M of the DNA.

The linearized plasmids may be gapped in such a way that the overlap between the fragments is deleted in the plasmid. The repair of the gap in the plasmid then requires that the fragments recombine with one another in addition to recombining with the ends of the gapped plasmid in order to reconstitute a circular, autonomously replicating plasmid. In a preferred embodiment, the linearization of the plasmid or vector creates a sufficient gap in the coding sequence of the nucleotide sequence to force the homologous recombination of the DNA fragments with the corresponding regions of the nucleotide sequence, recreating a circular replicating plasmid.

Variants

In the present invention, the isolated variants of a parent glycoside hydrolase comprise a substitution at one or more positions corresponding to positions 21, 94, 157, 205, 206, 247, 337, 350, 373, 383, 438, 455, 467, and 486 of amino acids 1 to 513 of SEQ ID NO: 2, and optionally further comprise a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2, wherein the variants, having glycoside hydrolase activity, comprise amino acid sequences which have a degree of identity of at least 70%, preferably at least 75%, more preferably at least 80%, more preferably at least 85%, even more preferably at least 90%, most preferably at least 95%, and even most preferably at least 97% to the amino acid sequence of the parent glycoside hydrolase. For purposes of the present invention, the degree of identity between two amino acid sequences is determined by the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

As defined herein, an "isolated variant" of a parent glycoside hydrolase is a polypeptide which is essentially free of other non-glycoside hydrolase polypeptides, e.g., at least 20% pure, preferably at least 40% pure, more preferably at least 60% pure, even more preferably at least 80% pure, most preferably at least 90% pure, and even most preferably at least 95% pure, as determined by SDS-PAGE.

In a preferred embodiment, the number of amino acid substitutions in the variants of the present invention comprise preferably 33, more preferably 32, even more preferably 31, even more preferably 30, even more preferably 29, even more preferably 28, even more preferably 27, even more preferably 26, even more preferably 25, even more preferably 24, even more preferably 23, even more preferably 22, even more preferably 21, even more preferably 20, even more preferably 19, even more preferably 18, even more preferably 17, even more preferably 16, even more preferably 15, even more preferably 14, even more preferably 13, even more preferably 12, even more preferably 11, even more preferably 10, even more preferably 9, even more preferably 8, even more preferably 7, even more preferably 6, even more preferably 5, even more preferably 4, even more preferably 3, even more preferably 2, and most preferably 1.

In a preferred embodiment, the variant of a parent glycoside hydrolase comprises a substitution at one or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at two or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at three or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at four or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at five or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at six or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at seven or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at eight or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at nine or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at ten or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at eleven or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at twelve or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at thirteen or more positions corresponding to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the variant of a parent glycoside hydrolase comprises substitutions at positions corresponding at least to positions 21, 94, 157, 205, 206, 247, 337, 350, 373, 383, 438, 455, 467, and 486 of amino acids 1 to 513 of SEQ ID NO: 2, and optionally further comprises a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2.

In another preferred embodiment, the variant comprises a substitution at a position corresponding to position 21 of amino acids 1 to 513 of SEQ ID NO: 2. In another more preferred embodiment, the variant comprises a substitution at a position corresponding to position 21 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Pro as a substitution at a position corresponding to position 21 of amino acids 1 to 513 of SEQ ID NO: 2. In another most preferred embodiment, the variant comprises the substitution S21P of amino acids 1 to 513 of SEQ ID NO: 2.

In another preferred embodiment, the variant comprises a substitution at a position corresponding to position 94 of amino acids 1 to 513 of SEQ ID NO: 2. In another more preferred embodiment, the variant comprises a substitution at a position corresponding to position 94 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Ser as a substitution at a position corresponding to position 94 of amino acids 1 to 513 of SEQ ID NO: 2. In another most preferred embodiment, the variant comprises the substitution G94S of amino acids 1 to 513 of SEQ ID NO: 2. In another even more preferred embodiment, the variant comprises Ala as a substitution at a position corresponding to position 94 of amino acids 1 to 513 of SEQ ID NO: 2. In another most preferred embodiment, the variant comprises the substitution G94A of amino acids 1 to 513 of SEQ ID NO: 2. In another even more preferred embodiment, the variant comprises Arg as a substitution at a position corresponding to position 94 of amino acids 1 to 513 of SEQ ID NO: 2. In another most preferred embodiment, the variant comprises the substitution G94R of amino acids 1 to 513 of SEQ ID NO: 2. In another even more preferred embodiment, the variant comprises Gln as a substitution at a position corresponding to position 94 of amino acids 1 to 513 of SEQ ID NO: 2. In another most preferred embodiment, the variant comprises the substitution G94Q of amino acids 1 to 513 of SEQ ID NO: 2.

In another preferred embodiment, the variant comprises a substitution at a position corresponding to position 157 of amino acids 1 to 513 of SEQ ID NO: 2. In another more preferred embodiment, the variant comprises a substitution at a position corresponding to position 157 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Arg as a substitution at a position corresponding to position 157 of amino acids 1 to 513 of SEQ ID NO: 2. In another most preferred embodiment, the variant comprises the substitution K157R of amino acids 1 to 513 of SEQ ID NO: 2.

In another preferred embodiment, the variant comprises a substitution at a position corresponding to position 205 of amino acids 1 to 513 of SEQ ID NO: 2. In another more preferred embodiment, the variant comprises a substitution at a position corresponding to position 205 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Arg as a substitution at a position corresponding to position 205 of amino acids 1 to 513 of SEQ ID NO: 2. In another most preferred embodiment, the variant comprises the substitution G205R of amino acids 1 to 513 of SEQ ID NO: 2.

In another preferred embodiment, the variant comprises a substitution at a position corresponding to position 206 of amino acids 1 to 513 of SEQ ID NO: 2. In another more preferred embodiment, the variant comprises a substitution at a position corresponding to position 206 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Tyr as a substitution at a position corresponding to position 206 of amino acids 1 to 513 of SEQ ID NO: 2. In another most preferred embodiment, the variant comprises the substitution H206Y of amino acids 1 to 513 of SEQ ID NO: 2.

In another preferred embodiment, the variant comprises a substitution at a position corresponding to position 247 of amino acids 1 to 513 of SEQ ID NO: 2. In another more preferred embodiment, the variant comprises a substitution at a position corresponding to position 247 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Cys as a substitution at a position corresponding to position 247 of amino acids 1 to 513 of SEQ ID NO: 2. In another most preferred embodiment, the variant comprises the substitution Y247C of amino acids 1 to 513 of SEQ ID NO: 2.

In another preferred embodiment, the variant comprises a substitution at a position corresponding to position 337 of amino acids 1 to 513 of SEQ ID NO: 2. In another more preferred embodiment, the variant comprises a substitution at a position corresponding to position 337 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Val as a substitution at a position corresponding to position 337 of amino acids 1 to 513 of SEQ ID NO: 2. In another most preferred embodiment, the variant comprises the substitution E337V of amino acids 1 to 513 of SEQ ID NO: 2.

In another preferred embodiment, the variant comprises a substitution at a position corresponding to position 350 of amino acids 1 to 513 of SEQ ID NO: 2. In another more preferred embodiment, the variant comprises a substitution at a position corresponding to position 350 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Ser as a substitution at a position corresponding to position 350 of amino acids 1 to 513 of SEQ ID NO: 2. In another most preferred embodiment, the variant comprises the substitution T350S of amino acids 1 to 513 of SEQ ID NO: 2.

In another preferred embodiment, the variant comprises a substitution at a position corresponding to position 373 of amino acids 1 to 513 of SEQ ID NO: 2. In another more preferred embodiment, the variant comprises a substitution at a position corresponding to position 373 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises His as a substitution at a position corresponding to position 373 of amino acids 1 to 513 of SEQ ID NO: 2. In another most preferred embodiment, the variant comprises the substitution N373H of amino acids 1 to 513 of SEQ ID NO: 2.

In another preferred embodiment, the variant comprises a substitution at a position corresponding to position 383 of amino acids 1 to 513 of SEQ ID NO: 2. In another more preferred embodiment, the variant comprises a substitution at a position corresponding to position 383 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Ala as a substitution at a position corresponding to position 383 of amino acids 1 to 513 of SEQ ID NO: 2. In another most preferred embodiment, the variant comprises the substitution T383A of amino acids 1 to 513 of SEQ ID NO: 2.

In another preferred embodiment, the variant comprises a substitution at a position corresponding to position 438 of amino acids 1 to 513 of SEQ ID NO: 2. In another more preferred embodiment, the variant comprises a substitution at a position corresponding to position 438 of amino acids 1 to 513 of SEQ ID NO: 2 with Ala, Arg, Asn, Asp, Cys, Gin, Glu, Gly, His, Ile, Leu, Lys, Met, Phe, Pro, Ser, Thr, Trp, Tyr, or Val. In another even more preferred embodiment, the variant comprises Leu as a substitution at a position corresponding to position 438 of amino acids 1 to 513 of SEQ ID NO: 2. In another most preferred embodiment, the variant comprises the substitution P438L of amino acids 1 to 513 of SEQ ID NO: 2.

In another preferred embodiment, the variant comprises a substitution at a position corresponding to position 455 of amino acids 1 to 513 of SEQ ID NO: 2. In another more preferred embodiment, the variant comprises a substitution at a position corresponding to position 455 of amino acids 1 to 513 of SEQ ID NO: 2 with Ala, Arg, Asn, Asp, Cys, Gin, Glu, Gly, His, Ile, Leu, Lys, Met, Phe, Pro, Ser, Thr, Trp, Tyr, or Val. In another even more preferred embodiment, the variant comprises Ala as a substitution at a position corresponding to position 455 of amino acids 1 to 513 of SEQ ID NO: 2. In another most preferred embodiment, the variant comprises the substitution T455A of amino acids 1 to 513 of SEQ ID NO: 2.

In another preferred embodiment, the variant comprises a substitution at a position corresponding to position 467 of amino acids 1 to 513 of SEQ ID NO: 2. In another more preferred embodiment, the variant comprises a substitution at a position corresponding to position 467 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Ser as a substitution at a position corresponding to position 467 of amino acids 1 to 513 of SEQ ID NO: 2. In another most preferred embodiment, the variant comprises the substitution G467S of amino acids 1 to 513 of SEQ ID NO: 2.

In another preferred embodiment, the variant comprises a substitution at a position corresponding to position 486 of amino acids 1 to 513 of SEQ ID NO: 2. In another more preferred embodiment, the variant comprises a substitution at a position corresponding to position 486 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant comprises Trp as a substitution at a position corresponding to position 486 of amino acids 1 to 513 of SEQ ID NO: 2. In another most preferred embodiment, the variant comprises the substitution C486W of amino acids 1 to 513 of SEQ ID NO: 2.

In a preferred embodiment, the variant further comprises a substitution at a position corresponding to position 8 of amino acids 1 to 513 of SEQ ID NO: 2. In a more preferred embodiment, the variant further comprises a substitution at a position corresponding to position 8 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant further comprises Pro as a substitution at a position corresponding to position 8 of amino acids 1 to 513 of SEQ ID NO: 2. In a most preferred embodiment, the variant further comprises the substitution S8P of amino acids 1 to 513 of SEQ ID NO: 2.

In another preferred embodiment, the variant further comprises a substitution at a position corresponding to position 22 of amino acids 1 to 513 of SEQ ID NO: 2. In another more preferred embodiment, the variant further comprises a substitution at a position corresponding to position 22 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Asp as a substitution at a position corresponding to position 22 of amino acids 1 to 513 of SEQ ID NO: 2. In another most preferred embodiment, the variant further comprises the substitution G22D of amino acids 1 to 513 of SEQ ID NO: 2.

In another preferred embodiment, the variant further comprises a substitution at a position corresponding to position 41 of amino acids 1 to 513 of SEQ ID NO: 2. In another more preferred embodiment, the variant further comprises a substitution at a position corresponding to position 41 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Ile as a substitution at a position corresponding to position 41 of amino acids 1 to 513 of SEQ ID NO: 2. In another most preferred embodiment, the variant further comprises the substitution T41I of amino acids 1 to 513 of SEQ ID NO: 2.

In another preferred embodiment, the variant further comprises a substitution at a position corresponding to position 49 of amino acids 1 to 513 of SEQ ID NO: 2. In another more preferred embodiment, the variant further comprises a substitution at a position corresponding to position 49 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Ser as a substitution at a position corresponding to position 49 of amino acids 1 to 513 of SEQ ID NO: 2. In another most preferred embodiment, the variant further comprises the substitution N49S of amino acids 1 to 513 of SEQ ID NO: 2.

In another preferred embodiment, the variant further comprises a substitution at a position corresponding to position 57 of amino acids 1 to 513 of SEQ ID NO: 2. In another more preferred embodiment, the variant further comprises a substitution at a position corresponding to position 57 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Asn as a substitution at a position corresponding to position 57 of amino acids 1 to 513 of SEQ ID NO: 2. In another most preferred embodiment, the variant further comprises the substitution S57N of amino acids 1 to 513 of SEQ ID NO: 2.

In another preferred embodiment, the variant further comprises a substitution at a position corresponding to position 113 of amino acids 1 to 513 of SEQ ID NO: 2. In another more preferred embodiment, the variant further comprises a substitution at a position corresponding to position 113 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Asn as a substitution at a position corresponding to position 113 of amino acids 1 to 513 of SEQ ID NO: 2. In another most preferred embodiment, the variant further comprises the substitution S113N of amino acids 1 to 513 of SEQ ID NO: 2.

In another preferred embodiment, the variant further comprises a substitution at a position corresponding to position 193 of amino acids 1 to 513 of SEQ ID NO: 2. In another more preferred embodiment, the variant further comprises a substitution at a position corresponding to position 193 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Lys as a substitution at a position corresponding to position 193 of amino acids 1 to 513 of SEQ ID NO: 2. In another most preferred embodiment, the variant further comprises the substitution E193K of amino acids 1 to 513 of SEQ ID NO: 2.

In another preferred embodiment, the variant further comprises a substitution at a position corresponding to position 196 of amino acids 1 to 513 of SEQ ID NO: 2. In another more preferred embodiment, the variant further comprises a substitution at a position corresponding to position 196 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Pro as a substitution at a position corresponding to position 196 of amino acids 1 to 513 of SEQ ID NO: 2. In another most preferred embodiment, the variant further comprises the substitution S196P of amino acids 1 to 513 of SEQ ID NO: 2. In another even more preferred embodiment, the variant further comprises Thr as a substitution at a position corresponding to position 196 of amino acids 1 to 513 of SEQ ID NO: 2. In another most preferred embodiment, the variant further comprises the substitution S196T of amino acids 1 to 513 of SEQ ID NO: 2. In another even more preferred embodiment, the variant further comprises Phe as a substitution at a position corresponding to position 196 of amino acids 1 to 513 of SEQ ID NO: 2. In another most preferred embodiment, the variant further comprises the substitution S196F of amino acids 1 to 513 of SEQ ID NO: 2.

In another preferred embodiment, the variant further comprises a substitution at a position corresponding to position 226 of amino acids 1 to 513 of SEQ ID NO: 2. In another more preferred embodiment, the variant further comprises a substitution at a position corresponding to position 226 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Ala as a substitution at a position corresponding to position 226 of amino acids 1 to 513 of SEQ ID NO: 2. In another most preferred embodiment, the variant further comprises the substitution T226A of amino acids 1 to 513 of SEQ ID NO: 2.

In another preferred embodiment, the variant further comprises a substitution at a position corresponding to position 227 of amino acids 1 to 513 of SEQ ID NO: 2. In another more preferred embodiment, the variant further comprises a substitution at a position corresponding to position 227 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Ala as a substitution at a position corresponding to position 227 of amino acids 1 to 513 of SEQ ID NO: 2. In another most preferred embodiment, the variant further comprises the substitution P227A of amino acids 1 to 513 of SEQ ID NO: 2. In another even more preferred embodiment, the variant further comprises Leu as a substitution at a position corresponding to position 227 of amino acids 1 to 513 of SEQ ID NO: 2. In another most preferred embodiment, the variant further comprises the substitution P227L of amino acids 1 to 513 of SEQ ID NO: 2. In another even more preferred embodiment, the variant further comprises Gly as a substitution at a position corresponding to position 227 of amino acids 1 to 513 of SEQ ID NO: 2. In another most preferred embodiment, the variant further comprises the substitution P227G of amino acids 1 to 513 of SEQ ID NO: 2.

In another preferred embodiment, the variant further comprises a substitution at a position corresponding to position 246 of amino acids 1 to 513 of SEQ ID NO: 2. In another more preferred embodiment, the variant further comprises a substitution at a position corresponding to position 246 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Ile as a substitution at a position corresponding to position 246 of amino acids 1 to 513 of SEQ ID NO: 2. In another most preferred embodiment, the variant further comprises the substitution T246I of amino acids 1 to 513 of SEQ ID NO: 2.

In another preferred embodiment, the variant further comprises a substitution at a position corresponding to position 251 of amino acids 1 to 513 of SEQ ID NO: 2. In another more preferred embodiment, the variant further comprises a substitution at a position corresponding to position 251 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Lys as a substitution at a position corresponding to position 251 of amino acids 1 to 513 of SEQ ID NO: 2. In another most preferred embodiment, the variant further comprises the substitution R251K of amino acids 1 to 513 of SEQ ID NO: 2.

In another preferred embodiment, the variant further comprises a substitution at a position corresponding to position 255 of amino acids 1 to 513 of SEQ ID NO: 2. In another more preferred embodiment, the variant further comprises a substitution at a position corresponding to position 255 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Pro as a substitution at a position corresponding to position 255 of amino acids 1 to 513 of SEQ ID NO: 2. In another most preferred embodiment, the variant further comprises the substitution T255P of amino acids 1 to 513 of SEQ ID NO: 2.

In another preferred embodiment, the variant further comprises a substitution at a position corresponding to position 259 of amino acids 1 to 513 of SEQ ID NO: 2. In another more preferred embodiment, the variant further comprises a substitution at a position corresponding to position 259 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Asn as a substitution at a position corresponding to position 259 ofino acids 1 to 513 of SEQ ID NO: 2. In another most preferred embodiment, the variant further comprises the substitution D259N of amino acids 1 to 513 of SEQ ID NO: 2.

In another preferred embodiment, the variant further comprises a substitution at a position corresponding to position 301 of amino acids 1 to 513 of SEQ ID NO: 2. In another more preferred embodiment, the variant further comprises a substitution at a position corresponding to position 301 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Ser as a substitution at a position corresponding to position 301 of amino acids 1 to 513 of SEQ ID NO: 2. In another most preferred embodiment, the variant further comprises the substitution N301S of amino acids 1 to 513 of SEQ ID NO: 2.

In another preferred embodiment, the variant further comprises a substitution at a position corresponding to position 356 of amino acids 1 to 513 of SEQ ID NO: 2. In another more preferred embodiment, the variant further comprises a substitution at a position corresponding to position 356 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Ile as a substitution at a position corresponding to position 356 of amino acids 1 to 513 of SEQ ID NO: 2. In another most preferred embodiment, the variant further comprises the substitution T356I of amino acids 1 to 513 of SEQ ID NO: 2.

In another preferred embodiment, the variant further comprises a substitution at a position corresponding to position 371 of amino acids 1 to 513 of SEQ ID NO: 2. In another more preferred embodiment, the variant further comprises a substitution at a position corresponding to position 371 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Cys as a substitution at a position corresponding to position 371 of amino acids 1 to 513 of SEQ ID NO: 2. In another most preferred embodiment, the variant further comprises the substitution Y371C of amino acids 1 to 513 of SEQ ID NO: 2.

In another preferred embodiment, the variant further comprises a substitution at a position corresponding to position 411 of amino acids 1 to 513 of SEQ ID NO: 2. In another more preferred embodiment, the variant further comprises a substitution at a position corresponding to position 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Phe as a substitution at a position corresponding to position 411 of amino acids 1 to 513 of SEQ ID NO: 2. In another most preferred embodiment, the variant further comprises the substitution S411F of amino acids 1 to 513 of SEQ ID NO: 2.

In another preferred embodiment, the variant further comprises a substitution at a position corresponding to position 462 of amino acids 1 to 513 of SEQ ID NO: 2. In another more preferred embodiment, the variant further comprises a substitution at a position corresponding to position 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the variant further comprises Ala as a substitution at a position corresponding to position 462 of amino acids 1 to 513 of SEQ ID NO: 2. In another most preferred embodiment, the variant further comprises the substitution T462A of amino acids 1 to 513 of SEQ ID NO: 2.

In another preferred embodiment, the variant comprises substitutions at positions corresponding to positions 227 and 259 of amino acids 1 to 513 of SEQ ID NO: 2. In a more preferred embodiment, the variant comprises substitutions at positions corresponding to positions 227 and 259 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Gly (or Ala or Leu) and Asn as substitutions at positions corresponding to positions 227 and 259, respectively, of amino acids 1 to 513 of SEQ ID NO: 2. In another most preferred embodiment, the variant comprises the substitutions P227G (or P227A or P227L)+D259N of amino acids 1 to 513 of SEQ ID NO: 2.

In another preferred embodiment, the variant comprises substitutions at positions corresponding to positions 227 and 486 of amino acids 1 to 513 of SEQ ID NO: 2. In a more preferred embodiment, the variant comprises substitutions at positions corresponding to positions 227 and 486 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ala (or Leu or Gly) and Trp as substitutions at positions corresponding to positions 227 and 486, respectively, of amino acids 1 to 513 of SEQ ID NO: 2. In another most preferred embodiment, the variant comprises the substitutions P227A (or P227L or P227G)+C486W of amino acids 1 to 513 of SEQ ID NO: 2.

In another preferred embodiment, the variant comprises substitutions at positions corresponding to positions 301 and 337 of amino acids 1 to 513 of SEQ ID NO: 2. In a more preferred embodiment, the variant comprises substitutions at positions corresponding to positions 301 and 337 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser and Val as substitutions at positions corresponding to positions 301 and 337, respectively, of amino acids 1 to 513 of SEQ ID NO: 2. In another most preferred embodiment, the variant comprises the substitutions N301S+E337V of amino acids 1 to 513 of SEQ ID NO: 2.

In another preferred embodiment, the variant comprises substitutions at positions corresponding to positions 196 and 350 of amino acids 1 to 513 of SEQ ID NO: 2. In a more preferred embodiment, the variant comprises substitutions at positions corresponding to positions 196 and 350 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Pro (or Thr or Phe) and Ser as substitutions at positions corresponding to positions 196 and 350, respectively, of amino acids 1 to 513 of SEQ ID NO: 2. In another most preferred embodiment, the variant comprises the substitutions S196P (or S196T or S196F)+T350S of amino acids 1 to 513 of SEQ ID NO: 2.

In another preferred embodiment, the variant comprises substitutions at positions corresponding to positions 22 and 467 of amino acids 1 to 513 of SEQ ID NO: 2. In a more preferred embodiment, the variant comprises substitutions at positions corresponding to positions 22 and 467 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asp and Ser as substitutions at positions corresponding to positions 22 and 467, respectively, of amino acids 1 to 513 of SEQ ID NO: 2. In another most preferred embodiment, the variant comprises the substitutions G22D+G467S of amino acids 1 to 513 of SEQ ID NO: 2.

In another preferred embodiment, the variant comprises substitutions at positions corresponding to positions 21 and 57 of amino acids 1 to 513 of SEQ ID NO: 2. In a more preferred embodiment, the variant comprises substitutions at positions corresponding to positions 21 and 57 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Pro and Asn as substitutions at positions corresponding to positions 21 and 57, respectively, of amino acids 1 to 513 of SEQ ID NO: 2. In another most preferred embodiment, the variant comprises the substitutions S21P+S57N of amino acids 1 to 513 of SEQ ID NO: 2.

In another preferred embodiment, the variant comprises substitutions at positions corresponding to positions 205 and 411 of amino acids 1 to 513 of SEQ ID NO: 2. In a more preferred embodiment, the variant comprises substitutions at positions corresponding to positions 205 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Phe as substitutions at positions corresponding to positions 205 and 411, respectively, of amino acids 1 to 513 of SEQ ID NO: 2. In another most preferred embodiment, the variant comprises the substitutions G205R+S411F of amino acids 1 to 513 of SEQ ID NO: 2.

In another preferred embodiment, the variant comprises substitutions at positions corresponding to positions 205 and 227 of amino acids 1 to 513 of SEQ ID NO: 2. In a more preferred embodiment, the variant comprises substitutions at positions corresponding to positions 205 and 227 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Ala (or Leu or Gly) as substitutions at positions corresponding to positions 205 and 227, respectively, of amino acids 1 to 513 of SEQ ID NO: 2. In another most preferred embodiment, the variant comprises the substitutions G205R+P227A (or P227L or P227L) of amino acids 1 to 513 of SEQ ID NO: 2.

In another preferred embodiment, the variant comprises substitutions at positions corresponding to positions 205 and 206 of amino acids 1 to 513 of SEQ ID NO: 2. In a more preferred embodiment, the variant comprises substitutions at positions corresponding to positions 205 and 206 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Tyr as substitutions at positions corresponding to positions 205 and 206, respectively, of amino acids 1 to 513 of SEQ ID NO: 2. In another most preferred embodiment, the variant comprises the substitutions G205R+H206Y of amino acids 1 to 513 of SEQ ID NO: 2.

In another preferred embodiment, the variant comprises substitutions at positions corresponding to positions 8 and 205 of amino acids 1 to 513 of SEQ ID NO: 2. In a more preferred embodiment, the variant comprises substitutions at positions corresponding to positions 8 and 205 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Pro and Arg as substitutions at positions corresponding to positions 8 and 205, respectively, of amino acids 1 to 513 of SEQ ID NO: 2. In another most preferred embodiment, the variant comprises the substitutions S8P+G205R of amino acids 1 to 513 of SEQ ID NO: 2.

In another preferred embodiment, the variant comprises substitutions at positions corresponding to positions 94 and 205 of amino acids 1 to 513 of SEQ ID NO: 2. In a more preferred embodiment, the variant comprises substitutions at positions corresponding to positions 94 and 205 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser (or Ala or Arg or Gln) and Arg as substitutions at positions corresponding to positions 94 and 205, respectively, of amino acids 1 to 513 of SEQ ID NO: 2. In another most preferred embodiment, the variant comprises the substitutions G94S (or G94A or G94R or G94Q)+G205R of amino acids 1 to 513 of SEQ ID NO: 2.

In another preferred embodiment, the variant comprises substitutions at positions corresponding to positions 196 and 205 of amino acids 1 to 513 of SEQ ID NO: 2. In a more preferred embodiment, the variant comprises substitutions at positions corresponding to positions 196 and 205 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Pro (or Thr or Phe) and Arg as substitutions at positions corresponding to positions 196 and 205, respectively, of amino acids 1 to 513 of SEQ ID NO: 2. In another most preferred embodiment, the variant comprises the substitutions S196P (or S196T or S196F)+G205R of amino acids 1 to 513 of SEQ ID NO: 2.

In another preferred embodiment, the variant comprises substitutions at positions corresponding to positions 383 and 455 of amino acids 1 to 513 of SEQ ID NO: 2. In a more preferred embodiment, the variant comprises substitutions at positions corresponding to positions 383 and 455 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ala and Ala as substitutions at positions corresponding to positions 383 and 455, respectively, of amino acids 1 to 513 of SEQ ID NO: 2. In another most preferred embodiment, the variant comprises the substitutions T383A+T455A of amino acids 1 to 513 of SEQ ID NO: 2.

In another preferred embodiment, the variant comprises substitutions at positions corresponding to positions 113 and 411 of amino acids 1 to 513 of SEQ ID NO: 2. In a more preferred embodiment, the variant comprises substitutions at positions corresponding to positions 113 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn and Phe as substitutions at positions corresponding to positions 113 and 411, respectively, of amino acids 1 to 513 of SEQ ID NO: 2. In another most preferred embodiment, the variant comprises the substitutions S113N+S411F of amino acids 1 to 513 of SEQ ID NO: 2.

In another preferred embodiment, the variant comprises substitutions at positions corresponding to positions 113 and 196 of amino acids 1 to 513 of SEQ ID NO: 2. In a more preferred embodiment, the variant comprises substitutions at positions corresponding to positions 113 and 196 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn and Thr (or Pro or Phe) as substitutions at positions corresponding to positions 113 and 196, respectively, of amino acids 1 to 513 of SEQ ID NO: 2. In another most preferred embodiment, the variant comprises the substitutions S113N+S196T (or S196P or S196F) of amino acids 1 to 513 of SEQ ID NO: 2.

In another preferred embodiment, the variant comprises substitutions at positions corresponding to positions 113 and 462 of amino acids 1 to 513 of SEQ ID NO: 2. In a more preferred embodiment, the variant comprises substitutions at positions corresponding to positions 113 and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn and Ala as substitutions at positions corresponding to positions 113 and 462, respectively, of amino acids 1 to 513 of SEQ ID NO: 2. In another most preferred embodiment, the variant comprises the substitutions S113N+T462A of amino acids 1 to 513 of SEQ ID NO: 2.

In another preferred embodiment, the variant comprises substitutions at positions corresponding to positions 196 and 462 of amino acids 1 to 513 of SEQ ID NO: 2. In a more preferred embodiment, the variant comprises substitutions at positions corresponding to positions 196 and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr (or Pro or Phe) and Ala as substitutions at positions corresponding to positions 196 and 462, respectively, of amino acids 1 to 513 of SEQ ID NO: 2. In another most preferred embodiment, the variant comprises the substitutions S196T (or S196P or S196F)+T462A of amino acids 1 to 513 of SEQ ID NO: 2.

In another preferred embodiment, the variant comprises substitutions at positions corresponding to positions 196 and 462 of amino acids 1 to 513 of SEQ ID NO: 2. In a more preferred embodiment, the variant comprises substitutions at positions corresponding to positions 41 and 196 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ile and Phe (or Pro or Thr) as substitutions at positions corresponding to positions 41 and 196, respectively, of amino acids 1 to 513 of SEQ ID NO: 2. In another most preferred embodiment, the variant comprises the substitutions T41I+S196F (or S196P or S196T) of amino acids 1 to 513 of SEQ ID NO: 2.

In another preferred embodiment, the variant comprises substitutions at positions corresponding to positions 94 and 226 of amino acids 1 to 513 of SEQ ID NO: 2. In a more preferred embodiment, the variant comprises substitutions at positions corresponding to positions 94 and 226 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ala (or Ser or Arg or Gln) and Ala as substitutions at positions corresponding to positions 94 and 226, respectively, of amino acids 1 to 513 of SEQ ID NO: 2. In another most preferred embodiment, the variant comprises the substitutions G94A (or G94S or G94R or G94Q)+T226A of amino acids 1 to 513 of SEQ ID NO: 2.

In another preferred embodiment, the variant comprises substitutions at positions corresponding to positions 113, 196, and 462 of amino acids 1 to 513 of SEQ ID NO: 2. In a more preferred embodiment, the variant comprises substitutions at positions corresponding to positions 113, 196, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Thr (or Pro or Phe), and Ala as substitutions at positions corresponding to positions 113, 196, and 462, respectively, of amino acids 1 to 513 of SEQ ID NO: 2. In another most preferred embodiment, the variant comprises the substitutions S113N+S196T (or S196P or S196F)+T462A of amino acids 1 to 513 of SEQ ID NO: 2.

In another preferred embodiment, the variant comprises substitutions at positions corresponding to positions 157 and 205 of amino acids 1 to 513 of SEQ ID NO: 2. In a more preferred embodiment, the variant comprises substitutions at positions corresponding to positions 157 and 205 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Arg as substitutions at positions corresponding to positions 157 and 205, respectively, of amino acids 1 to 513 of SEQ ID NO: 2. In another most preferred embodiment, the variant comprises the substitutions K157R+G205R of amino acids 1 to 513 of SEQ ID NO: 2.

In another preferred embodiment, the variant comprises substitutions at positions corresponding to positions 157 and 255 of amino acids 1 to 513 of SEQ ID NO: 2. In a more preferred embodiment, the variant comprises substitutions at positions corresponding to positions 157 and 255 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Pro as substitutions at positions corresponding to positions 157 and 255, respectively, of amino acids 1 to 513 of SEQ ID NO: 2. In another most preferred embodiment, the variant comprises the substitutions K157R+T255P of amino acids 1 to 513 of SEQ ID NO: 2.

In another preferred embodiment, the variant comprises substitutions at positions corresponding to positions 205 and 255 of amino acids 1 to 513 of SEQ ID NO: 2. In a more preferred embodiment, the variant comprises substitutions at positions corresponding to positions 205 and 255 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Pro as substitutions at positions corresponding to positions 205 and 255, respectively, of amino acids 1 to 513 of SEQ ID NO: 2. In another most preferred embodiment, the variant comprises the substitutions G205R+T255P of amino acids 1 to 513 of SEQ ID NO: 2.

In another preferred embodiment, the variant comprises substitutions at positions corresponding to positions 157, 205, and 255 of amino acids 1 to 513 of SEQ ID NO: 2. In a more preferred embodiment, the variant comprises substitutions at positions corresponding to positions 157, 205, and 255 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg, Arg, and Pro as substitutions at positions corresponding to positions 157, 205, and 255, respectively, of amino acids 1 to 513 of SEQ ID NO: 2. In another most preferred embodiment, the variant comprises the substitutions K157R+G205R+T255P of amino acids 1 to 513 of SEQ ID NO: 2.

In another preferred embodiment, the variant comprises substitutions at positions corresponding to positions 41 and 193 of amino acids 1 to 513 of SEQ ID NO: 2. In a more preferred embodiment, the variant comprises substitutions at positions corresponding to positions 41 and 193 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ile and Lys as substitutions at positions corresponding to positions 41 and 193, respectively, of amino acids 1 to 513 of SEQ ID NO: 2. In another most preferred embodiment, the variant comprises the substitutions T41I+E193K of amino acids 1 to 513 of SEQ ID NO: 2.

In another preferred embodiment, the variant comprises substitutions at positions corresponding to positions 41 and 411 of amino acids 1 to 513 of SEQ ID NO: 2. In a more preferred embodiment, the variant comprises substitutions at positions corresponding to positions 41 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ile and Phe as substitutions at positions corresponding to positions 41 and 411, respectively, of amino acids 1 to 513 of SEQ ID NO: 2. In another most preferred embodiment, the variant comprises the substitutions T41I+S411F of amino acids 1 to 513 of SEQ ID NO: 2.

In another preferred embodiment, the variant comprises substitutions at positions corresponding to positions 193 and 411 of amino acids 1 to 513 of SEQ ID NO: 2. In a more preferred embodiment, the variant comprises substitutions at positions corresponding to positions 193 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Lys and Phe as substitutions at positions corresponding to positions 193 and 411, respectively, of amino acids 1 to 513 of SEQ ID NO: 2. In another most preferred embodiment, the variant comprises the substitutions E193K+S411F of amino acids 1 to 513 of SEQ ID NO: 2.

In another preferred embodiment, the variant comprises substitutions at positions corresponding to positions 41, 193, and 411 of amino acids 1 to 513 of SEQ ID NO: 2. In a more preferred embodiment, the variant comprises substitutions at positions corresponding to positions 41, 193, and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ile, Lys, and Phe as substitutions at positions corresponding to positions 41, 193, and 411, respectively, of amino acids 1 to 513 of SEQ ID NO: 2. In another most preferred embodiment, the variant comprises the substitutions T41I+E193K+S411F of amino acids 1 to 513 of SEQ ID NO: 2.

In another preferred embodiment, the variant comprises substitutions at positions corresponding to positions 247 and 371 of amino acids 1 to 513 of SEQ ID NO: 2. In a more preferred embodiment, the variant comprises substitutions at positions corresponding to positions 247 and 371 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Cys and Cys as substitutions at positions corresponding to positions 247 and 371, respectively, of amino acids 1 to 513 of SEQ ID NO: 2. In another most preferred embodiment, the variant comprises the substitutions Y247C+Y371C of amino acids 1 to 513 of SEQ ID NO: 2.

In another preferred embodiment, the variant comprises substitutions at positions corresponding to positions 247 and 411 of amino acids 1 to 513 of SEQ ID NO: 2. In a more preferred embodiment, the variant comprises substitutions at positions corresponding to positions 247 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Cys and Phe as substitutions at positions corresponding to positions 247 and 411, respectively, of amino acids 1 to 513 of SEQ ID NO: 2. In another most preferred embodiment, the variant comprises the substitutions Y247C+S411F of amino acids 1 to 513 of SEQ ID NO: 2.

In another preferred embodiment, the variant comprises substitutions at positions corresponding to positions 371 and 411 of amino acids 1 to 513 of SEQ ID NO: 2. In a more preferred embodiment, the variant comprises substitutions at positions corresponding to positions 371 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Cys and Phe as substitutions at positions corresponding to positions 371 and 411, respectively, of amino acids 1 to 513 of SEQ ID NO: 2. In another most preferred embodiment, the variant comprises the substitutions Y371C+S411F of amino acids 1 to 513 of SEQ ID NO: 2.

In another preferred embodiment, the variant comprises substitutions at positions corresponding to positions 247, 371, and 411 of amino acids 1 to 513 of SEQ ID NO: 2. In a more preferred embodiment, the variant comprises substitutions at positions corresponding to positions 247, 371, and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Cys, Cys, and Phe as substitutions at positions corresponding to positions 247, 371, and 411, respectively, of amino acids 1 to 513 of SEQ ID NO: 2. In another most preferred embodiment, the variant comprises the substitutions Y247C+Y371C+S411F of amino acids 1 to 513 of SEQ ID NO: 2.

In another preferred embodiment, the variant comprises substitutions at positions corresponding to positions 113 and 227 of amino acids 1 to 513 of SEQ ID NO: 2. In a more preferred embodiment, the variant comprises substitutions at positions corresponding to positions 113 and 227 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn and Ala (or Leu or Gly) as substitutions at positions corresponding to positions 113 and 227, respectively, of amino acids 1 to 513 of SEQ ID NO: 2. In another most preferred embodiment, the variant comprises the substitutions S113N+P227A (or P227L or P227G) of amino acids 1 to 513 of SEQ ID NO: 2.

In another preferred embodiment, the variant comprises substitutions at positions corresponding to positions 196 and 227 of amino acids 1 to 513 of SEQ ID NO: 2. In a more preferred embodiment, the variant comprises substitutions at positions corresponding to positions 196 and 227 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr (or Pro or Phe) and Ala (or Leu or Gly) as substitutions at positions corresponding to positions 196 and 227, respectively, of amino acids 1 to 513 of SEQ ID NO: 2. In another most preferred embodiment, the variant comprises the substitutions S196T (or S196P or S196F)+P227A (or P227L or P227G) of amino acids 1 to 513 of SEQ ID NO: 2.

In another preferred embodiment, the variant comprises substitutions at positions corresponding to positions 227 and 462 of amino acids 1 to 513 of SEQ ID NO: 2. In a more preferred embodiment, the variant comprises substitutions at positions corresponding to positions 227 and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ala (or Leu or Gly) and Ala as substitutions at positions corresponding to positions 227 and 462, respectively, of amino acids 1 to 513 of SEQ ID NO: 2. In another most preferred embodiment, the variant comprises the substitutions P227A (or P227L or P227G)+T462A of amino acids 1 to 513 of SEQ ID NO: 2.

In another preferred embodiment, the variant comprises substitutions at positions corresponding to positions 113, 196, and 227 of amino acids 1 to 513 of SEQ ID NO: 2. In a more preferred embodiment, the variant comprises substitutions at positions corresponding to positions 142, 196, and 227 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Thr (or Pro or Phe), and Ala as substitutions at positions corresponding to positions 142, 196, and 227, respectively, of amino acids 1 to 513 of SEQ ID NO: 2.

In another preferred embodiment, the variant comprises substitutions at positions corresponding to positions 113, 227, and 462 of amino acids 1 to 513 of SEQ ID NO: 2. In a more preferred embodiment, the variant comprises substitutions at positions corresponding to positions 113, 227, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Ala (or Leu or Gly), and Ala as substitutions at positions corresponding to positions 113, 227, and 462, respectively, of amino acids 1 to 513 of SEQ ID NO: 2. In another most preferred embodiment, the variant comprises the substitutions S113N+P227A (or P227L or P227G)+T462A of amino acids 1 to 513 of SEQ ID NO: 2.

In another preferred embodiment, the variant comprises substitutions at positions corresponding to positions 196, 227, and 462 of amino acids 1 to 513 of SEQ ID NO: 2. In a more preferred embodiment, the variant comprises substitutions at positions corresponding to positions 196, 227, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr (or Pro or Phe), Ala (or Leu or Gly), and Ala as substitutions at positions corresponding to positions 196, 227, and 462, respectively, of amino acids 1 to 513 of SEQ ID NO: 2. In another most preferred embodiment, the variant comprises the substitutions S196T (or S196P or S196F)+P227A (or P227L or P227G)+T462A of amino acids 1 to 513 of SEQ ID NO: 2.

In another preferred embodiment, the variant comprises substitutions at positions corresponding to positions 113, 196, 227, and 462 of amino acids 1 to 513 of SEQ ID NO: 2. In a more preferred embodiment, the variant comprises substitutions at positions corresponding to positions 113, 196, 227, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Thr (or Pro or Phe), Ala (or Leu or Gly), and Ala as substitutions at positions corresponding to positions 113, 196, 227, and 462, respectively, of amino acids 1 to 513 of SEQ ID NO: 2. In another most preferred embodiment, the variant comprises the substitutions S113N+S196T (or S196P or S196F)+P227A (or P227L or P227G)+T462A of amino acids 1 to 513 of SEQ ID NO: 2.

In another preferred embodiment, the variant comprises substitutions at positions corresponding to positions 49 and 113 of amino acids 1 to 513 of SEQ ID NO: 2. In a more preferred embodiment, the variant comprises substitutions at positions corresponding to positions 49 and 113 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser and Asn as substitutions at positions corresponding to positions 49 and 113, respectively, of amino acids 1 to 513 of SEQ ID NO: 2. In another most preferred embodiment, the variant comprises the substitutions N49S+S113N of amino acids 1 to 513 of SEQ ID NO: 2.

In another preferred embodiment, the variant comprises substitutions at positions corresponding to positions 49 and 227 of amino acids 1 to 513 of SEQ ID NO: 2. In a more preferred embodiment, the variant comprises substitutions at positions corresponding to positions 49 and 227 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser and Ala (or Leu or Gly) as substitutions at positions corresponding to positions 49 and 227, respectively, of amino acids 1 to 513 of SEQ ID NO: 2. In another most preferred embodiment, the variant comprises the substitutions N49S+P227A (or P227L or P227G) of amino acids 1 to 513 of SEQ ID NO: 2.

In another preferred embodiment, the variant comprises substitutions at positions corresponding to positions 49 and 438 of amino acids 1 to 513 of SEQ ID NO: 2. In a more preferred embodiment, the variant comprises substitutions at positions corresponding to positions 49 and 438 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser and Leu as substitutions at positions corresponding to positions 49 and 438, respectively, of amino acids 1 to 513 of SEQ ID NO: 2. In another most preferred embodiment, the variant comprises the substitutions N49S+P438L of amino acids 1 to 513 of SEQ ID NO: 2.

In another preferred embodiment, the variant comprises substitutions at positions corresponding to positions 113 and 438 of amino acids 1 to 513 of SEQ ID NO: 2. In a more preferred embodiment, the variant comprises substitutions at positions corresponding to positions 113 and 438 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn and Leu as substitutions at positions corresponding to positions 113 and 438, respectively, of amino acids 1 to 513 of SEQ ID NO: 2. In another most preferred embodiment, the variant comprises the substitutions S113N+P438L of amino acids 1 to 513 of SEQ ID NO: 2.

In another preferred embodiment, the variant comprises substitutions at positions corresponding to positions 227 and 438 of amino acids 1 to 513 of SEQ ID NO: 2. In a more preferred embodiment, the variant comprises substitutions at positions corresponding to positions 227 and 438 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ala (or Leu or Gly) and Leu as substitutions at positions corresponding to positions 227 and 438, respectively, of amino acids 1 to 513 of SEQ ID NO: 2. In another most preferred embodiment, the variant comprises the substitutions P227A (or P227L or P227G)+P438L of amino acids 1 to 513 of SEQ ID NO: 2.

In another preferred embodiment, the variant comprises substitutions at positions corresponding to positions 49, 113, and 227 of amino acids 1 to 513 of SEQ ID NO: 2. In a more preferred embodiment, the variant comprises substitutions at positions corresponding to positions 49, 113, and 227 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser, Asn, and Ala (or Leu or Gly) as substitutions at positions corresponding to positions 49, 113, and 227, respectively, of amino acids 1 to 513 of SEQ ID NO: 2. In another most preferred embodiment, the variant comprises the substitutions N49S+S113N+P227A (or P227L or P227G) of amino acids 1 to 513 of SEQ ID NO: 2.

In another preferred embodiment, the variant comprises substitutions at positions corresponding to positions 49, 227, and 438 of amino acids 1 to 513 of SEQ ID NO: 2. In a more preferred embodiment, the variant comprises substitutions at positions corresponding to positions 49, 227, and 438 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser, Ala (or Leu or Gly), and Leu as substitutions at positions corresponding to positions 49, 227, and 438, respectively, of amino acids 1 to 513 of SEQ ID NO: 2. In another most preferred embodiment, the variant comprises the substitutions N49S+P227A (or P227L or P227G)+P438L of amino acids 1 to 513 of SEQ ID NO: 2.

In another preferred embodiment, the variant comprises substitutions at positions corresponding to positions 113, 227, and 438 of amino acids 1 to 513 of SEQ ID NO: 2. In a more preferred embodiment, the variant comprises substitutions at positions corresponding to positions 113, 227, and 438 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Ala (or Leu or Gly), and Leu as substitutions at positions corresponding to positions 113, 227, and 438, respectively, of amino acids 1 to 513 of SEQ ID NO: 2. In another most preferred embodiment, the variant comprises the substitutions S113N+P227A (or P227L or P227G)+P438L of amino acids 1 to 513 of SEQ ID NO: 2.

In another preferred embodiment, the variant comprises substitutions at positions corresponding to positions 49, 113, and 438 of amino acids 1 to 513 of SEQ ID NO: 2. In a more preferred embodiment, the variant comprises substitutions at positions corresponding to positions 49, 113, and 438 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser, Asn, and Leu as substitutions at positions corresponding to positions 49, 113, and 438, respectively, of amino acids 1 to 513 of SEQ ID NO: 2. In another most preferred embodiment, the variant comprises the substitutions N49S+S113N+P438L of amino acids 1 to 513 of SEQ ID NO: 2.

In another preferred embodiment, the variant comprises substitutions at positions corresponding to positions 49, 113, 227, and 438 of amino acids 1 to 513 of SEQ ID NO: 2. In a more preferred embodiment, the variant comprises substitutions at positions corresponding to positions 49, 113, 227, and 438 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ser, Asn, Ala (or Leu or Gly), and Leu as substitutions at positions corresponding to positions 49, 113, 227, and 438, respectively, of amino acids 1 to 513 of SEQ ID NO: 2. In another most preferred embodiment, the variant comprises the substitutions N49S+S113N+P227A (or P227L or P227G)+P438L of amino acids 1 to 513 of SEQ ID NO: 2.

In another preferred embodiment, the variant comprises substitutions at positions corresponding to positions 157 and 411 of amino acids 1 to 513 of SEQ ID NO: 2. In a more preferred embodiment, the variant comprises substitutions at positions corresponding to positions 157 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Phe as substitutions at positions corresponding to positions 157 and 411, respectively, of amino acids 1 to 513 of SEQ ID NO: 2. In another most preferred embodiment, the variant comprises the substitutions K157R+S411F of amino acids 1 to 513 of SEQ ID NO: 2.

In another preferred embodiment, the variant comprises substitutions at positions corresponding to positions 205 and 411 of amino acids 1 to 513 of SEQ ID NO: 2. In a more preferred embodiment, the variant comprises substitutions at positions corresponding to positions 205 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg and Phe as substitutions at positions corresponding to positions 205 and 411, respectively, of amino acids 1 to 513 of SEQ ID NO: 2. In another most preferred embodiment, the variant comprises the substitutions G205R+S411F of amino acids 1 to 513 of SEQ ID NO: 2.

In another preferred embodiment, the variant comprises substitutions at positions corresponding to positions 255 and 411 of amino acids 1 to 513 of SEQ ID NO: 2. In a more preferred embodiment, the variant comprises substitutions at positions corresponding to positions 255 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Pro and Phe as substitutions at positions corresponding to positions 255 and 411, respectively, of amino acids 1 to 513 of SEQ ID NO: 2. In another most preferred embodiment, the variant comprises the substitutions T255P+S411F of amino acids 1 to 513 of SEQ ID NO: 2.

In another preferred embodiment, the variant comprises substitutions at positions corresponding to positions 157, 255, and 411 of amino acids 1 to 513 of SEQ ID NO: 2. In a more preferred embodiment, the variant comprises substitutions at positions corresponding to positions 157, 255, and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg, Pro, and Phe as substitutions at positions corresponding to positions 157, 255, and 411, respectively, of amino acids 1 to 513 of SEQ ID NO: 2. In another most preferred embodiment, the variant comprises the substitutions K157R+T255P+S411F of amino acids 1 to 513 of SEQ ID NO: 2.

In another preferred embodiment, the variant comprises substitutions at positions corresponding to positions 205, 255, and 411 of amino acids 1 to 513 of SEQ ID NO: 2. In a more preferred embodiment, the variant comprises substitutions at positions corresponding to positions 205, 255, and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg, Pro, and Phe as substitutions at positions corresponding to positions 205, 255, and 411, respectively, of amino acids 1 to 513 of SEQ ID NO: 2. In another most preferred embodiment, the variant comprises the substitutions G205R+T255P+S411F of amino acids 1 to 513 of SEQ ID NO: 2.

In another preferred embodiment, the variant comprises substitutions at positions corresponding to positions 157, 205, and 411 of amino acids 1 to 513 of SEQ ID NO: 2. In a more preferred embodiment, the variant comprises substitutions at positions corresponding to positions 157, 205, and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg, Arg, and Phe as substitutions at positions corresponding to positions 157, 205, and 411, respectively, of amino acids 1 to 513 of SEQ ID NO: 2. In another most preferred embodiment, the variant comprises the substitutions K157R+G205R+S411F of amino acids 1 to 513 of SEQ ID NO: 2.

In another preferred embodiment, the variant comprises substitutions at positions corresponding to positions 157, 205, 255, and 411 of amino acids 1 to 513 of SEQ ID NO: 2. In a more preferred embodiment, the variant comprises substitutions at positions corresponding to positions 157, 205, 255, and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Arg, Arg, Pro, and Phe as substitutions at positions corresponding to positions 157, 205, 255, and 411, respectively, of amino acids 1 to 513 of SEQ ID NO: 2. In another most preferred embodiment, the variant comprises the substitutions K157R, G205R+T255P+S411F of amino acids 1 to 513 of SEQ ID NO: 2.

In another preferred embodiment, the variant comprises substitutions at positions corresponding to positions 196 and 411 of amino acids 1 to 513 of SEQ ID NO: 2. In a more preferred embodiment, the variant comprises substitutions at positions corresponding to positions 196 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr (or Pro or Phe) and Phe as substitutions at positions corresponding to positions 196 and 411, respectively, of amino acids 1 to 513 of SEQ ID NO: 2. In another most preferred embodiment, the variant comprises the substitutions S196T (or S196P or S196F)+S411F of amino acids 1 to 513 of SEQ ID NO: 2.

In another preferred embodiment, the variant comprises substitutions at positions corresponding to positions 227 and 411 of amino acids 1 to 513 of SEQ ID NO: 2. In a more preferred embodiment, the variant comprises substitutions at positions corresponding to positions 227 and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ala (or Leu or Gly) and Phe as substitutions at positions corresponding to positions 227 and 411, respectively, of amino acids 1 to 513 of SEQ ID NO: 2. In another most preferred embodiment, the variant comprises the substitutions P227A (or P227L or P227G)+S411F of amino acids 1 to 513 of SEQ ID NO: 2.

In another preferred embodiment, the variant comprises substitutions at positions corresponding to positions 113, 227, and 411 of amino acids 1 to 513 of SEQ ID NO: 2. In a more preferred embodiment, the variant comprises substitutions at positions corresponding to positions 113, 227, and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Ala (or Leu or Gly), and Phe as substitutions at positions corresponding to positions 113, 227, and 411, respectively, of amino acids 1 to 513 of SEQ ID NO: 2. In another most preferred embodiment, the variant comprises the substitutions S113N+P227A (or P227L or P227G)+S411F of amino acids 1 to 513 of SEQ ID NO: 2.

In another preferred embodiment, the variant comprises substitutions at positions corresponding to positions 196, 227, and 411 of amino acids 1 to 513 of SEQ ID NO: 2. In a more preferred embodiment, the variant comprises substitutions at positions corresponding to positions 196, 227, and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr (or Pro or Phe), Ala (or Leu or Gly), and Phe as substitutions at positions corresponding to positions 196, 227, and 411, respectively, of amino acids 1 to 513 of SEQ ID NO: 2. In another most preferred embodiment, the variant comprises the substitutions S196T (or S196P or S196F)+P227A (or P227L or P227G)+S411F of amino acids 1 to 513 of SEQ ID NO: 2.

In another preferred embodiment, the variant comprises substitutions at positions corresponding to positions 113, 196, and 411 of amino acids 1 to 513 of SEQ ID NO: 2. In a more preferred embodiment, the variant comprises substitutions at positions corresponding to positions 113, 196, and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Thr (or Pro or Phe), and Phe as substitutions at positions corresponding to positions 113, 196, and 411, respectively, of amino acids 1 to 513 of SEQ ID NO: 2. In another most preferred embodiment, the variant comprises the substitutions S113N+S196T (or S196P or S196F)+S411F of amino acids 1 to 513 of SEQ ID NO: 2.

In another preferred embodiment, the variant comprises substitutions at positions corresponding to positions 113, 196, 227, and 411 of amino acids 1 to 513 of SEQ ID NO: 2. In a more preferred embodiment, the variant comprises substitutions at positions corresponding to positions 113, 196, 227, and 411 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Thr (or Pro or Phe), Ala (or Leu or Gly), and Phe as substitutions at positions corresponding to positions 113, 196, 227, and 411, respectively, of amino acids 1 to 513 of SEQ ID NO: 2. In another most preferred embodiment, the variant comprises the substitutions S113N+S196T (or S196P or S196F)+P227A (or P227L or P227G)+S411F of amino acids 1 to 513 of SEQ ID NO: 2.

In another preferred embodiment, the variant comprises substitutions at positions corresponding to positions 113 and 356 of amino acids 1 to 513 of SEQ ID NO: 2. In a more preferred embodiment, the variant comprises substitutions at positions corresponding to positions 113 and 356 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn and Ile as substitutions at positions corresponding to positions 113 and 356, respectively, of amino acids 1 to 513 of SEQ ID NO: 2. In another most preferred embodiment, the variant comprises the substitutions S113N+T356I of amino acids 1 to 513 of SEQ ID NO: 2.

In another preferred embodiment, the variant comprises substitutions at positions corresponding to positions 196 and 356 of amino acids 1 to 513 of SEQ ID NO: 2. In a more preferred embodiment, the variant comprises substitutions at positions corresponding to positions 196 and 356 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr (or Pro or Phe) and Ile as substitutions at positions corresponding to positions 196 and 356, respectively, of amino acids 1 to 513 of SEQ ID NO: 2. In another most preferred embodiment, the variant comprises the substitutions S196T (or S196P or S196F)+T356I of amino acids 1 to 513 of SEQ ID NO: 2.

In another preferred embodiment, the variant comprises substitutions at positions corresponding to positions 227 and 356 of amino acids 1 to 513 of SEQ ID NO: 2. In a more preferred embodiment, the variant comprises substitutions at positions corresponding to positions 227 and 356 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ala (or Leu or Gly) and Ile as substitutions at positions corresponding to positions 227 and 356, respectively, of amino acids 1 to 513 of SEQ ID NO: 2. In another most preferred embodiment, the variant comprises the substitutions P227A (or P227L or P227G)+T356I of amino acids 1 to 513 of SEQ ID NO: 2.

In another preferred embodiment, the variant comprises substitutions at positions corresponding to positions 356 and 462 of amino acids 1 to 513 of SEQ ID NO: 2. In a more preferred embodiment, the variant comprises substitutions at positions corresponding to positions 356 and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ile and Ala as substitutions at positions corresponding to positions 356 and 462, respectively, of amino acids 1 to 513 of SEQ ID NO: 2. In another most preferred embodiment, the variant comprises the substitutions T356I+T462A of amino acids 1 to 513 of SEQ ID NO: 2.

In another preferred embodiment, the variant comprises substitutions at positions corresponding to positions 113, 227, and 356 of amino acids 1 to 513 of SEQ ID NO: 2. In a more preferred embodiment, the variant comprises substitutions at positions corresponding to positions 113, 227, and 356 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Ala (or Leu or Gly), and Ile as substitutions at positions corresponding to positions 113, 227, and 356, respectively, of amino acids 1 to 513 of SEQ ID NO: 2. In another most preferred embodiment, the variant comprises the substitutions S113N+P227A (or P227L or P227G)+T356I of amino acids 1 to 513 of SEQ ID NO: 2.

In another preferred embodiment, the variant comprises substitutions at positions corresponding to positions 196, 227, and 356 of amino acids 1 to 513 of SEQ ID NO: 2. In a more preferred embodiment, the variant comprises substitutions at positions corresponding to positions 196, 227, and 356 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr (or Pro or Phe), Ala (or Leu or Gly), and Ile as substitutions at positions corresponding to positions 196, 227, and 356, respectively, of amino acids 1 to 513 of SEQ ID NO: 2. In another most preferred embodiment, the variant comprises the substitutions S196T (or S196P or S196F)+P227A (or P227L or P227G)+T356I of amino acids 1 to 513 of SEQ ID NO: 2.

In another preferred embodiment, the variant comprises substitutions at positions corresponding to positions 196, 227, and 462 of amino acids 1 to 513 of SEQ ID NO: 2. In a more preferred embodiment, the variant comprises substitutions at positions corresponding to positions 196, 227, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr (or Pro or Phe), Ala (or Leu or Gly), and Ala as substitutions at positions corresponding to positions 196, 227, and 462, respectively, of amino acids 1 to 513 of SEQ ID NO: 2. In another most preferred embodiment, the variant comprises the substitutions S196T (or S196P or S196F)+P227A (or P227L or P227G)+T462A of amino acids 1 to 513 of SEQ ID NO: 2.

In another preferred embodiment, the variant comprises substitutions at positions corresponding to positions 196, 356, and 462 of amino acids 1 to 513 of SEQ ID NO: 2. In a more preferred embodiment, the variant comprises substitutions at positions corresponding to positions 196, 356, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr (or Pro or Phe), Ile, and Ala as substitutions at positions corresponding to positions 196, 356, and 462, respectively, of amino acids 1 to 513 of SEQ ID NO: 2. In another most preferred embodiment, the variant comprises the substitutions S196T (or S196P or S196F)+T356I+T462A of amino acids 1 to 513 of SEQ ID NO: 2.

In another preferred embodiment, the variant comprises substitutions at positions corresponding to positions 113, 196, and 356 of amino acids 1 to 513 of SEQ ID NO: 2. In a more preferred embodiment, the variant comprises substitutions at positions corresponding to positions 113, 196, and 356 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Thr (or Pro or Phe), and Ile as substitutions at positions corresponding to positions 113, 196, and 356, respectively, of amino acids 1 to 513 of SEQ ID NO: 2. In another most preferred embodiment, the variant comprises the substitutions S113N+S196T (or S196P or S196F)+T356I of amino acids 1 to 513 of SEQ ID NO: 2.

In another preferred embodiment, the variant comprises substitutions at positions corresponding to positions 227, 356, and 462 of amino acids 1 to 513 of SEQ ID NO: 2. In a more preferred embodiment, the variant comprises substitutions at positions corresponding to positions 227, 356, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Ala (or Leu or Gly), Ile, and Ala as substitutions at positions corresponding to positions 227, 356, and 462, respectively, of amino acids 1 to 513 of SEQ ID NO: 2. In another most preferred embodiment, the variant comprises the substitutions P227A (or P227L or P227G)+T356I+T462A of amino acids 1 to 513 of SEQ ID NO: 2.

In another preferred embodiment, the variant comprises substitutions at positions corresponding to positions 113, 196, 227, and 356 of amino acids 1 to 513 of SEQ ID NO: 2. In a more preferred embodiment, the variant comprises substitutions at positions corresponding to positions 113, 196, 227, and 356 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Thr (or Pro or Phe), Ala (or Leu or Gly), and Ile as substitutions at positions corresponding to positions 113, 196, 227, and 356 respectively, of amino acids 1 to 513 of SEQ ID NO: 2. In another most preferred embodiment, the variant comprises the substitutions S113N+S196T (or S196P or S196F)+P227A (or P227L or P227G)+T356I of amino acids 1 to 513 of SEQ ID NO: 2.

In another preferred embodiment, the variant comprises substitutions at positions corresponding to positions 113, 227, 356, and 462 of amino acids 1 to 513 of SEQ ID NO: 2. In a more preferred embodiment, the variant comprises substitutions at positions corresponding to positions 113, 227, 356, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Ala (or Leu or Gly), Ile, and Ala as substitutions at positions corresponding to positions 113, 227, 356, and 462, respectively, of amino acids 1 to 513 of SEQ ID NO: 2. In another most preferred embodiment, the variant comprises the substitutions S113N+P227A (or P227L or P227G)+T356I+T462A of amino acids 1 to 513 of SEQ ID NO: 2.

In another preferred embodiment, the variant comprises substitutions at positions corresponding to positions 113, 196, 356, and 462 of amino acids 1 to 513 of SEQ ID NO: 2. In a more preferred embodiment, the variant comprises substitutions at positions corresponding to positions 113, 196, 356, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Thr (or Pro or Phe), Ile, and Ala as substitutions at positions corresponding to positions 113, 196, 356, and 462, respectively, of amino acids 1 to 513 of SEQ ID NO: 2. In another most preferred embodiment, the variant comprises the substitutions S113N+S196T (or S196P or S196F)+T356I+T462A of amino acids 1 to 513 of SEQ ID NO: 2.

In another preferred embodiment, the variant comprises substitutions at positions corresponding to positions 196, 227, 356, and 462 of amino acids 1 to 513 of SEQ ID NO: 2. In a more preferred embodiment, the variant comprises substitutions at positions corresponding to positions 196, 227, 356, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Thr (or Pro or Phe), Ala (or Leu or Gly), Ile, and Ala as substitutions at positions corresponding to positions 196, 227, 356, and 462, respectively, of amino acids 1 to 513 of SEQ ID NO: 2. In another most preferred embodiment, the variant comprises the substitutions S196T (or S196P or S196F)+P227A (or P227L or P227G)+T356I+T462A of amino acids 1 to 513 of SEQ ID NO: 2.

In another preferred embodiment, the variant comprises substitutions at positions corresponding to positions 113, 196, 227, 356, and 462 of amino acids 1 to 513 of SEQ ID NO: 2. In a more preferred embodiment, the variant comprises substitutions at positions corresponding to positions 113, 196, 227, 356, and 462 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Thr (or Pro or Phe), Ala (or Leu or Gly), Ile, and Ala as substitutions at positions corresponding to positions 113, 196, 227, 356, and 462, respectively, of amino acids 1 to 513 of SEQ ID NO: 2. In another most preferred embodiment, the variant comprises the substitutions S113N+S196T (or S196P or S196F)+P227A (or P227L or P227L)+T356I+T462A of amino acids 1 to 513 of SEQ ID NO: 2.

In another preferred embodiment, the variant comprises substitutions at positions corresponding to positions 21 and 246 of amino acids 1 to 513 of SEQ ID NO: 2. In a more preferred embodiment, the variant comprises substitutions at positions corresponding to positions 21 and 246 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Pro and Ile as substitutions at positions corresponding to positions 21 and 246, respectively, of amino acids 1 to 513 of SEQ ID NO: 2. In another most preferred embodiment, the variant comprises the substitutions S21P+T246I of amino acids 1 to 513 of SEQ ID NO: 2.

In another preferred embodiment, the variant comprises substitutions at positions corresponding to positions 21 and 251 of amino acids 1 to 513 of SEQ ID NO: 2. In a more preferred embodiment, the variant comprises substitutions at positions corresponding to positions 21 and 251 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Pro and Lys as substitutions at positions corresponding to positions 21 and 251, respectively, of amino acids 1 to 513 of SEQ ID NO: 2. In another most preferred embodiment, the variant comprises the substitutions S21P+R251K of amino acids 1 to 513 of SEQ ID NO: 2.

In another preferred embodiment, the variant comprises substitutions at positions corresponding to positions 21 and 411 of amino acids 1 to 513 of SEQ ID NO: 2. In a more preferred embodiment, the variant comprises substitutions at positions corresponding to positions 21 and 411 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Pro and Phe as substitutions at positions corresponding to positions 21 and 411, respectively, of amino acids 1 to 513 of SEQ ID NO: 2. In another most preferred embodiment, the variant comprises the substitutions S21P+S411F of amino acids 1 to 513 of SEQ ID NO: 2.

In another preferred embodiment, the variant comprises substitutions at positions corresponding to positions 57 and 246 of amino acids 1 to 513 of SEQ ID NO: 2. In a more preferred embodiment, the variant comprises substitutions at positions corresponding to positions 57 and 246 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Asn and Ile as substitutions at positions corresponding to positions 57 and 246, respectively, of amino acids 1 to 513 of SEQ ID NO: 2. In another most preferred embodiment, the variant comprises the substitutions S57N+T246I of amino acids 1 to 513 of SEQ ID NO: 2.

In another preferred embodiment, the variant comprises substitutions at positions corresponding to positions 57 and 251 of amino acids 1 to 513 of SEQ ID NO: 2. In a more preferred embodiment, the variant comprises substitutions at positions corresponding to positions 57 and 251 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Asn and Lys as substitutions at positions corresponding to positions 57 and 251, respectively, of amino acids 1 to 513 of SEQ ID NO: 2. In another most preferred embodiment, the variant comprises the substitutions S57N+R251K of amino acids 1 to 513 of SEQ ID NO: 2.

In another preferred embodiment, the variant comprises substitutions at positions corresponding to positions 57 and 411 of amino acids 1 to 513 of SEQ ID NO: 2. In a more preferred embodiment, the variant comprises substitutions at positions corresponding to positions 57 and 251 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Asn and Phe as substitutions at positions corresponding to positions 57 and 411, respectively, of amino acids 1 to 513 of SEQ ID NO: 2. In another most preferred embodiment, the variant comprises the substitutions S57N+S411F of amino acids 1 to 513 of SEQ ID NO: 2.

In another preferred embodiment, the variant comprises substitutions at positions corresponding to positions 246 and 251 of amino acids 1 to 513 of SEQ ID NO: 2. In a more preferred embodiment, the variant comprises substitutions at positions corresponding to positions 246 and 251 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Ile and Lys as substitutions at positions corresponding to positions 246 and 251, respectively, of amino acids 1 to 513 of SEQ ID NO: 2. In another most preferred embodiment, the variant comprises the substitutions T246I+R251K of amino acids 1 to 513 of SEQ ID NO: 2.

In another preferred embodiment, the variant comprises substitutions at positions corresponding to positions 246 and 411 of amino acids 1 to 513 of SEQ ID NO: 2. In a more preferred embodiment, the variant comprises substitutions at positions corresponding to positions 246 and 411 of amino acids 1 to 513 of SEQ ID NO: 2 with Ala, Arg, Pro, Asp, Cys, Gin, Glu, Gly, His, Ile, Leu, Lys, Met, Phe, Pro, Ser, Thr, Trp, Tyr, or Val. In an even more preferred embodiment, the variant comprises Ile and Phe as substitutions at positions corresponding to positions 246 and 411, respectively, of amino acids 1 to 513 of SEQ ID NO: 2. In another most preferred embodiment, the variant comprises the substitutions T246I+S411F of amino acids 1 to 513 of SEQ ID NO: 2.

In another preferred embodiment, the variant comprises substitutions at positions corresponding to positions 251 and 411 of amino acids 1 to 513 of SEQ ID NO: 2. In a more preferred embodiment, the variant comprises substitutions at positions corresponding to positions 251 and 411 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Lys and Phe as substitutions at positions corresponding to positions 251 and 411, respectively, of amino acids 1 to 513 of SEQ ID NO: 2. In another most preferred embodiment, the variant comprises the substitutions R251K+S411F of amino acids 1 to 513 of SEQ ID NO: 2.

In another preferred embodiment, the variant comprises substitutions at positions corresponding to positions 21, 57, and 246 of amino acids 1 to 513 of SEQ ID NO: 2. In a more preferred embodiment, the variant comprises substitutions at positions corresponding to positions 21, 57, and 246 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Pro, Asn, and Ile as substitutions at positions corresponding to positions 21, 57, and 246, respectively, of amino acids 1 to 513 of SEQ ID NO: 2. In another most preferred embodiment, the variant comprises the substitutions S21P+S57N+T246I of amino acids 1 to 513 of SEQ ID NO: 2.

In another preferred embodiment, the variant comprises substitutions at positions corresponding to positions 21, 246, and 251 of amino acids 1 to 513 of SEQ ID NO: 2. In a more preferred embodiment, the variant comprises substitutions at positions corresponding to positions 21, 246, and 251 of amino acids 1 to 513 of SEQ ID NO: 2 with Ala, Arg, Pro, Asp, Cys, Gin, Glu, Gly, His, Ile, Leu, Lys, Met, Phe, Pro, Ser, Thr, Trp, Tyr, or Val. In an even more preferred embodiment, the variant comprises Pro, Ile, and Lys as substitutions at positions corresponding to positions 21, 246, and 251, respectively, of amino acids 1 to 513 of SEQ ID NO: 2. In another most preferred embodiment, the variant comprises the substitutions S21P+T246I+R251K of amino acids 1 to 513 of SEQ ID NO: 2.

In another preferred embodiment, the variant comprises substitutions at positions corresponding to positions 21, 246, and 411 of amino acids 1 to 513 of SEQ ID NO: 2. In a more preferred embodiment, the variant comprises substitutions at positions corresponding to positions 21, 246, and 411 of amino acids 1 to 513 of SEQ ID NO: 2 with Ala, Arg, Pro, Asp, Cys, Gin, Glu, Gly, His, Ile, Leu, Lys, Met, Phe, Pro, Ser, Thr, Trp, Tyr, or Val. In an even more preferred embodiment, the variant comprises Pro, Ile, and Phe as substitutions at positions corresponding to positions 21, 246, and 411, respectively, of amino acids 1 to 513 of SEQ ID NO: 2. In another most preferred embodiment, the variant comprises the substitutions S21P+T246I+S411F of amino acids 1 to 513 of SEQ ID NO: 2.

In another preferred embodiment, the variant comprises substitutions at positions corresponding to positions 57, 246, and 251 of amino acids 1 to 513 of SEQ ID NO: 2. In a more preferred embodiment, the variant comprises substitutions at positions corresponding to positions 57, 246, and 251 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Ile, and Lys as substitutions at positions corresponding to positions 57, 246, and 251, respectively, of amino acids 1 to 513 of SEQ ID NO: 2. In another most preferred embodiment, the variant comprises the substitutions S57N+T246I+R251K of amino acids 1 to 513 of SEQ ID NO: 2.

In another preferred embodiment, the variant comprises substitutions at positions corresponding to positions 57, 246, and 411 of amino acids 1 to 513 of SEQ ID NO: 2. In a more preferred embodiment, the variant comprises substitutions at positions corresponding to positions 57, 246, and 411 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Ile, and Phe as substitutions at positions corresponding to positions 57, 246, and 411, respectively, of amino acids 1 to 513 of SEQ ID NO: 2. In another most preferred embodiment, the variant comprises the substitutions S57N+T246I+S411F of amino acids 1 to 513 of SEQ ID NO: 2.

In another preferred embodiment, the variant comprises substitutions at positions corresponding to positions 57, 251, and 411 of amino acids 1 to 513 of SEQ ID NO: 2. In a more preferred embodiment, the variant comprises substitutions at positions corresponding to positions 57, 251, and 411 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Lys, and Phe as substitutions at positions corresponding to positions 57, 251, and 411, respectively, of amino acids 1 to 513 of SEQ ID NO: 2. In another most preferred embodiment, the variant comprises the substitutions S57N+R251K+S411F of amino acids 1 to 513 of SEQ ID NO: 2.

In another preferred embodiment, the variant comprises substitutions at positions corresponding to positions 21, 57, and 251 of amino acids 1 to 513 of SEQ ID NO: 2. In a more preferred embodiment, the variant comprises substitutions at positions corresponding to positions 21, 57, and 251 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Pro, Asn, and Lys as substitutions at positions corresponding to positions 21, 57, and 251, respectively, of amino acids 1 to 513 of SEQ ID NO: 2. In another most preferred embodiment, the variant comprises the substitutions S21P+S57N+R251K of amino acids 1 to 513 of SEQ ID NO: 2.

In another preferred embodiment, the variant comprises substitutions at positions corresponding to positions 246, 251, and 411 of amino acids 1 to 513 of SEQ ID NO: 2. In a more preferred embodiment, the variant comprises substitutions at positions corresponding to positions 246, 251, and 411 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Ile, Lys, and Phe as substitutions at positions corresponding to positions 246, 251, and 411, respectively, of amino acids 1 to 513 of SEQ ID NO: 2. In another most preferred embodiment, the variant comprises the substitutions T246I+R251K+S411F of amino acids 1 to 513 of SEQ ID NO: 2.

In another preferred embodiment, the variant comprises substitutions at positions corresponding to positions 21, 57, 246, and 251 of amino acids 1 to 513 of SEQ ID NO: 2. In a more preferred embodiment, the variant comprises substitutions at positions corresponding to positions 21, 57, 246, and 251 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Pro, Asn, Ile, and Lys as substitutions at positions corresponding to positions 21, 57, 246, and 251 respectively, of amino acids 1 to 513 of SEQ ID NO: 2. In another most preferred embodiment, the variant comprises the substitutions S21P+S57N+T246I+R251K of amino acids 1 to 513 of SEQ ID NO: 2.

In another preferred embodiment, the variant comprises substitutions at positions corresponding to positions 21, 246, 251, and 411 of amino acids 1 to 513 of SEQ ID NO: 2. In a more preferred embodiment, the variant comprises substitutions at positions corresponding to positions 21, 246, 251, and 411 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Pro, Ile, Lys, and Phe as substitutions at positions corresponding to positions 21, 246, 251, and 411, respectively, of amino acids 1 to 513 of SEQ ID NO: 2. In another most preferred embodiment, the variant comprises the substitutions S21P+T246I+R251K+S411F of amino acids 1 to 513 of SEQ ID NO: 2.

In another preferred embodiment, the variant comprises substitutions at positions corresponding to positions 21, 57, 251, and 411 of amino acids 1 to 513 of SEQ ID NO: 2. In a more preferred embodiment, the variant comprises substitutions at positions corresponding to positions 21, 57, 251, and 411 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Pro, Asn, Lys, and Phe as substitutions at positions corresponding to positions 21, 57, 251, and 411, respectively, of amino acids 1 to 513 of SEQ ID NO: 2. In another most preferred embodiment, the variant comprises the substitutions S21P+S57N+R251K+S411F of amino acids 1 to 513 of SEQ ID NO: 2.

In another preferred embodiment, the variant comprises substitutions at positions corresponding to positions 57, 246, 251, and 411 of amino acids 1 to 513 of SEQ ID NO: 2. In a more preferred embodiment, the variant comprises substitutions at positions corresponding to positions 57, 246, 251, and 411 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Asn, Ile, Lys, and Phe as substitutions at positions corresponding to positions 57, 246, 251, and 411, respectively, of amino acids 1 to 513 of SEQ ID NO: 2. In another most preferred embodiment, the variant comprises the substitutions S57N+T246I+R251K+S411F of amino acids 1 to 513 of SEQ ID NO: 2.

In another preferred embodiment, the variant comprises substitutions at positions corresponding to positions 21, 57, 246, and 411 of amino acids 1 to 513 of SEQ ID NO: 2. In a more preferred embodiment, the variant comprises substitutions at positions corresponding to positions 21, 57, 246, and 411 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Pro, Asn, Ile, and Phe as substitutions at positions corresponding to positions 21, 57, 246, and 411, respectively, of amino acids 1 to 513 of SEQ ID NO: 2. In another most preferred embodiment, the variant comprises the substitutions S21P+S57N+T246I+S411F of amino acids 1 to 513 of SEQ ID NO: 2.

In another preferred embodiment, the variant comprises substitutions at positions corresponding to positions 21, 57, 246, 251, and 411 of amino acids 1 to 513 of SEQ ID NO: 2. In a more preferred embodiment, the variant comprises substitutions at positions corresponding to positions 21, 57, 246, 251, and 411 of amino acids 1 to 513 of SEQ ID NO: 2 with Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the variant comprises Pro, Asn, Ile, Lys, and Phe as substitutions at positions corresponding to positions 21, 57, 246, 251, and 411, respectively, of amino acids 1 to 513 of SEQ ID NO: 2. In another most preferred embodiment, the variant comprises the substitutions S21P+S57N+T246I+R251K+S411F of amino acids 1 to 513 of SEQ ID NO: 2.

In another preferred embodiment, the variant comprises at least one substitution selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least two substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least three substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least four substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least five substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least six substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least seven substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least eight substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least nine substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least ten substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least eleven substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least twelve substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least thirteen substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least fourteen substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least fifteen substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least sixteen substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least seventeen substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least eighteen substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least nineteen substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises at least twenty substitutions selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

In another preferred embodiment, the variant comprises substitutions consisting of at least S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further comprises one or more substitutions selected from the group consisting of S8P, G22D, T41I, N49S, S57N, S113N, S196T, T226A, P227A, T255P, T356I, Y371C, S411F, and T462A.

The variants of the present invention may further comprise one or more deletions and/or insertions of the amino acid sequence.

In a preferred embodiment, a variant of the present invention consists of 341 to 350, 351 to 360, 361 to 370, 371 to 380, 381 to 390, 391 to 400, 401 to 410, 411 to 420, 421 to 430, 431 to 440, 441 to 450, 451 to 460, 461 to 470, 471 to 480, 481 to 490, 491 to 500, or 501 to 513 amino acids.

In another preferred embodiment, the variant comprising the substitution T226A of amino acids 1 to 513 of SEQ ID NO: 2 is encoded by the nucleotide sequence contained in *E. coli* NRRL B-30657. In another preferred embodiment, the variant comprising the substitutions S113N+S196T+T462A of amino acids 1 to 513 of SEQ ID NO: 2 is encoded by the nucleotide sequence contained in *E. coli* NRRL B-30658. In another preferred embodiment, the variant comprising the substitutions G22D+G467S of amino acids 1 to 513 of SEQ ID NO: 2 is encoded by the nucleotide sequence contained in *E. coli* NRRL B-30659. In another preferred embodiment, the variant comprising the substitutions S21P+S57N of amino acids 1 to 513 of SEQ ID NO: 2 is encoded by the nucleotide sequence contained in *E. coli* NRRL B-30661. In another preferred embodiment, the variant comprising the substitutions K157R+G205R+T255P of amino acids 1 to 513 of SEQ ID NO: 2 is encoded by the nucleotide sequence contained in *E. coli* NRRL B-30662. In another preferred embodiment, the variant comprising the substitutions S196P+G205R of amino acids 1 to 513 of SEQ ID NO: 2 is encoded by the nucleotide sequence contained in *E. coli* NRRL B-30663. In another preferred embodiment, the variant comprising the substitutions S113N+S196T+P227A+T462A of amino acids 1 to 513 of SEQ ID NO: 2 is encoded by the nucleotide sequence contained in *E. coli* NRRL B-30664. In another preferred embodiment, the variant comprising the substitutions T41I+E193K+S411F of amino acids 1 to 513 of SEQ ID NO: 2 is encoded by the nucleotide sequence contained in *E. coli* NRRL B-30665. In another preferred embodiment, the variant comprising the substitutions N49S+S113N+P227A+P438L of amino acids 1 to 513 of SEQ ID NO: 2 is encoded by the nucleotide sequence contained in *E. coli* NRRL B-30666. In another preferred embodiment, the variant comprising the substitutions N301S+E337V of amino acids 1 to 513 of SEQ ID NO: 2 is encoded by the nucleotide sequence contained in *E. coli* NRRL B-30674. In another preferred embodiment, the variant comprising the substitutions S196P+T350S of amino acids 1 to 513 of SEQ ID NO: 2 is encoded by the nucleotide sequence contained in *E. coli* NRRL B-30675. In another preferred embodiment, the variant comprising the substitutions G205R+H206Y of amino acids 1 to 513 of SEQ ID NO: 2 is encoded by the nucleotide sequence contained in *E. coli* NRRL B-30676. In another preferred embodiment, the variant comprising the substitutions S8P+G205R of amino acids 1 to 513 of SEQ ID NO: 2 is encoded by the nucleotide sequence contained in E. coli NRRL B-30677. In another preferred embodiment, the variant comprising the substitutions G94S+G205R of amino acids 1 to 513 of SEQ ID NO: 2 is encoded by the nucleotide sequence contained in E. coli NRRL B-30678. In another preferred embodiment, the variant comprising the substitutions T383A+T455A of amino acids 1 to 513 of SEQ ID NO: 2 is encoded by the nucleotide sequence contained in E. coli NRRL B-30679. In another preferred embodiment, the variant comprising the substitution N373H of amino acids 1 to 513 of SEQ ID NO: 2 is encoded by the nucleotide sequence contained in E. coli NRRL B-30680. In another preferred embodiment, the variant comprising the substitutions Y247C+Y371C+S411F of amino acids 1 to 513 of SEQ ID NO: 2 is encoded by the nucleotide sequence contained in E. coli NRRL B-30681. In another preferred embodiment, the variant comprising the substitutions S21P+S57N+T246I+R251K+S411F of amino acids 1 to 513 of SEQ ID NO: 2 is encoded by the nucleotide sequence contained in E. coli NRRL B-30682. In another preferred embodiment, the variant comprising the substitutions P227G+D259N of amino acids 1 to 513 of SEQ ID NO: 2 is encoded by the nucleotide sequence contained in E. coli NRRL B-30762.

The present invention also relates to methods for obtaining a variant of a parent glycoside hydrolase, comprising: (a) introducing into the parent glycoside hydrolase a substitution at one or more positions corresponding to positions 21, 94, 157, 205, 206, 247, 337, 350, 373, 383, 438, 455, 467, and 486 of amino acids 1 to 513 of SEQ ID NO: 2, and optionally further introducing a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2, wherein the variant has glycoside hydrolase activity; and (b) recovering the variant.

Nucleotide Sequences

The present invention also relates to isolated nucleotide sequences which encode variants of a parent glycoside hydrolase, wherein the nucleotide sequences have been modified to encode the variants described herein comprising a substitution at one or more positions corresponding to positions 21, 94, 157, 205, 206, 247, 337, 350, 373, 383, 438, 455, 467, and 486 of amino acids 1 to 513 of SEQ ID NO: 2, and optionally further comprising a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2.

The term "isolated nucleotide sequence" as used herein refers to a nucleotide sequence which is essentially free of other nucleotide sequences, e.g., at least 20% pure, preferably at least 40% pure, more preferably at least 60% pure, even more preferably at least 80% pure, and most preferably at least 90% pure as determined by agarose electrophoresis.

In a preferred embodiment, the isolated nucleotide sequence encoding the variant comprising the substitution T226A of amino acids 1 to 513 of SEQ ID NO: 2 is contained in E. coli NRRL B-30657. In another preferred embodiment, the isolated nucleotide sequence encoding the variant comprising the substitutions S113N+S196T+T462A of amino acids 1 to 513 of SEQ ID NO: 2 is contained in E. coli NRRL B-30658. In another preferred embodiment, the isolated nucleotide sequence encoding the variant comprising the substitutions G22D+G467S of amino acids 1 to 513 of SEQ ID NO: 2 is contained in E. coli NRRL B-30659. In another preferred embodiment, the isolated nucleotide sequence encoding the variant comprising the substitutions S21P+S57N of amino acids 1 to 513 of SEQ ID NO: 2 is contained in E. coli NRRL B-30661. In another preferred embodiment, the isolated nucleotide sequence encoding the variant comprising the substitutions K157R+G205R+T255P of amino acids 1 to 513 of SEQ ID NO: 2 is contained in E. coli NRRL B-30662. In another preferred embodiment, the isolated nucleotide sequence encoding the variant comprising the substitutions S196P+G205R of amino acids 1 to 513 of SEQ ID NO: 2 is contained in E. coli NRRL B-30663. In another preferred embodiment, the isolated nucleotide sequence encoding the variant comprising the substitutions S113N+S196T+P227A+T462A of amino acids 1 to 513 of SEQ ID NO: 2 is contained in E. coli NRRL B-30664. In another preferred embodiment, the isolated nucleotide sequence encoding the variant comprising the substitutions T41I+E193K+S411F of amino acids 1 to 513 of SEQ ID NO: 2 is contained in E. coli NRRL B-30665. In another preferred embodiment, the isolated nucleotide sequence encoding the variant comprising the substitutions N49S+S113N+P227A+P438L of amino acids 1 to 513 of SEQ ID NO: 2 is contained in E. coli NRRL B-30666. In another preferred embodiment, the variant comprising the substitutions N301S+E337V of amino acids 1 to 513 of SEQ ID NO: 2 is contained in E. coli NRRL B-30674. In another preferred embodiment, the isolated nucleotide sequence encoding the variant comprising the substitutions S196P+T350S of amino acids 1 to 513 of SEQ ID NO: 2 is contained in E. coli NRRL B-30675. In another preferred embodiment, the isolated nucleotide sequence encoding the variant comprising the substitutions G205R+H206Y of amino acids 1 to 513 of SEQ ID NO: 2 is contained in E. coli NRRL B-30676. In another preferred embodiment, the isolated nucleotide sequence encoding the variant comprising the substitutions S8P+G205R of amino acids 1 to 513 of SEQ ID NO: 2 is contained in E. coli NRRL B-30677. In another preferred embodiment, the isolated nucleotide sequence encoding the variant comprising the substitutions G94S+G205R of amino acids 1 to 513 of SEQ ID NO: 2 is contained in E. coli NRRL B-30678. In another preferred embodiment, the isolated nucleotide sequence encoding the variant comprising the substitutions T383A+T455A of amino acids 1 to 513 of SEQ ID NO: 2 is contained in E. coli NRRL B-30679. In another preferred embodiment, the isolated nucleotide sequence encoding the variant comprising the substitution N373H of amino acids 1 to 513 of SEQ ID NO: 2 is contained in E. coli NRRL B-30680. In another preferred embodiment, the isolated nucleotide sequence encoding the variant comprising the substitutions Y247C+Y371C+S411F of amino acids 1 to 513 of SEQ ID NO: 2 is contained in E. coli NRRL B-30681. In another preferred embodiment, the isolated nucleotide sequence encoding the variant comprising the substitutions S21P+S57N+T246I+R251K+S411F of amino acids 1 to 513 of SEQ ID NO: 2 is contained in E. coli NRRL B-30682. In another preferred embodiment, the isolated nucleotide sequence encoding the variant comprising the substitutions P227G+D259N of amino acids 1 to 513 of SEQ ID NO: 2 is contained in E. coli NRRL B-30762.

Nucleic Acid Constructs

The present invention also relates to nucleic acid constructs comprising a nucleotide sequence encoding a glycoside hydrolase variant of the present invention operably linked to one or more control sequences which direct the expression of the coding sequence in a suitable host cell under conditions compatible with the control sequences. Expression will be understood to include any step involved in the production of the variant including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of a variant of the present invention. The term "coding sequence" is defined herein as a nucleotide sequence which directly specifies the amino acid sequence of its protein product. The boundaries of a genomic coding sequence are generally determined by the ATG start codon, or alternative start codons such as GTG and TTG, located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleotide sequences.

An isolated nucleotide sequence encoding a glycoside hydrolase variant of the present invention may be manipulated in a variety of ways to provide for expression of the variant. Manipulation of the nucleotide sequence prior to its insertion into a vector may be desirable or necessary depending on the expression vector. The techniques for modifying nucleotide sequences utilizing recombinant DNA methods are well known in the art.

The term "control sequences" is defined herein to include all components which are necessary or advantageous for the expression of a glycoside hydrolase variant of the present invention. Each control sequence may be native or foreign to the nucleotide sequence encoding the variant. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a variant glycoside hydrolase of the present invention. The term "operably linked" is defined herein as a configuration in which a control sequence is appropriately placed at a position relative to the coding sequence of the nucleotide sequence such that the control sequence directs the expression of a variant glycoside hydrolase.

The control sequence may be an appropriate promoter sequence, which is recognized by a host cell for expression of the nucleotide sequence. The promoter sequence contains transcriptional control sequences which mediate the expression of the variant glycoside hydrolase. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); equivalents thereof; and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, which is recognized by a host cell to terminate transcription. The terminator sequence is operably linked to the 3'-terminus of the nucleotide sequence encoding the variant glycoside hydrolase. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleotide sequence encoding the variant glycoside hydrolase. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polypeptide-encoding sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger*glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular* Cellular Biology 15: 5983-5990.

The control sequence may also be a signal peptide coding region that codes for an amino acid sequence linked to the amino terminus of a variant glycoside hydrolase and directs the encoded polypeptide into the cell's secretory pathway. The 5'-end of the coding sequence of the nucleotide sequence may inherently contain a signal peptide coding region naturally linked in translation reading frame with the segment of the coding region which encodes the secreted variant glycoside hydrolase. Alternatively, the 5'-end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant glycoside hydrolase. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* Cel45A cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a variant glycoside hydrolase. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the variant glycoside hydrolase relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger*glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the variant glycoside hydrolase would be operably linked with the regulatory sequence.

Expression Vectors

The present invention also relates to recombinant expression vectors comprising a nucleotide sequence encoding a variant glycoside hydrolase of the present invention, a promoter, and transcriptional and translational stop signals. The various nucleotide and control sequences described above may be joined together to produce a recombinant expression vector which may include one or more convenient restriction sites to allow for insertion or substitution of the nucleotide sequence encoding the variant at such sites. Alternatively, the nucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector may be an autonomously replicating vector, i.e., a vector which exists as an extrachromosomal entity, the replication of which is distinct from chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain an element(s) that permits integration of the vector into the host cell's genome or autonomous replication of the vector in the cell independent of the genome.

For integration into the host cell genome, the vector may rely on the nucleotide sequence encoding the variant or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector mayfurther comprise an origin of replication enabling the vector to replicate autonomously in the host cell in question. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes functioning temperature-sensitive in the host cell (see, e.g., Ehrlich, 1978, *Proceedings of the National Academy of Sciences USA* 75: 1433). Examples of a plasmid replicator useful in a filamentous fungal cell are AMA1 and ANSI (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a nucleotide sequence of the present invention may be inserted into the host cell to increase production of a glycoside hydrolase variant. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra) to obtain substantially pure glycoside hydrolase variants.

Host Cells

The present invention also relates to recombinant host cells, comprising a nucleotide sequence encoding a variant glycoside hydrolase, which are advantageously used in the recombinant production of the variant. A vector comprising a nucleotide sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any eukaryote, such as a mammalian, insect, plant, or fungal cell.

The host cell may be any fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In a more preferred embodiment, the yeast host cell is a *Candida, Hansenula, Kluyveromyces, Pichia, Saccharomyces, Schizosaccharomyces,* or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal host cell is, but not limited to, an *Acremonium, Aspergillus, Fusarium, Humicola, Mucor, Myceliophthora, Neurospora, Penicillium, Thielavia, Tolypocladium,* or *Trichoderma* cell.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal host cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell. In another even most preferred embodiment, the filamentous fungal host cell is *Trichoderma reesei* RutC30.

Fungal cells may be transformed according to the procedures described herein.

Methods of Production

The present invention also relates to methods for producing a glycoside hydrolase variant, comprising:

(a) cultivating a host cell under conditions suitable for the expression of the variant, wherein the host cell comprises a nucleotide sequence which has been modified to encode the variant comprising a substitution at one or more positions corresponding to positions 21, 94, 157, 205, 206, 247, 337, 350, 373, 383, 438, 455, 467, and 486 of amino acids 1 to 513 of SEQ ID NO: 2, and optionally further comprising a substitution at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2, as described herein; and (b) recovering the variant from the cultivation medium.

In the production methods of the present invention, the host cells are cultivated in a nutrient medium suitable for production of the glycoside hydrolase variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

In an alternative embodiment, the glycoside hydrolase variant is not recovered, but rather a host cell of the present invention expressing a variant is used as a source of the variant.

The glycoside hydrolase variant may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein in the Examples.

The resulting glycoside hydrolase variant may be recovered by methods known in the art. For example, the polypeptide may be recovered from the nutrient medium by conventional procedures including, but not limited to, collection, centrifugation, filtration, extraction, spray-drying, evaporation, or precipitation.

A glycoside hydrolase variant of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure glycoside hydrolase variants.

Other Polypeptides Having Glycoside Hydrolase Activity (1994)

The present invention also relates to isolated polypeptides having glycoside hydrolase activity, wherein the amino acid sequence of the polypeptide differs from SEQ ID NO: 2 at one or more positions corresponding to positions 21, 94, 157, 205, 206, 247, 337, 350, 373, 383, 438, 455, 467, and 486 of amino acids 1 to 513 of SEQ ID NO: 2, and optionally further differs at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2.

In a preferred embodiment, the amino acid sequence of the polypeptide differs from amino acids 1 to 513 of SEQ ID NO: 2 by preferably 33 amino acids, more preferably 32 amino acids, even more preferably 31 amino acids, even more preferably 30 amino acids, even more preferably 29 amino acids, even more preferably 28 amino acids, even more preferably 27 amino acids, even more preferably 26 amino acids, even more preferably 25 amino acids, even more preferably 24 amino acids, even more preferably 23 amino acids, even more preferably 22 amino acids, even more preferably 21 amino acids, even more preferably 20 amino acids, even more preferably 19 amino acids, even more preferably 18 amino acids, even more preferably 17 amino acids, even more preferably 16 amino acids, even more preferably 15 amino acids, even more preferably 14 amino acids, even more preferably 13 amino acids, even more preferably 12 amino acids, even more preferably 11 amino acids, even more preferably 10 amino acids, even more preferably 9 amino acids, even more preferably 8 amino acids, even more preferably 7 amino acids, even more preferably 6 amino acids, even more preferably 5 amino acids, even more preferably 4 amino acids, even more preferably 3 amino acids, even more preferably 2 amino acids, and most preferably 1 amino acid.

In a preferred embodiment, the amino acid sequence of the polypeptide differs from SEQ ID NO: 2 at one or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at two or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at three or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at four or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at five or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at six or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at seven or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at eight or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at nine or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at ten or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at eleven or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at twelve or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at thirteen or more positions corresponding to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2. In another preferred embodiment, the amino acid sequence of the polypeptide differs from SEQ ID NO: 2 at positions corresponding at least to positions 21, 94, 157, 205, 206, 247, 337, 350, 373, 383, 438, 455, 467, and 486 of amino acids 1 to 513 of SEQ ID NO: 2, and optionally further differs from SEQ ID NO: 2 at one or more positions corresponding to positions 8, 22, 41, 49, 57, 113, 193, 196, 226, 227, 246, 251, 255, 259, 301, 356, 371, 411, and 462 of amino acids 1 to 513 of SEQ ID NO: 2.

In another preferred embodiment, the amino acid sequence of the polypeptide differs from SEQ ID NO: 2 at a position corresponding to position 21 of amino acids 1 to 513 of SEQ ID NO: 2. In another more preferred embodiment, the amino acid sequence of the polypeptide differs from SEQ ID NO: 2 at a position corresponding to position 21 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Pro at a position corresponding to position 21 of amino acids 1 to 513 of SEQ ID NO: 2. In another most preferred embodiment, the amino acid sequence of the polypeptide differs from SEQ ID NO: 2 by S21P of amino acids 1 to 513 of SEQ ID NO: 2.

In another preferred embodiment, the amino acid sequence of the polypeptide differs from SEQ ID NO: 2 at a position corresponding to position 94 of amino acids 1 to 513 of SEQ ID NO: 2.

In another more preferred embodiment, the amino acid sequence of the polypeptide differs from SEQ ID NO: 2 at a position corresponding to position 94 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Ser at a position corresponding to position 94 of amino acids 1 to 513 of SEQ ID NO: 2. In another most preferred embodiment, the amino acid sequence of the polypeptide differs from SEQ ID NO: 2 by G94S of amino acids 1 to 513 of SEQ ID NO: 2. In another even more preferred embodiment, the amino acid sequence of the polypeptide differs from SEQ ID NO: 2 by Ala at a position corresponding to position 94 of amino acids 1 to 513 of SEQ ID NO: 2. In another most preferred embodiment, the amino acid sequence of the polypeptide differs from SEQ ID NO: 2 by G94A of amino acids 1 to 513 of SEQ ID NO: 2. In another even more preferred embodiment, the amino acid sequence of the polypeptide differs from SEQ ID NO: 2 by Arg at a position corresponding to position 94 of amino acids 1 to 513 of SEQ ID NO: 2. In another most preferred embodiment, the amino acid sequence of the polypeptide differs from SEQ ID NO: 2 by G94R of amino acids 1 to 513 of SEQ ID NO: 2. In another even more preferred embodiment, the amino acid sequence of the polypeptide differs from SEQ ID NO: 2 by Gln at a position corresponding to position 94 of amino acids 1 to 513 of SEQ ID NO: 2. In another most preferred embodiment, the amino acid sequence of the polypeptide differs from SEQ ID NO: 2 by G94Q of amino acids 1 to 513 of SEQ ID NO: 2.

In another preferred embodiment, the amino acid sequence of the polypeptide differs from SEQ ID NO: 2 at a position corresponding to position 157 of amino acids 1 to 513 of SEQ ID NO: 2. In another more preferred embodiment, the amino acid sequence of the polypeptide differs from SEQ ID NO: 2 at a position corresponding to position 157 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Arg at a position corresponding to position 157 of amino acids 1 to 513 of SEQ ID NO: 2. In another most preferred embodiment, the amino acid sequence of the polypeptide differs from SEQ ID NO: 2 by K157R of amino acids 1 to 513 of SEQ ID NO: 2.

In another preferred embodiment, the amino acid sequence of the polypeptide differs from SEQ ID NO: 2 at a position corresponding to position 205 of amino acids 1 to 513 of SEQ ID NO: 2. In another more preferred embodiment, the amino acid sequence of the polypeptide differs from SEQ ID NO: 2 at a position corresponding to position 205 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Arg at a position corresponding to position 205 of amino acids 1 to 513 of SEQ ID NO: 2. In another most preferred embodiment, the amino acid sequence of the polypeptide differs from SEQ ID NO: 2 by G205R of amino acids 1 to 513 of SEQ ID NO: 2.

In another preferred embodiment, the amino acid sequence of the polypeptide differs from SEQ ID NO: 2 at a position corresponding to position 206 of amino acids 1 to 513 of SEQ ID NO: 2. In another more preferred embodiment, the amino acid sequence of the polypeptide differs from SEQ ID NO: 2 at a position corresponding to position 206 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Tyr at a position corresponding to position 206 of amino acids 1 to 513 of SEQ ID NO: 2. In another most preferred embodiment, the amino acid sequence of the polypeptide differs from SEQ ID NO: 2 by H206Y of amino acids 1 to 513 of SEQ ID NO: 2.

In another preferred embodiment, the amino acid sequence of the polypeptide differs from SEQ ID NO: 2 at a position corresponding to position 247 of amino acids 1 to 513 of SEQ ID NO: 2. In another more preferred embodiment, the amino acid sequence of the polypeptide differs from SEQ ID NO: 2 at a position corresponding to position 247 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Cys at a position corresponding to position 247 of amino acids 1 to 513 of SEQ ID NO: 2. In another most preferred embodiment, the amino acid sequence of the polypeptide differs from SEQ ID NO: 2 by Y247C of amino acids 1 to 513 of SEQ ID NO: 2.

In another preferred embodiment, the amino acid sequence of the polypeptide differs from SEQ ID NO: 2 at a position corresponding to position 337 of amino acids 1 to 513 of SEQ ID NO: 2. In another more preferred embodiment, the amino acid sequence of the polypeptide differs from SEQ ID NO: 2 at a position corresponding to position 337 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Val at a position corresponding to position 337 of amino acids 1 to 513 of SEQ ID NO: 2. In another most preferred embodiment, the amino acid sequence of the polypeptide differs from SEQ ID NO: 2 by E337V of amino acids 1 to 513 of SEQ ID NO: 2.

In another preferred embodiment, the amino acid sequence of the polypeptide differs from SEQ ID NO: 2 at a position corresponding to position 350 of amino acids 1 to 513 of SEQ ID NO: 2. In another more preferred embodiment, the amino acid sequence of the polypeptide differs from SEQ ID NO: 2 at a position corresponding to position 350 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val.

In another even more preferred embodiment, the amino acid sequence of the polypeptide differs from SEQ ID NO: 2 by Ser at a position corresponding to position 350 of amino acids 1 to 513 of SEQ ID NO: 2. In another most preferred embodiment, the amino acid sequence of the polypeptide differs from SEQ ID NO: 2 by T350S of amino acids 1 to 513 of SEQ ID NO: 2.

In another preferred embodiment, the amino acid sequence of the polypeptide differs from SEQ ID NO: 2 at a position corresponding to position 373 of amino acids 1 to 513 of SEQ ID NO: 2. In another more preferred embodiment, the amino acid sequence of the polypeptide differs from SEQ ID NO: 2 at a position corresponding to position 373 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by His at a position corresponding to position 373 of amino acids 1 to 513 of SEQ ID NO: 2. In another most preferred embodiment, the amino acid sequence of the polypeptide differs from SEQ ID NO: 2 by N373H of amino acids 1 to 513 of SEQ ID NO: 2.

In another preferred embodiment, the amino acid sequence of the polypeptide differs from SEQ ID NO: 2 at a position corresponding to position 383 of amino acids 1 to 513 of SEQ ID NO: 2. In another more preferred embodiment, the amino acid sequence of the polypeptide differs from SEQ ID NO: 2 at a position corresponding to position 383 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val.

In another even more preferred embodiment, the amino acid sequence of the polypeptide differs from SEQ ID NO:

2 by Ala at a position corresponding to position 383 of amino acids 1 to 513 of SEQ ID NO: 2. In another most preferred embodiment, the amino acid sequence of the polypeptide differs from SEQ ID NO: 2 by T383A of amino acids 1 to 513 of SEQ ID NO: 2. In another preferred embodiment, the amino acid sequence of the polypeptide differs from SEQ ID NO: 2 at a position corresponding to position 438 of amino acids 1 to 513 of SEQ ID NO: 2.

In another more preferred embodiment, the amino acid sequence of the polypeptide differs from SEQ ID NO: 2 at a position corresponding to position 438 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Leu at a position corresponding to position 438 of amino acids 1 to 513 of SEQ ID NO: 2. In another most preferred embodiment, the amino acid sequence of the polypeptide differs from SEQ ID NO: 2 by P438L of amino acids 1 to 513 of SEQ ID NO: 2.

In another preferred embodiment, the amino acid sequence of the polypeptide differs from SEQ ID NO: 2 at a position corresponding to position 455 of amino acids 1 to 513 of SEQ ID NO: 2. In another more preferred embodiment, the amino acid sequence of the polypeptide differs from SEQ ID NO: 2 at a position corresponding to position 455 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Ala at a position corresponding to position 455 of amino acids 1 to 513 of SEQ ID NO: 2. In another most preferred embodiment, the amino acid sequence of the polypeptide differs from SEQ ID NO: 2 by T455A of amino acids 1 to 513 of SEQ ID NO: 2.

In another preferred embodiment, the amino acid sequence of the polypeptide differs from SEQ ID NO: 2 at a position corresponding to position 467 of amino acids 1 to 513 of SEQ ID NO: 2. In another more preferred embodiment, the amino acid sequence of the polypeptide differs from SEQ ID NO: 2 at a position corresponding to position 467 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Ser at a position corresponding to position 467 of amino acids 1 to 513 of SEQ ID NO: 2. In another most preferred embodiment, the amino acid sequence of the polypeptide differs from SEQ ID NO: 2 by G467S of amino acids 1 to 513 of SEQ ID NO: 2.

In another preferred embodiment, the amino acid sequence of the polypeptide differs from SEQ ID NO: 2 at a position corresponding to position 486 of amino acids 1 to 513 of SEQ ID NO: 2. In another more preferred embodiment, the amino acid sequence of the polypeptide differs from SEQ ID NO: 2 at a position corresponding to position 486 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide differs from SEQ ID NO: 2 by Trp at a position corresponding to position 486 of amino acids 1 to 513 of SEQ ID NO: 2. In another most preferred embodiment, the amino acid sequence of the polypeptide differs from SEQ ID NO: 2 by C486W of amino acids 1 to 513 of SEQ ID NO: 2.

In a preferred embodiment, the amino acid sequence of the polypeptide further differs from SEQ ID NO: 2 at a position corresponding to position 8 of amino acids 1 to 513 of SEQ ID NO: 2. In a more preferred embodiment, the amino acid sequence of the polypeptide further differs from SEQ ID NO: 2 at a position corresponding to position 8 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide further differs from SEQ ID NO: 2 by Pro at a position corresponding to position 8 of amino acids 1 to 513 of SEQ ID NO: 2. In a most preferred embodiment, the amino acid sequence of the polypeptide further differs from SEQ ID NO: 2 by S8P of amino acids 1 to 513 of SEQ ID NO: 2.

In another preferred embodiment, the amino acid sequence of the polypeptide further differs from SEQ ID NO: 2 at a position corresponding to position 22 of amino acids 1 to 513 of SEQ ID NO: 2. In another more preferred embodiment, the amino acid sequence of the polypeptide further differs from SEQ ID NO: 2 at a position corresponding to position 22 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Asp at a position corresponding to position 22 of amino acids 1 to 513 of SEQ ID NO: 2. In another most preferred embodiment, the amino acid sequence of the polypeptide further differs from SEQ ID NO: 2 by G22D of amino acids 1 to 513 of SEQ ID NO: 2.

In another preferred embodiment, the amino acid sequence of the polypeptide further differs from SEQ ID NO: 2 at a position corresponding to position 41 of amino acids 1 to 513 of SEQ ID NO: 2. In another more preferred embodiment, the amino acid sequence of the polypeptide further differs from SEQ ID NO: 2 at a position corresponding to position 41 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Ile at a position corresponding to position 41 of amino acids 1 to 513 of SEQ ID NO: 2. In another most preferred embodiment, the amino acid sequence of the polypeptide further differs from SEQ ID NO: 2 by T41I of amino acids 1 to 513 of SEQ ID NO: 2.

In another preferred embodiment, the amino acid sequence of the polypeptide further differs from SEQ ID NO: 2 at a position corresponding to position 49 of amino acids 1 to 513 of SEQ ID NO: 2. In another more preferred embodiment, the amino acid sequence of the polypeptide further differs from SEQ ID NO: 2 at a position corresponding to position 49 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Ser at a position corresponding to position 49 of amino acids 1 to 513 of SEQ ID NO: 2. In another most preferred embodiment, the amino acid sequence of the polypeptide further differs from SEQ ID NO: 2 by N49S of amino acids 1 to 513 of SEQ ID NO: 2.

In another preferred embodiment, the amino acid sequence of the polypeptide further differs from SEQ ID NO: 2 at a position corresponding to position 57 of amino acids 1 to 513 of SEQ ID NO: 2. In another more preferred embodiment, the amino acid sequence of the polypeptide further differs from SEQ ID NO: 2 at a position corresponding to position 57 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Asn at a position corresponding to position 57 of amino acids 1 to 513 of SEQ ID NO: 2. In another most preferred embodiment, the amino acid sequence of the polypeptide further differs from SEQ ID NO: 2 by S57N of amino acids 1 to 513 of SEQ ID NO: 2.

In another preferred embodiment, the amino acid sequence of the polypeptide further differs from SEQ ID NO: 2 at a position corresponding to position 113 of amino acids 1 to 513 of SEQ ID NO: 2. In another more preferred embodiment, the amino acid sequence of the polypeptide further differs from SEQ ID NO: 2 at a position corresponding to position 113 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Asn at a position corresponding to position 113 of amino acids 1 to 513 of SEQ ID NO: 2. In another most preferred embodiment, the amino acid sequence of the polypeptide further differs from SEQ ID NO: 2 by S113N of amino acids 1 to 513 of SEQ ID NO: 2.

In another preferred embodiment, the amino acid sequence of the polypeptide further differs from SEQ ID NO: 2 at a position corresponding to position 193 of amino acids 1 to 513 of SEQ ID NO: 2. In another more preferred embodiment, the amino acid sequence of the polypeptide further differs from SEQ ID NO: 2 at a position corresponding to position 193 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Lys at a position corresponding to position 193 of amino acids 1 to 513 of SEQ ID NO: 2. In another most preferred embodiment, the amino acid sequence of the polypeptide further differs from SEQ ID NO: 2 by E193K of amino acids 1 to 513 of SEQ ID NO: 2.

In another preferred embodiment, the amino acid sequence of the polypeptide further differs from SEQ ID NO: 2 at a position corresponding to position 196 of amino acids 1 to 513 of SEQ ID NO: 2. In another more preferred embodiment, the amino acid sequence of the polypeptide further differs from SEQ ID NO: 2 at a position corresponding to position 196 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Pro at a position corresponding to position 196 of amino acids 1 to 513 of SEQ ID NO: 2. In another most preferred embodiment, the amino acid sequence of the polypeptide further differs from SEQ ID NO: 2 by S196P of amino acids 1 to 513 of SEQ ID NO: 2. In another even more preferred embodiment, the amino acid sequence of the polypeptide further differs from SEQ ID NO: 2 by Thr at a position corresponding to position 196 of amino acids 1 to 513 of SEQ ID NO: 2. In another most preferred embodiment, the amino acid sequence of the polypeptide further differs from SEQ ID NO: 2 by S196T of amino acids 1 to 513 of SEQ ID NO: 2. In another even more preferred embodiment, the amino acid sequence of the polypeptide further differs from SEQ ID NO: 2 by Phe at a position corresponding to position 196 of amino acids 1 to 513 of SEQ ID NO: 2. In another most preferred embodiment, the amino acid sequence of the polypeptide further differs from SEQ ID NO: 2 by S196F of amino acids 1 to 513 of SEQ ID NO: 2.

In another preferred embodiment, the amino acid sequence of the polypeptide further differs from SEQ ID NO: 2 at a position corresponding to position 226 of amino acids 1 to 513 of SEQ ID NO: 2. In another more preferred embodiment, the amino acid sequence of the polypeptide further differs from SEQ ID NO: 2 at a position corresponding to position 226 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Ala at a position corresponding to position 226 of amino acids 1 to 513 of SEQ ID NO: 2. In another most preferred embodiment, the amino acid sequence of the polypeptide further differs from SEQ ID NO: 2 by T226A of amino acids 1 to 513 of SEQ ID NO: 2.

In another preferred embodiment, the amino acid sequence of the polypeptide further differs from SEQ ID NO: 2 at a position corresponding to position 227 of amino acids 1 to 513 of SEQ ID NO: 2. In another more preferred embodiment, the amino acid sequence of the polypeptide further differs from SEQ ID NO: 2 at a position corresponding to position 227 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Ala at a position corresponding to position 227 of amino acids 1 to 513 of SEQ ID NO: 2. In another most preferred embodiment, the amino acid sequence of the polypeptide further differs from SEQ ID NO: 2 by P227A of amino acids 1 to 513 of SEQ ID NO: 2. In another even more preferred embodiment, the amino acid sequence of the polypeptide further differs from SEQ ID NO: 2 by Leu at a position corresponding to position 227 of amino acids 1 to 513 of SEQ ID NO: 2. In another most preferred embodiment, the amino acid sequence of the polypeptide further differs from SEQ ID NO: 2 by P227L of amino acids 1 to 513 of SEQ ID NO: 2. In another even more preferred embodiment, the amino acid sequence of the polypeptide further differs from SEQ ID NO: 2 by Gly at a position corresponding to position 227 of amino acids 1 to 513 of SEQ ID NO: 2. In another most preferred embodiment, the amino acid sequence of the polypeptide further differs from SEQ ID NO: 2 by P227G of amino acids 1 to 513 of SEQ ID NO: 2.

In another preferred embodiment, the amino acid sequence of the polypeptide further differs from SEQ ID NO: 2 at a position corresponding to position 246 of amino acids 1 to 513 of SEQ ID NO: 2. In another more preferred embodiment, the amino acid sequence of the polypeptide further differs from SEQ ID NO: 2 at a position corresponding to position 246 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Ile at a position corresponding to position 246 of amino acids 1 to 513 of SEQ ID NO: 2. In another most preferred embodiment, the amino acid sequence of the polypeptide further differs from SEQ ID NO: 2 by T246I of amino acids 1 to 513 of SEQ ID NO: 2.

In another preferred embodiment, the amino acid sequence of the polypeptide further differs from SEQ ID NO: 2 at a position corresponding to position 251 of amino acids 1 to 513 of SEQ ID NO: 2. In another more preferred embodiment, the amino acid sequence of the polypeptide further differs from SEQ ID NO: 2 at a position corresponding to position 251 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Lys at a position corresponding to position 251 of amino acids 1 to 513 of SEQ ID NO: 2. In another most preferred embodiment, the amino acid sequence of the polypeptide further differs from SEQ ID NO: 2 by R251K of amino acids 1 to 513 of SEQ ID NO: 2.

In another preferred embodiment, the amino acid sequence of the polypeptide further differs from SEQ ID NO: 2 at a position corresponding to position 255 of amino acids 1 to 513 of SEQ ID NO: 2. In another more preferred embodiment, the amino acid sequence of the polypeptide further differs from SEQ ID NO: 2 at a position corresponding to position 255 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Pro at a position corresponding to position 255 of amino acids 1 to 513 of SEQ ID NO: 2. In another most preferred embodiment, the amino acid sequence of the polypeptide further differs from SEQ ID NO: 2 by T255P of amino acids 1 to 513 of SEQ ID NO: 2.

In another preferred embodiment, the amino acid sequence of the polypeptide further differs from SEQ ID NO: 2 at a position corresponding to position 259 of amino acids 1 to 513 of SEQ ID NO: 2. In another more preferred embodiment, the amino acid sequence of the polypeptide further differs from SEQ ID NO: 2 at a position corresponding to position 259 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Asn at a position corresponding to position 259 of amino acids 1 to 513 of SEQ ID NO: 2. In another most preferred embodiment, the amino acid sequence of the polypeptide further differs from SEQ ID NO: 2 by D259N of amino acids 1 to 513 of SEQ ID NO: 2.

In another preferred embodiment, the amino acid sequence of the polypeptide further differs from SEQ ID NO: 2 at a position corresponding to position 301 of amino acids 1 to 513 of SEQ ID NO: 2. In another more preferred embodiment, the amino acid sequence of the polypeptide further differs from SEQ ID NO: 2 at a position corresponding to position 301 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Ser at a position corresponding to position 301 of amino acids 1 to 513 of SEQ ID NO: 2. In another most preferred embodiment, the amino acid sequence of the polypeptide further differs from SEQ ID NO: 2 by N301S of amino acids 1 to 513 of SEQ ID NO: 2.

In another preferred embodiment, the amino acid sequence of the polypeptide further differs from SEQ ID NO: 2 at a position corresponding to position 356 of amino acids 1 to 513 of SEQ ID NO: 2. In another more preferred embodiment, the amino acid sequence of the polypeptide further differs from SEQ ID NO: 2 at a position corresponding to position 356 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Ile at a position corresponding to position 356 of amino acids 1 to 513 of SEQ ID NO: 2. In another most preferred embodiment, the amino acid sequence of the polypeptide further differs from SEQ ID NO: 2 by T356I of amino acids 1 to 513 of SEQ ID NO: 2.

In another preferred embodiment, the amino acid sequence of the polypeptide further differs from SEQ ID NO: 2 at a position corresponding to position 371 of amino acids 1 to 513 of SEQ ID NO: 2. In another more preferred embodiment, the amino acid sequence of the polypeptide further differs from SEQ ID NO: 2 at a position corresponding to position 371 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Cys at a position corresponding to position 371 of amino acids 1 to 513 of SEQ ID NO: 2. In another most preferred embodiment, the amino acid sequence of the polypeptide further differs from SEQ ID NO: 2 by Y371C of amino acids 1 to 513 of SEQ ID NO: 2.

In another preferred embodiment, the amino acid sequence of the polypeptide further differs from SEQ ID NO: 2 at a position corresponding to position 411 of amino acids 1 to 513 of SEQ ID NO: 2. In another more preferred embodiment, the amino acid sequence of the polypeptide further differs from SEQ ID NO: 2 at a position corresponding to position 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Phe at a position corresponding to position 411 of amino acids 1 to 513 of SEQ ID NO: 2. In another most preferred embodiment, the amino acid sequence of the polypeptide further differs from SEQ ID NO: 2 by S411F of amino acids 1 to 513 of SEQ ID NO: 2.

In another preferred embodiment, the amino acid sequence of the polypeptide further differs from SEQ ID NO: 2 at a position corresponding to position 462 of amino acids 1 to 513 of SEQ ID NO: 2. In another more preferred embodiment, the amino acid sequence of the polypeptide further differs from SEQ ID NO: 2 at a position corresponding to position 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In another even more preferred embodiment, the amino acid sequence of the polypeptide further differs from SEQ ID NO: 2 by Ala at a position corresponding to position 462 of amino acids 1 to 513 of SEQ ID NO: 2. In another most preferred embodiment, the amino acid sequence of the polypeptide further differs from SEQ ID NO: 2 by T462A of amino acids 1 to 513 of SEQ ID NO: 2.

In another preferred embodiment, the amino acid sequence of the polypeptide differs from SEQ ID NO: 2 at positions corresponding to positions 227 and 259 of amino acids 1 to 513 of SEQ ID NO: 2. In a more preferred embodiment, the amino acid sequence of the polypeptide differs from SEQ ID NO: 2 at positions corresponding to positions 227 and 259 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Gly (or Ala or Leu) and Asn at positions corresponding to positions 227 and 259, respectively, of amino acids 1 to 513 of SEQ ID NO: 2. In another most preferred embodiment, the amino acid sequence of the polypeptide differs from SEQ ID NO: 2 by P227G (or P227A or P227L)+D259N of amino acids 1 to 513 of SEQ ID NO: 2.

In another preferred embodiment, the amino acid sequence of the polypeptide differs from SEQ ID NO: 2 at positions corresponding to positions 227 and 486 of amino acids 1 to 513 of SEQ ID NO: 2. In a more preferred embodiment, the amino acid sequence of the polypeptide differs from SEQ ID NO: 2 at positions corresponding to positions 227 and 486 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ala (or Leu or Gly) and Trp at positions corresponding to positions 227 and 486, respectively, of amino acids 1 to 513 of SEQ ID NO: 2. In another most preferred embodiment, the amino acid sequence of the polypeptide differs from SEQ ID NO: 2 by P227A (or P227L or P227G)+C486W of amino acids 1 to 513 of SEQ ID NO: 2.

In another preferred embodiment, the amino acid sequence of the polypeptide differs from SEQ ID NO: 2 at positions corresponding to positions 301 and 337 of amino acids 1 to 513 of SEQ ID NO: 2. In a more preferred embodiment, the amino acid sequence of the polypeptide differs from SEQ ID NO: 2 at positions corresponding to positions 301 and 337 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser and Val at positions corresponding to positions 301 and 337, respectively, of amino acids 1 to 513 of SEQ ID NO: 2. In another most preferred embodiment, the amino acid sequence of the polypeptide differs from SEQ ID NO: 2 by N301S+E337V of amino acids 1 to 513 of SEQ ID NO: 2.

In another preferred embodiment, the amino acid sequence of the polypeptide differs from SEQ ID NO: 2 at positions corresponding to positions 196 and 350 of amino acids 1 to 513 of SEQ ID NO: 2. In a more preferred embodiment, the amino acid sequence of the polypeptide differs from SEQ ID NO: 2 at positions corresponding to positions 196 and 350 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro (or Thr or Phe) and Ser at positions corresponding to positions 196 and 350, respectively, of amino acids 1 to 513 of SEQ ID NO: 2. In another most preferred embodiment, the amino acid sequence of the polypeptide differs from SEQ ID NO: 2 by S196P (or S196T or S196F)+T350S of amino acids 1 to 513 of SEQ ID NO: 2.

In another preferred embodiment, the amino acid sequence of the polypeptide differs from SEQ ID NO: 2 at positions corresponding to positions 22 and 467 of amino acids 1 to 513 of SEQ ID NO: 2. In a more preferred embodiment, the amino acid sequence of the polypeptide differs from SEQ ID NO: 2 at positions corresponding to positions 22 and 467 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asp and Ser at positions corresponding to positions 22 and 467, respectively, of amino acids 1 to 513 of SEQ ID NO: 2. In another most preferred embodiment, the amino acid sequence of the polypeptide differs from SEQ ID NO: 2 by G22D+G467S of amino acids 1 to 513 of SEQ ID NO: 2.

In another preferred embodiment, the amino acid sequence of the polypeptide differs from SEQ ID NO: 2 at positions corresponding to positions 21 and 57 of amino acids 1 to 513 of SEQ ID NO: 2. In a more preferred embodiment, the amino acid sequence of the polypeptide differs from SEQ ID NO: 2 at positions corresponding to positions 21 and 57 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro and Asn at positions corresponding to positions 21 and 57, respectively, of amino acids 1 to 513 of SEQ ID NO: 2. In another most preferred embodiment, the amino acid sequence of the polypeptide differs from SEQ ID NO: 2 by S21P+S57N of amino acids 1 to 513 of SEQ ID NO: 2.

In another preferred embodiment, the amino acid sequence of the polypeptide differs from SEQ ID NO: 2 at positions corresponding to positions 205 and 411 of amino acids 1 to 513 of SEQ ID NO: 2. In a more preferred embodiment, the amino acid sequence of the polypeptide differs from SEQ ID NO: 2 at positions corresponding to positions 205 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg and Phe at positions corresponding to positions 205 and 411, respectively, of amino acids 1 to 513 of SEQ ID NO: 2. In another most preferred embodiment, the amino acid sequence of the polypeptide differs from SEQ ID NO: 2 by G205R+S411F of amino acids 1 to 513 of SEQ ID NO: 2.

In another preferred embodiment, the amino acid sequence of the polypeptide differs from SEQ ID NO: 2 at positions corresponding to positions 205 and 227 of amino acids 1 to 513 of SEQ ID NO: 2. In a more preferred embodiment, the amino acid sequence of the polypeptide differs from SEQ ID NO: 2 at positions corresponding to positions 205 and 227 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg and Ala (or Leu or Gly) at positions corresponding to positions 205 and 227, respectively, of amino acids 1 to 513 of SEQ ID NO: 2. In another most preferred embodiment, the amino acid sequence of the polypeptide differs from SEQ ID NO: 2 by G205R+P227A (or P227L or P227G) of amino acids 1 to 513 of SEQ ID NO: 2.

In another preferred embodiment, the amino acid sequence of the polypeptide differs from SEQ ID NO: 2 at positions corresponding to positions 205 and 206 of amino acids 1 to 513 of SEQ ID NO: 2. In a more preferred embodiment, the amino acid sequence of the polypeptide differs from SEQ ID NO: 2 at positions corresponding to positions 205 and 206 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg and Tyr at positions corresponding to positions 205 and 206, respectively, of amino acids 1 to 513 of SEQ ID NO: 2. In another most preferred embodiment, the amino acid sequence of the polypeptide differs from SEQ ID NO: 2 by G205R+H206Y of amino acids 1 to 513 of SEQ ID NO: 2.

In another preferred embodiment, the amino acid sequence of the polypeptide differs from SEQ ID NO: 2 at positions corresponding to positions 8 and 205 of amino acids 1 to 513 of SEQ ID NO: 2. In a more preferred embodiment, the amino acid sequence of the polypeptide differs from SEQ ID NO: 2 at positions corresponding to positions 8 and 205 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro and Arg at positions corresponding to positions 8 and 205, respectively, of amino acids 1 to 513 of SEQ ID NO: 2. In another most preferred embodiment, the amino acid sequence of the polypeptide differs from SEQ ID NO: 2 by S8P+G205R of amino acids 1 to 513 of SEQ ID NO: 2.

In another preferred embodiment, the amino acid sequence of the polypeptide differs from SEQ ID NO: 2 at positions corresponding to positions 94 and 205 of amino acids 1 to 513 of SEQ ID NO: 2. In a more preferred embodiment, the amino acid sequence of the polypeptide differs from SEQ ID NO: 2 at positions corresponding to positions 94 and 205 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser (or Ala or Arg or Gln) and Arg at positions corresponding to positions 94 and 205, respectively, of amino acids 1 to 513 of SEQ ID NO: 2. In another most preferred embodiment, the amino acid sequence of the polypeptide differs from SEQ ID NO: 2 by G94S (or G94A or G94R or G94Q)+G205R of amino acids 1 to 513 of SEQ ID NO: 2.

In another preferred embodiment, the amino acid sequence of the polypeptide differs from SEQ ID NO: 2 at positions corresponding to positions 196 and 205 of amino acids 1 to 513 of SEQ ID NO: 2. In a more preferred embodiment, the amino acid sequence of the polypeptide differs from SEQ ID NO: 2 at positions corresponding to positions 196 and 205 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro (or Thr or Phe) and Arg at positions corresponding to positions 196 and 205, respectively, of amino acids 1 to 513 of SEQ ID NO: 2. In another most preferred embodiment, the amino acid sequence of the polypeptide differs from SEQ ID NO: 2 by S196P (or S196T or S196F)+G205R of amino acids 1 to 513 of SEQ ID NO: 2.

In another preferred embodiment, the amino acid sequence of the polypeptide differs from SEQ ID NO: 2 at positions corresponding to positions 383 and 455 of amino acids 1 to 513 of SEQ ID NO: 2. In a more preferred embodiment, the amino acid sequence of the polypeptide differs from SEQ ID NO: 2 at positions corresponding to positions 383 and 455 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ala and Ala at positions corresponding to positions 383 and 455, respectively, of amino acids 1 to 513 of SEQ ID NO: 2. In another most preferred embodiment, the amino acid sequence of the polypeptide differs from SEQ ID NO: 2 by T383A+T455A of amino acids 1 to 513 of SEQ ID NO: 2.

In another preferred embodiment, the amino acid sequence of the polypeptide differs from SEQ ID NO: 2 at positions corresponding to positions 113 and 411 of amino acids 1 to 513 of SEQ ID NO: 2. In a more preferred embodiment, the amino acid sequence of the polypeptide differs from SEQ ID NO: 2 at positions corresponding to positions 113 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn and Phe at positions corresponding to positions 113 and 411, respectively, of amino acids 1 to 513 of SEQ ID NO: 2. In another most preferred embodiment, the amino acid sequence of the polypeptide differs from SEQ ID NO: 2 by S113N+S411F of amino acids 1 to 513 of SEQ ID NO: 2.

In another preferred embodiment, the amino acid sequence of the polypeptide differs from SEQ ID NO: 2 at positions corresponding to positions 113 and 196 of amino acids 1 to 513 of SEQ ID NO: 2. In a more preferred embodiment, the amino acid sequence of the polypeptide differs from SEQ ID NO: 2 at positions corresponding to positions 113 and 196 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn and Thr (or Pro or Phe) at positions corresponding to positions 113 and 196, respectively, of amino acids 1 to 513 of SEQ ID NO: 2. In another most preferred embodiment, the amino acid sequence of the polypeptide differs from SEQ ID NO: 2 by S113N+S196T (or S196P or S196F) of amino acids 1 to 513 of SEQ ID NO: 2.

In another preferred embodiment, the amino acid sequence of the polypeptide differs from SEQ ID NO: 2 at positions corresponding to positions 113 and 462 of amino acids 1 to 513 of SEQ ID NO: 2. In a more preferred embodiment, the amino acid sequence of the polypeptide differs from SEQ ID NO: 2 at positions corresponding to positions 113 and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn and Ala at positions corresponding to positions 113 and 462, respectively, of amino acids 1 to 513 of SEQ ID NO: 2. In another most preferred embodiment, the amino acid sequence of the polypeptide differs from SEQ ID NO: 2 by S113N+T462A of amino acids 1 to 513 of SEQ ID NO: 2.

In another preferred embodiment, the amino acid sequence of the polypeptide differs from SEQ ID NO: 2 at positions corresponding to positions 196 and 462 of amino acids 1 to 513 of SEQ ID NO: 2. In a more preferred embodiment, the amino acid sequence of the polypeptide differs from SEQ ID NO: 2 at positions corresponding to positions 196 and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Thr (or Pro or Phe) and Ala at positions corresponding to positions 196 and 462, respectively, of amino acids 1 to 513 of SEQ ID NO: 2. In another most preferred embodiment, the amino acid sequence of the polypeptide differs from SEQ ID NO: 2 by S196T (or S196P or S196F)+T462A of amino acids 1 to 513 of SEQ ID NO: 2.

In another preferred embodiment, the amino acid sequence of the polypeptide differs from SEQ ID NO: 2 at positions corresponding to positions 196 and 462 of amino acids 1 to 513 of SEQ ID NO: 2. In a more preferred embodiment, the amino acid sequence of the polypeptide differs from SEQ ID NO: 2 at positions corresponding to positions 41 and 196 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ile and Phe (or Pro or Thr) at positions corresponding to positions 41 and 196, respectively, of amino acids 1 to 513 of SEQ ID NO: 2. In another most preferred embodiment, the amino acid sequence of the polypeptide differs from SEQ ID NO: 2 by T41I+S196F (or S196P or S196T) of amino acids 1 to 513 of SEQ ID NO: 2.

In another preferred embodiment, the amino acid sequence of the polypeptide differs from SEQ ID NO: 2 at positions corresponding to positions 94 and 226 of amino acids 1 to 513 of SEQ ID NO: 2. In a more preferred embodiment, the amino acid sequence of the polypeptide differs from SEQ ID NO: 2 at positions corresponding to positions 94 and 226 of amino acids 1 to 513 of SEQ ID NO: 2 with Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ala (or Ser or Arg or Gln) and Ala at positions corresponding to positions 94 and 226, respectively, of amino acids 1 to 513 of SEQ ID NO: 2. In another most preferred embodiment, the amino acid sequence of the polypeptide differs from SEQ ID NO: 2 by G94A (or G94S or G94R or G94Q)+T226A of amino acids 1 to 513 of SEQ ID NO: 2.

In another preferred embodiment, the amino acid sequence of the polypeptide differs from SEQ ID NO: 2 at positions corresponding to positions 113, 196, and 462 of amino acids 1 to 513 of SEQ ID NO: 2. In a more preferred embodiment, the amino acid sequence of the polypeptide differs from SEQ ID NO: 2 at positions corresponding to positions 113, 196, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Thr (or Pro or Phe), and Ala at positions corresponding to positions 113, 196, and 462, respectively, of amino acids 1 to 513 of SEQ ID NO: 2. In another most preferred embodiment, the amino acid sequence of the polypeptide differs from SEQ ID NO: 2 by S113N+S196T (or S196P or S196F)+T462A of amino acids 1 to 513 of SEQ ID NO: 2.

In another preferred embodiment, the amino acid sequence of the polypeptide differs from SEQ ID NO: 2 at positions corresponding to positions 157 and 205 of amino acids 1 to 513 of SEQ ID NO: 2. In a more preferred embodiment, the amino acid sequence of the polypeptide differs from SEQ ID NO: 2 at positions corresponding to positions 157 and 205 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg and Arg at positions corresponding to positions 157 and 205, respectively, of amino acids 1 to 513 of SEQ ID NO: 2. In another most preferred embodiment, the amino acid sequence of the polypeptide differs from SEQ ID NO: 2 by K157R+G205R of amino acids 1 to 513 of SEQ ID NO: 2.

In another preferred embodiment, the amino acid sequence of the polypeptide differs from SEQ ID NO: 2 at positions corresponding to positions 157 and 255 of amino acids 1 to 513 of SEQ ID NO: 2. In a more preferred embodiment, the amino acid sequence of the polypeptide differs from SEQ ID NO: 2 at positions corresponding to positions 157 and 255 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg and Pro at positions corresponding to positions 157 and 255, respectively, of amino acids 1 to 513 of SEQ ID NO: 2. In another most preferred embodiment, the amino acid sequence of the polypeptide differs from SEQ ID NO: 2 by K157R+T255P of amino acids 1 to 513 of SEQ ID NO: 2.

In another preferred embodiment, the amino acid sequence of the polypeptide differs from SEQ ID NO: 2 at positions corresponding to positions 205 and 255 of amino acids 1 to 513 of SEQ ID NO: 2. In a more preferred embodiment, the amino acid sequence of the polypeptide differs from SEQ ID NO: 2 at positions corresponding to positions 205 and 255 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg and Pro at positions corresponding to positions 205 and 255, respectively, of amino acids 1 to 513 of SEQ ID NO: 2. In another most preferred embodiment, the amino acid sequence of the polypeptide differs from SEQ ID NO: 2 by G205R+T255P of amino acids 1 to 513 of SEQ ID NO: 2.

In another preferred embodiment, the amino acid sequence of the polypeptide differs from SEQ ID NO: 2 at positions corresponding to positions 157, 205, and 255 of amino acids 1 to 513 of SEQ ID NO: 2. In a more preferred embodiment, the amino acid sequence of the polypeptide differs from SEQ ID NO: 2 at positions corresponding to positions 157, 205, and 255 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg, Arg, and Pro at positions corresponding to positions 157, 205, and 255, respectively, of amino acids 1 to 513 of SEQ ID NO: 2. In another most preferred embodiment, the amino acid sequence of the polypeptide differs from SEQ ID NO: 2 by K157R+G205R+T255P of amino acids 1 to 513 of SEQ ID NO: 2.

In another preferred embodiment, the amino acid sequence of the polypeptide differs from SEQ ID NO: 2 at positions corresponding to positions 41 and 193 of amino acids 1 to 513 of SEQ ID NO: 2. In a more preferred embodiment, the amino acid sequence of the polypeptide differs from SEQ ID NO: 2 at positions corresponding to positions 41 and 193 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ile and Lys at positions corresponding to positions 41 and 193, respectively, of amino acids 1 to 513 of SEQ ID NO: 2. In another most preferred embodiment, the amino acid sequence of the polypeptide differs from SEQ ID NO: 2 by T41I+E193K of amino acids 1 to 513 of SEQ ID NO: 2.

In another preferred embodiment, the amino acid sequence of the polypeptide differs from SEQ ID NO: 2 at positions corresponding to positions 41 and 411 of amino acids 1 to 513 of SEQ ID NO: 2. In a more preferred embodiment, the amino acid sequence of the polypeptide differs from SEQ ID NO: 2 at positions corresponding to positions 41 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ile and Phe at positions corresponding to positions 41 and 411, respectively, of amino acids 1 to 513 of SEQ ID NO: 2. In another most preferred embodiment, the amino acid sequence of the polypeptide differs from SEQ ID NO: 2 by T41 I+S411F of amino acids 1 to 513 of SEQ ID NO: 2.

In another preferred embodiment, the amino acid sequence of the polypeptide differs from SEQ ID NO: 2 at positions corresponding to positions 193 and 411 of amino acids 1 to 513 of SEQ ID NO: 2. In a more preferred embodiment, the amino acid sequence of the polypeptide differs from SEQ ID NO: 2 at positions corresponding to positions 193 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Lys and Phe at positions corresponding to positions 193 and 411, respectively, of amino acids 1 to 513 of SEQ ID NO: 2. In another most preferred embodiment, the amino acid sequence of the polypeptide differs from SEQ ID NO: 2 by E193K+S411F of amino acids 1 to 513 of SEQ ID NO: 2.

In another preferred embodiment, the amino acid sequence of the polypeptide differs from SEQ ID NO: 2 at positions corresponding to positions 41, 193, and 411 of amino acids 1 to 513 of SEQ ID NO: 2. In a more preferred embodiment, the amino acid sequence of the polypeptide differs from SEQ ID NO: 2 at positions corresponding to positions 41, 193, and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ile, Lys, and Phe at positions corresponding to positions 41, 193, and 411, respectively, of amino acids 1 to 513 of SEQ ID NO: 2. In another most preferred embodiment, the amino acid sequence of the polypeptide differs from SEQ ID NO: 2 by T41I+E193K+S411F of amino acids 1 to 513 of SEQ ID NO: 2.

In another preferred embodiment, the amino acid sequence of the polypeptide differs from SEQ ID NO: 2 at positions corresponding to positions 247 and 371 of amino acids 1 to 513 of SEQ ID NO: 2. In a more preferred embodiment, the amino acid sequence of the polypeptide differs from SEQ ID NO: 2 at positions corresponding to positions 247 and 371 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Cys and Cys at positions corresponding to positions 247 and 371, respectively, of amino acids 1 to 513 of SEQ ID NO: 2. In another most preferred embodiment, the amino acid sequence of the polypeptide differs from SEQ ID NO: 2 by Y247C+Y371C of amino acids 1 to 513 of SEQ ID NO: 2.

In another preferred embodiment, the amino acid sequence of the polypeptide differs from SEQ ID NO: 2 at positions corresponding to positions 247 and 411 of amino acids 1 to 513 of SEQ ID NO: 2. In a more preferred embodiment, the amino acid sequence of the polypeptide differs from SEQ ID NO: 2 at positions corresponding to positions 247 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Cys and Phe at positions corresponding to positions 247 and 411, respectively, of amino acids 1 to 513 of SEQ ID NO: 2. In another most preferred embodiment, the amino acid sequence of the polypeptide differs from SEQ ID NO: 2 by Y247C+S411F of amino acids 1 to 513 of SEQ ID NO: 2.

In another preferred embodiment, the amino acid sequence of the polypeptide differs from SEQ ID NO: 2 at positions corresponding to positions 371 and 411 of amino acids 1 to 513 of SEQ ID NO: 2. In a more preferred embodiment, the amino acid sequence of the polypeptide differs from SEQ ID NO: 2 at positions corresponding to positions 371 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Cys and Phe at positions corresponding to positions 371 and 411, respectively, of amino acids 1 to 513 of SEQ ID NO: 2. In another most preferred embodiment, the amino acid sequence of the polypeptide differs from SEQ ID NO: 2 by Y371C+S411F of amino acids 1 to 513 of SEQ ID NO: 2.

In another preferred embodiment, the amino acid sequence of the polypeptide differs from SEQ ID NO: 2 at positions corresponding to positions 247, 371, and 411 of amino acids 1 to 513 of SEQ ID NO: 2. In a more preferred embodiment, the amino acid sequence of the polypeptide differs from SEQ ID NO: 2 at positions corresponding to positions 247, 371, and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Cys, Cys, and Phe at positions corresponding to positions 247, 371, and 411, respectively, of amino acids 1 to 513 of SEQ ID NO: 2. In another most preferred embodiment, the amino acid sequence of the polypeptide differs from SEQ ID NO: 2 by Y247C+Y371C+S411F of amino acids 1 to 513 of SEQ ID NO: 2.

In another preferred embodiment, the amino acid sequence of the polypeptide differs from SEQ ID NO: 2 at positions corresponding to positions 113 and 227 of amino acids 1 to 513 of SEQ ID NO: 2. In a more preferred embodiment, the amino acid sequence of the polypeptide differs from SEQ ID NO: 2 at positions corresponding to positions 113 and 227 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn and Ala (or Leu or Gly) at positions corresponding to positions 113 and 227, respectively, of amino acids 1 to 513 of SEQ ID NO: 2. In another most preferred embodiment, the amino acid sequence of the polypeptide differs from SEQ ID NO: 2 by S113N+P227A (or P227L or P227G) of amino acids 1 to 513 of SEQ ID NO: 2.

In another preferred embodiment, the amino acid sequence of the polypeptide differs from SEQ ID NO: 2 at positions corresponding to positions 196 and 227 of amino acids 1 to 513 of SEQ ID NO: 2. In a more preferred embodiment, the amino acid sequence of the polypeptide differs from SEQ ID NO: 2 at positions corresponding to positions 196 and 227 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Thr (or Pro or Phe) and Ala (or Leu or Gly) at positions corresponding to positions 196 and 227, respectively, of amino acids 1 to 513 of SEQ ID NO: 2. In another most preferred embodiment, the amino acid sequence of the polypeptide differs from SEQ ID NO: 2 by S196T (or S196P or S196F)+P227A (or P227L or P227G) of amino acids 1 to 513 of SEQ ID NO: 2.

In another preferred embodiment, the amino acid sequence of the polypeptide differs from SEQ ID NO: 2 at positions corresponding to positions 227 and 462 of amino acids 1 to 513 of SEQ ID NO: 2. In a more preferred embodiment, the amino acid sequence of the polypeptide differs from SEQ ID NO: 2 at positions corresponding to positions 227 and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ala (or Leu or Gly) and Ala at positions corresponding to positions 227 and 462, respectively, of amino acids 1 to 513 of SEQ ID NO: 2. In another most preferred embodiment, the amino acid sequence of the polypeptide differs from SEQ ID NO: 2 by P227A (or P227L or P227G)+T462A of amino acids 1 to 513 of SEQ ID NO: 2.

In another preferred embodiment, the amino acid sequence of the polypeptide differs from SEQ ID NO: 2 at positions corresponding to positions 113, 196, and 227 of amino acids 1 to 513 of SEQ ID NO: 2. In a more preferred embodiment, the amino acid sequence of the polypeptide differs from SEQ ID NO: 2 at positions corresponding to positions 142, 196, and 227 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Thr (or Pro or Phe), and Ala (or Leu or Gly) at positions corresponding to positions 142, 196, and 227, respectively, of amino acids 1 to 513 of SEQ ID NO: 2. In another most preferred embodiment, the amino acid sequence of the polypeptide differs from SEQ ID NO: 2 by S113N+S196T (or S196P or S196F)+P227A (or P227L or P227G) of amino acids 1 to 513 of SEQ ID NO: 2.

In another preferred embodiment, the amino acid sequence of the polypeptide differs from SEQ ID NO: 2 at positions corresponding to positions 113, 227, and 462 of amino acids 1 to 513 of SEQ ID NO: 2. In a more preferred embodiment, the amino acid sequence of the polypeptide differs from SEQ ID NO: 2 at positions corresponding to positions 113, 227, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Ala (or Leu or Gly), and Ala at positions corresponding to positions 113, 227, and 462, respectively, of amino acids 1 to 513 of SEQ ID NO: 2. In another most preferred embodiment, the amino acid sequence of the polypeptide differs from SEQ ID NO: 2 by S113N+P227A (or P227L or P227G)+T462A of amino acids 1 to 513 of SEQ ID NO: 2.

In another preferred embodiment, the amino acid sequence of the polypeptide differs from SEQ ID NO: 2 at positions corresponding to positions 196, 227, and 462 of amino acids 1 to 513 of SEQ ID NO: 2. In a more preferred embodiment, the amino acid sequence of the polypeptide differs from SEQ ID NO: 2 at positions corresponding to positions 196, 227, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Thr (or Pro or Phe), Ala (or Leu or Gly), and Ala at positions corresponding to positions 196, 227, and 462, respectively, of amino acids 1 to 513 of SEQ ID NO: 2. In another most preferred embodiment, the amino acid sequence of the polypeptide differs from SEQ ID NO: 2 by S196T (or S196P or S196F)+P227A (or P227L or P227G)+T462A of amino acids 1 to 513 of SEQ ID NO: 2.

In another preferred embodiment, the amino acid sequence of the polypeptide differs from SEQ ID NO: 2 at positions corresponding to positions 113, 196, and 462 of amino acids 1 to 513 of SEQ ID NO: 2. In a more preferred embodiment, the amino acid sequence of the polypeptide differs from SEQ ID NO: 2 at positions corresponding to positions 113, 196, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Thr (or Pro or Phe), and Ala at positions corresponding to positions 113, 196, and 462, respectively, of amino acids 1 to 513 of SEQ ID NO: 2. In another most preferred embodiment, the amino acid sequence of the polypeptide differs from SEQ ID NO: 2 by S113N+S196T (or S196P or S196F)+T462A of amino acids 1 to 513 of SEQ ID NO: 2.

In another preferred embodiment, the amino acid sequence of the polypeptide differs from SEQ ID NO: 2 at positions corresponding to positions 113, 196, 227, and 462 of amino acids 1 to 513 of SEQ ID NO: 2. In a more preferred embodiment, the amino acid sequence of the polypeptide differs from SEQ ID NO: 2 at positions corresponding to positions 113, 196, 227, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Thr (or Pro or Phe), Ala (or Leu or Gly), and Ala at positions corresponding to positions 113, 196, 227, and 462, respectively, of amino acids 1 to 513 of SEQ ID NO: 2. In another most preferred embodiment, the amino acid sequence of the polypeptide differs from SEQ ID NO: 2 by S113N+S196T (or S196F or S196F)+P227A (or P227L or P227G)+T462A of amino acids 1 to 513 of SEQ ID NO: 2.

In another preferred embodiment, the amino acid sequence of the polypeptide differs from SEQ ID NO: 2 at positions corresponding to positions 49 and 113 of amino acids 1 to 513 of SEQ ID NO: 2. In a more preferred embodiment, the amino acid sequence of the polypeptide differs from SEQ ID NO: 2 at positions corresponding to positions 49 and 113 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser and Asn at positions corresponding to positions 49 and 113, respectively, of amino acids 1 to 513 of SEQ ID NO: 2. In another most preferred embodiment, the amino acid sequence of the polypeptide differs from SEQ ID NO: 2 by N49S+S113N of amino acids 1 to 513 of SEQ ID NO: 2.

In another preferred embodiment, the amino acid sequence of the polypeptide differs from SEQ ID NO: 2 at positions corresponding to positions 49 and 227 of amino acids 1 to 513 of SEQ ID NO: 2. In a more preferred embodiment, the amino acid sequence of the polypeptide differs from SEQ ID NO: 2 at positions corresponding to positions 49 and 227 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser and Ala (or Leu or Gly) at positions corresponding to positions 49 and 227, respectively, of amino acids 1 to 513 of SEQ ID NO: 2. In another most preferred embodiment, the amino acid sequence of the polypeptide differs from SEQ ID NO: 2 by N49S+P227A (or P227L or P227G) of amino acids 1 to 513 of SEQ ID NO: 2.

In another preferred embodiment, the amino acid sequence of the polypeptide differs from SEQ ID NO: 2 at positions corresponding to positions 49 and 438 of amino acids 1 to 513 of SEQ ID NO: 2. In a more preferred embodiment, the amino acid sequence of the polypeptide differs from SEQ ID NO: 2 at positions corresponding to positions 49 and 438 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser and Leu at positions corresponding to positions 49 and 438, respectively, of amino acids 1 to 513 of SEQ ID NO: 2. In another most preferred embodiment, the amino acid sequence of the polypeptide differs from SEQ ID NO: 2 by N49S+P438L of amino acids 1 to 513 of SEQ ID NO: 2.

In another preferred embodiment, the amino acid sequence of the polypeptide differs from SEQ ID NO: 2 at positions corresponding to positions 113 and 438 of amino acids 1 to 513 of SEQ ID NO: 2. In a more preferred embodiment, the amino acid sequence of the polypeptide differs from SEQ ID NO: 2 at positions corresponding to positions 113 and 438 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn and Leu at positions corresponding to positions 113 and 438, respectively, of amino acids 1 to 513 of SEQ ID NO: 2. In another most preferred embodiment, the amino acid sequence of the polypeptide differs from SEQ ID NO: 2 by S113N+P438L of amino acids 1 to 513 of SEQ ID NO: 2.

In another preferred embodiment, the amino acid sequence of the polypeptide differs from SEQ ID NO: 2 at positions corresponding to positions 227 and 438 of amino acids 1 to 513 of SEQ ID NO: 2. In a more preferred embodiment, the amino acid sequence of the polypeptide differs from SEQ ID NO: 2 at positions corresponding to positions 227 and 438 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ala (or Leu or Gly) and Leu at positions corresponding to positions 227 and 438, respectively, of amino acids 1 to 513 of SEQ ID NO: 2. In another most preferred embodiment, the amino acid sequence of the polypeptide differs from SEQ ID NO: 2 by P227A (or P227L or P227G)+P438L of amino acids 1 to 513 of SEQ ID NO: 2.

In another preferred embodiment, the amino acid sequence of the polypeptide differs from SEQ ID NO: 2 at positions corresponding to positions 49, 113, and 227 of amino acids 1 to 513 of SEQ ID NO: 2. In a more preferred embodiment, the amino acid sequence of the polypeptide differs from SEQ ID NO: 2 at positions corresponding to positions 49, 113, and 227 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser, Asn, and Ala (or Leu or Gly) at positions corresponding to positions 49, 113, and 227, respectively, of amino acids 1 to 513 of SEQ ID NO: 2. In another most preferred embodiment, the amino acid sequence of the polypeptide differs from SEQ ID NO: 2 by N49S+S113N+P227A (or P227L or P227G) of amino acids 1 to 513 of SEQ ID NO: 2.

In another preferred embodiment, the amino acid sequence of the polypeptide differs from SEQ ID NO: 2 at positions corresponding to positions 49, 227, and 438 of amino acids 1 to 513 of SEQ ID NO: 2. In a more preferred embodiment, the amino acid sequence of the polypeptide differs from SEQ ID NO: 2 at positions corresponding to positions 49, 227, and 438 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser, Ala (or Leu or Gly), and Leu at positions corresponding to positions 49, 227, and 438, respectively, of amino acids 1 to 513 of SEQ ID NO: 2. In another most preferred embodiment, the amino acid sequence of the polypeptide differs from SEQ ID NO: 2 by N49S+P227A (or P227L or P227G)+P438L of amino acids 1 to 513 of SEQ ID NO: 2.

In another preferred embodiment, the amino acid sequence of the polypeptide differs from SEQ ID NO: 2 at positions corresponding to positions 113, 227, and 438 of amino acids 1 to 513 of SEQ ID NO: 2. In a more preferred embodiment, the amino acid sequence of the polypeptide differs from SEQ ID NO: 2 at positions corresponding to positions 113, 227, and 438 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Ala (or Leu or Gly), and Leu at positions corresponding to positions 113, 227, and 438, respectively, of amino acids 1 to 513 of SEQ ID NO: 2. In another most preferred embodiment, the amino acid sequence of the polypeptide differs from SEQ ID NO: 2 by S113N+P227A (or P227L or P227G)+P438L of amino acids 1 to 513 of SEQ ID NO: 2.

In another preferred embodiment, the amino acid sequence of the polypeptide differs from SEQ ID NO: 2 at positions corresponding to positions 49, 113, and 438 of amino acids 1 to 513 of SEQ ID NO: 2. In a more preferred embodiment, the amino acid sequence of the polypeptide differs from SEQ ID NO: 2 at positions corresponding to positions 49, 113, and 438 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser, Asn, and Leu at positions corresponding to positions 49, 113, and 438, respectively, of amino acids 1 to 513 of SEQ ID NO: 2. In another most preferred embodiment, the amino acid sequence of the polypeptide differs from SEQ ID NO: 2 by N49S+S113N+P438L of amino acids 1 to 513 of SEQ ID NO: 2.

In another preferred embodiment, the amino acid sequence of the polypeptide differs from SEQ ID NO: 2 at positions corresponding to positions 49, 113, 227, and 438 of amino acids 1 to 513 of SEQ ID NO: 2. In a more preferred embodiment, the amino acid sequence of the polypeptide differs from SEQ ID NO: 2 at positions corresponding to positions 49, 113, 227, and 438 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ser, Asn, Ala (or Leu or Gly), and Leu at positions corresponding to positions 49, 113, 227, and 438, respectively, of amino acids 1 to 513 of SEQ ID NO: 2. In another most preferred embodiment, the amino acid sequence of the polypeptide differs from SEQ ID NO: 2 by N49S, S113N+P227A (or P227L or P227G)+P438L of amino acids 1 to 513 of SEQ ID NO: 2.

In another preferred embodiment, the amino acid sequence of the polypeptide differs from SEQ ID NO: 2 at positions corresponding to positions 157 and 411 of amino acids 1 to 513 of SEQ ID NO: 2. In a more preferred embodiment, the amino acid sequence of the polypeptide differs from SEQ ID NO: 2 at positions corresponding to positions 157 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg and Phe at positions corresponding to positions 157 and 411, respectively, of amino acids 1 to 513 of SEQ ID NO: 2. In another most preferred embodiment, the amino acid sequence of the polypeptide differs from SEQ ID NO: 2 by K157R+S411F of amino acids 1 to 513 of SEQ ID NO: 2.

In another preferred embodiment, the amino acid sequence of the polypeptide differs from SEQ ID NO: 2 at positions corresponding to positions 205 and 411 of amino acids 1 to 513 of SEQ ID NO: 2. In a more preferred embodiment, the amino acid sequence of the polypeptide differs from SEQ ID NO: 2 at positions corresponding to positions 205 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg and Phe at positions corresponding to positions 205 and 411, respectively, of amino acids 1 to 513 of SEQ ID NO: 2. In another most preferred embodiment, the amino acid sequence of the polypeptide differs from SEQ ID NO: 2 by G205R+S411F of amino acids 1 to 513 of SEQ ID NO: 2.

In another preferred embodiment, the amino acid sequence of the polypeptide differs from SEQ ID NO: 2 at positions corresponding to positions 255 and 411 of amino acids 1 to 513 of SEQ ID NO: 2. In a more preferred embodiment, the amino acid sequence of the polypeptide differs from SEQ ID NO: 2 at positions corresponding to positions 255 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro and Phe at positions corresponding to positions 255 and 411, respectively, of amino acids 1 to 513 of SEQ ID NO: 2. In another most preferred embodiment, the amino acid sequence of the polypeptide differs from SEQ ID NO: 2 by T255P+S411F of amino acids 1 to 513 of SEQ ID NO: 2.

In another preferred embodiment, the amino acid sequence of the polypeptide differs from SEQ ID NO: 2 at positions corresponding to positions 157, 255, and 411 of amino acids 1 to 513 of SEQ ID NO: 2. In a more preferred embodiment, the amino acid sequence of the polypeptide differs from SEQ ID NO: 2 at positions corresponding to positions 157, 255, and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg, Pro, and Phe at positions corresponding to positions 157, 255, and 411, respectively, of amino acids 1 to 513 of SEQ ID NO: 2. In another most preferred embodiment, the amino acid sequence of the polypeptide differs from SEQ ID NO: 2 by K157R+T255P+S411F of amino acids 1 to 513 of SEQ ID NO: 2.

In another preferred embodiment, the amino acid sequence of the polypeptide differs from SEQ ID NO: 2 at positions corresponding to positions 205, 255, and 411 of amino acids 1 to 513 of SEQ ID NO: 2. In a more preferred embodiment, the amino acid sequence of the polypeptide differs from SEQ ID NO: 2 at positions corresponding to positions 205, 255, and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg, Pro, and Phe at positions corresponding to positions 205, 255, and 411, respectively, of amino acids 1 to 513 of SEQ ID NO: 2. In another most preferred embodiment, the amino acid sequence of the polypeptide differs from SEQ ID NO: 2 by G205R+T255P+S411F of amino acids 1 to 513 of SEQ ID NO: 2.

In another preferred embodiment, the amino acid sequence of the polypeptide differs from SEQ ID NO: 2 at positions corresponding to positions 157, 205, and 411 of amino acids 1 to 513 of SEQ ID NO: 2. In a more preferred embodiment, the amino acid sequence of the polypeptide differs from SEQ ID NO: 2 at positions corresponding to positions 157, 205, and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg, Arg, and Phe at positions corresponding to positions 157, 205, and 411, respectively, of amino acids 1 to 513 of SEQ ID NO: 2. In another most preferred embodiment, the amino acid sequence of the polypeptide differs from SEQ ID NO: 2 by K157R+G205R+S411F of amino acids 1 to 513 of SEQ ID NO: 2.

In another preferred embodiment, the amino acid sequence of the polypeptide differs from SEQ ID NO: 2 at positions corresponding to positions 157, 205, 255, and 411 of amino acids 1 to 513 of SEQ ID NO: 2. In a more preferred embodiment, the amino acid sequence of the polypeptide differs from SEQ ID NO: 2 at positions corresponding to positions 157, 205, 255, and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Arg, Arg, Pro, and Phe at positions corresponding to positions 157, 205, 255, and 411, respectively, of amino acids 1 to 513 of SEQ ID NO: 2. In another most preferred embodiment, the amino acid sequence of the polypeptide differs from SEQ ID NO: 2 by K157R, G205R+T255P+S411F of amino acids 1 to 513 of SEQ ID NO: 2.

In another preferred embodiment, the amino acid sequence of the polypeptide differs from SEQ ID NO: 2 at positions corresponding to positions 196 and 411 of amino acids 1 to 513 of SEQ ID NO: 2. In a more preferred embodiment, the amino acid sequence of the polypeptide differs from SEQ ID NO: 2 at positions corresponding to positions 196 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Thr (or Pro or Phe) and Phe at positions corresponding to positions 196 and 411, respectively, of amino acids 1 to 513 of SEQ ID NO: 2. In another most preferred embodiment, the amino acid sequence of the polypeptide differs from SEQ ID NO: 2 by S196T (or S196P or S196F)+S411F of amino acids 1 to 513 of SEQ ID NO: 2.

In another preferred embodiment, the amino acid sequence of the polypeptide differs from SEQ ID NO: 2 at positions corresponding to positions 227 and 411 of amino acids 1 to 513 of SEQ ID NO: 2. In a more preferred embodiment, the amino acid sequence of the polypeptide differs from SEQ ID NO: 2 at positions corresponding to positions 227 and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ala (or Leu or Gly) and Phe at positions corresponding to positions 227 and 411, respectively, of amino acids 1 to 513 of SEQ ID NO: 2. In another most preferred embodiment, the amino acid sequence of the polypeptide differs from SEQ ID NO: 2 by P227A (or P227L or P227G)+S411F of amino acids 1 to 513 of SEQ ID NO: 2.

In another preferred embodiment, the amino acid sequence of the polypeptide differs from SEQ ID NO: 2 at positions corresponding to positions 113, 227, and 411 of amino acids 1 to 513 of SEQ ID NO: 2. In a more preferred embodiment, the amino acid sequence of the polypeptide differs from SEQ ID NO: 2 at positions corresponding to positions 113, 227, and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Ala (or Leu or Gly), and Phe at positions corresponding to positions 113, 227, and 411, respectively, of amino acids 1 to 513 of SEQ ID NO: 2. In another most preferred embodiment, the amino acid sequence of the polypeptide differs from SEQ ID NO: 2 by S113N+P227A (or P227L or P227G)+S411F of amino acids 1 to 513 of SEQ ID NO: 2.

In another preferred embodiment, the amino acid sequence of the polypeptide differs from SEQ ID NO: 2 at positions corresponding to positions 196, 227, and 411 of amino acids 1 to 513 of SEQ ID NO: 2. In a more preferred embodiment, the amino acid sequence of the polypeptide differs from SEQ ID NO: 2 at positions corresponding to positions 196, 227, and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Thr (or Pro or Phe), Ala (or Leu or Gly), and Phe at positions corresponding to positions 196, 227, and 411, respectively, of amino acids 1 to 513 of SEQ ID NO: 2. In another most preferred embodiment, the amino acid sequence of the polypeptide differs from SEQ ID NO: 2 by S196T (or S196P or S196F)+P227A (or P227L or P227G)+S411F of amino acids 1 to 513 of SEQ ID NO: 2.

In another preferred embodiment, the amino acid sequence of the polypeptide differs from SEQ ID NO: 2 at positions corresponding to positions 113, 196, and 411 of amino acids 1 to 513 of SEQ ID NO: 2. In a more preferred embodiment, the amino acid sequence of the polypeptide differs from SEQ ID NO: 2 at positions corresponding to positions 113, 196, and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Thr (or Pro or Phe), and Phe at positions corresponding to positions 113, 196, and 411, respectively, of amino acids 1 to 513 of SEQ ID NO: 2. In another most preferred embodiment, the amino acid sequence of the polypeptide differs from SEQ ID NO: 2 by S113N+S196T (or S196P or S196F)+S411F of amino acids 1 to 513 of SEQ ID NO: 2.

In another preferred embodiment, the amino acid sequence of the polypeptide differs from SEQ ID NO: 2 at positions corresponding to positions 113, 196, 227, and 411 of amino acids 1 to 513 of SEQ ID NO: 2. In a more preferred embodiment, the amino acid sequence of the polypeptide differs from SEQ ID NO: 2 at positions corresponding to positions 113, 196, 227, and 411 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Thr (or Pro or Phe), Ala (or Leu or Gly), and Phe at positions corresponding to positions 113, 196, 227, and 411, respectively, of amino acids 1 to 513 of SEQ ID NO: 2. In another most preferred embodiment, the amino acid sequence of the polypeptide differs from SEQ ID NO: 2 by S113N+S196T (or S196P or S196F)+P227A (or P227L or P227G)+S411F of amino acids 1 to 513 of SEQ ID NO: 2.

In another preferred embodiment, the amino acid sequence of the polypeptide differs from SEQ ID NO: 2 at positions corresponding to positions 113 and 356 of amino acids 1 to 513 of SEQ ID NO: 2. In a more preferred embodiment, the amino acid sequence of the polypeptide differs from SEQ ID NO: 2 at positions corresponding to positions 113 and 356 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn and Ile at positions corresponding to positions 113 and 356, respectively, of amino acids 1 to 513 of SEQ ID NO: 2. In another most preferred embodiment, the amino acid sequence of the polypeptide differs from SEQ ID NO: 2 by S113N+T356I of amino acids 1 to 513 of SEQ ID NO: 2.

In another preferred embodiment, the amino acid sequence of the polypeptide differs from SEQ ID NO: 2 at positions corresponding to positions 196 and 356 of amino acids 1 to 513 of SEQ ID NO: 2. In a more preferred embodiment, the amino acid sequence of the polypeptide differs from SEQ ID NO: 2 at positions corresponding to positions 196 and 356 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Thr (or Pro or Phe) and Ile at positions corresponding to positions 196 and 356, respectively, of amino acids 1 to 513 of SEQ ID NO: 2. In another most preferred embodiment, the amino acid sequence of the polypeptide differs from SEQ ID NO: 2 by S196T (or S196P or S196F)+T356I of amino acids 1 to 513 of SEQ ID NO: 2.

In another preferred embodiment, the amino acid sequence of the polypeptide differs from SEQ ID NO: 2 at positions corresponding to positions 227 and 356 of amino acids 1 to 513 of SEQ ID NO: 2. In a more preferred embodiment, the amino acid sequence of the polypeptide differs from SEQ ID NO: 2 at positions corresponding to positions 227 and 356 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ala (or Leu or Gly) and Ile at positions corresponding to positions 227 and 356, respectively, of amino acids 1 to 513 of SEQ ID NO: 2. In another most preferred embodiment, the amino acid sequence of the polypeptide differs from SEQ ID NO: 2 by P227A (or P227L or P227G)+T356I of amino acids 1 to 513 of SEQ ID NO: 2.

In another preferred embodiment, the amino acid sequence of the polypeptide differs from SEQ ID NO: 2 at positions corresponding to positions 356 and 462 of amino acids 1 to 513 of SEQ ID NO: 2. In a more preferred embodiment, the amino acid sequence of the polypeptide differs from SEQ ID NO: 2 at positions corresponding to positions 356 and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ile and Ala at positions corresponding to positions 356 and 462, respectively, of amino acids 1 to 513 of SEQ ID NO: 2. In another most preferred embodiment, the amino acid sequence of the polypeptide differs from SEQ ID NO: 2 by T356I+T462A of amino acids 1 to 513 of SEQ ID NO: 2.

In another preferred embodiment, the amino acid sequence of the polypeptide differs from SEQ ID NO: 2 at positions corresponding to positions 113, 227, and 356 of amino acids 1 to 513 of SEQ ID NO: 2. In a more preferred embodiment, the amino acid sequence of the polypeptide differs from SEQ ID NO: 2 at positions corresponding to positions 113, 227, and 356 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Ala (or Leu or Gly), and Ile at positions corresponding to positions 113, 227, and 356, respectively, of amino acids 1 to 513 of SEQ ID NO: 2. In another most preferred embodiment, the amino acid sequence of the polypeptide differs from SEQ ID NO: 2 by S113N+P227A (or P227L or P227G)+T356I of amino acids 1 to 513 of SEQ ID NO: 2.

In another preferred embodiment, the amino acid sequence of the polypeptide differs from SEQ ID NO: 2 at positions corresponding to positions 196, 227, and 356 of amino acids 1 to 513 of SEQ ID NO: 2. In a more preferred embodiment, the amino acid sequence of the polypeptide differs from SEQ ID NO: 2 at positions corresponding to positions 196, 227, and 356 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Thr (or Pro or Phe), Ala (or Leu or Gly), and Ile at positions corresponding to positions 196, 227, and 356, respectively, of amino acids 1 to 513 of SEQ ID NO: 2. In another most preferred embodiment, the amino acid sequence of the polypeptide differs from SEQ ID NO: 2 by S196T (or S196P or S196F)+ P227A (or P227L or P227G)+T356I of amino acids 1 to 513 of SEQ ID NO: 2.

In another preferred embodiment, the amino acid sequence of the polypeptide differs from SEQ ID NO: 2 at positions corresponding to positions 196, 227, and 462 of amino acids 1 to 513 of SEQ ID NO: 2. In a more preferred embodiment, the amino acid sequence of the polypeptide differs from SEQ ID NO: 2 at positions corresponding to positions 196, 227, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Thr (or Pro or Phe), Ala (or Leu or Gly), and Ala at positions corresponding to positions 196, 227, and 462, respectively, of amino acids 1 to 513 of SEQ ID NO: 2. In another most preferred embodiment, the amino acid sequence of the polypeptide differs from SEQ ID NO: 2 by S196T (or S196P or S196F)+ P227A (or P227L or P227G)+T462A of amino acids 1 to 513 of SEQ ID NO: 2.

In another preferred embodiment, the amino acid sequence of the polypeptide differs from SEQ ID NO: 2 at positions corresponding to positions 196, 356, and 462 of amino acids 1 to 513 of SEQ ID NO: 2. In a more preferred embodiment, the amino acid sequence of the polypeptide differs from SEQ ID NO: 2 at positions corresponding to positions 196, 356, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Thr (or Pro or Phe), Ile, and Ala at positions corresponding to positions 196, 356, and 462, respectively, of amino acids 1 to 513 of SEQ ID NO: 2. In another most preferred embodiment, the amino acid sequence of the polypeptide differs from SEQ ID NO: 2 by S196T (or S196P or S196F)+T356I+T462A of amino acids 1 to 513 of SEQ ID NO: 2.

In another preferred embodiment, the amino acid sequence of the polypeptide differs from SEQ ID NO: 2 at positions corresponding to positions 113, 196, and 356 of amino acids 1 to 513 of SEQ ID NO: 2. In a more preferred embodiment, the amino acid sequence of the polypeptide differs from SEQ ID NO: 2 at positions corresponding to positions 113, 196, and 356 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Thr (or Pro or Phe), and Ile at positions corresponding to positions 113, 196, and 356, respectively, of amino acids 1 to 513 of SEQ ID NO: 2. In another most preferred embodiment, the amino acid sequence of the polypeptide differs from SEQ ID NO: 2 by S113N+S196T (or S196P or S196F)+T356I of amino acids 1 to 513 of SEQ ID NO: 2.

In another preferred embodiment, the amino acid sequence of the polypeptide differs from SEQ ID NO: 2 at positions corresponding to positions 227, 356, and 462 of amino acids 1 to 513 of SEQ ID NO: 2. In a more preferred embodiment, the amino acid sequence of the polypeptide differs from SEQ ID NO: 2 at positions corresponding to positions 227, 356, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ala (or Leu or Gly), Ile, and Ala at positions corresponding to positions 227, 356, and 462, respectively, of amino acids 1 to 513 of SEQ ID NO: 2. In another most preferred embodiment, the amino acid sequence of the polypeptide differs from SEQ ID NO: 2 by P227A (or P227L or P227G)+T356I+T462A of amino acids 1 to 513 of SEQ ID NO: 2.

In another preferred embodiment, the amino acid sequence of the polypeptide differs from SEQ ID NO: 2 at positions corresponding to positions 113, 196, 227, and 356 of amino acids 1 to 513 of SEQ ID NO: 2. In a more preferred embodiment, the amino acid sequence of the polypeptide differs from SEQ ID NO: 2 at positions corresponding to positions 113, 196, 227, and 356 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Thr (or Pro or Phe), Ala (or Leu or Gly), and Ile at positions corresponding to positions 113, 196, 227, and 356 respectively, of amino acids 1 to 513 of SEQ ID NO: 2. In another most preferred embodiment, the amino acid sequence of the polypeptide differs from SEQ ID NO: 2 by S113N+S196T (or S196P or S196F)+P227A (or P227L or P227G)+T356I of amino acids 1 to 513 of SEQ ID NO: 2.

In another preferred embodiment, the amino acid sequence of the polypeptide differs from SEQ ID NO: 2 at positions corresponding to positions 113, 227, 356, and 462 of amino acids 1 to 513 of SEQ ID NO: 2. In a more preferred embodiment, the amino acid sequence of the polypeptide differs from SEQ ID NO: 2 at positions corresponding to positions 113, 227, 356, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Ala (or Leu or Gly), Ile, and Ala at positions corresponding to positions 113, 227, 356, and 462, respectively, of amino acids 1 to 513 of SEQ ID NO: 2. In another most preferred embodiment, the amino acid sequence of the polypeptide differs from SEQ ID NO: 2 by S113N+P227A (or P227L or P227G)+T356I+T462A of amino acids 1 to 513 of SEQ ID NO: 2.

In another preferred embodiment, the amino acid sequence of the polypeptide differs from SEQ ID NO: 2 at positions corresponding to positions 113, 196, 356, and 462 of amino acids 1 to 513 of SEQ ID NO: 2. In a more preferred embodiment, the amino acid sequence of the polypeptide differs from SEQ ID NO: 2 at positions corresponding to positions 113, 196, 356, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Thr (or Pro or Phe), Ile, and Ala at positions corresponding to positions 113, 196, 356, and 462, respectively, of amino acids 1 to 513 of SEQ ID NO: 2. In another most preferred embodiment, the amino acid sequence of the polypeptide differs from SEQ ID NO: 2 by S113N+S196T (or S196P or S196F)+T356I+T462A of amino acids 1 to 513 of SEQ ID NO: 2.

In another preferred embodiment, the amino acid sequence of the polypeptide differs from SEQ ID NO: 2 at positions corresponding to positions 196, 227, 356, and 462 of amino acids 1 to 513 of SEQ ID NO: 2. In a more preferred embodiment, the amino acid sequence of the polypeptide differs from SEQ ID NO: 2 at positions corresponding to positions 196, 227, 356, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Thr (or Pro or Phe), Ala (or Leu or Gly), Ile, and Ala at positions corresponding to positions 196, 227, 356, and 462, respectively, of amino acids 1 to 513 of SEQ ID NO: 2. In another most preferred embodiment, the amino acid sequence of the polypeptide differs from SEQ ID NO: 2 by S196T (or S196P or S196F)+P227A (or P227L or P227G)+T356I+T462A of amino acids 1 to 513 of SEQ ID NO: 2.

In another preferred embodiment, the amino acid sequence of the polypeptide differs from SEQ ID NO: 2 at positions corresponding to positions 113, 196, 227, 356, and 462 of amino acids 1 to 513 of SEQ ID NO: 2. In a more preferred embodiment, the amino acid sequence of the polypeptide differs from SEQ ID NO: 2 at positions corresponding to positions 113, 196, 227, 356, and 462 of amino acids 1 to 513 of SEQ ID NO: 2 by Ala, Arg, Asn, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Thr (or Pro or Phe), Ala (or Leu or Gly), Ile, and Ala at positions corresponding to positions 113, 196, 227, 356, and 462, respectively, of amino acids 1 to 513 of SEQ ID NO: 2. In another most preferred embodiment, the amino acid sequence of the polypeptide differs from SEQ ID NO: 2 by S113N+S196T (or S196P or S196F)+P227A (or P227L or P227G)+T356I+T462A of amino acids 1 to 513 of SEQ ID NO: 2.

In another preferred embodiment, the amino acid sequence of the polypeptide differs from SEQ ID NO: 2 at positions corresponding to positions 21 and 246 of amino acids 1 to 513 of SEQ ID NO: 2. In a more preferred embodiment, the amino acid sequence of the polypeptide differs from SEQ ID NO: 2 at positions corresponding to positions 21 and 246 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro and Ile at positions corresponding to positions 21 and 246, respectively, of amino acids 1 to 513 of SEQ ID NO: 2. In another most preferred embodiment, the amino acid sequence of the polypeptide differs from SEQ ID NO: 2 by S21P+T246I of amino acids 1 to 513 of SEQ ID NO: 2.

In another preferred embodiment, the amino acid sequence of the polypeptide differs from SEQ ID NO: 2 at positions corresponding to positions 21 and 251 of amino acids 1 to 513 of SEQ ID NO: 2. In a more preferred embodiment, the amino acid sequence of the polypeptide differs from SEQ ID NO: 2 at positions corresponding to positions 21 and 251 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro and Lys at positions corresponding to positions 21 and 251, respectively, of amino acids 1 to 513 of SEQ ID NO: 2. In another most preferred embodiment, the amino acid sequence of the polypeptide differs from SEQ ID NO: 2 by S21P+R251K of amino acids 1 to 513 of SEQ ID NO: 2.

In another preferred embodiment, the amino acid sequence of the polypeptide differs from SEQ ID NO: 2 at positions corresponding to positions 21 and 411 of amino acids 1 to 513 of SEQ ID NO: 2. In a more preferred embodiment, the amino acid sequence of the polypeptide differs from SEQ ID NO: 2 at positions corresponding to positions 21 and 411 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro and Phe at positions corresponding to positions 21 and 411, respectively, of amino acids 1 to 513 of SEQ ID NO: 2. In another most preferred embodiment, the amino acid sequence of the polypeptide differs from SEQ ID NO: 2 by S21P+S411F of amino acids 1 to 513 of SEQ ID NO: 2.

In another preferred embodiment, the amino acid sequence of the polypeptide differs from SEQ ID NO: 2 at positions corresponding to positions 57 and 246 of amino acids 1 to 513 of SEQ ID NO: 2. In a more preferred embodiment, the amino acid sequence of the polypeptide differs from SEQ ID NO: 2 at positions corresponding to positions 57 and 246 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn and Ile at positions corresponding to positions 57 and 246, respectively, of amino acids 1 to 513 of SEQ ID NO: 2. In another most preferred embodiment, the amino acid sequence of the polypeptide differs from SEQ ID NO: 2 by S57N+T246I of amino acids 1 to 513 of SEQ ID NO: 2.

In another preferred embodiment, the amino acid sequence of the polypeptide differs from SEQ ID NO: 2 at positions corresponding to positions 57 and 251 of amino acids 1 to 513 of SEQ ID NO: 2. In a more preferred embodiment, the amino acid sequence of the polypeptide differs from SEQ ID NO: 2 at positions corresponding to positions 57 and 251 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn and Lys at positions corresponding to positions 57 and 251, respectively, of amino acids 1 to 513 of SEQ ID NO: 2. In another most preferred embodiment, the amino acid sequence of the polypeptide differs from SEQ ID NO: 2 by S57N+R251K of amino acids 1 to 513 of SEQ ID NO: 2.

In another preferred embodiment, the amino acid sequence of the polypeptide differs from SEQ ID NO: 2 at positions corresponding to positions 57 and 411 of amino acids 1 to 513 of SEQ ID NO: 2. In a more preferred embodiment, the amino acid sequence of the polypeptide differs from SEQ ID NO: 2 at positions corresponding to positions 57 and 251 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn and Phe at positions corresponding to positions 57 and 411, respectively, of amino acids 1 to 513 of SEQ ID NO: 2. In another most preferred embodiment, the amino acid sequence of the polypeptide differs from SEQ ID NO: 2 by S57N+S411F of amino acids 1 to 513 of SEQ ID NO: 2.

In another preferred embodiment, the amino acid sequence of the polypeptide differs from SEQ ID NO: 2 at positions corresponding to positions 246 and 251 of amino acids 1 to 513 of SEQ ID NO: 2. In a more preferred embodiment, the amino acid sequence of the polypeptide differs from SEQ ID NO: 2 at positions corresponding to positions 246 and 251 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ile and Lys at positions corresponding to positions 246 and 251, respectively, of amino acids 1 to 513 of SEQ ID NO: 2. In another most preferred embodiment, the amino acid sequence of the polypeptide differs from SEQ ID NO: 2 by T246I+R251K of amino acids 1 to 513 of SEQ ID NO: 2.

In another preferred embodiment, the amino acid sequence of the polypeptide differs from SEQ ID NO: 2 at positions corresponding to positions 246 and 411 of amino acids 1 to 513 of SEQ ID NO: 2. In a more preferred embodiment, the amino acid sequence of the polypeptide differs from SEQ ID NO: 2 at positions corresponding to positions 246 and 411 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ile and Phe at positions corresponding to positions 246 and 411, respectively, of amino acids 1 to 513 of SEQ ID NO: 2. In another most preferred embodiment, the amino acid sequence of the polypeptide differs from SEQ ID NO: 2 by T246I+S411F of amino acids 1 to 513 of SEQ ID NO: 2.

In another preferred embodiment, the amino acid sequence of the polypeptide differs from SEQ ID NO: 2 at positions corresponding to positions 251 and 411 of amino acids 1 to 513 of SEQ ID NO: 2. In a more preferred embodiment, the amino acid sequence of the polypeptide differs from SEQ ID NO: 2 at positions corresponding to positions 251 and 411 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Lys and Phe at positions corresponding to positions 251 and 411, respectively, of amino acids 1 to 513 of SEQ ID NO: 2. In another most preferred embodiment, the amino acid sequence of the polypeptide differs from SEQ ID NO: 2 by R251K+S411F of amino acids 1 to 513 of SEQ ID NO: 2.

In another preferred embodiment, the amino acid sequence of the polypeptide differs from SEQ ID NO: 2 at positions corresponding to positions 21, 57, and 246 of amino acids 1 to 513 of SEQ ID NO: 2. In a more preferred embodiment, the amino acid sequence of the polypeptide differs from SEQ ID NO: 2 at positions corresponding to positions 21, 57, and 246 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro, Asn, and Ile at positions corresponding to positions 21, 57, and 246, respectively, of amino acids 1 to 513 of SEQ ID NO: 2. In another most preferred embodiment, the amino acid sequence of the polypeptide differs from SEQ ID NO: 2 by S21P+S57N+T246I of amino acids 1 to 513 of SEQ ID NO: 2.

In another preferred embodiment, the amino acid sequence of the polypeptide differs from SEQ ID NO: 2 at positions corresponding to positions 21, 246, and 251 of amino acids 1 to 513 of SEQ ID NO: 2. In a more preferred embodiment, the amino acid sequence of the polypeptide differs from SEQ ID NO: 2 at positions corresponding to positions 21, 246, and 251 of amino acids 1 to 513 of SEQ ID NO: 2 by Ala, Arg, Pro, Asp, Cys, Gin, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro, Ile, and Lys at positions corresponding to positions 21, 246, and 251, respectively, of amino acids 1 to 513 of SEQ ID NO: 2. In another most preferred embodiment, the amino acid sequence of the polypeptide differs from SEQ ID NO: 2 by S21P+T246I+R251K of amino acids 1 to 513 of SEQ ID NO: 2.

In another preferred embodiment, the amino acid sequence of the polypeptide differs from SEQ ID NO: 2 at positions corresponding to positions 21, 246, and 411 of amino acids 1 to 513 of SEQ ID NO: 2. In a more preferred embodiment, the amino acid sequence of the polypeptide differs from SEQ ID NO: 2 at positions corresponding to positions 21, 246, and 411 of amino acids 1 to 513 of SEQ ID NO: 2 by Ala, Arg, Pro, Asp, Cys, Gin, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro, Ile, and Phe at positions corresponding to positions 21, 246, and 411, respectively, of amino acids 1 to 513 of SEQ ID NO: 2. In another most preferred embodiment, the amino acid sequence of the polypeptide differs from SEQ ID NO: 2 by S21P+T246I+S411F of amino acids 1 to 513 of SEQ ID NO: 2.

In another preferred embodiment, the amino acid sequence of the polypeptide differs from SEQ ID NO: 2 at positions corresponding to positions 57, 246, and 251 of amino acids 1 to 513 of SEQ ID NO: 2. In a more preferred embodiment, the amino acid sequence of the polypeptide differs from SEQ ID NO: 2 at positions corresponding to positions 57, 246, and 251 of amino acids 1 to 513 of SEQ ID NO: 2 by Ala, Arg, Pro, Asp, Cys, Gin, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Ile, and Lys at positions corresponding to positions 57, 246, and 251, respectively, of amino acids 1 to 513 of SEQ ID NO: 2. In another most preferred embodiment, the amino acid sequence of the polypeptide differs from SEQ ID NO: 2 by S57N+T246I+R251K of amino acids 1 to 513 of SEQ ID NO: 2.

In another preferred embodiment, the amino acid sequence of the polypeptide differs from SEQ ID NO: 2 at positions corresponding to positions 57, 246, and 411 of amino acids 1 to 513 of SEQ ID NO: 2. In a more preferred embodiment, the amino acid sequence of the polypeptide differs from SEQ ID NO: 2 at positions corresponding to positions 57, 246, and 411 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Ile, and Phe at positions corresponding to positions 57, 246, and 411, respectively, of amino acids 1 to 513 of SEQ ID NO: 2. In another most preferred embodiment, the amino acid sequence of the polypeptide differs from SEQ ID NO: 2 by S57N+T246I+S411F of amino acids 1 to 513 of SEQ ID NO: 2.

In another preferred embodiment, the amino acid sequence of the polypeptide differs from SEQ ID NO: 2 at positions corresponding to positions 57, 251, and 411 of amino acids 1 to 513 of SEQ ID NO: 2. In a more preferred embodiment, the amino acid sequence of the polypeptide differs from SEQ ID NO: 2 at positions corresponding to positions 57, 251, and 411 of amino acids 1 to 513 of SEQ ID NO: 2 by Ala, Arg, Pro, Asp, Cys, Gin, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Lys, and Phe at positions corresponding to positions 57, 251, and 411, respectively, of amino acids 1 to 513 of SEQ ID NO: 2. In another most preferred embodiment, the amino acid sequence of the polypeptide differs from SEQ ID NO: 2 by S57N+R251K+S411F of amino acids 1 to 513 of SEQ ID NO: 2.

In another preferred embodiment, the amino acid sequence of the polypeptide differs from SEQ ID NO: 2 at positions corresponding to positions 21, 57, and 251 of amino acids 1 to 513 of SEQ ID NO: 2. In a more preferred embodiment, the amino acid sequence of the polypeptide differs from SEQ ID NO: 2 at positions corresponding to positions 21, 57, and 251 of amino acids 1 to 513 of SEQ ID NO: 2 by Ala, Arg, Pro, Asp, Cys, Gin, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro, Asn, and Lys at positions corresponding to positions 21, 57, and 251, respectively, of amino acids 1 to 513 of SEQ ID NO: 2. In another most preferred embodiment, the amino acid sequence of the polypeptide differs from SEQ ID NO: 2 by S21P+S57N+R251K of amino acids 1 to 513 of SEQ ID NO: 2.

In another preferred embodiment, the amino acid sequence of the polypeptide differs from SEQ ID NO: 2 at positions corresponding to positions 246, 251, and 411 of amino acids 1 to 513 of SEQ ID NO: 2. In a more preferred embodiment, the amino acid sequence of the polypeptide differs from SEQ ID NO: 2 at positions corresponding to positions 246, 251, and 411 of amino acids 1 to 513 of SEQ ID NO: 2 by Ala, Arg, Pro, Asp, Cys, Gin, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Ile, Lys, and Phe at positions corresponding to positions 246, 251, and 411, respectively, of amino acids 1 to 513 of SEQ ID NO: 2. In another most preferred embodiment, the amino acid sequence of the polypeptide differs from SEQ ID NO: 2 by T246I+R251K+S411F of amino acids 1 to 513 of SEQ ID NO: 2.

In another preferred embodiment, the amino acid sequence of the polypeptide differs from SEQ ID NO: 2 at positions corresponding to positions 21, 57, 246, and 251 of amino acids 1 to 513 of SEQ ID NO: 2. In a more preferred embodiment, the amino acid sequence of the polypeptide differs from SEQ ID NO: 2 at positions corresponding to positions 21, 57, 246, and 251 of amino acids 1 to 513 of SEQ ID NO: 2 by Ala, Arg, Pro, Asp, Cys, Gin, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro, Asn, Ile, and Lys at positions corresponding to positions 21, 57, 246, and 251 respectively, of amino acids 1 to 513 of SEQ ID NO: 2. In another most preferred embodiment, the amino acid sequence of the polypeptide differs from SEQ ID NO: 2 by S21P+S57N+T246I+R251K of amino acids 1 to 513 of SEQ ID NO: 2.

In another preferred embodiment, the amino acid sequence of the polypeptide differs from SEQ ID NO: 2 at positions corresponding to positions 21, 246, 251, and 411 of amino acids 1 to 513 of SEQ ID NO: 2. In a more preferred embodiment, the amino acid sequence of the polypeptide differs from SEQ ID NO: 2 at positions corresponding to positions 21, 246, 251, and 411 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro, Ile, Lys, and Phe at positions corresponding to positions 21, 246, 251, and 411, respectively, of amino acids 1 to 513 of SEQ ID NO: 2. In another most preferred embodiment, the amino acid sequence of the polypeptide differs from SEQ ID NO: 2 by S21P+T246I+R251K+S411F of amino acids 1 to 513 of SEQ ID NO: 2.

In another preferred embodiment, the amino acid sequence of the polypeptide differs from SEQ ID NO: 2 at positions corresponding to positions 21, 57, 251, and 411 of amino acids 1 to 513 of SEQ ID NO: 2. In a more preferred embodiment, the amino acid sequence of the polypeptide differs from SEQ ID NO: 2 at positions corresponding to positions 21, 57, 251, and 411 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro, Asn, Lys, and Phe at positions corresponding to positions 21, 57, 251, and 411, respectively, of amino acids 1 to 513 of SEQ ID NO: 2. In another most preferred embodiment, the amino acid sequence of the polypeptide differs from SEQ ID NO: 2 by S21P+S57N+R251K+S411F of amino acids 1 to 513 of SEQ ID NO: 2.

In another preferred embodiment, the amino acid sequence of the polypeptide differs from SEQ ID NO: 2 at positions corresponding to positions 57, 246, 251, and 411 of amino acids 1 to 513 of SEQ ID NO: 2. In a more preferred embodiment, the amino acid sequence of the polypeptide differs from SEQ ID NO: 2 at positions corresponding to positions 57, 246, 251, and 411 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Asn, Ile, Lys, and Phe at positions corresponding to positions 57, 246, 251, and 411, respectively, of amino acids 1 to 513 of SEQ ID NO: 2. In another most preferred embodiment, the amino acid sequence of the polypeptide differs from SEQ ID NO: 2 by S57N+T246I+R251K+S411F of amino acids 1 to 513 of SEQ ID NO: 2.

In another preferred embodiment, the amino acid sequence of the polypeptide differs from SEQ ID NO: 2 at positions corresponding to positions 21, 57, 246, and 411 of amino acids 1 to 513 of SEQ ID NO: 2. In a more preferred embodiment, the amino acid sequence of the polypeptide differs from SEQ ID NO: 2 at positions corresponding to positions 21, 57, 246, and 411 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro, Asn, Ile, and Phe at positions corresponding to positions 21, 57, 246, and 411, respectively, of amino acids 1 to 513 of SEQ ID NO: 2. In another most preferred embodiment, the amino acid sequence of the polypeptide differs from SEQ ID NO: 2 by S21P+S57N+T246I+S411F of amino acids 1 to 513 of SEQ ID NO: 2.

In another preferred embodiment, the amino acid sequence of the polypeptide differs from SEQ ID NO: 2 at positions corresponding to positions 21, 57, 246, 251, and 411 of amino acids 1 to 513 of SEQ ID NO: 2. In a more preferred embodiment, the amino acid sequence of the polypeptide differs from SEQ ID NO: 2 at positions corresponding to positions 21, 57, 246, 251, and 411 of amino acids 1 to 513 of SEQ ID NO: 2 by Ala, Arg, Pro, Asp, Cys, Gln, Glu, Gly, His, Ile, Leu, Lys, Met, Phe, Pro, Ser, Thr, Trp, Tyr, or Val. In an even more preferred embodiment, the amino acid sequence of the polypeptide differs from SEQ ID NO: 2 by Pro, Asn, Ile, Lys, and Phe at positions corresponding to positions 21, 57, 246, 251, and 411, respectively, of amino acids 1 to 513 of SEQ ID NO: 2. In another most preferred embodiment, the amino acid sequence of the polypeptide differs from SEQ ID NO: 2 by S21P+S57N+T246I+R251K+S411F of amino acids 1 to 513 of SEQ ID NO: 2.

In another preferred embodiment, the amino acid sequence of the polypeptide differs from SEQ ID NO: 2 by at least one difference selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least two differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least three differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least four differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least five differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least six differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least seven differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least eight differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least nine differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least ten differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, AND T462A.

In another preferred embodiment, the amino acid sequence of the polypeptide differs from SEQ ID NO: 2 by at least eleven differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least twelve differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least thirteen differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least fourteen differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least fifteen differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least sixteen differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least seventeen differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least eighteen differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least nineteen differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by at least twenty differences selected from the group consisting of S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of S8P, G22D, T41I, N49S, S57N, S113N, S196T, T226A, P227A, T255P, T356I, Y371C, S411F, and T462A.

In another preferred embodiment, the amino acid sequence of the polypeptide differs from SEQ ID NO: 2 by the differences consisting of at least S21P, G94S, G94A, G94R, G94Q, K157R, E193K, S196P, S196F, G205R, H206Y, P227L, P227G, T246I, Y247C, D259N, R251K, N301S, E337V, T350S, N373H, T383A, P438L, T455A, G467S, and C486W of amino acids 1 to 513 of SEQ ID NO: 2, and optionally further differ by one or more differences selected from the group consisting of SBP, G22D, T41I, N49S, S57N, S113N, S196T, T226A, P227A, T255P, T356I, Y371C, S411F, and T462A.

In a preferred embodiment, the polypeptide consists of 341 to 350, 351 to 360, 361 to 370, 371 to 380, 381 to 390, 391 to 400, 401 to 410, 411 to 420, 421 to 430, 431 to 440, 441 to 450, 451 to 460, 461 to 470, 471 to 480, 481 to 490, 491 to 500, or 501 to 513 amino acids.

The isolated polypeptides have one or more improved properties compared to the polypeptide of SEQ ID NO: 2, wherein the improved properties are selected from the group consisting of thermal activity, thermostability, pH activity, pH stability, substrate specificity, product specificity, and chemical stability, as described herein.

The present invention also relates to isolated nucleotide sequences encoding such polypeptides, nucleic acid constructs, expression vectors, and host cells comprising the nucleotide sequences, and methods of producing the polypeptides having glycoside hydrolase activity, according to the same disclosure herein for glycoside hydrolase variants.

Cellobiohydrolase I and Nucleotide Sequences Thereof

The present invention also relates to an isolated polypeptide having cellobiohydrolase I activity and to an isolated nucleotide sequence encoding the polypeptide.

In a preferred embodiment, the isolated polypeptide having cellobiohydrolase I activity comprises the amino acid sequence of SEQ ID NO: 2 or an allelic variant thereof; or a fragment thereof that has cellobiohydrolase I activity. In a more preferred embodiment, the polypeptide of the present invention comprises the amino acid sequence of SEQ ID NO: 2. In another preferred embodiment, the polypeptide of the present invention comprises amino acids 1 to 513 of SEQ ID NO: 2, or an allelic variant thereof; or a fragment thereof that has cellobiohydrolase I activity. In another preferred embodiment, the polypeptide of the present invention comprises amino acids 1 to 513 of SEQ ID NO: 2. In another preferred embodiment, the polypeptide of the present invention consists of the amino acid sequence of SEQ ID NO: 2 or an allelic variant thereof; or a fragment thereof that has cellobiohydrolase I activity. In another preferred embodiment, the polypeptide of the present invention consists of the amino acid sequence of SEQ ID NO: 2. In another preferred embodiment, the polypeptide consists of amino acids 1 to 513 of SEQ ID NO: 2 or an allelic variant thereof; or a fragment thereof that has cellobiohydrolase I activity. In another preferred embodiment, the polypeptide consists of amino acids 1 to 513 of SEQ ID NO: 2.

In another preferred embodiment, the nucleotide sequence is set forth in SEQ ID NO: 1. In another more preferred embodiment, the nucleic acid sequence is the sequence contained in plasmid pAJO52 that is contained in *Escherichia coli* NRRL B-30683. In another preferred embodiment, the nucleotide sequence is the mature polypeptide coding region of SEQ ID NO: 1. In another more preferred embodiment, the nucleotide sequence is the mature polypeptide coding region contained in plasmid pAJO52 that is contained in *Escherichia coli* NRRL B-30683. The present invention also encompasses nucleotide sequences encoding a polypeptide having the amino acid sequence of SEQ ID NO: 2, or the mature polypeptide thereof, which differ from SEQ ID NO: 1 by virtue of the degeneracy of the genetic code. The present invention also relates to subsequences of SEQ ID NO: 1 which encode fragments of SEQ ID NO: 2 that have cellobiohydrolase I activity.

A fragment of SEQ ID NO: 2 is a polypeptide having one or more amino acids deleted from the amino and/or carboxyl terminus of this amino acid sequence. Preferably, a fragment contains at least 450 amino acid residues, more preferably at least 470 amino acid residues, and most preferably at least 490 amino acid residues.

A subsequence of SEQ ID NO:1 is a nucleic acid sequence encompassed by SEQ ID NO:1 except that one or more nucleotides from the 5' and/or 3' end have been deleted. Preferably, a subsequence contains at least 1350 nucleotides, more preferably at least 1410 nucleotides, and most preferably at least 1470 nucleotides.

The present invention also relates to mutant nucleic acid sequences comprising at least one mutation in the mature polypeptide coding sequence of SEQ ID NO:1, in which the mutant nucleic acid sequence encodes a polypeptide which consists of amino acids 1 to 513 of SEQ ID NO: 2.

The present invention also relates to nucleic acid constructs, expression vectors, and host cells comprising the nucleotide sequence encoding the polypeptide having cellobiohydrolase activity comprising amino acids 1 to 513 of SEQ ID NO: 2. Nucleic acid constructs, expression vectors, and host cells may be constructed as described herein.

The present invention further relates to methods for producing the polypeptide having cellobiohydrolase activity, comprising: (a) cultivating a strain, which in its wild-type form is capable of producing the polypeptide, to produce the polypeptide; and (b) recovering the polypeptide, according to the methods described herein. Preferably, the strain is of the genus *Trichoderma*, and more preferably *Trichoderma reesei*.

The present invention also relates to methods for producing a polypeptide of the present invention comprising (a) cultivating a host cell, comprising a nucleotide sequence encoding the polypeptide, under conditions conducive for production of the polypeptide; and (b) recovering the polypeptide, according to the methods described herein.

Degradation of Biomass to Monosaccharides, Disaccharides, and Polysaccharides

The glycoside hydrolase variants, polypeptides having glycoside hydrolase activity, and host cells of the present invention may be used in the production of monosaccharides, disaccharides, and polysaccharides as chemical or fermentation feedstocks from biomass for the production of ethanol, plastics, or other products or intermediates. The glycoside variants and polypeptides having glycoside hydrolase activity may be in the form of a crude fermentation broth with or without the cells removed or in the form of a semi-purified or purified enzyme preparation. Alternatively, a host cell of the present invention may be used as a source of the variant or polypeptide having glycoside hydrolase activity in a fermentation process with the biomass.

Biomass can include, but is not limited to, wood resources, municipal solid waste, wastepaper, and crop residues (see, for example, Wiselogel et al., 1995, in *Handbook on Bioethanol* (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, *Recent Progress in Bioconversion of Lignocellulosics*, in *Advances in Biochemical Engineering/Biotechnology*, T. Scheper, managing editor, Volume 65, pp. 23-40, Springer-Verlag, New York).

The predominant polysaccharide in the primary cell wall of biomass is cellulose, the second most abundant is hemicellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Three major classes of glycohydrolases are used to breakdown cellulosic biomass:

(1) The "endo-1,4-beta-glucanases" or 1,4-beta-D-glucan-4-glucanohydrolases (EC 3.2.1.4), which act randomly on soluble and insoluble 1,4-beta-glucan substrates.

(2) The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and cellobiohydrolases (1,4-beta-D-glucan cellobiohydrolases, EC 3.2.1.91), which liberate D-cellobiose from 1,4-beta-glucans.

(3) The "beta-D-glucosidases" or beta-D-glucoside glucohydrolases (EC 3.2.1.21), which act to release D-glucose units from cellobiose and soluble cellodextrins, as well as an array of glycosides.

These three classes of enzymes work together synergistically resulting in efficient decrystallization and hydrolysis of native cellulose from biomass to yield reducing sugars.

The glycoside hydrolase variants and polypeptides having glycoside hydrolase activity of the present invention may be used in conjunction with the above-noted enzymes to further degrade the cellulose component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24).

Ethanol can be produced by enzymatic degradation of biomass and conversion of the released saccharides to ethanol. This kind of ethanol is often referred to as bioethanol or biofuel. It can be used as a fuel additive or extender in blends of from less than 1% and up to 100% (a fuel substitute).

Detergent Compositions

The variants and polypeptides having glycoside hydrolase activity of the present invention may be added to and thus become a component of a detergent composition.

The detergent composition of the present invention may be, for example, formulated as a hand or machine laundry detergent composition including a laundry additive composition suitable for pre-treatment of stained fabrics and a rinse added fabric softener composition, or formulated as a detergent composition for use in general household hard surface cleaning operations, or formulated for hand or machine dishwashing operations.

In a specific aspect, the present invention provides a detergent additive comprising the variants and polypeptides having glycoside hydrolase activity of the present invention. The detergent additive as well as the detergent composition may comprise one or more other enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the enzymatic components should be compatible with the selected detergent, (i.e., pH-optimum, compatibility with other enzymatic and non-enzymatic ingredients, etc.), and the enzymatic components should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™ Primase™, Duralase™, Esperase™, and Kannase™ (Novozymes A/S), Maxatase™, Maxacal™ Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipases include Lipolase™ and Lipolase Ultra™ (Novozymes A/S).

Amylases: Suitable amylases (α and/or β) include those of bacterial or fungal origin. Chemically modified or protein engineered mutants are included. Amylases include, for example, a-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The enzymatic component(s) may be included in a detergent composition by adding separate additives containing one or more enzymes, or by adding a combined additive comprising all of these enzymes. A detergent additive of the present invention, i.e., a separate additive ora combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the present invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system that may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzymatic component(s) of the detergent composition of the present invention may be stabilized using conventional stabilizing agents, e.g., a polyol such as propylene glycol or glycerol, a sugar or sugar alcohol, lactic acid, boric acid, ora boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzymatic component, in particular the variants and polypeptides having glycoside hydrolase activity of the present invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The variants and polypeptides having glycoside hydrolase activity of the present invention may additionally be incorporated in the detergent formulations disclosed in WO 97/07202 which is hereby incorporated as reference.

Plants

The present invention also relates to a transgenic plant, plant part, or plant cell which has been transformed with a nucleotide sequence encoding a variant or polypeptides having glycoside hydrolase activity of the present invention so as to express and produce the variant or polypeptide in recoverable quantities. The variant or polypeptide may be recovered from the plant or plant part. Alternatively, the plant or plant part containing the variant or polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a variant or polypeptide of the present invention may be constructed in accordance with methods known in the art. In short, the plant or plant cell is constructed by incorporating one or more expression constructs encoding a variant or polypeptide of the present invention into the plant host genome and propagating the resulting modified plant or plant cell into a transgenic plant or plant cell.

Conveniently, the expression construct is a nucleic acid construct which comprises a nucleic acid sequence encoding a variant or polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant or polypeptide is desired to be expressed. For example, the expression of the gene encoding a variant or polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For example, the promoter enhancer element may be an intron which is placed between the promoter and the nucleotide sequence encoding a polypeptide of the present invention. Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, Agrobacterium tumefaciens-mediated gene transfer is the method of choice for generating transgenic dicots (for a review, see Hooykas and Schilperoort, 1992, Plant Molecular Biology 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a variant or polypeptide of the present invention comprising (a) cultivating a transgenic plant or a plant cell comprising a nucleic acid sequence encoding a variant or polypeptide having glycoside hydrolase activity of the present invention under conditions conducive for production of the variant; and (b) recovering the variant or polypeptide.

Other Uses

The glycoside hydrolase variants or polypeptides having glycoside hydrolase activity of the present invention may also be used in the treatment of textiles as biopolishing agents and for reducing fuzz, pilling, texture modification, and stonewashing (N. K. Lange, in P. Suominen, T. Reinikainen (Eds.), Trichoderma reesei Cellulases and Other Hydrolases, Foundation for Biotechnical and Industrial Fermentation research, Helsinki, 1993, pp. 263-272). In addition, the described variants or polypeptides having glycoside hydrolase activity may also be used in wood processing for biopulping or debarking, paper manufacturing for fiber modification, bleaching, and reduction of refining energy costs, whitewater treatment, important to wastewater recycling, lignocellulosic fiber recycling such as deinking and secondary fiber processing, and wood residue utilization (S. D, Mansfield and A. R. Esteghlalian in S. D, Mansfield and J. N. Saddler (Eds.), Applications of Enzymes to Lignocellulosics, ACS Symposium Series 855, Washington, D.C., 2003, pp. 2-29).

The present invention is further described by the following examples which should not be construed as limiting the scope of the invention.

EXAMPLES

Strains

Trichoderma reesei RutC30 (ATCC 56765; Montenecourt and Eveleigh, 1979, Adv. Chem. Ser. 181: 289-301) was derived from Trichoderma reesei Qm6A (ATCC 13631; Mandels and Reese, 1957, J. Bacteriol. 73: 269-278).

Aspergillus oryzae Ja1250 strain (WO 99/61651) was used for expression of the thermostable beta-glucosidase.

Saccharomyces cerevisiae YNG 344 (MATα, ura3-52, leu-2Δ2, pep4Δ1, his4-539, cir$^0$) was used to generate libraries of mutagenized glycoside hydrolase (Cel7A).

Bacterial strains used to generate plasmids were Epicurian coli XL-10 Gold ultracompetent cells, (Stratagene, Inc., La Jolla, Calif.).

Media and Solutions

Yeast selection medium was composed per liter of 6.7 g of yeast nitrogen base, 0.8 g of complete supplement mixture (CSM-URA, Qbiogene, Inc., Carlsbad, Calif.; lacking uracil and containing 40 mg/ml of adenine), 5 g of casamino acid, and 20 g of Noble agar. The medium also contained 50 mM succinate pH 5.0, 2% glucose, and 25 mg of chloramphenicol per ml.

Yeast screening medium was composed per liter of 6.7 g of yeast nitrogen base, 0.8 g of CSM-URA, 5 g of casamino acid, and 20 g of Noble agar. The medium also contained 50 mM succinate pH 5.0, 2% galactose, 0.1% glucose, and 25 mg of chloramphenicol per ml.

YPD medium was composed per liter of 10 g of yeast extract, 20 g of bacto peptone, and 40 ml of 50% glucose.

Cellulase-inducing media was composed per liter of 20 g of Arbocel B800-natural cellulose fibers (J. Rettenmaier USA LP, Schoolcraft, Michigan), 10 g of corn steep solids (Sigma Chemical Co., St. Louis, Mo.), 1.45 g of $(NH_4)_2SO_4$, 2.08 g of $KH_2PO_4$, 0.28 g of $CaCl_2$, 0.42 g of $MgSO_4.7H_2O$, 0.42 ml of Trichoderma reesei trace metals solution, and 2 drops of pluronic acid; pH to 6.0 with 10 N NaoH.

Trichoderma reesei trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid.

COVE selection plates were composed per liter of 342.3 g of sucrose, 20 ml of COVE salt solution, 10 mM acetamide, 15 mM $CsCl_2$, and 25 g of Noble agar.

COVE2 plus uridine plates were composed per liter of 30 g of sucrose, 20 ml COVE salt solution, 10 mM acetamide, 10 mM uridine, and 25 g of Noble agar.

COVE salt solution was composed per liter of 26 g of KCl, 26 g of $MgSO_4.7H_2O$, 76 g of $KH_2PO_4$, and 50 ml of COVE trace metals.

COVE trace metals solution was composed per liter of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

PDA medium was composed per liter of 39 g potato dextrose agar.

1×SSC was composed per liter of 8.765 g sodium chloride and 4.41 g sodium citrate.

PEG Buffer was composed per liter of 500 g of PEG 4000 (BDH, Poole, England), 10 mM $CaCl_2$, and 10 mM Tris-HCl pH 7.5 (filter sterilized).

STC was composed per liter of 1 M sorbitol, 10 mM $CaCl_2$, and 10 mM Tris-HCl pH 7.5, and was filter sterilized.

Trichoderma reesei Inoculum Medium was composed per liter of 20 g of glucose, 10 g of corn steep solids (Sigma Chemical Co., St. Louis, Mo.), 1.45 g of $(NH_4)_2SO_4$, 2.08 g of $KH_2PO_4$, 0.28 g of $CaCl_2$, 0.42 g of $MgSO_4.7H_2O$, 0.42 ml of Trichoderma reesei trace metals solution, and 2 drops of pluronic acid; final pH 5.0.

Trichoderma reesei Fermentation Medium was composed per liter of 4 g of glucose, 10 g of corn steep solids, 30 g of Arbocel B800-natural cellulose fibers (J. Rettenmaier USA LP, Schoolcraft, Michigan), 3.8 g of $(NH_4)_2SO_4$, 2.8 g of $KH_2PO_4$, 2.08 g of $CaCl_2$, 1.63 g of $MgSO_4.7H_2O$, 0.75 ml of Trichoderma reesei trace metals solution, and 1.8 ml of pluronic acid.

Trichoderma reesei Feed Medium was composed per liter of 600 g of glucose, 20 g of Cellulose B800, 35.5 g of $H_3PO_4$, and 5 ml of pluronic acid.

Aspergillus oryzae Inoculum Medium was composed per liter of 50 g of glucose, 2 g of $MgSO_4.7H_2O$, 10 g of $KH_2PO_4$, 2 g of $K_2SO_4$, 2.08 g of $CaCl_2.2H_2O$, 2 g of citric acid, 10 g of yeast extract, 0.5 g of AMG trace metals, and 2 g of urea, final pH 6.0.

AMG trace metals is comprised per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

Aspergillus oryzae Fermentation Medium was composed per liter of 2 g $MgSO_4.7H_2O$, 2 g of $KH_2PO_4$, 3 g of $K_2SO_4$, 9 g of $(NH4)_2HPO_4$, 1 g of citric acid.$H_2O$, 10 g of yeast extract, 0.5 ml of AMG trace metals, 25 g of sucrose, and 0.55 mL of pluronic.

Aspergillus oryzae Feed Medium was composed per liter of 1 g of citric acid.$H_2O$, 320 g SatinSweet 65, and 5 g of pluronic.

MDU2BP medium is composed per liter of 45 g of maltose, 1 g of $MgSO_4.7H_2O$, 1 g of NaCl, 2 g of $K_2SO_4$, 12 g of $KH_2PO_4$, 7 g of yeast extract, 2 g of urea, 0.5 ml of AMG trace metals solution.

Example 1

Fermentation and Mycelial Tissue

Trichoderma reesei RutC30 was grown under cellulase inducing standard conditions as described in the art (Mandels and Weber, 1969, Adv. Chem. Ser. 95: 391-413). Mycelial samples were harvested by filtration through Whatman paper and quick-frozen in liquid nitrogen. The samples were stored at −80° C. until they were disrupted for RNA extraction.

Example 2

Expressed Sequence Tags (EST) cDNA Library Construction

Total cellular RNA was extracted from the mycelial samples described in Example 1 according to the method of Timberlake and Barnard (1981, Cell 26: 29-37), and the RNA samples were analyzed by Northern hybridization after blotting from 1% formaldehyde-agarose gels (Davis et al., 1986, Basic Methods in Molecular Biology, Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 µg of poly(A)+mRNA according to the method of Gubler and Hoffman (1983, Gene 25: 263-269), except a NotI-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

BamH I/EcoR I adaptors were ligated to the blunt ends of the cDNA. After digestion with NotI, the cDNA was size selected (ca. 0.7-4.5 kb) by 0.7% agarose gel electrophoresis using TAE buffer (4.84 g of Tris Base, 1.14 ml of glacial acetic acid, and 2 ml of 0.5 M EDTA pH 8.0 per liter), and ligated with pYES2 (Invitrogen Corporation, Carlsbad, Calif.) which had been cleaved with Not I plus BamH/and dephosphorylated with calf-intestine alkaline phosphatase (Boehringer Mannheim Corporation, Indianapolis, Ind.). The ligation mixture was used to transform competent E. coli TOP10 cells (Invitrogen Corporation, Carlsbad, Calif.). Transformants were selected on 2YT agar plates (Miller, 1992, A Short Course in Bacterial Genetics. A Laboratory Manual and Handbook for Escherichia coli and Related Bacteria, Cold Spring Harbor Press, Cold Spring Harbor, N.Y.) supplemented with ampicillin at a final concentration of 50 µg per ml.

Example 3

Template Preparation and Nucleotide Sequencing of cDNA Clones

From the cDNA library described in Example 2, approximately 7000 transformant colonies were picked directly from the transformation plates into 96-well microtiter dishes which contained 100 µl of 2YT broth supplemented with 50 µg of ampicillin per ml. The plates were incubated overnight at 37° C. with shaking at 200 rpm. After incubation, 100 µl of sterile 50% glycerol was added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 µg of ampicillin per ml in each well. The primary microtiter plates were stored frozen at −80° C. The secondary deep-dish plates were incubated at 37° C. overnight with vigorous agitation (300 rpm) on a rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover.

DNA was isolated from each well using a 96-well Miniprep Kit protocol of Advanced Genetic Technologies Corporation (Gaithersburg, Md.) as modified by Utterback et al. (1995, Genome Sci. Technol. 1: 1-8). Single-pass DNA sequencing (EST) was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, Journal of Virology Methods 38: 47-60) and a T7 sequencing primer:

```
                                                   (SEQ ID NO: 3)
       5'-TAATACGACTCACTATAGGG-3'
```

Example 4

Analysis of DNA Sequence Data of cDNA Clones

Nucleotide sequence data were scrutinized for quality and vector sequences and ambiguous base calls at the ends of the DNA sequences were trimmed, and all sequences were compared to each other with assistance of PHRED/PHRAP software (University of Washington, Seattle, Wash.). The resulting contigs and singletons were translated in six frames and searched against publicly available protein databases using GeneMatcher™ software (Paracel, Inc., Pasadena, Calif.) with a modified Smith-Waterman algorithm using the BLOSUM 62 matrix.

Example 5

Identification of cDNA Clones Encoding a Family 7 Cellobiohydrolase I (Cel7A)

Putative cDNA clones encoding a Family 7 cellobiohydrolase (Cel7A) were identified by comparing the deduced amino acid sequence of the assembled ESTs to protein sequences deposited in publicly available databases such as Swissprot, Genpept, and PIR. One clone, *Trichoderma reesei* EST Tr0221, was selected for nucleotide sequence analysis which revealed an 1821 by pYES2 insert which contained a 1452 by open reading-frame as shown in SEQ ID NO: 1 and a deduced amino acid sequence as shown in SEQ ID NO: 2. The plasmid containing *Trichoderma reesei* Cel7A cellobiohydrolase I was designated pTr0221.

Example 6

Construction of *Saccharomyces cerevisiae* Vectors for the Generation of Primary and Shuffled *Trichoderma reesei* Cel7A Cellobiohydrolase I Libraries Two vectors were utilized in the generation of primary and shuffled libraries, pJC106 (WO9510602) and pAJ052 (FIG. 1). Plasmid pJC106 is a derivative of pYES2 (Invitrogen Inc., Carlsbad, Calif.) but differs in that pJC106 has a full-length 2 micron replicon, which replaces the partial 2 micron in pYES2, and contains the *Coprinus cinereus* peroxidase (CIP) (Cherry et al., 1999, *Nat. Biotechnol.* 4: 379-384) coding sequence, which is regulated by the GAL1 promoter.

For pAJ052, a 1452 by DNA fragment spanning from the ATG start codon to the TAA stop codon of the *Trichoderma reesei* Cel 7A coding sequence was PCR amplified from pTr0221 (Example 5) using primers aGal 776.1 (sense) and aGal_776.1A (antisense) shown below:

Primers aGal_776.1 and aGal_776.1 A were designed to contain a homologous GAL1 promoter (Giniger and Ptashne, 1988, *Proc. Natl. Acad. Sci., USA* 85: 382-386) and the CYC1 terminator sequence (Osbourne and Guarente, 1988, *Genes Dev.* 2: 766-772) (underlined, respectively) of pJC106 for in vivo homologous recombination of the PCR product and pJC106. Primers aGal_776.1 and aGal_776.1 A were also designed to contain BamH I and Xho I restriction sites, respectively. Primer aGal_776.1 was further designed to contain the yeast Kozak sequence (ACC, −3 to −1 bp; Kozak, 1984, *Nature* 308: 241-246) immediately upstream of the *Trichoderma reesei* cellobiohydrolase I (Cel7A) gene ATG. The amplification reaction (50 µl) was composed of 1×PCR buffer (Applied Biosystems Inc., Foster City, Calif.), 0.2 mM dNTPs, 3.2 pM primer aGal_776.1, 3.2 pM primer aGal_776.1 A, approximately 100 ng of pTr0221, and 2.5 units of Taq DNA Polymerase (Roche Applied Science, Manheim, Germany). The reactions were incubated in an Eppendorf Mastercycler 5333 (Eppendorf EG, Hamburg, Germany) programmed for 1 cycle at 94° C. for 3 minutes followed by 30 cycles each at 94° C. for 30 seconds, 55° C. for 30 seconds, and 72° C. for 90 seconds followed by 1 cycle at 72° C. for 5 minutes. The PCR product was then purified using a QIAquick PCR Kit (QIAGEN Inc., Valencia, Calif.), according to the manufacturer's instructions, and was then introduced into *Saccharomyces cerevisiae* by in vivo recombination. To accomplish the in vivo recombination, approximately 100 ng of pJC016, digested with BamH I and Xho I, and approximately 500 ng of the purified PCR fragment, were co-transformed into *Saccharomyces cerevisiae* YNG 344 following the YEASTMAKER yeast transformation protocol (Clontech Laboratories Inc., Palo Alto, Calif.). The transformation was plated onto yeast selection medium for colony growth at 30° C. for 4 days.

A single colony was selected and plasmid DNA was isolated according to the protocol described by Kaiser and Auer, 1993, *Bio Techniques* 14: 552, which was subsequently transformed into *E. coli* strain XL-10 (Stratagene Inc., La Jolla, Calif.) according to the manufacturer's instructions. Plasmid derived from the transformed *E. coli* strain was sequenced to verify the fidelity of the PCR and recombination event.

Example 7

Generation of Primary Libraries of Mutagenized Cel7A Cellobiohydrolase I in *Saccharomyces cerevisiae*

Figure 2:
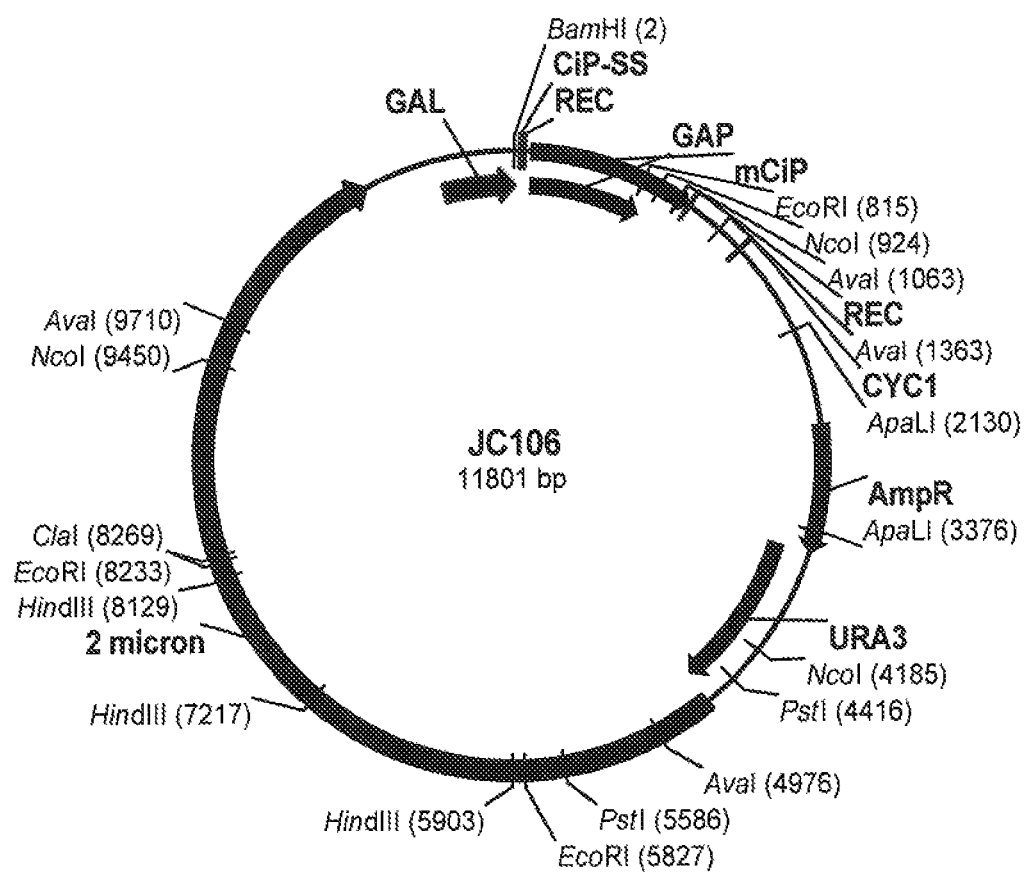
FIG. 2 shows a restriction map of pJC106.

In an effort to identify regions of the *Trichoderma reesei* Cel7A cellobiohydrolase I that are critical for protein thermostability and improved high-temperature activity, the entire wild-type *Trichoderma reesei* Cel7A cellobiohydrolase I gene was mutagenized using error-prone PCR with homologous sequences to the yeast expression vector pJC106 (FIG. 2), which can undergo in vivo recombination between homologous domains of distinct fragments, gener-

```
Primer aGal_776.1:
                                                                   (SEQ ID NO: 4)
5'-TATACCTCTATACTTTAACGTCAAGGAGAAAAAACTATAGGATCCACCATGTATCGGAAGT
TGGCCG-3'

Primer aGal_776.1A:
                                                                   (SEQ ID NO: 5)
5'-CATAACTAATTACATGATGCGGCCCTCTAGATGCACATGACTCGAGTTACAGGCACTGAG
AGTAG-3'
``` ating circular, replicating plasmids from a combination of linearized vector and PCR products.

PCR products for gap repair were generated using one of the following template/primer combinations:

1) Primer aGal_776.1 and primer aGal_776.1a, shown below, were used in the error-prone PCR amplification of the Cel7A cellobiohydrolase I gene from pTR0221 to generate mutagenized sequences.

2) Primer yes2term and primer CiPperdwn, shown below, were used in the error-prone PCR amplification of the Cel7A cellobiohydrolase I gene from pAJ052 to generate mutagenized sequences.

3) Primer cJC106.1a and primer CiPperdwn, shown below, were also used in the error-prone PCR amplification of the Cel7A cellobiohydrolase I gene from pAJ052 to generate mutagenized sequences.

The fragments were cloned into pJC106 for expression of the Cel7A cellobiohydrolase I variants in yeast.

```
Primer aGal_776.1:
                                                        (SEQ ID NO: 6)
5'-TATACCTCTATACTTTAACGTCAAGGAGAAAAAACTATAGGATCCACCATGTATCGGAAGT
TGGCCG-3'

Primer aGal_776.1a:
                                                        (SEQ ID NO: 7)
5'-CATAACTAATTACATGATGCGGCCCTCTAGATGCACATGACTCGAGTTACAGGCACTGAG
AGTAG-3'

Primer yes2term:
                                                        (SEQ ID NO: 8)
5'-GGCGTGAATGTAAGCGTGAC-3'

Primer CiPpcrdwn:
                                                        (SEQ ID NO: 9)
5'-CTGGGGTAATTAATCAGCGAAGCGATGA-3'

Primer cJC106.1a:
                                                       (SEQ ID NO: 10)
5'-GCGTACACGCGTCTGTACA-3'
```

The error-prone PCR amplifications (50 μl) were composed of 1×PCR buffer with MgCl$_2$, 0.2 mM dATP, 0.2 mM dGTP, 0.1 mM dCTP and 0.1 mM dTTP, 50 pmol of sense and antisense primer, 0.05 mM to 0.6 mM MnCl$_2$, and 10-50 ng of plasmid DNA (in some cases pTR0221, in other cases pAJ052). The reactions were incubated using a MJ Research thermocycler (MJ Research, Inc. Boston, Mass.) programmed for one cycle at 95° C. for 3 minutes after which 2.5 units of Amplitaq (Perkin Elmer, Foster City, Calif.) were added followed by 30 cycles each at 95° C. for 60 seconds, 55° C. for 60 seconds, and 72° C. for 90 seconds. The reactions were then incubated at 72° C. for a 5 minute extension. An aliquot of each PCR product was run on a 0.7% agarose gel using TAE buffer, as previously described, generating expected bands of approximately 1680 to 2030 bp. PCR reactions were purified using a MiniElute PCR Purification Kit (QIAGEN, Valencia, Calif.) eluted into 50 μl of EB buffer (QIAGEN, Valencia, Calif.).

Plasmid pJC106 was gapped by digestion with BamH I and Xho I, and then gel purified using a Qiaquick Minielute column (QIAGEN, Inc., Valencia, Calif.). The digestion was verified by fractionating an aliquot of the digestion on a 0.8% agarose gel using TAE buffer and staining with ethidium bromide where expected fragments of 10771 by (gapped) and 1030 by (from the *Coprinus cinereus* peroxidase gene) were obtained.

The PCR reactions were mixed at approximately a 3 to 1 ratio with the gapped pJC106 vector for cotransformation into *Saccharomyces cerevisiae* YNG344 competent cells.

The co-transformed fragments, amplified using primers aGal_776.1 and aGal_776.1a, contained at least 67 by of 5' and 66 by of 3' homologous DNA, amplified using yes2term and CiPperdwn contained at least 293 by of 5' and 41 by of 3' homologous DNA, and amplified using cJC106.1a and CiPperdwn contained at least 293 by of 5' and 190 by of 3' homologous DNA at the ends to facilitate gap repair of the expressed plasmid. Competent cells of *Saccharomyces cerevisiae* YNG 344 were prepared prior to each transformation following the YEASTMAKER Yeast Transformation Protocol with the following modifications: (1) The volume of yeast culture used to inoculate the overnight incubation (16-20 hours) was between 100-1,000 μl; (2) recovery of cells upon transformation was performed in YPD medium for 45 minutes at 30° C.; and (3) the transformation mixture was aliquoted for plating onto yeast selection medium plates and frozen at −80° C. in a controlled rate freezer (Nalge Nunc International, Rochester, N.Y.).

Example 8

Construction of pAILo1 and pAILo2 *Aspergillus oryzae* Expression Vectors

As a backbone vector for cloning several of the Cel7A cellobiohydrolase variants, two *Aspergillus oryzae* expression vectors were constructed. Vector pAlLo1 was constructed by modifying pBANe6 (U.S. Pat. No. 6,461,837), which comprises the *Aspergillus oryzae* alpha-amylase promoter (TAKA promoter), *Aspergillus niger* amyloglucosidase terminator sequence (AMG terminator), and *Aspergillus nidulans* acetamidase gene (amdS). Modification of pBANe6 was performed by first eliminating three Nco I restriction sites at positions 2051, 2722, and 3397 by from the amdS selection marker by site-directed mutagenesis. All changes were designed to be "silent" leaving the actual protein sequence of the amds gene product unchanged. Removal of these three sites was performed simultaneously with a GeneEditor Site-Directed Mutagenesis Kit (Promega, Madison, Wis.) according to the manufacturer's instructions using the following primers (underlined nucleotide represents the changed base):

```
Primer AMDS3NcoMut (2050):
                                                       (SEQ ID NO: 11)
5'-GTGCCCCATGATACGCCTCCGG-3'
```

-continued

```
Primer AMDS2NcoMut (2721):
                                     (SEQ ID NO: 12)
5'-GAGTCGTATTTCCAAGGCTCCTGACC-3'

Primer AMDS1NcoMut (3396):
                                     (SEQ ID NO: 13)
5'-GGAGGCCATGAAGTGGACCAACGG-3'
```

A plasmid comprising all three expected sequence changes was then submitted to site-directed mutagenesis, using a QuickChange Mutagenesis Kit (Stratagene, La Jolla, Calif.), to eliminate the Nco I restriction site at the end of the AMG terminator at position 1643. The following primers (underlined nucleotide represents the changed base) were used for mutagenesis:

Sense Primer to mutagenize the *Aspergillus niger* AMG terminator sequence:

```
                                     (SEQ ID NO: 14)
5'-CACCGTGAAAGCCATGCTCTTTCCTTCGTGTAGAAGACCAGACAG-3'
```

Antisense Primer to mutagenize the *Aspergillus niger* AMG terminator sequence:

```
                                     (SEQ ID NO: 15)
5'-CTGGTCTTCTACACGAAGGAAAGAGCATGGCTTTCACGGTGTCTG-3'
```

Figure 3:
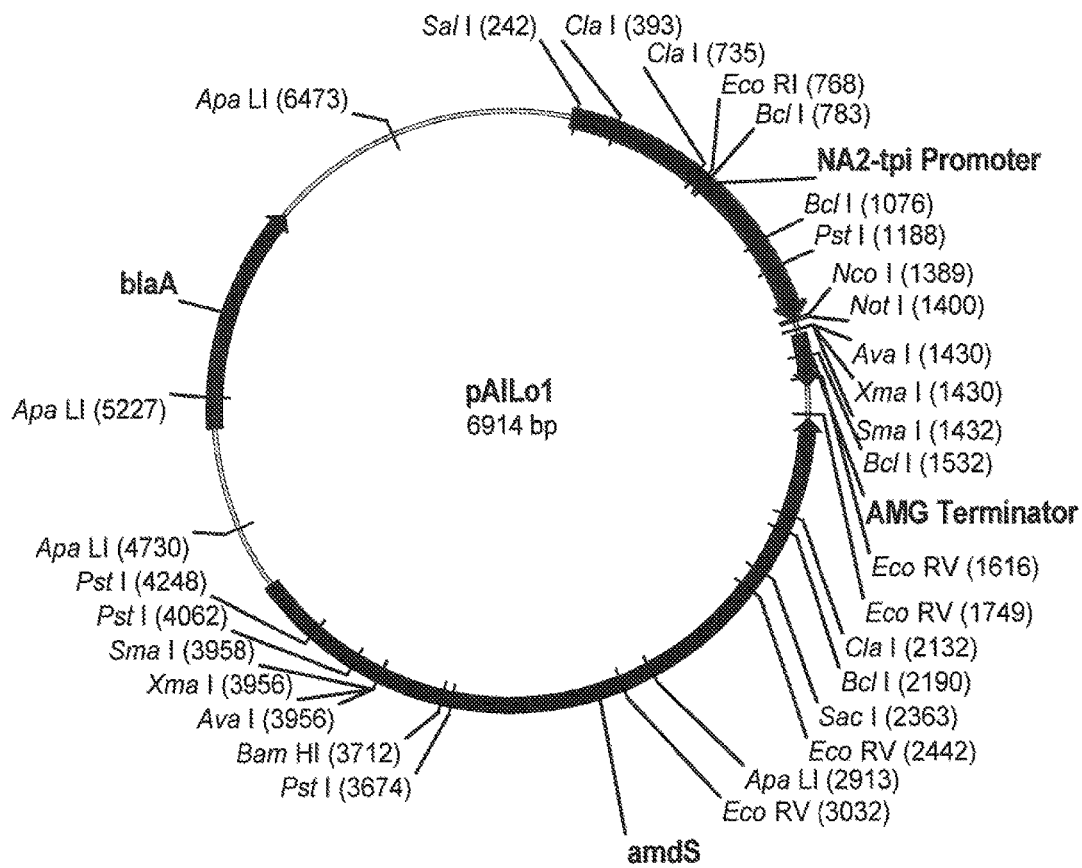
FIG. 3 shows a restriction map of pAILo1.

The last step in the modification of pBANe6 was the addition of a new Nco I restriction site at the beginning of the polylinker using a QuickChange Mutagenesis Kit and the following primers (underlined nucleotides represent the changed bases) to yield pAlLo1 (FIG. 3).

Sense Primer to mutagenize the *Aspergillus oryzae* TAKA promoter:

```
                                     (SEQ ID NO: 16)
5'-CTATATACACAACTGGATTTACCATGGGCCCGCGGCCGCAGATC-3'
```

Antisense Primer to mutagenize the *A. oryzae* TAKA promoter:

```
                                     (SEQ ID NO: 17)
5'-GATCTGCGGCCGCGGGCCCATGGTAAATCCAGTTGTGTATATAG-3'
```

Figure 4:
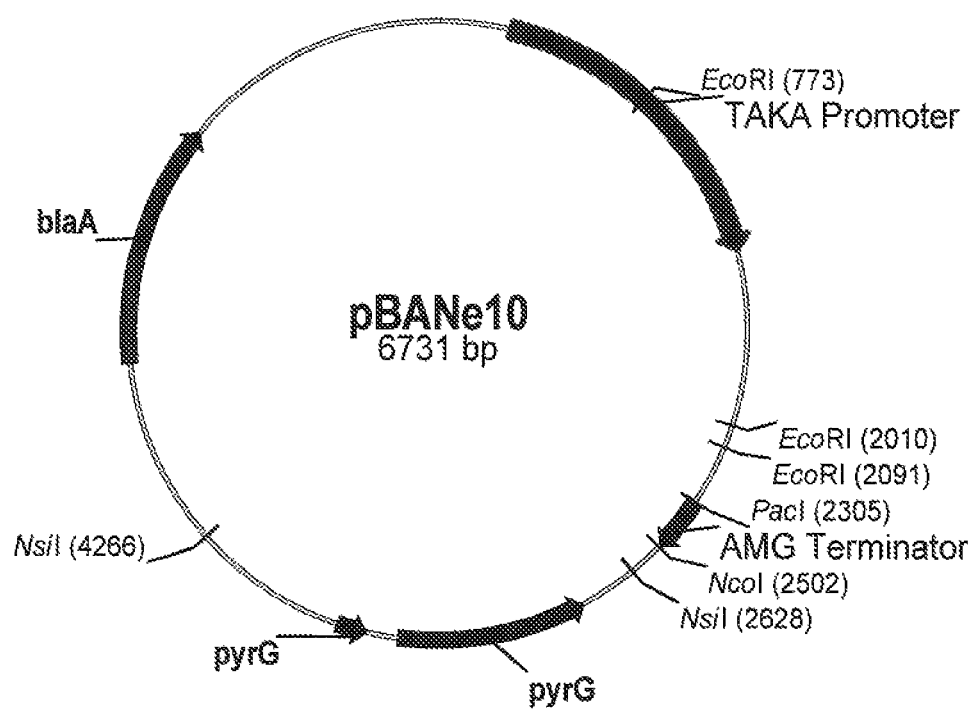
FIG. 4 shows a restriction map of pBANe10.

The amdS gene of pAlLo1 was swapped with the *Aspergillus nidulans* pyrG gene. Plasmid pBANe10 (FIG. 4) was used as a source for the pyrG gene as a selection marker. Analysis of the sequence of pBANe10 showed that the pyrG marker was contained within an Nsi I restriction fragment and does not contain either Nco I or Pac I restriction sites. Since the amdS was also flanked by Nsi I restriction sites, the strategy to switch the selection marker was a simple swap of Nsi I restriction fragments.

Figure 5:
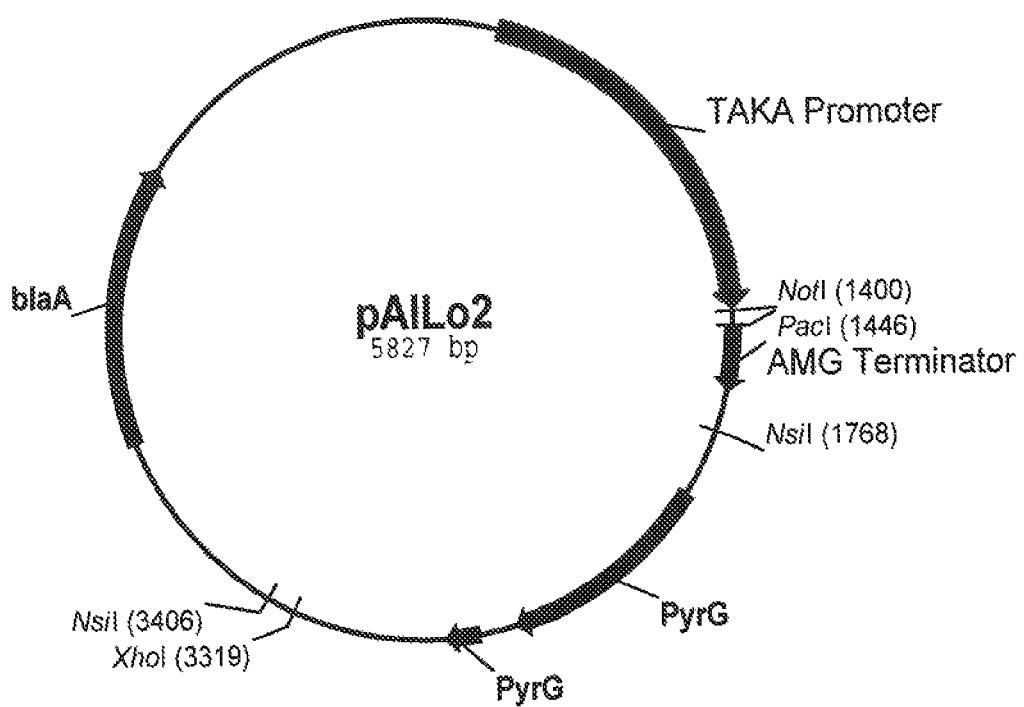
FIG. 5 shows a restriction map of pAILo2.

Plasmid DNA from pAlLo1 and pBANe10 were digested with the restriction enzyme Nsi I and the products purified by 0.7% agarose gel electrophoresis using TAE buffer. The Nsi I fragment from pBANe10 containing the pyrG gene was ligated to the backbone of pAlLo1 to replace the original Nsi I DNA fragment containing the amdS gene. Recombinant clones were analyzed by restriction enzyme digestion to determine insert orientation. A clone with the pyrG gene transcribed in the counterclockwise direction was selected. The new plasmid was designated pAlLo2 (FIG. 5).

Example 9

Rational Design of Improved Cel7A Cellobiohydrolase I Variant G205R and Generation of G205R Primary Libraries in *Saccharomyces cerevisiae*

The *Trichoderma reesei* Cel7A cellobiohydrolase I protein sequence (SEQ ID NO: 2) was compared to other proteins of the same enzyme family. Sequences included a Cel7A cellobiohydrolase I from *Chaetomium thermophilum* (WO 03/000941), *Humicola insolens* (WO 95/02675), and *Neurospora crassa* (SWISSPROT: P38676a close phylogenetic relative of *Chaetomium thermophilum*). Multiple alignments of the Cel7A cellobiohydrolase I protein sequences from *Chaetomium thermophilum, Humicola insolens, Trichoderma reesei*, and *Neurospora crassa* were made, using ClustalX software version 1.81, (National Center for Biotechnology Information, NIH Bethesda, Md.) (Thompson et al, 1994, Nucleic Acids Res 22: 4673-4680; Thompson et al, 1997, *Nucleic Acids Res* 25: 4876-4882), using the Gonnet matrix with default gap penalty parameters. Regions that appeared poorly aligned were iteratively realigned, sometimes using an alternative matrix (Blosum) and/or variable gap parameters. Homology models for publicly available Cel7A cellobiohydrolase I sequences were generated using the automated SwissModel service SwissModel service (Biozentrum, Basel, Switzerland). The homology model for the Cel7A cellobiohydrolase I from *Humicola insolens* was generated by using the Insight II programs (Accelrys, San Diego Calif.). The program DeepView (Guex and Peitsch, 1997, *Electrophoresis* 18: 2714-2723) was used to introduce virtual mutations and for all other structure manipulations and energy minimization. The reference structure used for the Cel7A cellobiohydrolase I from *Trichoderma reesei* was PDB: 7CEL (Divne et al, 1994, *Science* 265: 524-528; Stahlberg et al, 1996, 264:337-349). Based on the comparisons, potential mutations for *Trichoderma reesei* cellobiohydrolase I were prioritized based upon the likelihood that they would create a new stabilizing interaction (ion pair and/or H-bond) and also the probability of occurrence in the sequences and structures of Cel7A cellobiohydrolase I of the thermophilic fungi *Chaetomium thermophilum* and *Humicola insolens*, and their absence in the mesophilic fungus *Neurospora crassa*.

One of the amino acid substitutions suggested was a change from glycine at position 205 to arginine. The G205R variant was rationally designed to introduce ion-pairing with E190 and E239. To generate the G205R substitution, the *Trichoderma reesei* Cel7A cellobiohydrolase I gene was subcloned into the *Aspergillus oryzae* vector pAlLo02 digested with Nco I and Pac I to form a perfect junction with the ATG of the gene and the *Aspergillus oryzae* alpha-amylase promoter and the *Aspergillus niger* amyloglucosidase terminator sequence. Subcloning of the Cel7A cellobiohydrolase I gene into pAlLo2 was accomplished by designing two primers, shown below, that allowed cloning into the Nco I and Pac I sites. Primer cTR0221.7: 5'-GCAACATGTATCGGAAGTTGGC-3' (SEQ ID NO: 18) incorporated a BspLU II site, which was compatible to the Nco I site in pAlLo2, to the 5'-end of the Cel7A cellobiohydrolase I gene, and primer cTR0221.7a: 5'-AATTAATTT-TACAGGCACTGAG-3' (SEQ ID NO: 19) incorporated a BspLU II site at the-3'end.

Figure 6:
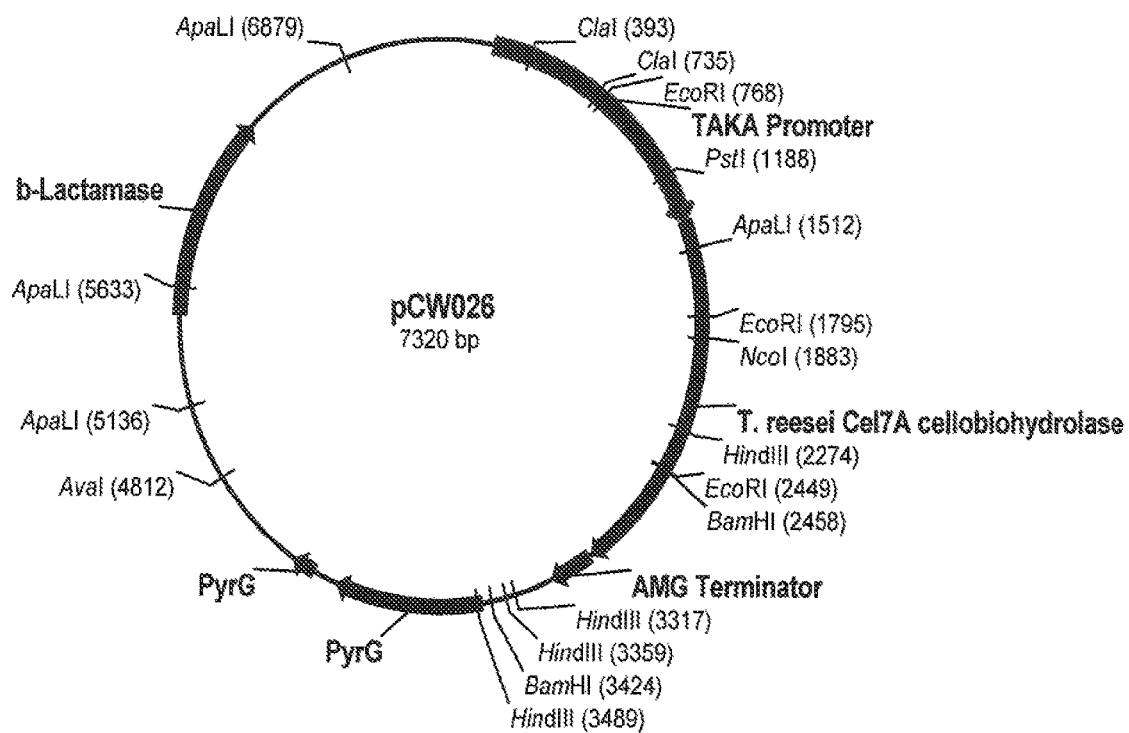
FIG. 6 shows a restriction map of pCW026.

Amplification of the Cel7A cellobiohydrolase I gene was accomplished using 1×Tgo Polymerase Reaction buffer (Boehringer Mannheim Co, Indianapolis, Ind.), 25 ng of pTR0221, 0.2 mM each of dATP, dGTP, dCTP, and dTTP, 50 pmole of each primer (cTR0221.7 and cTR0221.7a), and 1 unit of Tgo polymerase (Boehringer Mannheim Co, Indianapolis, Ind.). The reactions were incubated using a MJ Research Thermocycler programmed for one cycle at 95° C. for 5 minutes, followed by 35 cycles each at 94° C. for 60 seconds, 55° C. for 45 seconds, and 72° C. for 2 minutes. The reactions were then incubated at 72° C. for a 5 minute extension. An aliquot of each PCR product was run on a 0.7% agarose gel using TAE buffer generating expected bands of approximately 1545 bp. The 1545 by PCR product was subcloned using a TOPO Blunt PCR4 Cloning Kit (Invitrogen, Carlsbad, Calif.). The resulting plasmid was digested with BspLU II and Pac I and fractionated on a 0.7% agarose gel using TAE buffer generating an expected 1.5 kb coding sequence, which was excised and gel purified using an Amicon Ultra-free DA column (Millipore, Billerica, Mass.). The resulting fragment was subsequently ligated into pAlLo2, which was digested similarly, to generate the expression vector designated pCW026 (FIG. 6) containing the *Trichoderma reesei* Cel7A cellobiohydrolase I gene.

Working from the starting plasmid pCW026, the G205R variant was obtained by mutating a guanosine to cytidine at base 664 of the coding sequence of Cel7A cellobiohydrolase I, using a Quick Change Site Directed Mutagenesis Kit (Stratagene, La Jolla, Calif.) with pCW026 as the template. Primers used to incorporate this mutation were primer G205R.1 and primer G205R.1a shown below:

```
G205R.1:
                                    (SEQ ID NO: 20)
5'-GAACACGGGCATTGGACGACACGGAAGCTGCTG-3'

G205R.1a:
                                    (SEQ ID NO: 21)
5'-CAGCAGCTTCCGTGTCGTCCAATGCCCGTGTTC-3'
```

Figure 7:
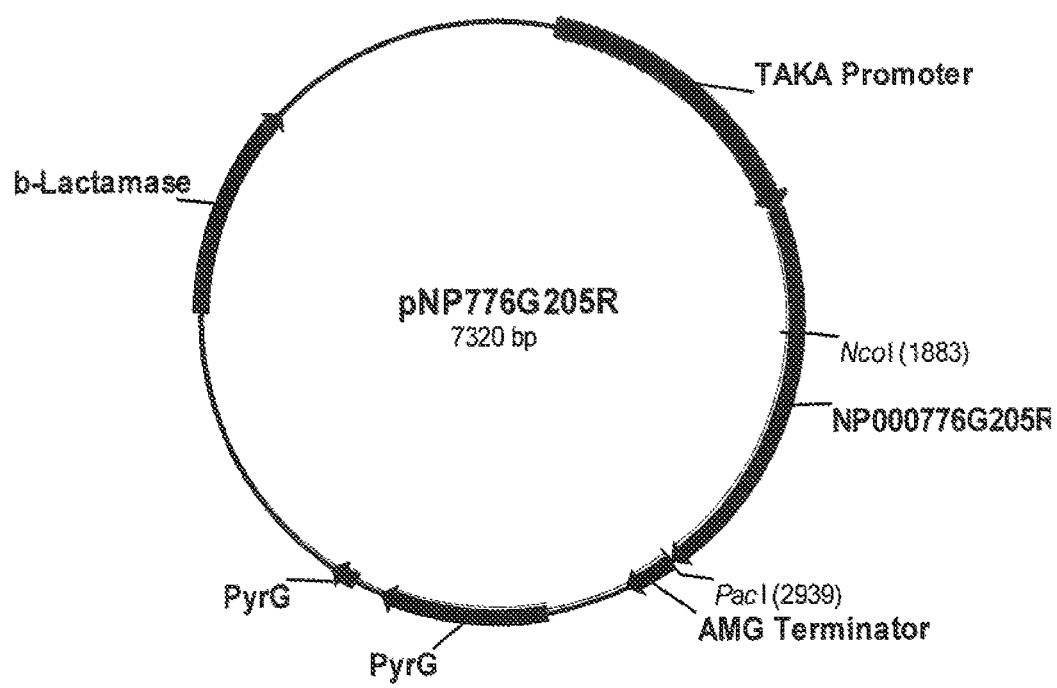
FIG. 7 shows a restriction map of pNP776G205R.

The resulting expression vector was designated pNP776G205R (FIG. 7).

Example 10

Screening of Cel7A Cellobiohydrolase I Libraries

Primary Cel7A cellobiohydrolase I libraries were spread on agar yeast selection medium in Genetix QTrays (22×22 cm Petri dishes, Genetics Ltd., Hampshire, United Kingdom) and incubated for 5 days at 30° C. Using a Genetix QPix (Genetix Ltd., Hampshire, United Kingdom), colonies were picked into 96-well plates containing yeast selection medium. Plates were incubated for 5-8 days at 30° C. Using an ORCA robot (Beckman Coulter, Fullerton, Calif.), the growth plates were transported to a Biomek Fx (Beckman Coulter, Fullerton, Calif.) and broth samples were removed from the growth plate and aliquoted into two 96-well polycarbonate v-bottom plates. The cellobiohydrolase I substrate 4-methylumbelliferyl-beta-D-lactoside (MUL, Marker Gene Tech. Inc., Eugene, Oreg.) was added to each V-bottom 96-well plate to a final concentration of 0.2, 0.1, or 0.05 mg of 4-methylumbelliferyl-beta-D-lactoside per ml, 0.1 M succinate pH 5.0, and 0.01% Tween-20. Assay plates were transferred to a temperature-controlled incubator, where one plate was incubated at a 50° C. for 45 minutes, and another was incubated at a pre-determined temperature, between 62° C. and 65° C. for 45 minutes. After this incubation, the plates were cooled to 4° C. for 1 minute, and then transferred to the Biomek Fx where assays were quenched by addition of Tris-CI, pH 9.5 to a final concentration of 0.75 M. Quenched reaction samples were diluted in water, and fluorescence of 4-methyl-umbelliferyl liberated by Cel7A cellobiohydrolase I hydrolysis of 4-methyl-umbelliferyl-beta-D-lactoside was measured using a BMG FLUOStar Galaxy fluorometer (Offenburg, Germany) (excitation 360 nm, emission 460 nm). The ratio of the fluorescence from the plate treated at high temperature ("high temperature activity") was compared to fluorescence from the same samples incubated at 50° C. ("low temperature activity"), using Microsoft Excel (Microsoft Corporation, Redmond, Wash.) to determine the relative thermal activity ratio for each variant. Based on the thermal activity ratios, screening of libraries constructed in Example 7 and Example 9 generated the variants listed in Table 1. Table 1 shows the degree of improvement for novel Cel7A cellobiohydrolase I variants as measured by assessing the thermal activity ratio of activity at 64° C. relative to activity at 50° C. For mutants obtained in the primary screen, improvements range from 2.60-fold higher to 10.20-fold improvement relative to the wild type enzyme. For mutants obtained from shuffling, the improvement observed was 12.40-fold to 19.20-fold better thermal activity than the wild type enzyme.

TABLE 1

Cel7A variants with improved thermal stability and thermal activity. "Fold Improvement" indicates relative improvement in thermal activity ratio, measured at 64° C./50° C.

| Cel7A Variant | Amino Acid Substitutions* | IFold Improvement |
|---|---|---|
| Wild type | none | 1 |
| G205R | G205R | 2.60 |
| 776-M1 | T226A | 6.20 |
| 776-M3 | P227A, C486W | 7.80 |
| 776-M4 | S113N, S196T, T462A | 6.00 |
| 776-M21 | N301S, E337V | 4.00 |
| 776-M22 | S196P, T350S | 1.60 |
| 776-M23 | G22D, G467S | 1.40 |
| 776-M26 | S21P, S57N | 3.80 |
| 776-M27 | S411F | 7.60 |
| 776-M30 | T41I | 2.60 |
| 776-M32 | K157R, G205R, T255P | 5.20 |
| 776-M35 | G205R, S411F | 8.40 |
| 776-M40 | G205R, P227A | 10.20 |
| 776-M41 | G205R, H206Y | 3.40 |
| 776-M42 | S8P, G205R | 4.60 |
| 776-M52 | G94S, G205R | 4.00 |
| 776-M53 | S196P, G205R | 4.80 |
| 776-M57 | S113N, S196T, P227A, T462A | 14.60 |
| 776-M65 | S57N | 5.00 |
| 776-M71 | T383A, T455A | 2.60 |
| 776-M73 | N373H | 4.80 |
| 776-M101 | S113N, S411F | 12.40 |
| 776-M108 | T41I, E193K, S411F | 15.60 |
| 776-M109 | N49S, S113N, P227A, P438L | 15.00 |
| 776-M124 | Y247C, Y371C, S411F | 17.40 |
| 776-M125 | S21P, S57N, T246I, R251K, S411F | 18.00 |
| 776-M192 | K157R, G205R, T255P, S411F | 15.00 |
| 776-M216 | S113N, S196T, P227A, S411F | 17.80 |
| 776-M252 | S113N, S196T, P227A, T356I, T462A | 19.20 |

*Numbering uses the first residue of the mature Cel7A enzyme as position 1.

Example 11

DNA Sequencing of Variants

To determine the sequence of the Cel7A cellobiohydrolase I variants derived from the libraries of Examples 7 and 9, plasmid DNA was isolated. Each variant was streaked onto agar yeast selection medium and incubated for 3-5 days at 30° C. Eight colonies were isolated and inoculated into 1 ml of yeast screening medium, and grown for 5-8 days at 30° C. The agar plates were re-grown at 30° C. for 3-5 days. Culture broth from the single colonies of each variant was assayed for improved thermal activity of the produced cellobiohydrolase I variant as described in Example 10 to determine which had improved thermal activity ratios relative to wild type (wt) CeI7A cellobiohydrolase I. Plasmid was rescued from the colonies which produced cellobiohydrolase I variants with improved thermal activity as described by Kaiser and Auer, 1993, *Bio Techniques* 14: 552, using *E. coli* strain XL-10 (Stratagene Inc., La Jolla, Calif.).

DNA sequencing was performed using an ABI 3700 sequencer (Applied Biosystems, Foster City, Calif.) using dye terminator chemistry (Giesecke et al., 1992, *Journal of ViroL Methods* 38: 47-60). Plasmid DNA for sequencing was prepared using a BioRobot 9604 (QIAGEN, Valencia, Calif.). The entire coding region for each *Trichoderma reesei* CeI7A cellobiohydrolase I variant was sequenced using 0.5 µl of plasmid DNA and 3.2 pmol of the following primers:

```
cTr0221.1:
                               (SEQ ID NO: 22)
5'-CTTCTTGGCCACAGCTCGTG-3' cTr0221.2:
                               (SEQ ID NO: 23)
5'-GGCTTTGTCACCCAGTCTGC-3' cTr0221.3:
                               (SEQ ID NO: 24)
5'-CGTCATCCAACAACGCGAAC-3' cTr0221.4:
                               (SEQ ID NO: 25)
5'-TTCGAGACGTCGGGTGCCAT-3' cTr0221.4:
                               (SEQ ID NO: 26)
5'-CGCGGAAGCTGCTCCACCAG-3' cTr0221.1A:
                               (SEQ ID NO: 27)
5'-AATGGAGAGGCTGTTACCGC-3'
```

Sequence trace files were edited and assembled using Vector NTI Contig Express (Informax, Inc., Bethesda, Md.).

Example 12

Generation of Error Prone Libraries Using Variant CeI7A Cellobiohydrolase I Genes as Templates Random mutagenesis of several of the improved variants was performed. Plasmid DNA was used that had been rescued from yeast as described in Example 10, and error-prone PCR was performed as described in Example 7. In addition, the G205R variant was mutagenized by using pNP776G205R as a template in error-prone PCR. The following primers were used to generate mutagenized sequences:

```
Primer aGal_776.1:
                               (SEQ ID NO: 28)
5' TATACCTCTATACTTTAACGTCAAGGAGAAAAA
CTATAGGATCCACCATGTATCGGAAGTTGGCCG-3'
```

```
-continued
Primer aGal_776.1a:
                               (SEQ ID NO: 29)
5' CATAACTAATTACATGATGCGGCCCTCTAGATG
CACATGACTCGAGTTACAGGCACTGAGAGTAG-3'
```

The error-prone PCR amplifications were analyzed on 0.7% agarose gels using TAE buffer and transformed with gapped pJC106 vector into *Saccharomyces cerevisiae* as described in Example 7.

Variants 76-M35, 776-M40, 776-M41, 776-M42, 776-M52, and 776-M53 were obtained from screening libraries created by error-prone amplification of the G205R template. Variant 776-252 was derived from a library created by mutagenic amplification of variant 776-M57. DNA from these variants was rescued and sequenced as described in Example 10.

Example 13

Shuffled libraries of CeI7A cellobiohydrolase I

To shuffle the CeI7A cellobiohydrolase I variants derived from mutagenesis of wild type CeI7A cellobiohydrolase I and G205R templates, plasmid DNA was isolated from the variants as described in Example 10. The CeI7A cellobiohydrolase I genes were amplified from the variants using the following primers:

```
Primer CiPpcrdwn:
                               (SEQ ID NO: 30)
5'-CTGGGGTAATTAATCAGCGAAGCGATGA-3'

Primer cJC106.1A:
                               (SEQ ID NO: 31)
5'-GCGTACACGCGTCTGTACA-3'
```

Each amplification reaction (50 µl) was composed of 1×PCR buffer, 0.2 mM dNTPs, 3.2 pM primer aGal_776.1, 3.2 pM primer aGal_776.1 A, approximately 100 ng of pTr0221, and 2.5 units of Taq DNA polymerase. The reactions were incubated in an Eppendorf Mastercycler 5333 programmed for 1 cycle at 94° C. for 3 minutes followed by 30 cycles each at 94° C. for 30 seconds, 55° C. for 30 seconds, and 72° C. for 90 seconds (5 minute final extension). PCR products were then purified using a QIAquick PCR Kit according to the manufacturer's instructions.

For shuffling of the CeI7A cellobiohydrolase I variants, PCR products from the amplified variant genes were combined with approximately 50 ng of pJC016 digested with BamH I and Xho I, and 100-200 ng of the assorted PCR fragments were co-transformed into *Saccharomyces cerevisiae* YNG 344 following the YEASTMAKER yeast transformation protocol to generate shuffled libraries, as described in Example 7. A large number of shuffled libraries were generated. The total number of variants included in a single library ranged from two to ten. The percentage of active variants in these libraries ranged from 87% to 94%, based on 50° C. activity determined in the 4-methylumbelliferyl-beta-D-lactoside assay described in Example 9. Since the Taq DNA polymerase used has low proofreading activity, the process of shuffling may have introduced new mutations in the CeI7A cellobiohydrolase I coding sequence.

Colonies from the shuffled libraries were picked and screened as described in Example 9, using a comparison of the 64° C. activity to the 50° C. activity using 4-methylumbelliferyl-beta-D-lactoside as substrate to assess the degree of improved thermal stability and thermal activity of each variant.

Screening of the shuffled libraries resulted in the isolation of improved variants, designated 776-M57, 776-M101, 776-M108, 776-M109, 776-M124, 776-M125, 776-M192, and 776-M216. DNA from these variants was rescued and sequenced as described in Example 10. Some of the substitutions identified by DNA sequencing of variants 776-M57, 776-M101, 776-M108, 776-M109, 776-M124, 776-M125, 776-M192, and 776-M216 contain substitutions previously identified by sequencing the mutants from error-prone libraries. For example, 776-M57 contained the S113N mutation that was also found in one parent (776-M4) of the shuffled library from which it was derived. Likewise, 776-M101 contained S411F, a substitution found in one of the parents (776-M27) of the shuffled library from which it was obtained. Other substitutions found in the variants derived from shuffled libraries, including N49S, E193K, R251K, T246I, Y247C, Y371C, and P438L, were not observed in the sequenced variants that comprised the parent variants for the corresponding shuffled libraries. These mutations may have been introduced by a PCR-mediated mutagenesis event during amplification of the variant DNA during construction of the shuffled libraries.

Example 14

Site-specific Saturation Mutagenesis

To screen for the optimal substitution for improved thermal activity at specific positions in Cel7A cellobiohydrolase I, site-specific randomization was performed. Amino acids G94, S196, and P227 were randomized by substitution of the wild-type codon with NN (G/C) using megaprimer PCR (Landt, et al., 1990 Gene 96: 125-128). Randomization at the three positions was performed using the following primers:

Randomization at position 94:

```
Primer aTrCBHI.2:
                                    (SEQ ID NO: 32)
5'-GCGGTAACAGCCTCTCCATTNNSTTTGTCAC-3'

Primer aTrCBHI.2a:
                                    (SEQ ID NO: 33)
5'-CTGCGCAGACTGGGTGACAAASNNAATGGAGAG-3'
```

Randomization at position 196:

```
Primer aTrCBHI.3:
                                    (SEQ ID NO: 34)
5'-CCATCTCCGAGGCTCTTACCNNSCACCCTTGC-3'

Primer aTrCBHI.3a:
                                    (SEQ ID NO: 35)
5'-GGCCGACAGTCGTGCAAGGGTGSNNGGTAAGAG-3'
```

Randomization at position 227:

```
Primer aTrCBHIR.1:
                                    (SEQ ID NO: 36)
5'-GAGGGCTGGGAGCCGTCANNSAACAACGCG-3'

Primer aTrCBHI.1bA:
                                    (SEQ ID NO: 37)
5'-CCAATGCCCGTGTTCGCGTTGTTSNNTGACGGC-3'
```

Each amplification reaction (50 µl) was composed of 1×PCR buffer, 0.2 mM dNTPs, 3.2 pM of the sense primer, 3.2 pM of the antisense primer, approximately 100 ng of pTr0221, and 2.5 units of Taq DNA Polymerase. The reactions were incubated in an Eppendorf Mastercycler 5333 programmed for 1 cycle at 95° C. for 3 minutes followed by 30 cycles each at 95° C. for 30 seconds, 55° C. for 60 seconds, and 72° C. for 90 seconds (5 minute final extension). PCR products were then purified using a QIAquick PCR Kit according to the manufacturer's instructions. Each PCR fragment generated for the individual site mutations served as megaprimers for the overlap extension amplification reaction to generate a complete cellobiohydrolase I gene fragment, with indicated site-specific mutations, for library generation. The first 5 rounds of the amplification reaction was composed of 1×PCR buffer, 0.2 mM dNTPs, 100 ng of the sense (5') megaprimer, 100 ng of the antisense (3') megaprimer, and 2.5 units of Taq DNA Polymerase. The reactions were incubated in an Eppendorf Mastercycler 5333 programmed for 1 cycle at 95° C. for 3 minutes followed by 5 cycles each at 95° C. for 30 seconds, 55° C. for 60 seconds, and 72° C. for 90 seconds. To this reaction, 50 pmol of primer aGal776.1 and aGal776.1A were added to amplify the newly generated site randomized fragment generated in the previous 5 cycle reaction. The reactions after the addition of the new primers were incubated in an Eppendorf Mastercycler 5333 programmed for 30 cycles each at 95° C. for 30 seconds, 55° C. for 60 seconds, and 72° C. for 90 seconds (5 minute final extension). The resulting PCR fragments were then purified using a QIAquick PCR Kit according to the manufacturer's instructions. The final PCR fragment was then transformed directly into yeast together with BamH I and Xho I-gapped pJC106 plasmid (Example 6).

Since the Taq DNA polymerase used has low proofreading activity, the process of saturation mutagenesis may have introduced new mutations in the coding sequence in addition to the designed changes at positions 94, 196, and 227. Libraries containing site-specific randomized amino acids were screened as described in Example 10. As shown in Table 2, a number of substitutions that improved the thermal activity ratio at 63° C./50° C. relative to wild type were discovered in addition to the substitutions identified by screening randomly-mutagenized libraries. For example, variant 776-M3 was obtained from screening a primary library, where a proline at position 227 was converted to an alanine. In screening the site-specific randomized library at this position, we indentified substitutions to leucine and to glycine as well as alanine.

In addition to uncovering the amino acid substitutions at positions 227, 94, and 196, which confer improved thermal stability and activity, a second site mutation was identified that could improve thermal activity. Specifically, the substitution D259N was identified in variant 776-M273 as shown in Table 2.

TABLE 2

Cel7A variants with improved thermal stability containing substitutions at positions 227, 94, and 196. "Fold Improvement" indicates relative improvement in thermal activity ratio, measured at 63° C./50° C.

| Cel7A Variant | Amino Acid Substitutions* | Fold-Improvement | Library Type |
| --- | --- | --- | --- |
| Wild type | none | 1 | none |
| 776-M3 | P227A, C486W | 2.67 | primary |
| 776-M259 | P227L | 1.50 | Site-specific randomization at 227 |
| 776-M273 | P227G, D259N | 3.00 | Site-specific randomization at 227 |

TABLE 2-continued

Cel7A variants with improved thermal stability containing substitutions at positions 227, 94, and 196. "Fold Improvement" indicates relative improvement in thermal activity ratio, measured at 63° C./50° C.

| Cel7A Variant | Amino Acid Substitutions* | Fold-Improve-ment | Library Type |
|---|---|---|---|
| 776-M274 | P227A | 2.67 | Site-specific randomization at 227 |
| 776-M275 | P227L | 2.00 | Site-specific randomization at 227 |
| 776-M52 | G94S, G205R | 2.00 | primary |
| 776-M268 | G94A, T226A | 2.67 | Site-specific randomization at 94 |
| 776-M264 | G94R | 2.07 | Site-specific randomization at 94 |
| 776-M266 | G94Q | 2.17 | Site-specific randomization at 94 |
| 776-M269 | G94A | 2.03 | Site-specific randomization at 94 |
| 776-M53 | S196P, G205R | 1.50 | primary |
| 776-M4 | S113N, S196T, T462A | n.a. | primary |
| 776-M261 | S196P | 1.33 | Site-specific randomization at 196 |
| 776-M263 | T41I, S196F | 1.67 | Site-specific randomization at 196 |

*Numbering uses the first residue of the mature Cel7A enzyme as position 1.

Example 15

Construction of pMJ04, pMJ06, and pMJ09 Expression Vectors

Expression vector pMJ04 was constructed by PCR amplifying the *Trichoderma reesei* cellobiohydrolase 1 gene (cbh1) terminator from *Trichoderma reesei* RutC30 genomic DNA using primers 993429 (antisense) and 993428 (sense) shown below. The antisense primer was engineered to have a Pac I site at the 5'-end and a Spe I site at the 3'-end of the sense primer.

```
Primer 993429 (antisense):
                          (SEQ ID NO: 38)
5'-AACGTTAATTAAGGAATCGTTTTGTGTTT-3'

Primer 993428 (sense):
                          (SEQ ID NO: 39)
5'-AGTACTAGTAGCTCCGTGGCGAAAGCCTG-3'
```

*Trichoderma reesei* RutC30 genomic DNA was isolated using a DNeasy Plant Maxi Kit (QIAGEN, Valencia, Calif.). The amplification reactions (50 µl) were composed of 1×ThermoPol Reaction Buffer (New England Biolabs, Beverly, Mass.), 0.3 mM dNTPs, 100 ng of *Trichoderma reesei* RutC30 genomic DNA, 0.3 µM primer 993429, 0.3 µM primer 993428, and 2 units of Vent polymerase (New England Biolabs, Beverly, Mass.). The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 229 by product band was excised from the gel and purified using a QIAquick Gel Extraction Kit (QIAGEN, Valencia, Calif.) according to the manufacturer's instructions.

Figure 8:
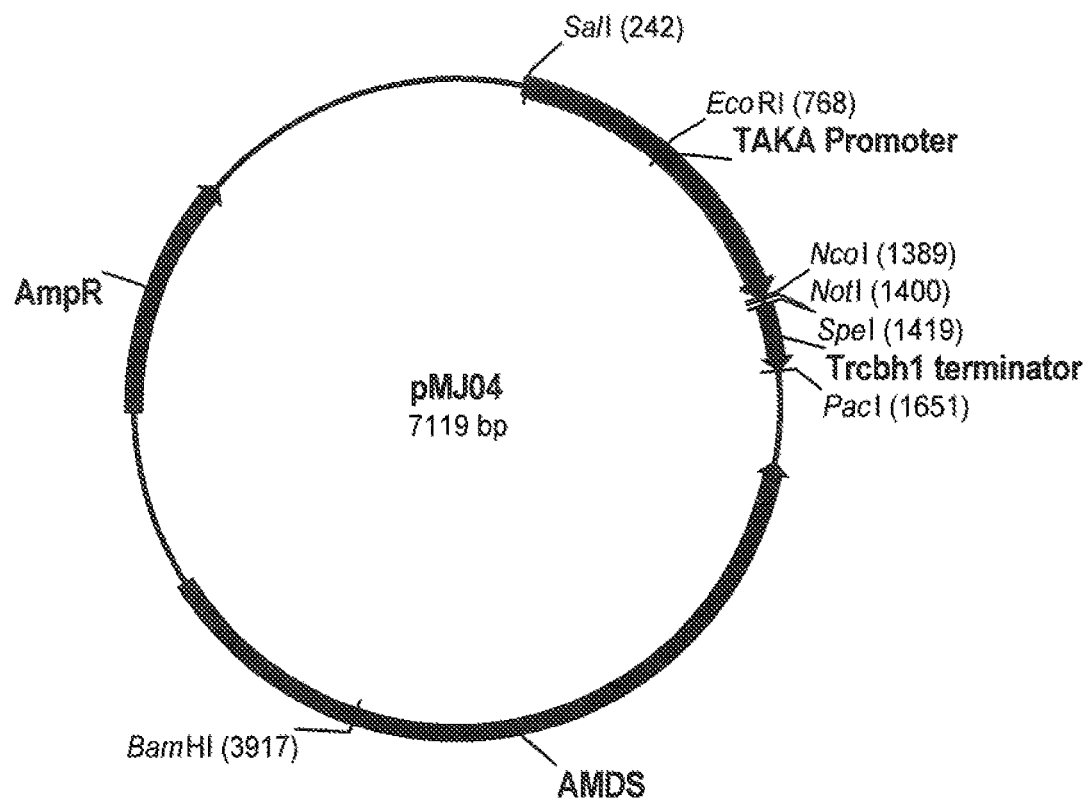
FIG. 8 shows a restriction map of pMJ04.

The resulting PCR fragment was digested with Pac I and Spe I and ligated into pAILo01 (Example 8) digested with the same restriction enzymes using a Rapid Ligation Kit (Roche, Indianapolis, Ind.) to generate pMJ04 (FIG. 8).

Expression vector pMJ06 was constructed by PCR amplifying the *Trichoderma reesei* Cel7A cellobiohydrolase 1 gene (cbh1) promoter from *Trichoderma reesei* RutC30 genomic DNA using primers 993696 (antisense) and 993695 (sense) shown below. The antisense primer was engineered to have a Sal I site at the 5'-end of the sense primer and an Nco I site at the 5'-end of the antisense primer.

```
Primer 993695 (sense):
                          (SEQ ID NO: 40)
5'-ACTAGTCGACCGAATGTAGGATTGTT-3'

Primer 993696 (antisense):
                          (SEQ ID NO: 41)
5'-TGACCATGGTGCGCAGTCC-3'
```

The amplification reactions (50 µl) were composed of 1×ThermoPol Reaction Buffer, 0.3 mM dNTPs, 100 ng of *Trichoderma reesei* RutC30 genomic DNA (which was prepared using a DNeasy Plant Maxi Kit, 0.3 µM primer 993696, 0.3 µM primer 993695, and 2 units of Vent polymerase. The reactions were incubated in an Eppendorf Mastercycler 5333 programmed as follows: 30 cycles each for 30 seconds at 94° C., 30 seconds at 55° C., and 60 seconds at 72° C. (15 minute final extension). The reaction products were isolated on a 1.0% agarose gel using TAE buffer where a 988 by product band was excised from the gel and purified using a QIAquick Gel Extraction Kit according to the manufacturer's instructions.

Figure 9:
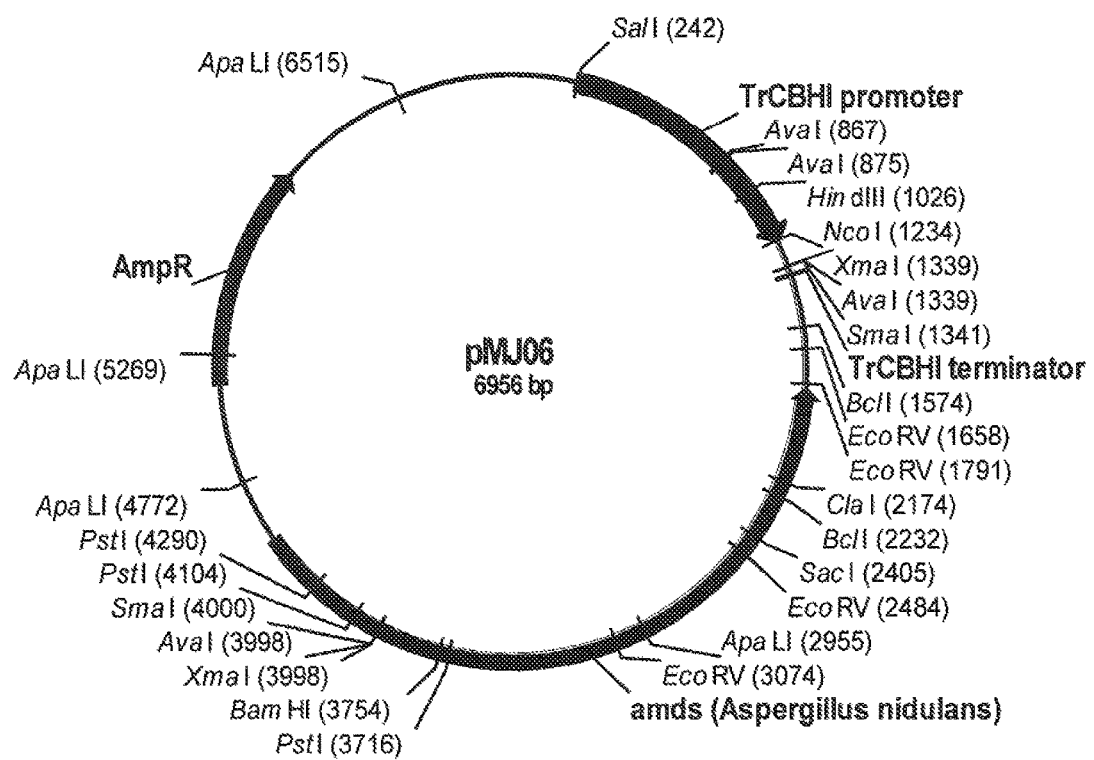
FIG. 9 shows a restriction map of pMJ06.

The resulting PCR fragment was digested with Nco I and Sal I and ligated into pMJ04 digested with the same restriction enzymes using a Rapid Ligation Kit to generate pMJ06 (FIG. 9).

Expression vector pMJ09 was constructed by PCR amplifying the *Trichoderma reesei* Cel7A cellobiohydrolase 1 gene (cbh1) terminator from *Trichoderma reesei* RutC30 genomic DNA using primers 993843 (antisense) and 99344 (sense) shown below. The antisense primer was engineered to have a Pac I and a Spe I sites at the 5'-end and a Pvu I site at the 5'-end of the sense primer.

```
Primer 993844 (sense):
                          (SEQ ID NO: 42)
5'-CGATCGTCTCCCTATGGGTCATTACC-3'

Primer 993843 (antisense):
                          (SEQ ID NO: 43)
5'-ACTAGTTAATTAAGCTCCGTGGCGAAAG-3'
```

The amplification reactions (50 µl) were composed of 1× ThermoPol Reaction Buffer, 0.3 mM dNTPs, 100 ng *Trichoderma reesei* RutC30 genomic DNA (which was extracted using a DNeasy Plant Maxi Kit), 0.3 µM primer 993844, 0.3 µM primer 993843, and 2 units of Vent polymerase. The reactions were incubated in an Eppendorf Mastercycler 5333 programmed as follows: 30 cycles each for 30 seconds at 94° C., 30 seconds at 55° C., and 60 seconds at 72° C. (15 minute final extension). The reaction products were isolated on a 1.0% agarose gel using TAE buffer where a 473 by product band was excised from the gel and purified using a QIAquick Gel Extraction Kit according to the manufacturer's instructions.

Figure 10:
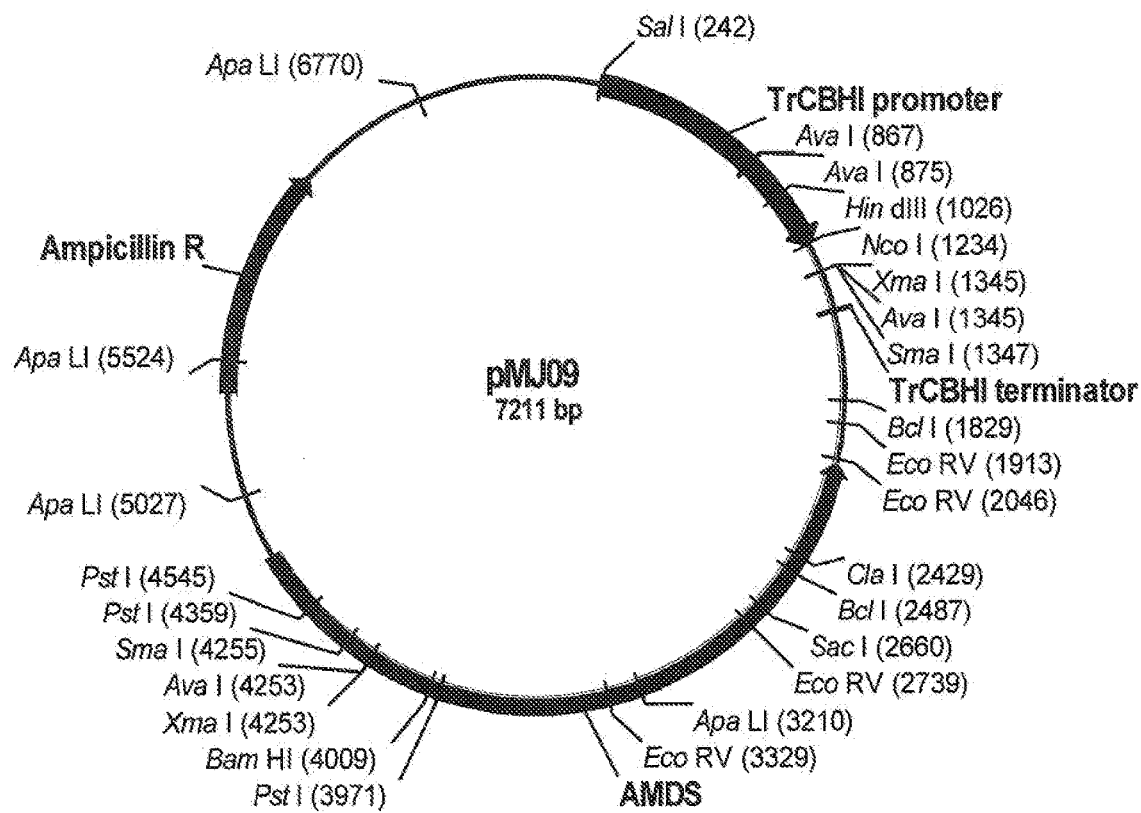
FIG. 10 shows a restriction map of pMJ09.

The resulting PCR fragment was digested with Pvu I and Spe I and ligated into pMJ06 digested with Pac I and Spe I using a Rapid Ligation Kit to generate pMJ09 (FIG. 10).

Example 16

Construction of pCW045 for Expression of Variant 776-M57 in *Trichoderma reesei*

Variant 776-M57 was subcloned into the *Trichoderma reesei* expression vector pMJ09 using an In-Fusion PCR Cloning Kit (BD Biosciences, Clonetech, Palo Alto, Calif.). PCR amplification of the variants was performed using Platinum Pfx DNA Polymerase (Invitrogen, Carlsbad, Calif.). Amplifications were composed of 1×Pfx amplification buffer, 0.3 mM each dCTP, dATP, dTTP, and dGTP; 1 mM MgSO$_4$, 1 pmol of primer IF-F1, 1 pmol of primer IF-R1, 50-100 ng of DNA template 776-57, and 1 unit of Pfx polymerase. The reactions were incubated using a MJ Research Thermocycler programmed for one cycle at 95° C. for 3 minutes followed by 30 cycles each at 95° C. for 15 seconds, 55° C. for 30 seconds, and 68° C. for 2 minutes 30 seconds. The reactions were then incubated at 72° C. for a 7 minute extension.

```
Primer IF-F1:
                                        (SEQ ID NO: 44)
5'-CGCGGACTGCGCACCATGTATCGGAAGTTG-3'

Primer IF-R1:
                                        (SEQ ID NO: 45)
5'-CGCCACGGAGCTTAATTACAGGCACTGAGA-3'
```

An aliquot of each PCR product was run on a 0.7% agarose gel using TAE buffer, as previously described, generating expected bands of approximately 1.575 kb. PCR reactions were purified using a MinElute PCR Purification Kit and eluting the DNA into 50 µl of EB buffer. The yield of each purified PCR product was estimated to be 125 ng per microliter by visualization on a 0.7% agarose gel using TAE buffer.

Figure 11:
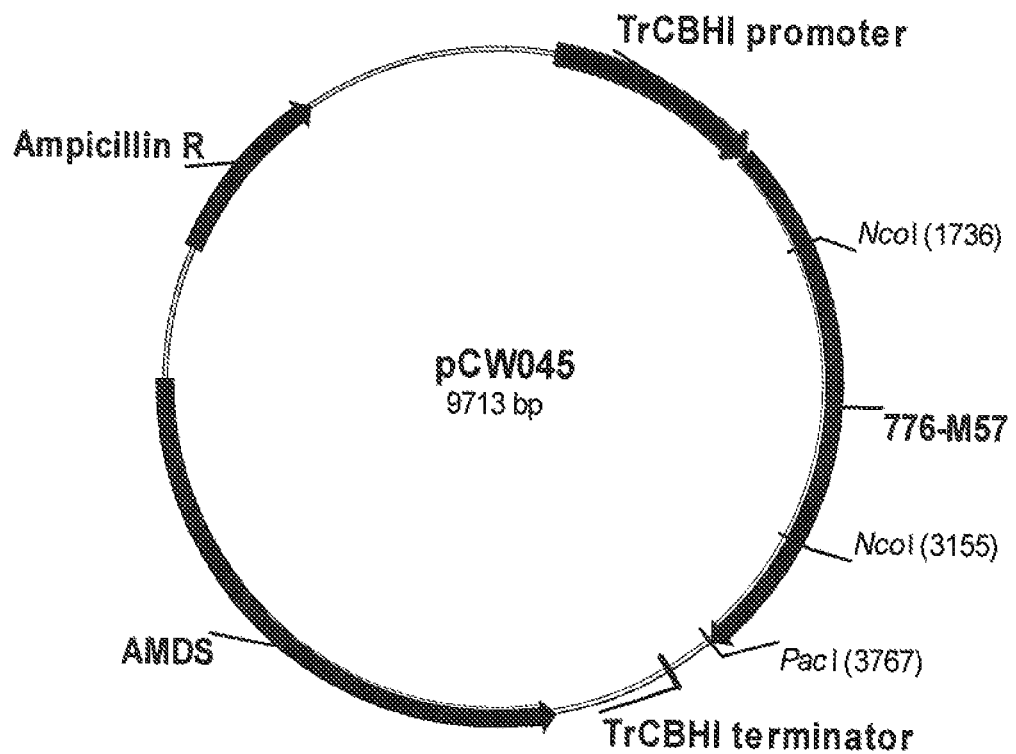
FIG. 11 shows a restriction map of pCW045.

Plasmid pMJ09 digested with Pac I and blunted at the Nco I site was purified using a Qiaquick Minielute Column Kit (QIAGEN, Valencia, Calif.). The plasmid had a concentration of 100 ng per microliter. The concentration was verified by visualization on a 0.7% agarose gel using TAE buffer. Cloning of the 776-M57 PCR product described above and the digested pMJ09 vector was accomplished by using the In-Fusion PCR Cloning Kit (BD Biosciences, Clonetech, Palo Alto, Calif.). The resulting *Trichoderma reesei* expression vector containing variant 776-M57 was designated pCW045 (FIG. 11).

Example 17

Expression Cel7A Cellobiohydrolase I in *Trichoderma reesei* as the Sole Cellobiohydrolase I In order to evaluate the 776-M57 variant as the sole cellobhiohydrolase I following expression in the native host, a *Trichoderma reesei* strain was constructed wherein the cellobiohydrolase I Cel7A gene, cbh1, had been disrupted. A disruption cassette was constructed using the hygromycin resistance gene (hph) from *Escherichia coli* as a selectable marker. The hph marker was flanked by homologous cbh1 sequence in order to target the native cbh1 gene.

Amplification of the genomic cbh1 gene was done using the polymerase chain reaction method with PWO Polymerase (Roche Applied Science, Manheim, Germany). The reactions were incubated in an Eppendorf Mastercycler 5333. Amplifications were composed of 1×PWO amplification buffer, 0.3 mM each of dCTP, dATP, dTTP, and dGTP, 1 mM MgSO$_4$, 1 pmol each of primer cbh1 N-term and cbh1 C-term described below, and 50-100 ng of DNA template. Amplifications utilized an initial denaturation of 2 minutes at 95° C. followed by 35 cycles of a 1 minute denaturation, 2 minute annealing at 55° C. and a 2 minute extension at 68° C.

```
Primer cbh1 N-term:
                                        (SEQ ID NO: 46)
5'-GCC TTC GGC CTT TGG GTG TA-3'

Primer cbh1 C-term:
                                        (SEQ ID NO: 47)
5'-GAG CGG CGA TTC TAC GGG TT-3'
```

Figure 12:
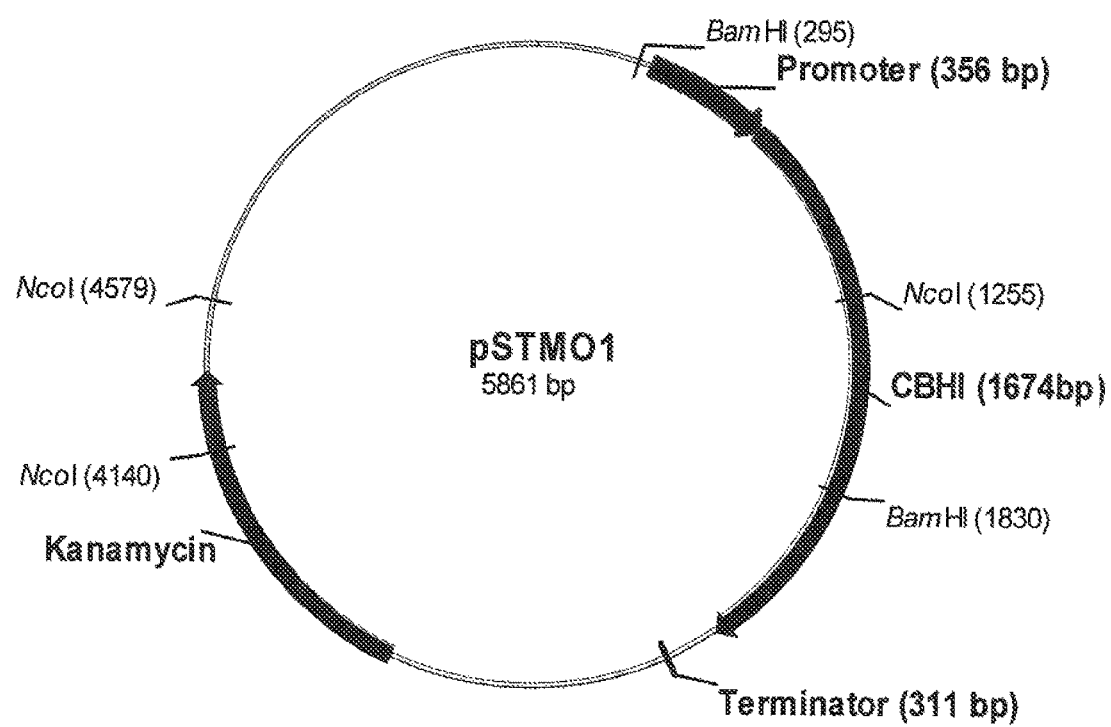
FIG. 12 shows a restriction map of pSTM01.

The 2.3 kb PCR fragment was cloned using the Zero Blunt TOPO PCR Cloning Kit (Invitrogen Corporation, Carlsbad, Calif.) and propagated in *E. coli* Top10 cells (Invitrogen Corporation, Carlsbad, Calif.). The resulting construct was a 5.8 kb plasmid designated pSTMO1 (FIG. 12).

The hph gene was amplified from the PHT1 plasmid (Cummings, et al., 1999, *Curr. Genet.* 36: 371-382) using the polymerase chain reaction method with PWO Polymerase. The reactions were incubated in an Eppendorf Mastercycler 5333, and were composed of 1×PWO amplification buffer, 0.3 mM each of dCTP, dATP, dTTP, and dGTP, 1 mM MgSO$_4$, 1 pmol each of primer hph N-term and hph C-term described below, and 50-100 ng of DNA template. The amplifications utilized an initial denaturation of 2 minutes at 95° C. followed by 35 cycles of a 1 minute denaturation, 2 minute annealing at 55° C. and a 2 minute extension at 68° C.

```
Primer hph N-term:
                                        (SEQ ID NO: 48)
5'-GCC GCG GCA CGC GCC ACA CGG AAA AT-3'

Primer hph C-term:
                                        (SEQ ID NO: 49)
5'-GAC CGG TCG CAA AAT GAC AAA TAG AAG-3'
```

Figure 13:
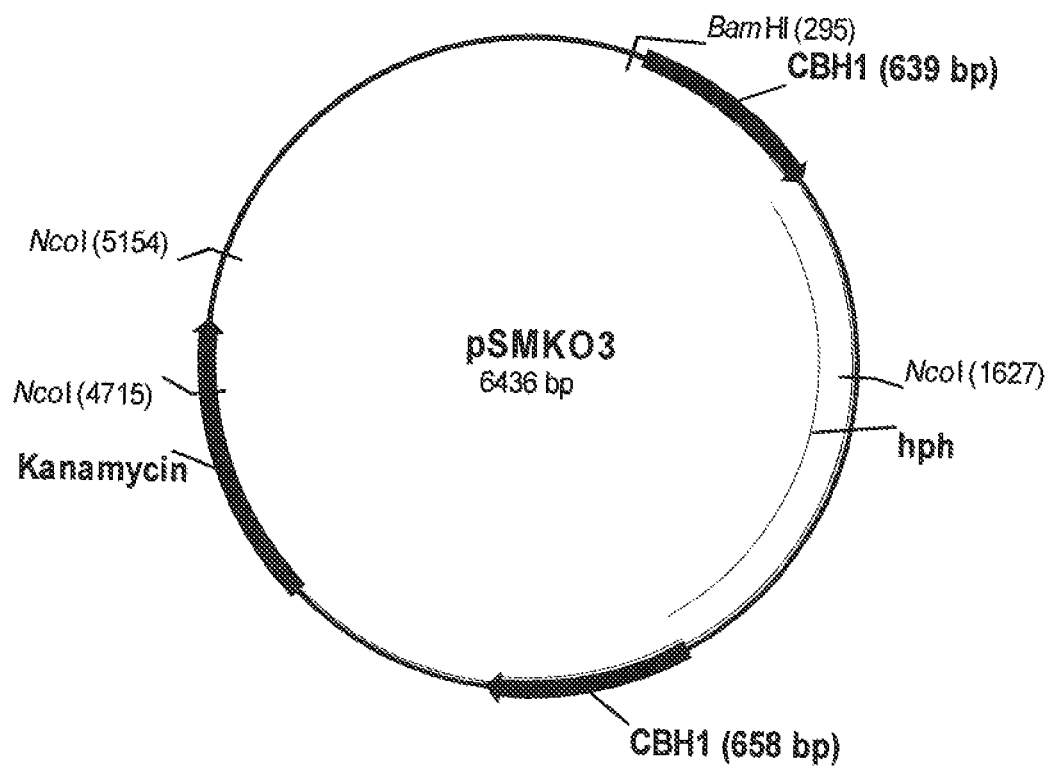
FIG. 13 shows a restriction map of pSMKO3.

To generate the cbh1 disruption cassette, pSTMO1 was digested with Mlu I and BstE II to create a 1.1 kb gap in the cbh1 coding sequence. T4 DNA polymerase (New England Biolabs, Beverly, Mass.) was then used to fill in and generate blunt ends in the digested plasmid. The T4 reaction was incubated for 20 minutes at 15° C. followed by a heat inactivation for 15 minutes at 65° C. The entire reaction mix was fractionated on a 1% agarose gel using TAE buffer, and the major band was excised and eluted from the gel using a Qiaquick Gel Extraction Kit. The 1.7 kb hph gene was then inserted into the gapped pSTMO1 vector using a Rapid DNA Ligation Kit and transformed into One Shot *E. coli* competent cells (Invitrogen Corporation, Carlsbad, Calif.). The resulting plasmid was designated pSMKO3 (FIG. 13).

Using pSMKO3 as a template, cbh1 DNA was amplified using PCR primers flanking the hph gene. A 2.7 kb fragment was amplified from pSMKO3 using the following primers:

```
Primer pSMK03-F1:
                                        (SEQ ID NO: 50)
5'-GCTCCGGGCAAATGCAAA GTG TG-3'

Primer pSMK03-R1:
                                        (SEQ ID NO: 51)
5'-AGCAGGCCGCATCTCCAGTGAAAG-3'
```

The amplification was performed using the polymerase chain reaction method with PWO Polymerase. The reactions were incubated in an Eppendorf Mastercycler 5333, and were composed of 1×PWO amplification buffer, 0.3 mM each of dCTP, dATP, dTTP, and dGTP, 1 mM MgSO$_4$, 1 pmol each of primer KO N-term and KO C-term described above, and 50-100 ng of DNA template. Amplifications utilized an initial denaturation of 2 minutes at 95° C. followed by 35 cycles of a 1 minute denaturation, 2 minute annealing at 55° C., and a 2 minute extension at 68° C. The resulting DNA fragment contained 639 kb of the cbhl promoter/gene sequence, the 1.7 kb of the hph coding region, and 659 bases of the cbhl gene/terminator sequence.

Protoplasts of *Trichoderma reesei* RutC30 were prepared for transformation by the following method. Shake flasks containing 25 ml of YPD medium were inoculated with 5×10$^7$ conidia. Following an overnight (approximately 18 hours) incubation at 34° C. (150 rpm), the mycelia were collected by filtration through sterile Miracloth™ (Calbiochem, San Diego, Calif.) and transferred to 20 mg/ml Glucanex (Novozymes A/S, Bagsvrd, Denmark) and 1.6 mg/ml chitinase (Sigma-Aldrich, St. Louis, Mo.) in 25 ml of 1 M sorbitol. Digestions were typically 25-40 minutes with gentle shaking (80-100 rpm) at 34° C. The protoplasts were then filtered through a gauze filter and washed with ice cold 1 M sorbitol and then centrifuged at 400×g for 8 minutes. Protoplasts were washed twice with 25 ml of 1 M sorbitol and twice with 25 ml of 1 M sorbitol, 50 mM Tris-HCl pH 8.0, 50 mM CaCl$_2$. Protoplasts were then counted using a haemacytometer and resuspended in a solution composed of 7 parts of 1 M sorbitol, 50 mM Tris-HCl pH 8.0, 50 mM CaCl$_2$ and 2 parts of 50% PEG-4000, 50 mM Tris-HCl pH 8.0, 50 mM CaCl$_2$ at a concentration of 1×10$^8$ protoplasts/ml. Protoplasts were either used immediately or stored at −80° C. in a controlled rate freezer (Nalge Nunc International, Rochester, N.Y.) until transformation.

Transformation of the protoplasts was performed using 5 µg of linear DNA and 5 µl of heparin (5 mg/ml), which were mixed and incubated on ice for 5 minutes. One hundered microliters of protoplasts were then added and the mixture was incubated for 15 minutes on ice. Five hundred microliters of 50% PEG-4000, 50 mM Tris-HCl pH 8.0, 50 mM CaCl$_2$ was then added and incubated at room temperature for 15 minutes. One milliliter of 50% PEG-4000, 50 mM Tris-HCl pH 8.0, 50 mM CaCl$_2$ was added to the mixture and incubated at 34° C. for 20 minutes. Following the incubation at 34° C., 2 ml of 1 M sorbitol, 50 mM Tris-HCl pH 8.0, 50 mM CaCl$_2$ was added. The contents were gently mixed before spreading 350 µl of the protoplast mixture on PDA plates. The plates were incubated at 29° C. for approximately 18 hours before overlaying with 100 µg/ml hygromycin B (Roche Applied Science, Manheim, Germany) in PDA medium. Transformants appeared within 3 days of the hygromycin overlay. Transformants were then subcultured to PDA plates containing 100 µg/ml hygromycin B. Transformants that grew on the secondary plates were then used for inoculation into cellulase inducing medium (CIM).

Strains were screened for cellobiohydrolase I disruption by the following method. Transformants were grown in cellulase-inducing medium in 24-well tissue culture plates (Corning, Acton, Mass.) for 3 days at 34° C. Ten microliters of culture broth was added to 10 µl of 2× sample buffer plus 1% beta-mercaptoethanol and run on an 8-16% Tris-glycine acrylamide gel (NUPAGE Novex Gels Invitrogen Corporation, Carlsbad, Calif.) using NuPAGE® MES SDS Running Buffer (NUPAGE Novex Gels Invitrogen Corporation, Carlsbad, Calif.). Potential knockouts were selected based on the absence of a cellobiohydrolase I Cel7A protein band in comparison to the parent strain.

To confirm deletion of the cbh1 gene in candidate strains that had been selected by SDS-PAGE analysis, Southern analysis was performed to assess whether the cbh1 gene had been disrupted. Mycelia were grown overnight in shake flasks containing 25 ml of YPD medium. The mycelia were then harvested, filtered, and ground using a mortar and pestle with liquid nitrogen. Genomic DNA was isolated using a DNeasy Plant Maxi Kit. One microgram of DNA was digested either with Hind III or Nde I and run on a 0.8% agarose gel in TAE buffer. The DNA was fragmented in the gel by treating with 0.25 M HCl, denatured with 0.5 M NaOH, 1.5 M NaCl, and neutralized with 1 M Tris, pH 8.0; 1.5 M NaCl for subsequent transfer in 10×SSC to Nytran Plus membrane (Schleicher & Schuell BioScience, GmbH, Dassel, Germany). The DNA was UV-crosslinked to the membrane and prehybridized for 1 hour at 60° C. in 20 ml of DIG Easy Hyb (Roche Applied Science, Manheim, Germany).

Two probes were prepared for Southern analysis. A 1.7 kb hygromycin probe was amplified from pSMK03, using polymerase chain reaction and the following primers:

```
Primer cpht-p:
                                    (SEQ ID NO: 52)
5'-GCACGCGCCACACGGAAAAT-3'

Primer cpht-t:
                                    (SEQ ID NO: 53)
5'-CGCAAAATGACAAATAGAAG-3'
```

In addition, a 2.1 kb cellobiohydrolase I probe was amplified from pSTMO1 by PCR using the primers pSMK03-F1 and pSMK03-R1. Probes were prepared with a PCR DIG Probe Synthesis Kit (Roche Applied Science, Manheim, Germany). The PCR DIG Probe Synthesis mix and PCR buffer with magnesium were used at 1×. Expand High Fidelity Polymerase (Roche Applied Science, Manheim, Germany) was added at 0.75 µl per reaction. One pmol each of primers and 50-100 ng of DNA template were used per reaction. Prior to use the probe was denatured by boiling for 5 minutes and then added to the hybridization buffer.

The denatured probe was added directly to the DIG Easy Hyb buffer and hybridization was overnight at 65° C. Following the post hybridization washes (twice in 2×SSC, once in 0.4×SSC, 60° C., 10 minutes each), chemiluminescent detection using the DIG detection system and CPD-Star (Roche Applied Science, Manheim, Germany) was done. The DIG-labeled DNA Molecular Weight Marker III Kit (Roche Applied Science, Manheim, Germany) was used as the source of standard markers.

Southern analysis indicated that the presence of a single hph intergration within the cbh1gene for a specific transformant. This cellobiohydrolase I gene deletion strain was designated *Trichoderma reesei* SaMe013.

Plasmid pCW045, containing the cellobiohydrolase I variant 776-M57 behind the cbh1 promoter, was introduced into *Trichoderma reesei* SaMe013 by PEG-mediated transformation (Penttila et al., 1987, *Gene* 61: 155-164). The plasmid contains the *Aspergillus nidulans* amdS gene to enable transformants to grow on acetamide as the sole nitrogen source. *Trichoderma reesei* RutC30 was cultivated at 27° C. and 90 rpm in 25 ml of YPD medium supplemented with 10 mM uridine for 17 hours. Mycelia were collected by filtration using Millipore's Vacuum Driven Disposable Filtration System (Millipore, Bedford, Mass.) and washed twice with deionized water and twice with 1.2 M sorbitol. Protoplasts were generated by suspending the washed mycelia in 20 ml of 1.2 M sorbitol containing 15 mg of Glucanex per ml and 0.36 units of chitinase per ml and incubating for 15-25 minutes at 34° C. with gentle shaking at 90 rpm. Protoplasts were collected by centrifuging for 7 minutes at 400×g and washed twice with ice cold 1.2 M sorbitol. The protoplasts were counted using a hemacytometer and resuspended in STC to a final concentration of $1 \times 10^8$ protoplasts per ml. Excess protoplasts were stored in a Cryo 1° C. Freezing Container (Nalgene, Rochester, N.Y.) at −80° C.

Approximately 1 μg of Pme I digested pCW045 was added to 100 μl of protoplast solution and mixed gently, followed by 260 μl of PEG buffer, mixed, and incubated at room temperature for 30 minutes. STC (3 ml) was then added, mixed and the transformation solution was plated onto COVE plates using *Aspergillus nidulans* amdS selection. The plates were incubated at 28° C. for 5-7 days. Transformants were sub-cultured onto COVE2 plus uridine plates and grown at 28° C. for 7 days.

The *Trichoderma reesei* transformants were cultivated in 125 ml baffled shake flasks containing 25 ml of cellulase-inducing media at pH 6.0 inoculated with spores of the transformants and incubated at 28° C. and 200 rpm for 7 days. *Trichoderma reesei* RutC30 was run as a control. Culture broth samples were removed at day 7. SDS-PAGE was carried out using Criterion Tris-HCl (8-16% polyacrylamide) gels (BioRad, Hercules, Calif.) with the Criterion SDS-PAGE System (BioRad, Hercules, Calif.). Five μl of day 7 supernatants were suspended in 5 μl of 2× Sample Buffer (BioRad, Hercules, Calif.) and heated in the presence of 1% beta-mercaptoethanol for 5 minutes. The supernatant samples were loaded onto a polyacrylamide gel and subjected to electrophoresis with 1× Tris/Glycine/SDS as running buffer (BioRad, Hercules, Calif.). The resulting gel was stained with Bio-Safe Coomassie Stain (BioRad, Hercules, Calif.). Candidate transformants were evaluated for their ability to express the variant Cel7A cellobiohydrolase I 776-M57 at levels that were apparently equivalent to levels observed in the *Trichoderma reesei* parent strain. A single transformant was selected on this basis for larger scale production in fermentation.

Fermentation was performed using the strain expressing cellobiohydrolase I variant 776-M57, and the *Trichoderma reesei* RutC30 (host strain) was run as a control. Spores of *Trichoderma reesei* RutC30 were inoculated into 500 ml shake flasks, containing 100 ml of *Trichoderma* Inoculum Medium. The flasks were placed into an orbital shaker at 28° C. for approximately 48 hours at which time 50 ml of the culture was inoculated into 1.8 liters of *Trichoderma* Fermentation Medium in a 2 liter fermentation vessel. The fermentations were run at pH 5.0, 28° C., with minimum dissolved oxygen at 25% at a 1.0 VVM air flow and an agitation of 1100. *Trichoderma* Feed Medium was administrated into the fermentation vessel at 18 hours with a feed rate of 3.6 g/hour for 33 hours and then 7.2 g/hour. The fermentations ran for 165 hours at which time the final fermentation broths were centrifuged and the supernatants stored at −20° C.

Example 18

Identification of a Glycosyl Hydrolase Family GH3A Gene in the Genomic Sequence of *Aspergillus fumigatus*

A tblastn search (Altschul et al., 1997, *Nucleic Acids Res.* 25: 3389-3402) of the *Aspergillus fumigatus* partial genome sequence (The Institute for Genomic Research, Rockville, Md.) was carried out using as query a beta-glucosidase protein sequence from *Aspergillus aculeatus* (Accession No. P48825). Several genes were identified as putative Family GH3A homologs based upon a high degree of similarity to the query sequence at the amino acid level. One genomic region of approximately 3000 by with greater than 70% identity to the query sequence at the amino acid level was chosen for further study.

Example 19

*Aspergillus fumigatus* Genomic DNA Extraction

*Aspergillus fumigatus* was grown in 250 ml of potato dextrose medium in a baffled shake flask at 37° C. and 240 rpm. Mycelia were harvested by filtration, washed twice in TE (10 mM Tris-1 mM EDTA) and frozen under liquid nitrogen. Frozen mycelia were ground, by mortar and pestle, to a fine powder, which was resuspended in pH 8.0 buffer containing 10 mM Tris, 100 mM EDTA, 1% Triton X-100, 0.5 M guanidine-HCl, and 200 mM NaCl. DNase free RNase A was added at a concentration of 20 mg/liter and the lysate was incubated at 37° C. for 30 minutes. Cellular debris was removed by centrifugation, and DNA was isolated by using a Qiagen Maxi 500 column (QIAGEN Inc., Valencia, Calif.). The columns were equilibrated in 10 ml of QBT washed with 30 ml of QC, and eluted with 15 ml of QF (all buffers from QIAGEN Inc., Valencia, Calif.). DNA was precipitated in isopropanol, washed in 70% ethanol, and recovered by centrifugation. The DNA was resuspended in TE buffer.

Example 20

Cloning of the Family GH3A Beta-glucosidase Gene and Construction of an *Aspergillus oryzae* Expression Vector Two synthetic oligonucleotide primers shown below were designed to PCR amplify a *Aspergillus fumigatus* gene encoding a putative Family GH3A beta-glucosidase from the genomic DNA prepared in Example 19. An InFusion Cloning Kit (BD Biosciences, Palo Alto, Calif.) was used to clone the fragment directly into the expression vector, pAlLo2 (Example 8; FIG. 5).

```
Forward primer:
                                (SEQ ID NO: 54)
5'-ACTGGATTTACCATGAGATTCGGTTGGCTCG-3'

Reverse primer:
                                (SEQ ID NO: 55)
5'-AGTCACCTCTAGTTACTAGTAGACACGGGGC-3'
```

Bold letters represent coding sequence. The remaining sequence contains sequence identity compared with the insertion sites of pAlLo2 (FIG. 5).

Fifty picomoles of each of the primers above were used in a PCR reaction containing 100 ng of *Aspergillus fumigatus* genomic DNA, 1×Pfx Amplification Buffer (Invitrogen, Carlsbad, Calif.), 1.5 μl of 10 mM blend of dATP, dTTP, dGTP, and dCTP, 2.5 units of Platinum Pfx DNA Polymerase (Invitrogen, Carlsbad, Calif.), 1 μl of 50 mM $MgSO_4$ and 2.5 μl of 10×pCRx Enhancer solution (Invitrogen, Carlsbad, Calif.) in a final volume of 50 μl. The amplification conditions were one cycle at 94° C. for 2 minutes; 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using 40 mM Tris base-20 mM sodium acetate-1 mM disodium EDTA (TAE) buffer where a 3 kb product band was excised from the gel and purified using a QIAquick Gel Extraction Kit (QIAGEN, Valencia, Calif.) according to the manufacturer's instructions.

Figure 14:
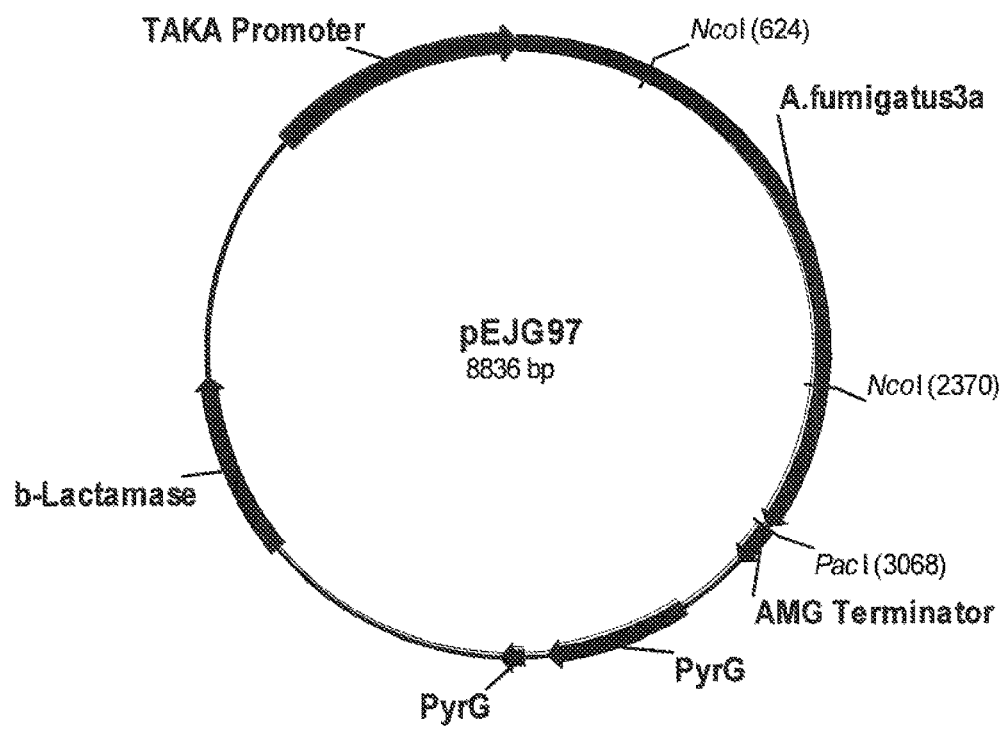
FIG. 14 shows a restriction map of pEJG97.

The fragment was then cloned into the pAlLo2 expression vector using an Infusion Cloning Kit. The vector was digested with restriction endonucleases Nco I and Pac I (using conditions specified by the manufacturer). The fragment was purified by gel electrophoresis and Qiaquick gel purification. The gene fragment and the cut vector were ligated together in a reaction resulting in the expression plasmid pEJG97 (FIG. 14) in which transcription of the Family GH3A beta-glucosidase gene was under the control of the NA2-tpi promoter. The reaction (50 μl) was composed of 1×InFusion Buffer (BD Biosciences, Palo Alto, Calif.), 1×BSA (BD Biosciences, Palo Alto, Calif.), 1 μl of Infusion enzyme (diluted 1:10) (BD Biosciences, Palo Alto, Calif.), 150 ng of pAlLo2 digested with Nco I and Pac I, and 50 ng of the *Aspergillus fumigatus* beta-glucosidase purified PCR product. The reaction was incubated at room temperature for 30 minutes. One μl of the reaction was used to transform *E. coli* XL10 Solopac Gold cells (Stratagene, La Jolla, Calif.). An *E. coli* transformant containing the pEJG97 plasmid was detected by restriction digestion and plasmid DNA was prepared using a BioRobot 9600 (QIAGEN, Inc., Valencia, Calif.).

Example 21

Characterization of the *Aspergillus fumigatus* Genomic Sequence Encoding a Family GH3A Beta-glucosidase DNA sequencing of the *Aspergillus fumigatus* beta-glucosidase gene from pEJG97 was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.).

Figure 15A:
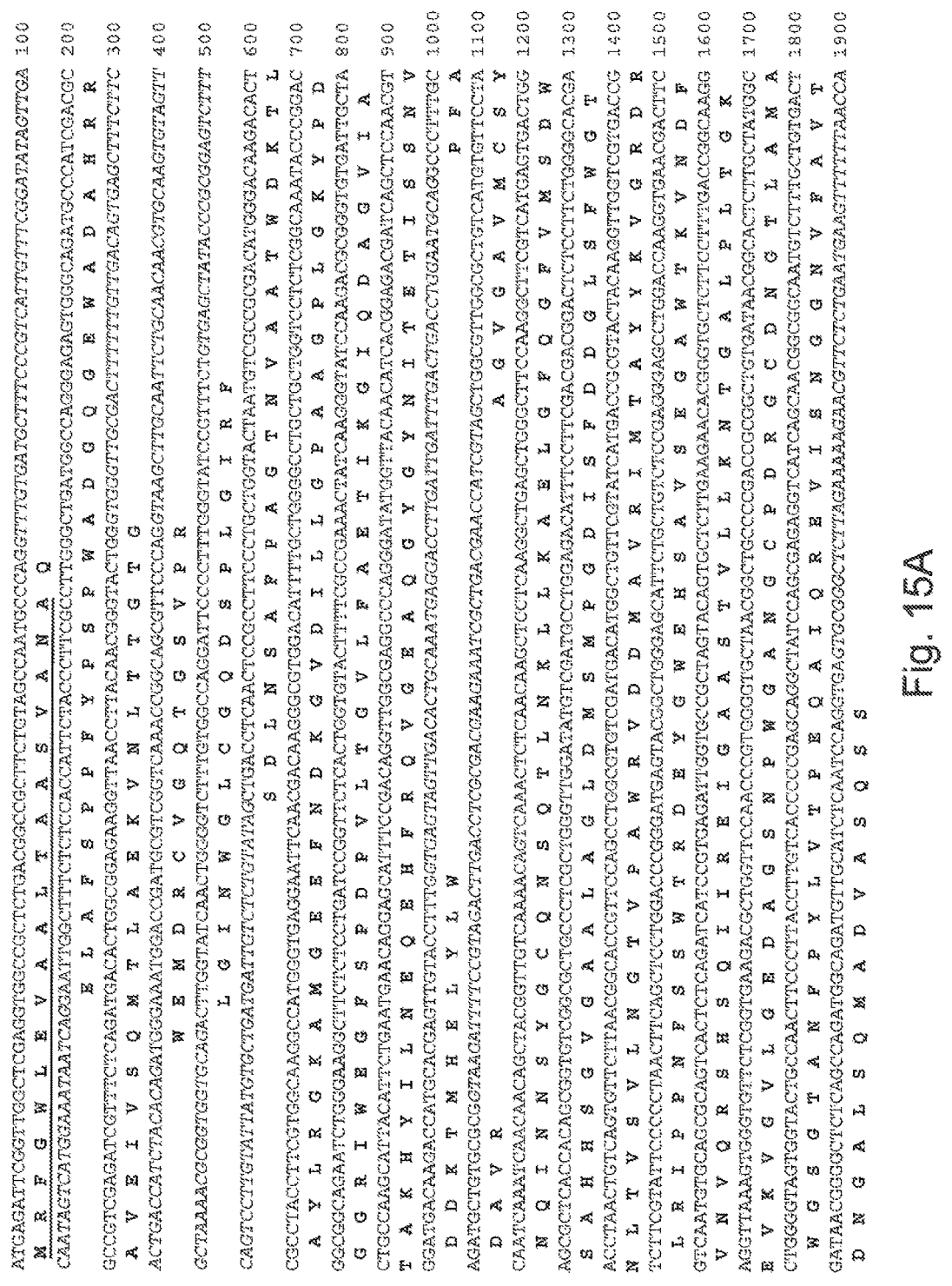
Figure 15B:
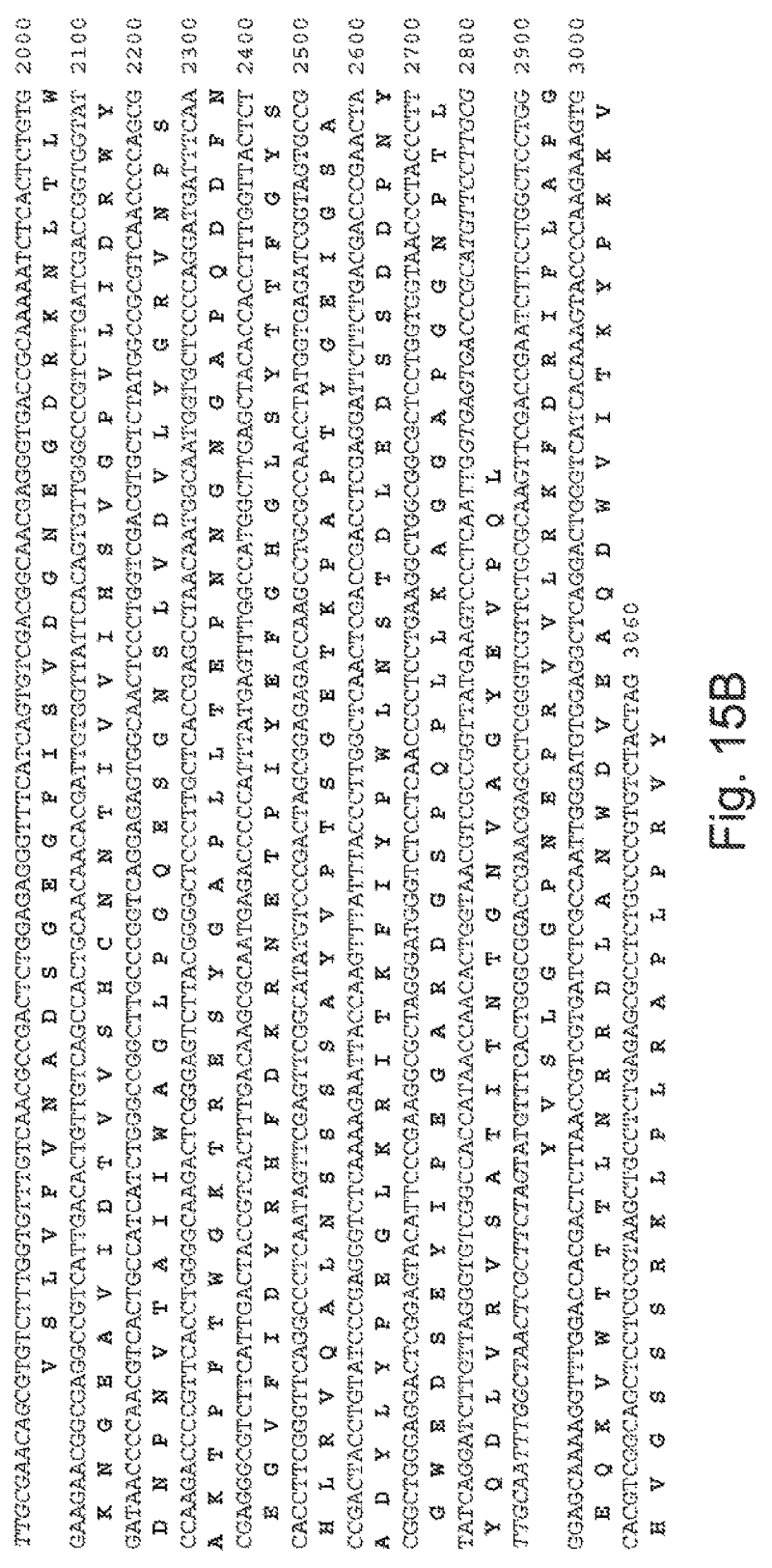

A gene model for the *Aspergillus fumigatus* sequence was constructed based on similarity to homologous genes from *Aspergillus aculeatus*, *Aspergillus niger*, and *Aspergillus kawachii*. The nucleotide sequence (SEQ ID NO: 56) and deduced amino acid sequence (SEQ ID NO: 57) are shown in FIG. 15. The genomic fragment encodes a polypeptide of 863 amino acids, interrupted by 8 introns of 62, 55, 58, 63, 58, 58, 63 and 51 bp. The % G+C content of the gene is 54.3%. Using the SignalP software program (Nielsen et al., 1997, *Protein Engineering* 10: 1-6), a signal peptide of 19 residues was predicted. The predicted mature protein contains 844 amino acids with a molecular mass of 91.7 kDa.

A comparative alignment of beta-glucosidase sequences was determined using the Clustal W method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* beta-glucosidase gene shared 78%, 76%, and 76% identity to the deduced amino acid sequences of the *Aspergillus aculeatus* (accession number P48825), *Aspergillus niger* (000089), and *Aspergillus kawachii* (P87076) beta-glucosidases.

Example 22

Expression of the *Aspergillus fumigatus* Family GH3A Beta-Glucosidase Gene in *Aspergillus oryzae* JAL250

*Aspergillus oryzae* Ja1250 protoplasts were prepared according to the method of Christensen et al., 1988, *Bio/Technology* 6: 1419-1422. Five μg of pEJG97 (as well as pAlLo2 as a vector control) was used to transform *Aspergillus oryzae* JAL250.

The transformation of *Aspergillus oryzae* Ja1250 with pEJG97 yielded about 100 transformants. Ten transformants were isolated to individual PDA plates.

Confluent PDA plates of five of the ten transformants were washed with 5 ml of 0.01% Tween 20 and inoculated separately into 25 ml of MDU2BP medium in 125 ml glass shake flasks and incubated at 34° C., 250 rpm. Five days after incubation, 0.5 μl of supernatant from each culture was analyzed using 8-16% Tris-Glycine SDS-PAGE gels (Invitrogen, Carlsbad, Calif.) according to the manufacturer's instructions. SDS-PAGE profiles of the cultures showed that one of the transformants (designated transformant 1) had a major band of approximately 130 kDa.

A confluent plate of transformant 1 (grown on PDA) was washed with 10 ml of 0.01% Tween 20 and inoculated into a 2 liter Fernbach containing 400 ml of MDU2BP medium to generate broth for characterization of the enzyme. The flask was harvested on day 5 and filtered using a 0.22 μm GP Express plus Membrane (Millipore, Bedford, Mass.).

A single transformant of pEJG97 in *Aspergillus oryzae* was grown in a fermentation tank. Spores of *Aspergillus oryzae* were inoculated into 500 ml shake flasks, containing 100 ml of Inoculum Medium. The flasks were placed into an orbital shaker at 34° C., at 200 rpm for approximately 24 hours at which time 50 ml of the culture was inoculated into 1.8 liters of Fermentation Medium in a 2 liter fermentation vessel. The fermentations were run at pH 7.0, 34° C., with minimum dissolved oxygen at 25% at a 1.0 VVM air flow and an agitation of 1100. Feed Medium was administrated into the fermentation vessel at the dissolved oxygen spike with a feed rate of 4 g/hour. The fermentations ran for 164 hours at which time the final fermentation broths were centrifuged and the supernatants stored at −20° C.

Example 23

Characterization of *Aspergillus fumigatus* Beta-glucosidase

A 3 ml aliquot of the *Aspergillus fumigatus* beta-glucosidase, obtained as described in Example 22, was desalted using a BioRad Econo-Pac 10DG desalting column (Bio-Rad, Hercules, Calif.), resulting in approx. 4 ml of desalted broth in 100 mM sodium citrate pH 5.0. The desalted broth was then concentrated to approximately 180 μl using an Amicon Centricon Plus-20 (Biomax-5, 5 kDa cutoff, PES membrane) and diluted with 100 mM sodium citrate pH 5.0 to a final volume of approximately 500 μl. BCA assay (Smith et al., 1985, *Anal. Biochem.* 150: 76-85) of the desalted, concentrated broth showed a concentration of 1.00 mg of protein per ml. A second aliquot was also desalted to obtain more material, which yielded similar results.

SDS-PAGE (BioRad Criterion 7.5% Tris-HCl) of the concentrated desalted samples showed a major band at approx. 130 kD. The major band at 130 kD was cut out of the gel and submitted to N-terminal amino acid sequencing.

The *Aspergillus fumigatus* beta-glucosidase from the desalted/concentrated broth was evaluated for thermal stability at 50°, 65°, and 70° C. Assay conditions at 50° and 65° C. were: 100 mM sodium citrate pH 5.0, 0.01% Tween-20, 4 mM p-nitrophenyl-beta-D-glucopyranoside, $[\text{protein}]_{AfumGH3A}=6.9\times10^{-6}$ mg/ml, incubated at 50° and 65° C. Aliquots were taken at 0.5, 1, 2, 3, 3.75, and 24 hours. To each aliquot was added 1 M sodium carbonate pH 10.0, and the p-nitrophenyl anion concentration was determined from the absorbance at 405 nm. At 70° C., the assay conditions were: 100 mM sodium citrate (pH 5.0), 0.01% Tween-20, 4 mM p-nitrophenyl-beta-D-glucopyranoside, $[\text{protein}]=5.6\times10^{-6}$ mg/ml. Aliquots were taken at 0.25, 0.5, 1, 2, 4, and 5 hours. To each aliquot was added 1 M sodium carbonate pH 10.0, and the p-nitrophenyl anion concentration was determined from the absorbance at 405 nm. Note that each of the above protein concentrations refers to total protein concentration in the assay, as they were all assayed as broths rather than purified enzymes.

Figure 16:
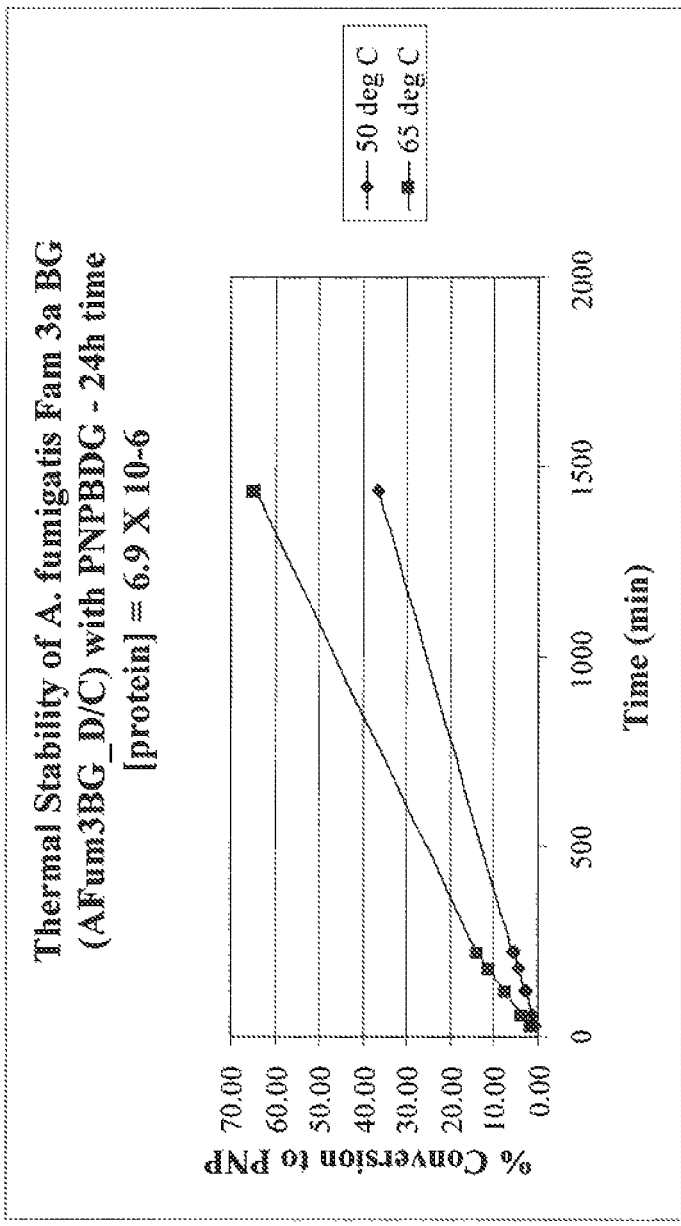
FIG. 16 shows the thermal stability of *Aspergillus fumigatus* beta-glucosidase at 50° and 65° C.
Figure 17:
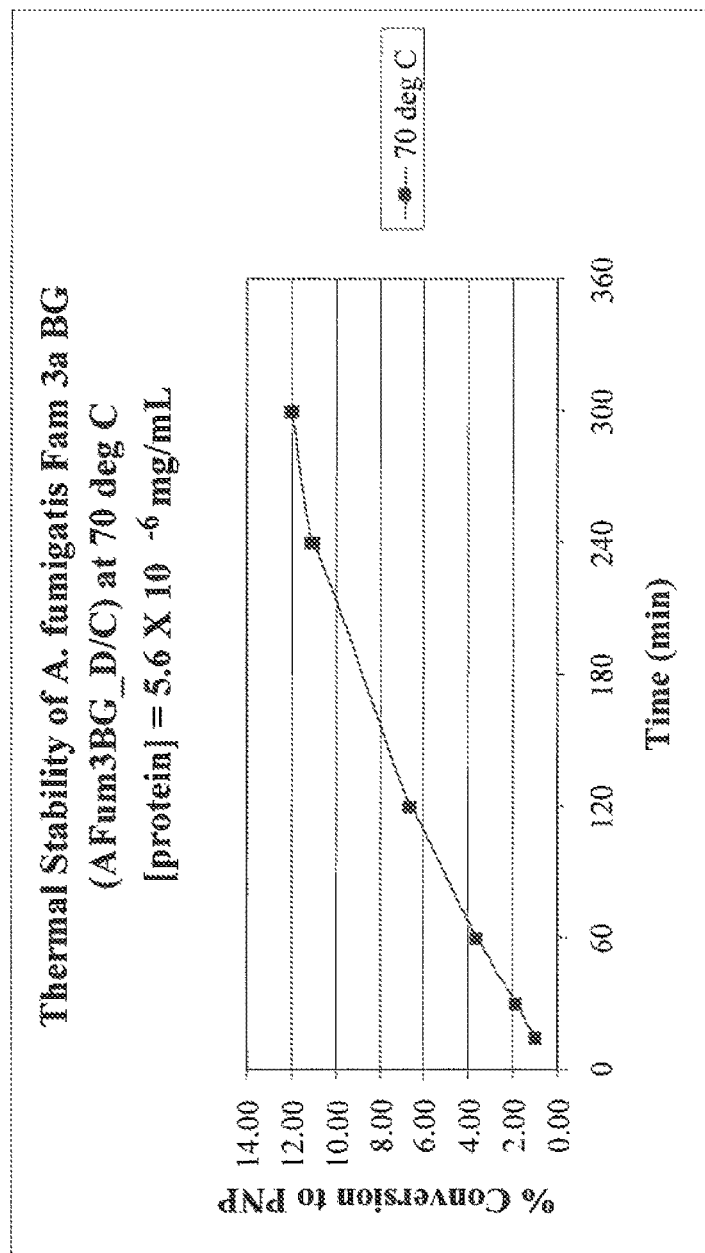
FIG. 17 shows the thermal stability of *Aspergillus fumigatus* beta-glucosidase at 70° C.

The results are shown in FIGS. 16 and 17. Thermal stability was defined as linear reaction kinetics for a given time interval, within a reasonable percent conversion (<15%) to p-nitrophenyl anion. The *Aspergillus fumigatus* beta-glucosidase appeared to be stable at least 24 hours at 50° C., although there were no time points between 4 hours and 24 hours. At 65° C. it appeared to be stable at least 3.75 hours, but afterward the stability gradually decreased with a 65% conversion to p-nitrophenyl anion at 24 hours. This conversion was quite high, so some of the observed decrease in rate may have been due to depletion of substrate and/or product inhibition in addition to possible thermal inactivation. At 70° C. it appeared to be stable for 1 hour, and reasonably stable to 2 hours.

Figure 18:
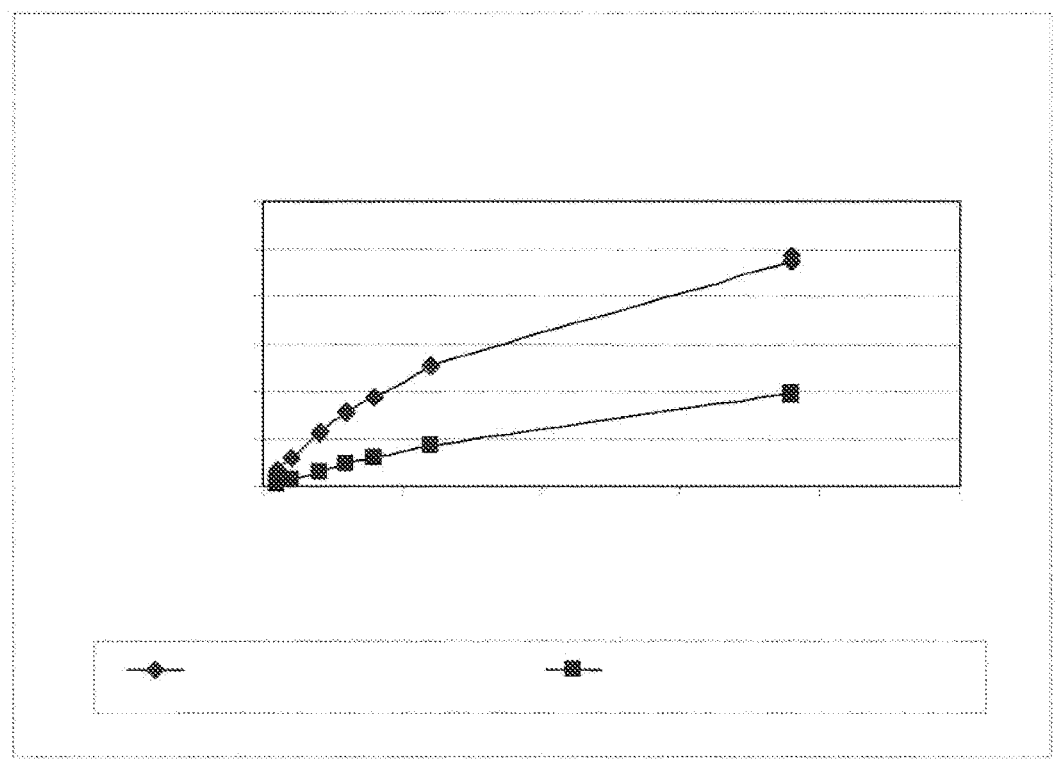
FIG. 18 shows the hydrolysis of cellobiose by *Aspergillus fumigatus* beta-glucosidase at 65° C.

Broth containing Family GH3A beta-glucosidase from *Aspergillus fumigatus*, obtained as described in Example 22, was first desalted (BioRad Econo-Pac 10DG column) and concentrated (Centricon Plus-20, Biomax-5, 5 kD cut-off), to a concentration of 0.92 mg/ml (BCA assay). Then, it was incubated at 0.037 and 0.0092 µg/ml total protein with 10 mM cellobiose in 100 mM sodium citrate pH 5.0 plus 0.01% Tween-20 at 65° C. Aliquots were taken at 0.5, 1, 2, 3, 4, 6, and 19 hours. Aliquots were boiled 6 minutes to terminate the reaction, and the glucose concentration determined using the Trinder assay (Sigma Chemical Co., St. Louis, Mo.) and external glucose standards. Results are shown in FIG. 18. The beta-glucosidase appeared to maintain 90% of its activity to 6 hours, and 65% to 19 hours at 65° C. at the lower protein loading (0.0092 µg/ml). The beta-glucosidase appeared to be reasonably stable up to 6 hours at 65° C.

Example 24

Assay of Cel7A Variant 776-M57 in Combination with *Trichoderma* Cellulases

Pretreated corn stover (PCS) was obtained from U.S. Department of Energy National Renewable Energy Laboratory (NREL). The water-insoluble solids in PCS include: 56.5% cellulose, 4.6% hemicellulose, and 28.4% lignin. Pretreatment conditions were: corn stover, 1.4% (wt/vol) sulfuric acid, 165° C., 107 p.s.i., for 8 minutes. Prior to assay, PCS was washed with a large volume of distilled deionized water on a glass filter. PCS was then milled using a coffee grinder to reduce particle size, then washed further with water on a 22 µm Millipore filter (6P Express Membrane, Stericup, Millipore, Billerica, Mass.). The washed PCS was resuspended in deionized water to make a 20 mg/ml suspension, and stored at 4° C.

*Trichoderma reesei* fermentation broths were filtered (0.4 µm Membrane, Stericup, Millipore, Billerica, Mass.), and protein content was assayed by BCA assay (Pierce Biotech., Inc., Rockford, Ill.). The thermostable beta-glucosidase from *Aspergillus fumigatus* was used in the PCS assays. The *Aspergillus fumigatus* beta-glucosidase was prepared as described in Example 22. Fermentation broths of the heterologously expressed *Aspergillus fumigatus* beta-glucosidase were filtered (0.4 µm Membrane, Stericup, Millipore, Billerica, Mass.), and protein content was assayed by BCA assay (Pierce, Biotech., Inc., Rockford, Ill.). PCS assays were carried out in a volume of 1.0 ml. Assays included 10 mg of PCS per ml, 50 mM sodium acetate buffer (pH 5.0), 8.5 mg of total fermentation broth protein per gram of cellulose, and 0.27 mg of *Aspergillus fumigatus* beta-glucosidase fermentation broth. Assays were maintained at 55° C. and at 60° C. in sealed assay tubes (ImmunoWare Microtubes, Pierece Biotech., Inc., Rockford, Ill.) for 5 days with intermittent inversion of assay tubes.

Approximately every 24 hours, time points were taken from the PCS reactions. Ten microliter aliquots were removed from the assay tubes into 90 µl of alkaline quench mixture (0.102 M $Na_2CO_3$ plus 0.058 M $NaHCO_3$). Dilution of the quenched samples to one-eighth or one-sixteenth of the starting concentration was performed. The concentration of reducing sugars in samples produced by degradation of PCS was determined by p-hydroxybenzoic acid hydrazide (PHBAH) assay (Lever, 1972, *Anal Biochem* 47: 273-279) using 2 parts of 1.25% PHBAH in alkaline quench mixture added to 3 parts of the quenched assay solution. This solution was then heated for 10 minutes at 95° C., samples were then diluted into water, and absorbance was measured at 405 nm using a UltraMark Plate Reader (Bio-Rad, Hercules, Calif.). The absorbance at 405 nm was converted into glucose equivalents using a glucose standard curve. Finally, the degree of cellulose conversion was calculated, using the initial concentration of cellulose, and a weight gain factor in converting cellulose to glucose. The degree of cellulose conversion to reducing sugar (RS yield, %) was calculated using the following equation:

$$RS\ \text{Yield}_{(\%)} = RS_{(mg/ml)} * 100 * 162/(5.65_{(mg/ml)} * 180)$$
$$= RS_{(mg/ml)} * 100/(5.65_{(mg/ml)} * 1.111)$$

Figure 19:
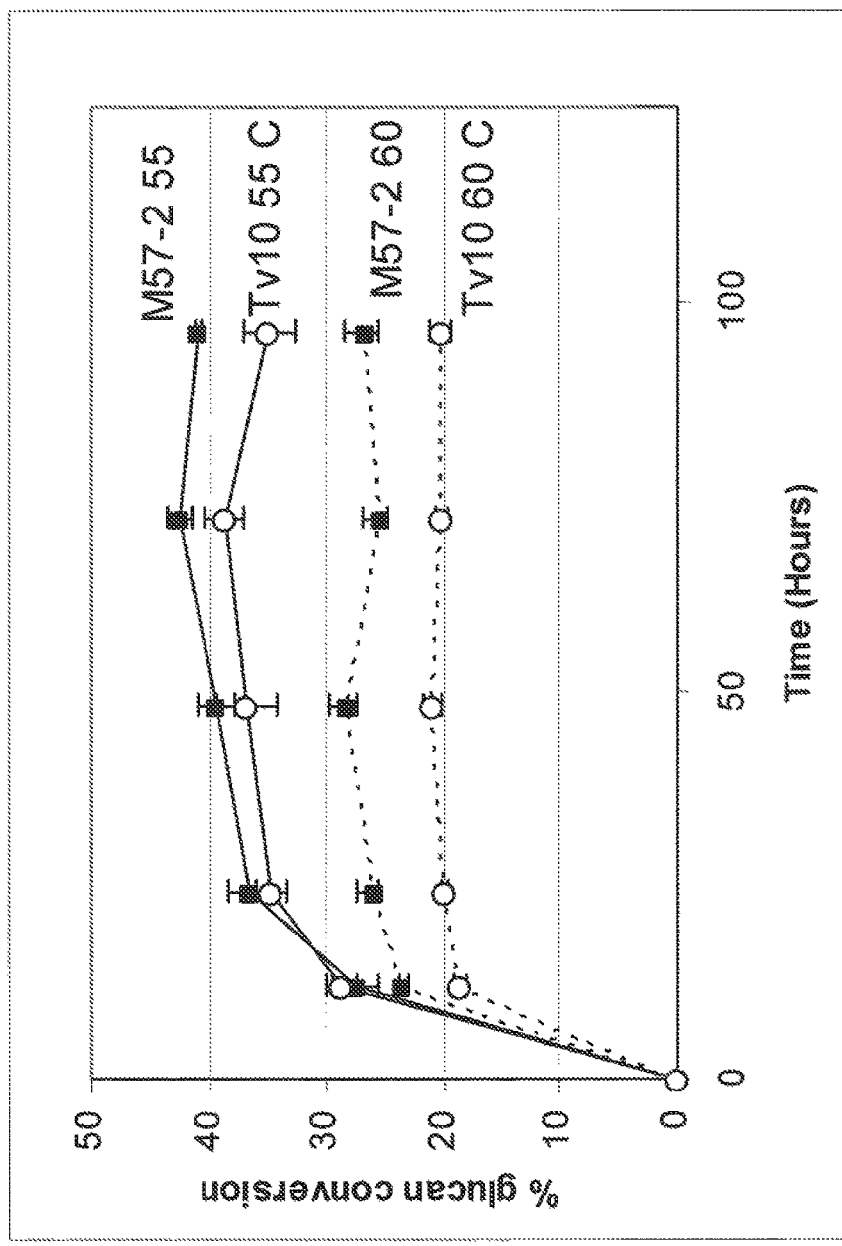
FIG. 19 shows the time course profiles of PCS hydrolysis by the parent *Trichoderma reesei* strain RutC30 and the strain expressing variant 776-M57.

FIG. 19 shows the time course profiles of PCS hydrolysis by the parent *Trichoderma reesei* strain, and the strain which expresses variant 776-M57 in place of the wild type Cel7A cellobiohydrolase I. It is apparent that the strain containing the variant outperforms the parent under these conditions.

Deposit of Biological Materials

The following biological materials have been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
|---|---|---|
| pAJO52 | NRRL B-30683 | Jul. 29, 2003 |
| 776-M1 | NRRL B-30657 | May 22, 2003 |
| 776-M4 | NRRL B-30658 | May 22, 2003 |
| 776-M23 | NRRL B-30659 | May 22, 2003 |
| 776-M26 | NRRL B-30661 | May 22, 2003 |
| 776-M32 | NRRL B-30662 | May 22, 2003 |
| 776-M53 | NRRL B-30663 | May 22, 2003 |
| 776-M57 | NRRL B-30664 | May 22, 2003 |
| 776-M108 | NRRL B-30665 | May 22, 2003 |
| 776-M109 | NRRL B-30666 | May 22, 2003 |
| 776-M21 | NRRL B-30674 | Jul. 28, 2003 |
| 776-M22 | NRRL B-30675 | Jul. 28, 2003 |
| 776-M41 | NRRL B-30676 | Jul. 28, 2003 |
| 776-M42 | NRRL B-30677 | Jul. 28, 2003 |
| 776-M52 | NRRL B-30678 | Jul. 28, 2003 |
| 776-M71 | NRRL B-30679 | Jul. 28, 2003 |
| 776-M73 | NRRL B-30680 | Jul. 28, 2003 |
| 776-M124 | NRRL B-30681 | Jul. 28, 2003 |
| 776-M125 | NRRL B-30682 | Jul. 28, 2003 |
| 776-M273 | NRRL B-30762 | Aug. 25, 2004 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A variant of a parent glycoside hydrolase, comprising a substitution at a position corresponding to position 157 of SEQ ID NO: 2, wherein the variant glycoside hydrolase has at least 95% sequence identity to amino acids 1 to 513 SEQ ID NO: 2, and wherein the variant has glycoside hydrolase activity.

2. The variant of claim 1, which has cellobiohydrolase activity.

3. The variant of claim 1, which has cellobiohydrolase I activity.

4. The variant of claim 1, which is a Family 7 cellobiohydrolase CBH I.

5. The variant of claim 4, which has at least 96% sequence identity to amino acids 1 to 513 of SEQ ID NO: 2.

6. The variant of claim 4, which has at least 97% sequence identity to amino acids 1 to 513 of SEQ ID NO: 2.

7. The variant of claim 4, wherein the substitution is with Arg.

8. The variant of claim 4, wherein the substitution is K157R.

9. The variant of claim 4, further comprising a substitution at one or more positions corresponding to positions 21, 94, 205, 206, 247, 337, 350, 373, 383, 438, 455, 467, and 486 of SEQ ID NO: 2.

10. The variant of claim 9, wherein
the substitution at a position corresponding to position 21 is with Pro,
the substitution at a position corresponding to position 94 is with Ser, Ala, Arg, or Gln,
the substitution at a position corresponding to position 205 is with Arg,
the substitution at a position corresponding to position 206 is with Tyr,
the substitution at a position corresponding to position 247 is with Cys,
the substitution at a position corresponding to position 337 is with Val,
the substitution at a position corresponding to position 350 is with Ser,
the substitution at a position corresponding to position 373 is with His,
the substitution at a position corresponding to position 383 is with Ala,
the substitution at a position corresponding to position 438 is with Leu,
the substitution at a position corresponding to position 455 is with Ala,
the substitution at a position corresponding to position 467 is with Ser, and
the substitution at a position corresponding to position 486 is with Trp.

11. The variant of claim 4, further comprising a substitution at positions corresponding to positions 205 and 255.

12. The variant of claim 11, wherein
the substitution at a position corresponding to position 205 is with Arg, and
the substitution at a position corresponding to position 255 is with Pro.

13. The variant of claim 4, further comprising substitutions at positions corresponding to positions 205, 255, and 411.

14. The variant of claim 13, wherein
the substitution at a position corresponding to position 205 is with Arg,
the substitution at a position corresponding to position 255 is with Pro, and
the substitution at a position corresponding to position 411 is with Phe.

15. The variant of claim 4, further comprising a substitution at one or more positions corresponding to positions 8, 22, 41, 49, 57, 113, 193, 196, 226, 227, 246, 251, 255, 259, 301, 356, 371, 411, and 462 of SEQ ID NO: 2.

16. The variant of claim 15, wherein
the substitution at a position corresponding to position 8 is with Pro, the substitution at a position corresponding to position 22 is with Asp,
the substitution at a position corresponding to position 41 is with Ile,
the substitution at a position corresponding to position 49 is with Ser,
the substitution at a position corresponding to position 57 is with Asn,
the substitution at a position corresponding to position 113 is with Asn,
the substitution at a position corresponding to position 193 is with Lys,
the substitution at a position corresponding to position 196 is with Thr,
the substitution at a position corresponding to position 226 is with Ala,
the substitution at a position corresponding to position 227 is with Ala,
the substitution at a position corresponding to position 246 is with Ile,
the substitution at a position corresponding to position 251 is with Lys,
the substitution at a position corresponding to position 255 is with Pro,
the substitution at a position corresponding to position 259 is with Asn,
the substitution at a position corresponding to position 301 is with Ser,
the substitution at a position corresponding to position 356 is with Ile,
the substitution at a position corresponding to position 371 is with Cys,
the substitution at a position corresponding to position 411 is with Phe, and
the substitution at a position corresponding to position 462 is with Ala.

17. A detergent composition comprising the variant of claim 4 and a surfactant.

18. A method for degrading cellulose- and hemicellulose-containing biomass, comprising treating the biomass with an effective amount of a variant of claim 1, an endoglucanase, and a beta-glucosidase.

19. The method of claim 18, further comprising recovering the degraded biomass.

20. A method for producing ethanol, comprising
(a) degrading biomass according to the method of claim 18; and
(b) converting the degraded biomass to ethanol.

21. The method of claim 20, further comprising recovering the ethanol.

* * * * *

SEQUENCE LISTING

```
<160> NUMBER OF SEQ ID NOS: 57

<210> SEQ ID NO 1
<211> LENGTH: 1545
<212> TYPE: DNA
<213> ORGANISM: Trichoderma reesei
<220> FEATURE:
<221> NAME/KEY: CDS
<222> LOCATION: (1)..(1539)
<220> FEATURE:
<221> NAME/KEY: sig_peptide
<222> LOCATION: (1)..(51)
<220> FEATURE:
<221> NAME/KEY: mat_peptide
<222> LOCATION: (52)..()

<400> SEQUENCE: 1 atg tat cgg aag ttg gcc gtc atc tcg gcc ttc ttg gcc aca gct cgt      48
Met Tyr Arg Lys Leu Ala Val Ile Ser Ala Phe Leu Ala Thr Ala Arg
        -15                 -10                  -5 gct cag tcg gcc tgc act ctc caa tcg gag act cac ccg cct ctg aca      96
Ala Gln Ser Ala Cys Thr Leu Gln Ser Glu Thr His Pro Pro Leu Thr
 -1   1               5                  10                  15 tgg cag aaa tgc tcg tct ggt ggc acg tgc act caa cag aca ggc tcc     144
Trp Gln Lys Cys Ser Ser Gly Gly Thr Cys Thr Gln Gln Thr Gly Ser
                 20                  25                  30 gtg gtc atc gac gcc aac tgg cgc tgg act cac gct acg aac agc agc     192
Val Val Ile Asp Ala Asn Trp Arg Trp Thr His Ala Thr Asn Ser Ser
             35                  40                  45 acg aac tgc tac gat ggc aac act tgg agc tcg acc cta tgt cct gac     240
Thr Asn Cys Tyr Asp Gly Asn Thr Trp Ser Ser Thr Leu Cys Pro Asp
         50                  55                  60 aac gag acc tgc gcg aag aac tgc tgt ctg gac ggt gcc gcc tac gcg     288
Asn Glu Thr Cys Ala Lys Asn Cys Cys Leu Asp Gly Ala Ala Tyr Ala
 65                  70                  75 tcc acg tac gga gtt acc acg agc ggt aac agc ctc tcc att ggc ttt     336
Ser Thr Tyr Gly Val Thr Thr Ser Gly Asn Ser Leu Ser Ile Gly Phe
 80                  85                  90                  95 gtc acc cag tct gcg cag aag aac gtt ggc gct cgc ctt tac ctt atg     384
```

```
       Val Thr Gln Ser Ala Gln Lys Asn Val Gly Ala Arg Leu Tyr Leu Met
                       100                 105                 110 gcg agc gac acg acc tac cag gaa ttc acc ctg ctt ggc aac gag ttc        432
Ala Ser Asp Thr Thr Tyr Gln Glu Phe Thr Leu Leu Gly Asn Glu Phe
            115                 120                 125 tct ttc gat gtt gat gtt tcg cag ctg ccg tgc ggc ttg aac gga gct        480
Ser Phe Asp Val Asp Val Ser Gln Leu Pro Cys Gly Leu Asn Gly Ala
        130                 135                 140 ctc tac ttc gtg tcc atg gac gcg gat ggt ggc gtg agc aag tat ccc        528
Leu Tyr Phe Val Ser Met Asp Ala Asp Gly Gly Val Ser Lys Tyr Pro
        145                 150                 155 acc aac acc gct ggc gcc aag tac ggc acg ggg tac tgt gac agc cag        576
Thr Asn Thr Ala Gly Ala Lys Tyr Gly Thr Gly Tyr Cys Asp Ser Gln
160                 165                 170                 175 tgt ccc cgc gat ctg aag ttc atc aat ggc cag gcc aac gtt gag ggc        624
Cys Pro Arg Asp Leu Lys Phe Ile Asn Gly Gln Ala Asn Val Glu Gly
                    180                 185                 190 tgg gag ccg tca tcc aac aac gcg aac acg ggc att gga gga cac gga        672
Trp Glu Pro Ser Ser Asn Asn Ala Asn Thr Gly Ile Gly Gly His Gly
                195                 200                 205 agc tgc tgc tct gag atg gat atc tgg gag gcc aac tcc atc tcc gag        720
Ser Cys Cys Ser Glu Met Asp Ile Trp Glu Ala Asn Ser Ile Ser Glu
            210                 215                 220 gct ctt acc ccc cac cct tgc acg act gtc ggc cag gag atc tgc gag        768
Ala Leu Thr Pro His Pro Cys Thr Thr Val Gly Gln Glu Ile Cys Glu
        225                 230                 235 ggt gat ggg tgc ggc gga act tac tcc gat aac aga tat ggc ggc act        816
Gly Asp Gly Cys Gly Gly Thr Tyr Ser Asp Asn Arg Tyr Gly Gly Thr
240                 245                 250                 255 tgc gat ccc gat ggc tgc gac tgg aac cca tac cgc ctg ggc aac acc        864
Cys Asp Pro Asp Gly Cys Asp Trp Asn Pro Tyr Arg Leu Gly Asn Thr
                    260                 265                 270 agc ttc tac ggc cct ggc tca agc ttt acc ctc gat acc acc aag aaa        912
Ser Phe Tyr Gly Pro Gly Ser Ser Phe Thr Leu Asp Thr Thr Lys Lys
                275                 280                 285 ttg acc gtt gtc acc cag ttc gag acg tcg ggt gcc atc aac cga tac        960
Leu Thr Val Val Thr Gln Phe Glu Thr Ser Gly Ala Ile Asn Arg Tyr
            290                 295                 300 tat gtc cag aat ggc gtc act ttc cag cag ccc aac gcc gag ctt ggt       1008
Tyr Val Gln Asn Gly Val Thr Phe Gln Gln Pro Asn Ala Glu Leu Gly
        305                 310                 315 agt tac tct ggc aac gag ctc aac gat gat tac tgc aca gct gag gag       1056
Ser Tyr Ser Gly Asn Glu Leu Asn Asp Asp Tyr Cys Thr Ala Glu Glu
320                 325                 330                 335 gca gaa ttc ggc gga tcc tct ttc tca gac aag ggc ggc ctg act cag       1104
Ala Glu Phe Gly Gly Ser Ser Phe Ser Asp Lys Gly Gly Leu Thr Gln
                    340                 345                 350 ttc aag aag gct acc tct ggc ggc atg gtt ctg gtc atg agt ctg tgg       1152
Phe Lys Lys Ala Thr Ser Gly Gly Met Val Leu Val Met Ser Leu Trp
                355                 360                 365 gat gat tac tac gcc aac atg ctg tgg ctg gac tcc acc tac ccg aca       1200
Asp Asp Tyr Tyr Ala Asn Met Leu Trp Leu Asp Ser Thr Tyr Pro Thr
            370                 375                 380 aac gag acc tcc tcc aca ccc ggt gcc gtg cgc gga agc tgc tcc acc       1248
Asn Glu Thr Ser Ser Thr Pro Gly Ala Val Arg Gly Ser Cys Ser Thr
        385                 390                 395 agc tcc ggt gtc cct gct cag gtc gaa tct cag tct ccc aac gcc aag       1296
Ser Ser Gly Val Pro Ala Gln Val Glu Ser Gln Ser Pro Asn Ala Lys
400                 405                 410                 415
```

```
gtc acc ttc tcc aac atc aag ttc gga ccc att ggc agc acc ggc aac    1344
Val Thr Phe Ser Asn Ile Lys Phe Gly Pro Ile Gly Ser Thr Gly Asn
            420             425             430 cct agc ggc ggc aac cct ccc ggc gga aac ccg cct ggc acc acc acc    1392
Pro Ser Gly Gly Asn Pro Pro Gly Gly Asn Pro Pro Gly Thr Thr Thr
            435             440             445 acc cgc cgc cca gcc act acc act gga agc tct ccc gga cct acc cag    1440
Thr Arg Arg Pro Ala Thr Thr Thr Gly Ser Ser Pro Gly Pro Thr Gln
            450             455             460 tct cac tac ggc cag tgc ggt att ggc tac agc ggc ccc acg gtc        1488
Ser His Tyr Gly Gln Cys Gly Ile Gly Tyr Ser Gly Pro Thr Val
            465             470             475 tgc gcc agc ggc aca act tgc cag gtc ctg aac cct tac tac tct cag    1536
Cys Ala Ser Gly Thr Thr Cys Gln Val Leu Asn Pro Tyr Tyr Ser Gln
480             485             490             495 tgc ctgtaa                                                         1545
Cys

<210> SEQ ID NO 2
<211> LENGTH: 513
<212> TYPE: PRT
<213> ORGANISM: Trichoderma reesei

<400> SEQUENCE: 2

Met Tyr Arg Lys Leu Ala Val Ile Ser Ala Phe Leu Ala Thr Ala Arg
        -15             -10                 -5

Ala Gln Ser Ala Cys Thr Leu Gln Ser Glu Thr His Pro Pro Leu Thr
-1  1               5                   10                  15

Trp Gln Lys Cys Ser Ser Gly Gly Thr Cys Thr Gln Thr Gly Ser
            20                  25                  30

Val Val Ile Asp Ala Asn Trp Arg Trp Thr His Ala Thr Asn Ser Ser
            35                  40                  45

Thr Asn Cys Tyr Asp Gly Asn Thr Trp Ser Ser Thr Leu Cys Pro Asp
            50                  55                  60

Asn Glu Thr Cys Ala Lys Asn Cys Cys Leu Asp Gly Ala Ala Tyr Ala
65                  70                  75

Ser Thr Tyr Gly Val Thr Thr Ser Gly Asn Ser Leu Ser Ile Gly Phe
80                  85                  90                  95

Val Thr Gln Ser Ala Gln Lys Asn Val Gly Ala Arg Leu Tyr Leu Met
            100                 105                 110

Ala Ser Asp Thr Thr Tyr Gln Glu Phe Thr Leu Leu Gly Asn Glu Phe
            115                 120                 125

Ser Phe Asp Val Asp Val Ser Gln Leu Pro Cys Gly Leu Asn Gly Ala
            130                 135                 140

Leu Tyr Phe Val Ser Met Asp Ala Asp Gly Gly Val Ser Lys Tyr Pro
            145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
            180                 185                 190

Trp Glu Pro Ser Ser Asn Asn Ala Asn Thr Gly Ile Gly Gly His Gly
            195                 200                 205

Ser Cys Cys Ser Glu Met Asp Ile Trp Glu Ala Asn Ser Ile Ser Glu
            210                 215                 220

Ala Leu Thr Pro His Pro Cys Thr Thr Val Gly Gln Glu Ile Cys Glu
225                 230                 235
```

Gly Asp Gly Cys Gly Thr Tyr Ser Asp Asn Arg Tyr Gly Gly Thr
240                 245                 250                 255

Cys Asp Pro Asp Gly Cys Asp Trp Asn Pro Tyr Arg Leu Gly Asn Thr
                260                 265                 270

Ser Phe Tyr Gly Pro Gly Ser Ser Phe Thr Leu Asp Thr Thr Lys Lys
            275                 280                 285

Leu Thr Val Val Thr Gln Phe Glu Thr Ser Gly Ala Ile Asn Arg Tyr
        290                 295                 300

Tyr Val Gln Asn Gly Val Thr Phe Gln Gln Pro Asn Ala Glu Leu Gly
    305                 310                 315

Ser Tyr Ser Gly Asn Glu Leu Asn Asp Asp Tyr Cys Thr Ala Glu Glu
320                 325                 330                 335

Ala Glu Phe Gly Gly Ser Ser Phe Ser Asp Lys Gly Gly Leu Thr Gln
                340                 345                 350

Phe Lys Lys Ala Thr Ser Gly Gly Met Val Leu Val Met Ser Leu Trp
            355                 360                 365

Asp Asp Tyr Tyr Ala Asn Met Leu Trp Leu Asp Ser Thr Tyr Pro Thr
        370                 375                 380

Asn Glu Thr Ser Ser Thr Pro Gly Ala Val Arg Gly Ser Cys Ser Thr
385                 390                 395

Ser Ser Gly Val Pro Ala Gln Val Glu Ser Gln Ser Pro Asn Ala Lys
400                 405                 410                 415

Val Thr Phe Ser Asn Ile Lys Phe Gly Pro Ile Gly Ser Thr Gly Asn
                420                 425                 430

Pro Ser Gly Gly Asn Pro Pro Gly Gly Asn Pro Pro Gly Thr Thr Thr
            435                 440                 445

Thr Arg Arg Pro Ala Thr Thr Thr Gly Ser Ser Pro Gly Pro Thr Gln
        450                 455                 460

Ser His Tyr Gly Gln Cys Gly Gly Ile Gly Tyr Ser Gly Pro Thr Val
    465                 470                 475

Cys Ala Ser Gly Thr Thr Cys Gln Val Leu Asn Pro Tyr Tyr Ser Gln
480                 485                 490                 495

Cys

<210> SEQ ID NO 3
<211> LENGTH: 20
<212> TYPE: DNA
<213> ORGANISM: E. coli

<400> SEQUENCE: 3
taatacgact cactataggg                                              20

<210> SEQ ID NO 4
<211> LENGTH: 67
<212> TYPE: DNA
<213> ORGANISM: Trichoderma reesei

<400> SEQUENCE: 4
tatacctcta tactttaacg tcaaggagaa aaaactatag gatccaccat gtatcggaag    60
ttggccg                                                             67

<210> SEQ ID NO 5
<211> LENGTH: 65
<212> TYPE: DNA
<213> ORGANISM: Trichoderma reesei

<400> SEQUENCE: 5

```
cataactaat tacatgatgc ggccctctag atgcacatga ctcgagttac aggcactgag    60
agtag                                                                65

<210> SEQ ID NO 6
<211> LENGTH: 67
<212> TYPE: DNA
<213> ORGANISM: Saccharomyces cerevisiae

<400> SEQUENCE: 6
tatacctcta tactttaacg tcaaggagaa aaaactatag gatccaccat gtatcggaag    60
ttggccg                                                              67

<210> SEQ ID NO 7
<211> LENGTH: 65
<212> TYPE: DNA
<213> ORGANISM: Saccharomyces cerevisiae

<400> SEQUENCE: 7
cataactaat tacatgatgc ggccctctag atgcacatga ctcgagttac aggcactgag    60
agtag                                                                65

<210> SEQ ID NO 8
<211> LENGTH: 20
<212> TYPE: DNA
<213> ORGANISM: Saccharomyces cerevisiae

<400> SEQUENCE: 8
ggcgtgaatg taagcgtgac                                                20

<210> SEQ ID NO 9
<211> LENGTH: 28
<212> TYPE: DNA
<213> ORGANISM: Saccharomyces cerevisiae

<400> SEQUENCE: 9
ctggggtaat taatcagcga agcgatga                                       28

<210> SEQ ID NO 10
<211> LENGTH: 19
<212> TYPE: DNA
<213> ORGANISM: Saccharomyces cerevisiae

<400> SEQUENCE: 10
gcgtacacgc gtctgtaca                                                 19

<210> SEQ ID NO 11
<211> LENGTH: 22
<212> TYPE: DNA
<213> ORGANISM: Aspergillus nidulans

<400> SEQUENCE: 11
gtgccccatg atacgcctcc gg                                             22

<210> SEQ ID NO 12
<211> LENGTH: 26
<212> TYPE: DNA
<213> ORGANISM: Aspergillus nidulans

<400> SEQUENCE: 12
gagtcgtatt tccaaggctc ctgacc                                         26
```

```
<210> SEQ ID NO 13
<211> LENGTH: 24
<212> TYPE: DNA
<213> ORGANISM: Aspergillus nidulans

<400> SEQUENCE: 13
ggaggccatg aagtggacca acgg                                              24

<210> SEQ ID NO 14
<211> LENGTH: 45
<212> TYPE: DNA
<213> ORGANISM: Aspergillus niger

<400> SEQUENCE: 14
caccgtgaaa gccatgctct tccttcgtg tagaagacca gacag                        45

<210> SEQ ID NO 15
<211> LENGTH: 45
<212> TYPE: DNA
<213> ORGANISM: Aspergillus niger

<400> SEQUENCE: 15
ctggtcttct acacgaagga aagagcatgg ctttcacggt gtctg                       45

<210> SEQ ID NO 16
<211> LENGTH: 44
<212> TYPE: DNA
<213> ORGANISM: Aspergillus oryzae

<400> SEQUENCE: 16
ctatatacac aactggattt accatgggcc cgcggccgca gatc                        44

<210> SEQ ID NO 17
<211> LENGTH: 44
<212> TYPE: DNA
<213> ORGANISM: Aspergillus oryzae

<400> SEQUENCE: 17
gatctgcggc cgcgggccca tggtaaatcc agttgtgtat atag                        44

<210> SEQ ID NO 18
<211> LENGTH: 22
<212> TYPE: DNA
<213> ORGANISM: Trichoderma reesei

<400> SEQUENCE: 18
gcaacatgta tcggaagttg gc                                                22

<210> SEQ ID NO 19
<211> LENGTH: 22
<212> TYPE: DNA
<213> ORGANISM: Trichoderma reesei

<400> SEQUENCE: 19
aattaatttt acaggcactg ag                                                22

<210> SEQ ID NO 20
<211> LENGTH: 33
<212> TYPE: DNA
<213> ORGANISM: Trichoderma reesei

<400> SEQUENCE: 20
gaacacgggc attggacgac acggaagctg ctg                                    33
```

<210> SEQ ID NO 21
<211> LENGTH: 33
<212> TYPE: DNA
<213> ORGANISM: Trichoderma reesei

<400> SEQUENCE: 21
cagcagcttc cgtgtcgtcc aatgcccgtg ttc          33

<210> SEQ ID NO 22
<211> LENGTH: 20
<212> TYPE: DNA
<213> ORGANISM: Trichoderma reesei

<400> SEQUENCE: 22
cttcttggcc acagctcgtg                         20

<210> SEQ ID NO 23
<211> LENGTH: 20
<212> TYPE: DNA
<213> ORGANISM: Trichoderma reesei

<400> SEQUENCE: 23
ggctttgtca cccagtctgc                         20

<210> SEQ ID NO 24
<211> LENGTH: 20
<212> TYPE: DNA
<213> ORGANISM: Trichoderma reesei

<400> SEQUENCE: 24
cgtcatccaa caacgcgaac                         20

<210> SEQ ID NO 25
<211> LENGTH: 20
<212> TYPE: DNA
<213> ORGANISM: Trichoderma reesei

<400> SEQUENCE: 25
ttcgagacgt cgggtgccat                         20

<210> SEQ ID NO 26
<211> LENGTH: 20
<212> TYPE: DNA
<213> ORGANISM: Trichoderma reesei

<400> SEQUENCE: 26
cgcggaagct gctccaccag                         20

<210> SEQ ID NO 27
<211> LENGTH: 20
<212> TYPE: DNA
<213> ORGANISM: Trichoderma reesei

<400> SEQUENCE: 27
aatggagagg ctgttaccgc                         20

<210> SEQ ID NO 28
<211> LENGTH: 67
<212> TYPE: DNA
<213> ORGANISM: Saccharomyces cerevisiae

<400> SEQUENCE: 28

-continued

```
tatacctcta tactttaacg tcaaggagaa aaaactatag gatccaccat gtatcggaag    60
ttggccg                                                              67

<210> SEQ ID NO 29
<211> LENGTH: 65
<212> TYPE: DNA
<213> ORGANISM: Saccharomyces cerevisiae

<400> SEQUENCE: 29
cataactaat tacatgatgc ggccctctag atgcacatga ctcgagttac aggcactgag    60
agtag                                                                65

<210> SEQ ID NO 30
<211> LENGTH: 28
<212> TYPE: DNA
<213> ORGANISM: Saccharomyces cerevisiae

<400> SEQUENCE: 30
ctggggtaat taatcagcga agcgatga                                       28

<210> SEQ ID NO 31
<211> LENGTH: 19
<212> TYPE: DNA
<213> ORGANISM: Saccharomyces cerevisiae

<400> SEQUENCE: 31
gcgtacacgc gtctgtaca                                                 19

<210> SEQ ID NO 32
<211> LENGTH: 31
<212> TYPE: DNA
<213> ORGANISM: Trichoderma reesei
<220> FEATURE:
<221> NAME/KEY: misc_feature
<222> LOCATION: (21)..(21)
<223> OTHER INFORMATION: N= A,C, G,OR T
<220> FEATURE:
<221> NAME/KEY: misc_feature
<222> LOCATION: (22)..(22)
<223> OTHER INFORMATION: N= A,C, G,OR T

<400> SEQUENCE: 32
gcggtaacag cctctccatt nnstttgtca c                                   31

<210> SEQ ID NO 33
<211> LENGTH: 33
<212> TYPE: DNA
<213> ORGANISM: Trichoderma reesei
<220> FEATURE:
<221> NAME/KEY: misc_feature
<222> LOCATION: (23)..(24)
<223> OTHER INFORMATION: N= A, C, G, OR T

<400> SEQUENCE: 33
ctgcgcagac tgggtgacaa asnnaatgga gag                                 33

<210> SEQ ID NO 34
<211> LENGTH: 32
<212> TYPE: DNA
<213> ORGANISM: Trichoderma reesei
<220> FEATURE:
<221> NAME/KEY: misc_feature
<222> LOCATION: (21)..(22)
<223> OTHER INFORMATION: N= A, C, G, OR T

<400> SEQUENCE: 34
```
ccatctccga ggctcttacc nnscaccctt gc    32

<210> SEQ ID NO 35
<211> LENGTH: 33
<212> TYPE: DNA
<213> ORGANISM: Trichoderma reesei
<220> FEATURE:
<221> NAME/KEY: misc_feature
<222> LOCATION: (24)..(25)
<223> OTHER INFORMATION: N= A, C, G, OR T

<400> SEQUENCE: 35
ggccgacagt cgtgcaaggg tgsnnggtaa gag    33

<210> SEQ ID NO 36
<211> LENGTH: 30
<212> TYPE: DNA
<213> ORGANISM: Trichoderma reesei
<220> FEATURE:
<221> NAME/KEY: misc_feature
<222> LOCATION: (19)..(20)
<223> OTHER INFORMATION: N= A, C, G, OR T

<400> SEQUENCE: 36
gagggctggg agccgtcann saacaacgcg    30

<210> SEQ ID NO 37
<211> LENGTH: 33
<212> TYPE: DNA
<213> ORGANISM: Trichoderma reesei
<220> FEATURE:
<221> NAME/KEY: misc_feature
<222> LOCATION: (25)..(26)
<223> OTHER INFORMATION: N= A, C, G, OR T

<400> SEQUENCE: 37
ccaatgcccg tgttcgcgtt gttsnntgac ggc    33

<210> SEQ ID NO 38
<211> LENGTH: 29
<212> TYPE: DNA
<213> ORGANISM: Trichoderma reesei

<400> SEQUENCE: 38
aacgttaatt aaggaatcgt tttgtgttt    29

<210> SEQ ID NO 39
<211> LENGTH: 29
<212> TYPE: DNA
<213> ORGANISM: Trichoderma reesei

<400> SEQUENCE: 39
agtactagta gctccgtggc gaaagcctg    29

<210> SEQ ID NO 40
<211> LENGTH: 26
<212> TYPE: DNA
<213> ORGANISM: Trichoderma reesei

<400> SEQUENCE: 40
actagtcgac cgaatgtagg attgtt    26

<210> SEQ ID NO 41
<211> LENGTH: 19
<212> TYPE: DNA

```
<213> ORGANISM: Trichoderma reesei

<400> SEQUENCE: 41
tgaccatggt gcgcagtcc                                         19

<210> SEQ ID NO 42
<211> LENGTH: 26
<212> TYPE: DNA
<213> ORGANISM: Trichoderma reesei

<400> SEQUENCE: 42
cgatcgtctc cctatgggtc attacc                                 26

<210> SEQ ID NO 43
<211> LENGTH: 28
<212> TYPE: DNA
<213> ORGANISM: Trichoderma reesei

<400> SEQUENCE: 43
actagttaat taagctccgt ggcgaaag                               28

<210> SEQ ID NO 44
<211> LENGTH: 30
<212> TYPE: DNA
<213> ORGANISM: Trichoderma reesei

<400> SEQUENCE: 44
cgcggactgc gcaccatgta tcggaagttg                             30

<210> SEQ ID NO 45
<211> LENGTH: 30
<212> TYPE: DNA
<213> ORGANISM: Trichoderma reesei

<400> SEQUENCE: 45
cgccacggag cttaattaca ggcactgaga                             30

<210> SEQ ID NO 46
<211> LENGTH: 20
<212> TYPE: DNA
<213> ORGANISM: Trichoderma reesei

<400> SEQUENCE: 46
gccttcggcc tttgggtgta                                        20

<210> SEQ ID NO 47
<211> LENGTH: 20
<212> TYPE: DNA
<213> ORGANISM: Trichoderma reesei

<400> SEQUENCE: 47
gagcggcgat tctacgggtt                                        20

<210> SEQ ID NO 48
<211> LENGTH: 26
<212> TYPE: DNA
<213> ORGANISM: Escherichia coli

<400> SEQUENCE: 48
gccgcggcac gcgccacacg gaaaat                                 26

<210> SEQ ID NO 49
<211> LENGTH: 27
```

```
<212> TYPE: DNA
<213> ORGANISM: Escherichia coli

<400> SEQUENCE: 49
gaccggtcgc aaaatgacaa atagaag                                          27

<210> SEQ ID NO 50
<211> LENGTH: 23
<212> TYPE: DNA
<213> ORGANISM: Trichoderma reesei

<400> SEQUENCE: 50
gctccgggca aatgcaaagt gtg                                              23

<210> SEQ ID NO 51
<211> LENGTH: 24
<212> TYPE: DNA
<213> ORGANISM: Trichoderma reesei

<400> SEQUENCE: 51
agcaggccgc atctccagtg aaag                                             24

<210> SEQ ID NO 52
<211> LENGTH: 20
<212> TYPE: DNA
<213> ORGANISM: Escherichia coli

<400> SEQUENCE: 52
gcacgcgcca cacggaaaat                                                  20

<210> SEQ ID NO 53
<211> LENGTH: 20
<212> TYPE: DNA
<213> ORGANISM: Escherichia coli

<400> SEQUENCE: 53
cgcaaaatga caaatagaag                                                  20

<210> SEQ ID NO 54
<211> LENGTH: 31
<212> TYPE: DNA
<213> ORGANISM: Aspergillus fumigatus

<400> SEQUENCE: 54
actggattta ccatgagatt cggttggctc g                                     31

<210> SEQ ID NO 55
<211> LENGTH: 31
<212> TYPE: DNA
<213> ORGANISM: Aspergillus fumigatus

<400> SEQUENCE: 55
agtcacctct agttactagt agacacgggg c                                     31

<210> SEQ ID NO 56
<211> LENGTH: 3060
<212> TYPE: DNA
<213> ORGANISM: Aspergillus fumigatus

<400> SEQUENCE: 56
atgagattcg gttggctcga ggtggccgct ctgacggccg cttctgtagc caatgcccag      60
gtttgtgatg ctttcccgtc attgtttcgg atatagttga caatagtcat ggaaataatc     120
```

-continued

```
aggaattggc tttctctcca ccattctacc cttcgccttg ggctgatggc cagggagagt    180
gggcagatgc ccatcgacgc gccgtcgaga tcgtttctca gatgacactg gcggagaagg    240
ttaaccttac aacgggtact gggtgggttg cgactttttt gttgacagtg agctttcttc    300
actgaccatc tacacagatg ggaaatggac cgatgcgtcg gtcaaaccgg cagcgttccc    360
aggtaagctt gcaattctgc aacaacgtgc aagtgtagtt gctaaaacgc ggtggtgcag    420
acttggtatc aactgggtc tttgtggcca ggattcccct ttgggtatcc gtttctgtga    480
gctatacccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660
gctggggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg gatatggtta caacatcacg gagacgatca gctccaacgt    900
ggatgacaag accatgcacg agttgtacct ttggtgagta gttgacactg caaatgagga    960
ccttgattga tttgactgac ctggaatgca ggcccttttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acgttgtca aaacagtcaa    1140 actctcaaca agctcctcaa ggctgagctg gcttccaag gcttcgtcat gagtgactgg    1200
agcgctcacc acagcggtgt cggcgctgcc ctcgctgggt tggatatgtc gatgcctgga   1260
gacatttcct tcgacgacgg actctccttc tggggcacga acctaactgt cagtgttctt    1320
aacggcaccg ttccagcctg gcgtgtcgat gacatggctg ttcgtatcat gaccgcgtac    1380
tacaaggttg gtcgtgaccg tcttcgtatt cccctaact tcagctcctg gacccgggat    1440
gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga acacggggtgc tcttcctttg accggcaagg aggttaaagt gggtgttctc    1620
ggtgaagacg ctggttccaa cccgtggggt gctaacggct gccccgaccg cggctgtgat    1680
aacggcactc ttgctatggc ctgggggtagt ggtactgcca acttcccttaa ccttgtcacc    1740 cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860 cttagaaaaaa gaacgttctc tgaatgaagt tttttaacca ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat   2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
```

-continued

```
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccccT cctgaaggct ggcggcgctc ctggtggtaa ccctacccTT    2700
tatcaggatc ttgttagggt gtcggccacc ataaccaaca ctggtaacgt cgccggttat    2760
gaagtccctc aattggtgag tgacccgcat gttccttgcg ttgcaatttg ctaactcgc    2820 ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc ctctgccccg tgtctactag    3060
```

<210> SEQ ID NO 57
<211> LENGTH: 863
<212> TYPE: PRT
<213> ORGANISM: Aspergillus fumigatus

<400> SEQUENCE: 57

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
                100                 105                 110

Val Ala Ala Thr Trp Asp Lys Thr Leu Ala Tyr Leu Arg Gly Lys Ala
            115                 120                 125

Met Gly Glu Glu Phe Asn Asp Lys Gly Val Asp Ile Leu Leu Gly Pro
130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
```

```
                275                 280                 285
Val Gly Ala Ala Leu Ala Gly Leu Asp Met Ser Met Pro Gly Asp Ile
290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
                340                 345                 350

Pro Pro Asn Phe Ser Ser Trp Thr Arg Asp Glu Tyr Gly Trp Glu His
                355                 360                 365

Ser Ala Val Ser Glu Gly Ala Trp Thr Lys Val Asn Asp Phe Val Asn
370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
                420                 425                 430

Ala Asn Gly Cys Pro Asp Arg Gly Cys Asp Asn Gly Thr Leu Ala Met
                435                 440                 445

Ala Trp Gly Ser Gly Thr Ala Asn Phe Pro Tyr Leu Val Thr Pro Glu
450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
                500                 505                 510

Ile Ser Val Asp Gly Asn Glu Gly Asp Arg Lys Asn Leu Thr Leu Trp
                515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
                580                 585                 590

Pro Ser Ala Lys Thr Pro Phe Thr Trp Gly Lys Thr Arg Glu Ser Tyr
                595                 600                 605

Gly Ala Pro Leu Leu Thr Glu Pro Asn Asn Gly Asn Gly Ala Pro Gln
                610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
                660                 665                 670

Ser Ala Tyr Val Pro Thr Ser Gly Glu Thr Lys Pro Ala Pro Thr Tyr
                675                 680                 685

Gly Glu Ile Gly Ser Ala Ala Asp Tyr Leu Tyr Pro Glu Gly Leu Lys
                690                 695                 700
```

```
Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
            725                 730                 735

Pro Glu Gly Ala Arg Asp Gly Ser Pro Gln Pro Leu Leu Lys Ala Gly
        740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
            805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
    850                 855                 860
```